US009815898B2

(12) United States Patent
Freeman et al.

(10) Patent No.: US 9,815,898 B2
(45) Date of Patent: Nov. 14, 2017

(54) ANTIBODY MOLECULES TO PD-1 AND USES THEREOF

(71) Applicants: Novartis AG, Basel (CH); DANA-FARBER CANCER INSTITUTE, INC., Boston, MA (US); PRESIDENT AND FELLOWS OF HARVARD COLLEGE, Cambridge, MA (US)

(72) Inventors: Gordon James Freeman, Brookline, MA (US); Arlene Helen Sharpe, Brookline, MA (US); Walter A. Blattler, Brookline, MA (US); Jennifer Marie Mataraza, Cambridge, MA (US); Catherine Anne Sabatos-Peyton, Cambridge, MA (US); Hwai Wen Chang, Cambridge, MA (US); Gerhard Johann Frey, San Diego, CA (US)

(73) Assignees: Novartis AG, Basel (CH); PRESIDENT AND FELLOWS OF HARVARD COLLEGE, Cambridge, MA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 15/595,618

(22) Filed: May 15, 2017

(65) Prior Publication Data

US 2017/0247456 A1 Aug. 31, 2017

Related U.S. Application Data

(62) Division of application No. 14/604,415, filed on Jan. 23, 2015, now Pat. No. 9,683,048.

(60) Provisional application No. 62/094,834, filed on Dec. 19, 2014, provisional application No. 62/059,676, filed on Oct. 3, 2014, provisional application No. 61/931,512, filed on Jan. 24, 2014.

(51) Int. Cl.
*C07K 16/28* (2006.01)

(52) U.S. Cl.
CPC ...... *C07K 16/2818* (2013.01); *C07K 2317/24* (2013.01); *C07K 2317/31* (2013.01); *C07K 2317/565* (2013.01); *C07K 2317/76* (2013.01); *C07K 2317/92* (2013.01)

(58) Field of Classification Search
CPC C07K 16/28; C07K 16/2827; C07K 16/2818; C07K 16/2896; A61K 39/395; A61K 39/3955; A61K 39/39558
See application file for complete search history.

(56) References Cited

U.S. PATENT DOCUMENTS

| | | | |
|---|---|---|---|
| 5,324,514 | A | 6/1994 | Sipos |
| 5,629,204 | A | 5/1997 | Honjo et al. |
| 5,698,520 | A | 12/1997 | Honjo et al. |
| 5,897,862 | A | 4/1999 | Hardy et al. |
| 5,968,511 | A | 10/1999 | Akita et al. |
| 6,051,227 | A | 4/2000 | Allison et al. |
| 6,632,927 | B2 | 10/2003 | Adair et al. |
| 6,632,976 | B1 | 10/2003 | Tomizuka et al. |
| 6,803,192 | B1 | 10/2004 | Chen |
| 6,808,710 | B1 | 10/2004 | Wood et al. |
| 6,936,704 | B1 | 8/2005 | Freeman et al. |
| 7,029,674 | B2 | 4/2006 | Carreno et al. |
| 7,038,013 | B2 | 5/2006 | Freeman et al. |
| 7,041,474 | B2 | 5/2006 | Kingsbury |
| 7,101,550 | B2 | 9/2006 | Wood et al. |
| 7,105,328 | B2 | 9/2006 | Wood et al. |
| 7,122,372 | B2 | 10/2006 | Hardy et al. |
| 7,329,639 | B2 | 2/2008 | Hardy et al. |
| 7,332,582 | B2 | 2/2008 | Hardy et al. |
| 7,414,171 | B2 | 8/2008 | Honjo et al. |
| 7,423,128 | B2 | 9/2008 | Gazit-Bornstein et al. |
| 7,488,802 | B2 | 2/2009 | Collins et al. |
| 7,521,051 | B2 | 4/2009 | Collins et al. |
| 7,524,498 | B2 | 4/2009 | Hardy et al. |
| 7,563,869 | B2 | 7/2009 | Honjo et al. |
| 7,595,048 | B2 | 9/2009 | Honjo et al. |
| 7,635,757 | B2 | 12/2009 | Freeman et al. |
| 7,695,715 | B2 | 4/2010 | Hardy et al. |
| 7,722,868 | B2 | 5/2010 | Freeman et al. |
| 7,794,710 | B2 | 9/2010 | Chen et al. |
| 7,858,746 | B2 | 12/2010 | Honjo et al. |
| 8,008,449 | B2 | 8/2011 | Korman et al. |
| 8,039,273 | B2 | 10/2011 | Jeffrey |

(Continued)

FOREIGN PATENT DOCUMENTS

| | | | |
|---|---|---|---|
| AU | 774391 | B2 | 6/2004 |
| EP | 0670369 | A2 | 9/1995 |

(Continued)

OTHER PUBLICATIONS

Pinzon-Ortiz et al: "S710: The combination of JAK inhibitor, ruxolitinib, pan-PIM inhibitor, LGH447, and CDK4/6 inhibitor, LEE011, in a preclinical mouse model of myeloproliferative neoplasia", Haematologica, The Hematology Journal: Official Organ of the European Hematology Association, vol. 99. No . Supp 1 (2014) p. 252.

Polyak, M.J. and Deans, J.P., "Alanine-170 and proline-172 are critical determinants for extracellular CD20 epitopes; heterogeneity in the fine specificity of CD20 monoclonal antibodies is defined by additional requirements imposed by both aminoacid sequence and quaternary structure," Blood 99(9):3256-3262, American Society of Hematology, United States (2002).

Prokunina, L. and Alarcon-Riquelme, M., "The genetic basis of systemic lupus erythematosus -knowledge of today and thoughts for tomorrow," Human Molecular Genetics 13(1):R143-R148, Oxford University Press, England (2004).

(Continued)

*Primary Examiner* — Jessica H Roark
(74) *Attorney, Agent, or Firm* — Lando & Anastasi, LLP

(57) ABSTRACT

Antibody molecules that specifically bind to PD-1 are disclosed. The anti-PD-1 antibody molecules can be used to treat, prevent and/or diagnose cancerous or infectious conditions and disorders.

30 Claims, 20 Drawing Sheets

(56) References Cited

U.S. PATENT DOCUMENTS

| | | | | |
|---|---|---|---|---|
| 8,088,905 | B2 | 1/2012 | Collins et al. | |
| 8,168,179 | B2 | 5/2012 | Honjo et al. | |
| 8,168,757 | B2 | 5/2012 | Finnefrock et al. | |
| 8,287,856 | B2 | 10/2012 | Li et al. | |
| 8,354,509 | B2 | 1/2013 | Carven et al. | |
| 8,460,886 | B2 | 6/2013 | Shibayama et al. | |
| 8,568,728 | B2 | 10/2013 | Jeffrey | |
| 8,580,247 | B2 | 11/2013 | Li et al. | |
| 8,609,089 | B2 | 12/2013 | Langermann et al. | |
| 8,709,416 | B2 | 4/2014 | Langermann et al. | |
| 8,728,474 | B2 | 5/2014 | Honjo et al. | |
| 8,735,553 | B1 | 5/2014 | Li et al. | |
| 8,779,105 | B2 | 7/2014 | Korman et al. | |
| 8,779,108 | B2 | 7/2014 | Queva et al. | |
| 8,900,587 | B2 | 12/2014 | Carven et al. | |
| 8,927,697 | B2 | 1/2015 | Davis et al. | |
| 8,952,136 | B2 | 2/2015 | Carven et al. | |
| 9,067,999 | B1 | 6/2015 | Honjo et al. | |
| 9,073,994 | B2 | 7/2015 | Honjo et al. | |
| 9,084,776 | B2 | 7/2015 | Korman et al. | |
| 9,102,727 | B2 * | 8/2015 | Freeman ............ | C07K 16/2818 |
| 9,683,048 | B2 * | 6/2017 | Freeman ............ | C07K 16/2896 |
| 2002/0164660 | A1 | 11/2002 | Spaulding et al. | |
| 2003/0039653 | A1 | 2/2003 | Chen et al. | |
| 2003/0232323 | A1 | 12/2003 | Freeman et al. | |
| 2004/0073957 | A1 | 4/2004 | Tomizuka et al. | |
| 2004/0241745 | A1 | 12/2004 | Honjo et al. | |
| 2006/0110383 | A1 | 5/2006 | Honjo et al. | |
| 2006/0210567 | A1 | 9/2006 | Collins et al. | |
| 2007/0065427 | A1 | 3/2007 | Freeman et al. | |
| 2007/0122378 | A1 | 5/2007 | Freeman et al. | |
| 2007/0202100 | A1 | 8/2007 | Wood et al. | |
| 2008/0025979 | A1 | 1/2008 | Honjo et al. | |
| 2008/0311117 | A1 | 12/2008 | Collins et al. | |
| 2009/0076250 | A1 | 3/2009 | Honjo et al. | |
| 2010/0266617 | A1 * | 10/2010 | Carven .............. | C07K 16/2818 424/172.1 |
| 2011/0081341 | A1 | 4/2011 | Honjo et al. | |
| 2011/0150892 | A1 | 6/2011 | Thudium et al. | |
| 2011/0171220 | A1 | 7/2011 | Davis | |
| 2011/0177088 | A1 | 7/2011 | Olive et al. | |
| 2011/0195068 | A1 | 8/2011 | Langermann et al. | |
| 2011/0229461 | A1 | 9/2011 | Tyson | |
| 2012/0076805 | A1 | 3/2012 | Sharpe et al. | |
| 2012/0114649 | A1 | 5/2012 | Langermann et al. | |
| 2013/0017199 | A1 | 1/2013 | Langermann | |
| 2013/0095098 | A1 | 4/2013 | Tyson | |
| 2013/0109843 | A1 | 5/2013 | Carven et al. | |
| 2013/0133091 | A1 | 5/2013 | Korman et al. | |
| 2013/0202623 | A1 | 8/2013 | Chomont et al. | |
| 2013/0230514 | A1 | 9/2013 | Langermann et al. | |
| 2014/0044738 | A1 | 2/2014 | Langermann et al. | |
| 2014/0155678 | A1 | 6/2014 | Zeng et al. | |
| 2014/0178370 | A1 | 6/2014 | Freeman et al. | |
| 2014/0212422 | A1 | 7/2014 | Korman et al. | |
| 2014/0294852 | A1 | 10/2014 | Korman et al. | |
| 2014/0314714 | A1 | 10/2014 | Honjo et al. | |
| 2014/0328833 | A1 | 11/2014 | Korman et al. | |
| 2014/0348743 | A1 | 11/2014 | Korman et al. | |
| 2015/0079109 | A1 | 3/2015 | Li et al. | |
| 2015/0093380 | A1 | 4/2015 | Honjo et al. | |
| 2015/0210769 | A1 | 7/2015 | Freeman et al. | |
| 2015/0232555 | A1 | 8/2015 | Carven et al. | |
| 2015/0259420 | A1 | 9/2015 | Triebel et al. | |
| 2016/0108123 | A1 | 4/2016 | Freeman et al. | |
| 2016/0222121 | A1 | 8/2016 | Johnson et al. | |
| 2017/0044259 | A1 * | 2/2017 | Tipton ............... | C07K 16/3069 |

FOREIGN PATENT DOCUMENTS

| | | | |
|---|---|---|---|
| EP | 0742795 | A1 | 11/1996 |
| EP | 1165616 | A1 | 1/2002 |
| EP | 1210424 | A1 | 6/2002 |
| EP | 1334659 | A1 | 8/2003 |
| EP | 1385533 | A1 | 2/2004 |
| EP | 1445264 | A1 | 8/2004 |
| EP | 1537878 | A1 | 6/2005 |
| EP | 1576014 | A1 | 9/2005 |
| EP | 1591527 | A1 | 11/2005 |
| EP | 1896582 | A1 | 3/2008 |
| EP | 2161336 | A1 | 3/2010 |
| EP | 2170959 | A1 | 4/2010 |
| EP | 2195347 | A1 | 6/2010 |
| EP | 2206517 | A1 | 7/2010 |
| EP | 2243493 | A1 | 10/2010 |
| EP | 2270051 | A2 | 1/2011 |
| EP | 2307050 | A1 | 4/2011 |
| EP | 2328920 | A2 | 6/2011 |
| EP | 2342228 | A1 | 7/2011 |
| EP | 2342229 | A1 | 7/2011 |
| EP | 2360254 | A1 | 8/2011 |
| EP | 2370593 | A2 | 10/2011 |
| EP | 2397155 | A1 | 12/2011 |
| EP | 2397156 | A1 | 12/2011 |
| EP | 2417984 | A1 | 2/2012 |
| EP | 2418278 | A2 | 2/2012 |
| EP | 2439272 | A2 | 4/2012 |
| EP | 2439273 | A2 | 4/2012 |
| EP | 2482849 | A2 | 8/2012 |
| EP | 2504364 | A1 | 10/2012 |
| EP | 2535354 | A1 | 12/2012 |
| EP | 2545076 | A1 | 1/2013 |
| EP | 2545078 | A1 | 1/2013 |
| EP | 2581113 | A1 | 4/2013 |
| EP | 2691112 | A1 | 2/2014 |
| EP | 2699264 | A1 | 2/2014 |
| EP | 2723381 | A2 | 4/2014 |
| EP | 2927240 | A1 | 10/2015 |
| JP | H07291996 | A | 11/1995 |
| JP | 2002194491 | A | 7/2002 |
| JP | 2003029846 | A | 1/2003 |
| JP | 2004512005 | A | 4/2004 |
| WO | 9520605 | A1 | 8/1995 |
| WO | 9707671 | A1 | 3/1997 |
| WO | 0032231 | A1 | 6/2000 |
| WO | 0058363 | A1 | 10/2000 |
| WO | 0071078 | A2 | 11/2000 |
| WO | 0114424 | A2 | 3/2001 |
| WO | 0114556 | A1 | 3/2001 |
| WO | 0114557 | A1 | 3/2001 |
| WO | 0183750 | A2 | 11/2001 |
| WO | 0200692 | | 1/2002 |
| WO | 0200730 | | 1/2002 |
| WO | 0232378 | A2 | 4/2002 |
| WO | 0234205 | A2 | 5/2002 |
| WO | 0239813 | A1 | 5/2002 |
| WO | 02078731 | A1 | 10/2002 |
| WO | 02079499 | A1 | 10/2002 |
| WO | 02086083 | A2 | 10/2002 |
| WO | 03000066 | A1 | 1/2003 |
| WO | 03011911 | A1 | 2/2003 |
| WO | 03033644 | A2 | 4/2003 |
| WO | 03042402 | A2 | 5/2003 |
| WO | 03099196 | A2 | 12/2003 |
| WO | 2004004771 | A1 | 1/2004 |
| WO | 2004056875 | A1 | 7/2004 |
| WO | 2004072286 | A1 | 8/2004 |
| WO | 2006021955 | A2 | 3/2006 |
| WO | 2006042237 | A2 | 4/2006 |
| WO | 2006/124269 | A2 | 11/2006 |
| WO | 2006121168 | A1 | 11/2006 |
| WO | 2006133396 | A2 | 12/2006 |
| WO | 2007005874 | A2 | 1/2007 |
| WO | 2007011968 | A2 | 1/2007 |
| WO | 2007082154 | A2 | 7/2007 |
| WO | 2007113648 | A2 | 10/2007 |
| WO | 2008071447 | A2 | 6/2008 |
| WO | 2008083174 | A2 | 7/2008 |
| WO | 2008085562 | A2 | 7/2008 |
| WO | 2008156712 | A1 | 12/2008 |
| WO | 2009014708 | A2 | 1/2009 |
| WO | 2009024531 | A1 | 2/2009 |
| WO | 2009101611 | A1 | 8/2009 |

(56) References Cited

FOREIGN PATENT DOCUMENTS

| | | | |
|---|---|---|---|
| WO | 2009114335 | A2 | 9/2009 |
| WO | 2010001617 | A1 | 1/2010 |
| WO | 2010019570 | A2 | 2/2010 |
| WO | 2010027423 | A2 | 3/2010 |
| WO | 2010027827 | A2 | 3/2010 |
| WO | 2010027828 | A2 | 3/2010 |
| WO | 2010029434 | A1 | 3/2010 |
| WO | 2010029435 | A1 | 3/2010 |
| WO | 2010036959 | A2 | 4/2010 |
| WO | 2010051502 | A2 | 5/2010 |
| WO | 2010063011 | A2 | 6/2010 |
| WO | 2010077634 | A1 | 7/2010 |
| WO | 2010089411 | A2 | 8/2010 |
| WO | 2010098788 | A2 | 9/2010 |
| WO | 2010102278 | A1 | 9/2010 |
| WO | 2011011027 | A1 | 1/2011 |
| WO | 2011041613 | A2 | 4/2011 |
| WO | 2011066342 | A2 | 6/2011 |
| WO | 2011066389 | A1 | 6/2011 |
| WO | 2011100841 | A1 | 8/2011 |
| WO | 2011110604 | A1 | 9/2011 |
| WO | 2011110621 | A1 | 9/2011 |
| WO | 2011159877 | A2 | 12/2011 |
| WO | 2012018538 | A2 | 2/2012 |
| WO | 2012022814 | A1 | 2/2012 |
| WO | 2012135408 | A1 | 10/2012 |
| WO | 2012145493 | A1 | 10/2012 |
| WO | 2012177624 | A2 | 12/2012 |
| WO | 2013006490 | A2 | 1/2013 |
| WO | 2013019906 | A1 | 2/2013 |
| WO | 2013043647 | A1 | 3/2013 |
| WO | 2013066761 | A1 | 5/2013 |
| WO | 2013079174 | A1 | 6/2013 |
| WO | 2013079945 | A1 | 6/2013 |
| WO | 2013169693 | A1 | 11/2013 |
| WO | 2013173223 | A1 | 11/2013 |
| WO | 2013181452 | A1 | 12/2013 |
| WO | 2014022138 | A2 | 2/2014 |
| WO | 2014047350 | A1 | 3/2014 |
| WO | 2014055648 | A1 | 4/2014 |
| WO | 2014179664 | A2 | 11/2014 |
| WO | 2014189805 | A1 | 11/2014 |
| WO | 2015009856 | A2 | 1/2015 |
| WO | 2015035606 | A1 | 3/2015 |
| WO | 2015036394 | A1 | 3/2015 |
| WO | 2015042246 | A1 | 3/2015 |
| WO | 2015048312 | A1 | 4/2015 |
| WO | 2015088847 | A1 | 6/2015 |
| WO | 2015095423 | A2 | 6/2015 |
| WO | 2015095811 | A2 | 6/2015 |
| WO | 2015112900 | A1 | 7/2015 |
| WO | 2015117002 | A1 | 8/2015 |
| WO | 2015134605 | A1 | 9/2015 |
| WO | 2015138920 | A1 | 9/2015 |
| WO | 2016028672 | A1 | 2/2016 |
| WO | 2016040880 | A1 | 3/2016 |
| WO | 2016040892 | A1 | 3/2016 |
| WO | 2016054555 | A2 | 4/2016 |
| WO | 2016061142 | A1 | 4/2016 |
| WO | 2016100882 | A1 | 6/2016 |
| WO | 2017019894 | A1 | 2/2017 |
| WO | 2017019896 | A1 | 2/2017 |
| WO | 2017019897 | A1 | 2/2017 |

OTHER PUBLICATIONS

Quintarelli et al: "Selective strong synergism of Ruxolitinib and second generation tyrosine kinase inhibitors to overcome bone marrow stroma related drug resistance in chronic myelogenous leukemia", Leukemia Research, New York,NY, US, vol. 38, No. 2, Nov. 15, 2013 (Nov. 15, 2013), pp. 236-242.

Riley, J.L. and June, C.H., "The CD28 family: a T-cell rheostat for therapeutic control of T-cell activation," Blood 105 (1):13-21, American Society of Hematology, United States (Jan. 2005).

Rudikoff, et al.; "Single Amino Acid Substitution Altering Antigen-binding Specificity"; Proc. Natl. Acad. Sci. USA; 79:1979-1983 (1982).

Salama, A.D., et al., "Critical role of the programmed death- I (PD-1) pathway in regulation of experimental autoimmune encephalomyelitis," The Journal of Experimental Medicine 198(1):71-78, The Rockefeller University Press, United States (2003).

Shinohara, T., et al., "Structure and chromosomal localization of the human PD-1 gene (PDCD1)," Genomics 23 (3):704-706, Academic Press, United States (1994).

Soh, E.Y., et al., "Neutralizing vascular endothelial growth factor activity inhibits thyroid cancer growth in vivo," Surgery 128(6):1059-1066, Mosby, United States (2000).

Song et al: "3681 Phenotypic and Functional Effects of Novel HDAC Inhibitor LBH589 on Human Lymphocyte Populations", 51st ASH Annual Meeting and Exposition (2009) Retrieved from the Internet: URL:https:jjash.confex.comjash/2889/webprogramjPaper22684.html [retrieved on 2816-84-14].

Song W et al: "HDAC inhibition by LBH589 affects the phenotype and function of human myeloid dendritic cells.", Leukemia Jan 2811, vol. 25, No. 1, Jan. 2011 (Jan. 2011), pp. 161-168.

Supplementary Partial European Search Report for European Application No. EP 1484888 dated Jan. 3, 2017.

Tamura, H., et al., "B7-H1 costimulation preferentially enhances CD28-independent T-helper cell function," Blood 97 (6)1809-1816, The American Society of Hematology, United States (2001).

Teeling, J.L., et al., "Characterization of new human CD20 monoclonal antibodies with potent cytolytic activity against non-Hodgkin Lymphomas," Blood 104(6):1793-1800, American Society of Hematology, United States (2004).

Thomas, M.L., "Of ITAMs and ITIMs: turning on and off the B cell antigen receptor," The Journal of Experimental Medicine 181(6):1953-1956, The Rockefeller University Press, United States (1995).

Thompson, R. Houston, et al.; "PD-1 is expressed by tumor-infiltrating immune cells and is associated with poor outcome for patients with renal cell carcinoma"; Clin. Cancer Res. 13(6):1757-1761 (2007).

Tomlinson, I.M., et al., "The repertoire of human germline VH sequences reveals about fifty groups of VH segments with different hypervariable loops," Journal of Molecular Biology 227(3):776-798, Elsevier, Netherlands (1992).

Topalian, S., "Q&A: Suzanne Topalian on Immune Terapies", Cancer Discovery 3(7):712, American Association for Cancer Research, United States, published online Jun. 27, 2013.

Topalian, S., et al., "Nivolumab (anti-PD-1; BMS-936558; ONO-4538) in patients with advanced solid tumors: Survival and long-term safety in a phase I trial," accessed at http://meetinglibrary.asco.org/content/113543-132, accessed on Jun. 1, 2016, 2pages.

Topalian, S.L., et al., "Safety, Activity, and Immune Correlates of Anti-PD-1 Antibody in Cancer," The New England Journal of Medicine 366(26):2443-2454, Massachusetts Medical Society, United States (2012).

Trautmann, Lydie, et al.; "Upregulation of PD-1 expression on HIV-specific CD8+ T cells leads to reversible immune dysfunction"; Nat. Med.; 12(10):1198-1202 (2006).

Tsai, C-J., et al., "Protein Allostery, signal transmission and dynamics: a classification scheme of allosteric mechanisms," Molecular BioSystems 5(3):207-216, Royal Society of Chemistry, England (2009).

Tsushima, Fumihiko, et al.; "Predominant expression of B7-H1 and its immunoregulatory roles in oral squamous cell carcinoma"; Oral Oncology; 42:268-274 (2006).

UniProtKB/Swiss-Prot Database entry, PDCD1.sub.—Human, accessed at http://www.uniprot.org/uniprot/Q15116.txt, accessed on Jun. 1, 2016, 5 pages.

Van Regenmortel, M.H.V., "The recognition of Proteins and Peptides by Antibodies," Journal of Immunoassay 21 (2-3):85-108, Taylor & Francis, England (2000).

Vanneman et al: "Combining immunotherapy and targeted therapies in cancer treatment" Nature Reviews Cancer (2012) vol. 12 No. 4 pp. 237-251.

(56) References Cited

OTHER PUBLICATIONS

Verbrugge et al: "The curative outcome of radioinmunotherapy in a mouse breast cancer model relies on mTOR signaling", Radiation Research. Radiation Research Society, GB, vol. 182 No. 2 pp. 219-229.
Waldmann, Thomas A.; "Effective cancer therapy through immunomodulation"; Annual Rev.; 57(1):65-81 (2006).
Wang et al. "In Vitro Characterization of the Anti-PD-1 Antibody Nivolumab, BMS-936558, and In Vivo Toxicology in Non-Human Primates" Cancer Immunol Res. (2014) vol. 2, No. 9, pp. 846-856.
Wang et al., "The Mdm2 inhibitor, NVP-CGM097, in combination with the BRAF inhibitor NVP-LGX818 elicits synergistic antitumor effects in melanoma" Cancer Research (2014) Retrieved from the Internet: URL:http://cancerres.aacrjournals.orgjcontent/74/19 Supplement/5466 [retrieved on Apr. 14, 2016].
Wang et al., "Vista, a novel mouse Ig superfamily ligand that negatively regulates T cell responses" The Journal of Experimental Medicine (2011) vol. 208 No. 3 pp. 577-592.
Wang et al: "Abstract 2929: The Mdm2 inhibitor NVP-CGM097 enhances the anti-tumor activityof NVP-LDK378 in ALK mutant neuroblastomamodels", Cancer Research (2014) Retrieved from the Internet: URL:http:jjcancerres.aacrjournals.orgjcontent/74/19 Supplement/2929 [retrieved on Apr. 14, 2016].
Weber, J.S., et al., "Safety, Efficacy, and Biomarkers of Nivolumab with Vaccine in Ipilimumab-Refractory or -Naive Melanoma," Journal of Clinical Oncology 31 (34):4311-4318, American Society of Clinical Oncology, United States (2013).
Wilson, I.A. and Stanfield, R.L., "Antibody-antigen interactions," Current Opinion in Sturctural Biology 3:113-118, Current Biology, United States (1993).
Winslow, R., "New Cancer Drugs Harness Power of Immune System", The Wall Street Journal, May 15, 2013, accessed at http://www.wsj.com/articles/ SB10001424127887323398204578485401089823868, accessed on Jun. 1, 2016, 4 pages.
Wolchok, J.D., et al., "Nivolumab plus Ipilimumab in Advanced Melanoma," The New England Journal of Medicine 369 (2):122-133, Massachusetts Medical Society, United States (2013).
Wong, R.M., et al., "Programmed death-1 blockade enhances expansion and functional capacity of human melanoma antigen-specific CTLs," International Immunology 19(10)1223-1234, Oxford University Press, England (2007).
Woods David M et al: "HDAC Inhibition Upregulates PD-1 Ligands in Melanoma and Augments Immunotherapy with PD-1 Blockade. ",Cancer Immunology Research, vol. 3, No. 12, Dec. 2815 (Dec. 2015), pp. 1375-1385.
Woods David M et al: "The antimelanoma activity of the histone deacetylase inhibitor panobinostat (LBH589) is mediated by direct tumor cytotoxicity and increased tumor immunogenicity.", Melanoma Research, vol. 23, No. 5, Oct. 2813 (Oct. 2013), pp. 341-348.
Woods et al: "Abstract 4090: Inhibition of class I histone deacetylases promotes robust and durable enhancement of PDL1 expression in melanoma: Rationale for combination therapy", Cancer Research (2014) AACR Annual Meeting 2014; San Deigo, CA; published Cancer Res. Oct. 1, 2014; 74:4090.
Wu, K-P., et al., "Structural Basis of a Flavivirus Recognized by Its Neutralizing Antibody: Solution Structure of the Domain III of the Japanese Encephalitis Virus Envelope Protein," The Journal of Biological Chemistry 278 (46):46007-46013, AmericanSociety for Biochemistry and Molecular Biology, Inc., United States (Nov. 2003).
Yamazaki, T., et al., "Expression of programmed death 1 ligands by murine T cells and APC," The Journal of Immunology 169(10):5538-5545, The American Association of Immunologists, United States (2002).
Yi, J., et al., "Mapping the Epitope of an Inhibitory Monoclonal Antibody to the C-terminal DNA-binding Domain of HIV-1 Integrase," The Journal of Biological Chemistry 277(14):12164-12174, American Society for Biochemistry and Molecular Biology,Inc., United States (2002).
Youngnak, Pompan, et al.; "Differential binding properties of B7-H1 and B7-DC to programmed death-1"; Biochem. Biophys. Res. Commun.; 307:672-677 (2003).
Yuan Z et al, "Blockade of inhibitors of apoptosis (IAPs) in combination with tumor-targeted delivery of tumor necrosis factor-[alpha] leads to synergistic antitumor activity" Cancer Gene Therapy (2013) vol. 20 No. 1 pp. 46-56.
Zehavi-Willner, Tova, et al.; "The mitogenic activity of staphylococcal enterotoxin B (Seb): a monovalent T cell mitogen that stimulates cytolytic T lymphocytes but cannot mediate their lytic interaction"; J. Immunol.; 137(8):2682-2687 (1986).
Zhang, Xuewu, et al.; "Structural and Functional Ana ysis of the Costimulatory Receptor Programmed Death-1"; Immunity; 20:337-347 (2004).
Zhou et al., "Coexpression of Tim-3 and PD-1 identifies a CD8 T-cell exhaustion phenotype in mice with disseminated acute myelogenous leukemia" Blood (2011) vol. 117 No. 17 pp. 4501-4510.
Zhuang J et al: "Selective IAP inhibition results in sensitization of unstimulated but not CD40-stimulated chronic lymphocytic leukaemia cells to TRAIL-induced apoptosis" Pharmacology Research & Perspectives. John Wiley & Sons Ltd, GB, vol. 2 No. 6 pp. 1-14.
Zou, W. and Chen, L., "Inhibitory B7-family Molecules in the Tumour Microenvironment," Nature Reviews Immunology 8(6):467-477, Nature Publishing Group, England (2008).
Zuberek, K., "The role of in vivo PD-1/PD-L1 interactions in syngeneic and allogeneic antitumor responses in murine tumor models," Blood 98(11):42B (2001).
Zuberek, Krystyna, et al.; "Invitro and in vivo expression regulation of PD-1 and PD-L1 in murine tumor models"; Blood; 98(11 Part 1):25a (2001).
"About the Internet Archive: General Information", Internet Archive, 2001, 10 pages, retrieved online from http://www.archive.org/about/about.php on Jun. 1, 2016.
Abbas, A.K., et al., Cellular and Molecular Immunobiology, 2nd ed., pp. 8, 47-50, W.B. Saunders Company, United States (1991).
Adams, G.P. and Weiner, L.M., "Monoclonal antibody therapy of cancer," Nature Biotechnology 23(9):1147-1157, Nature Publishing Group, United States (2005).
Agata, Y., et al., "Expression of the PD-1 antigen on the surface of stimulated mouse T and B lymphocytes," International Immunology 8(5):765-772, Oxford University Press, England (1996).
Allard et al. "Targeting CD73 Enhances the Antitumor Activity of Anti-FD-1 and Anti-CTLA-4 mAbs" Clinical Cancer Research (2013) vol. 19, No. 20, pp. 5626-5635.
Allison, J.P. and Krummel, M.F., "The Yin and Yang of T Cell Costimulation," Science 270(5238):932-933, American Association for the Advancement of Science, United States (1995).
Amin et al: "Nivolumab (anti-PD-1; BMS-936558, ONO-4538) in combination with sunitinib or pazopanib in patients (pts) with metastatic renal cell carcinoma (mRCC)" Journal of Clinical Oncology (2014) vol. 32, No. 15 suppl, Abstract 5010.
Anderson et al. "Tim-3, a negative regulator of anti-tumor immunity" Current Opinion in Immunology (2012) vol. 24, No. 2, pp. 213-216.
Andre, E., et al., "Precise Characterization of the Epitope Recognized by a Monoclonal Antibody Against *Escherichia coli* RNA Polymerase," Hybridoma 24(1):1-5, Mary Ann Liebert, Inc., United States (Feb. 2005).
Ansari, M.J., et al., "The programmed death-1 (PD-1) pathway regulates autoimmune diabetes in nonobese diabetic (NOD) mice," The Journal of Experimental Medicine 198(1):63-69, The Rockefeller University Press, United States (2003).
Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).
Armand, P., et al., "289 Nivolumab in Patients with relapsed or Refractory Hodgkin Lymphoma—Preliminary Safety, Efficacy and Biomarker Results of a Phase I Study," 56th ASH Annual Meeting and Exposition, Abstracts & Program, San Francisco, CA, Dec. 6-9, 2014.

(56) References Cited

OTHER PUBLICATIONS

Ashworth et al., "Management of a patient with advanced BRAF-mutant melanoma" Journal of the National Comprehensive Cancer Network (2014) vol. 12 No. 3 pp. 315-319.
Barber, Daniel L., et al.; "Restoring function in exhausted CD8 T cells during chronic viral infection"; Nature 439:682-687 (2006).
Batus et al., "Optimal management of metastatic melanoma: Current strategies and future directions" American Journal of Clinical Dermatology (2013) Retrieved from the Internet: URL:http://www.ncbi.nlm.nih.govjpmcjarticles/PMC3913474/pdf/nihms481840 .pdf [retrieved on 2015-12-82].
Bellucci et al: "JAKI and JAK2 Modulate Tumor Cell Susceptibility to Natural Killer (NK) Cells Through Regulation of PDLI Expression", Blood, 2013; 122:3472.
Bennett, F., et al., "Program death-1 engagement upon TCR activation has distinct effects on costimulation and cytokine-driven proliferation: attenuation of ICOS, IL-4, and IL-21, but not CD28, IL-7, and IL-15 responses," The Journal of Immunology170(2):711-718, The American Association of Immunologists, United States (2003).
Benson et al. "The PD-1/PD-L1 axis modulates the natural killer cell versus multiple myeloma effect: a therapeutic target for CT-011, a novel monoclonal anti-PD-1 antibody" Blood (2010) vol. 116, No. 13, pp. 2286-2294.
Berg, J.M., et al., "The Immune System," in Biochemistry 5th ed., pp. 921-950, W.H. Freeman and Company, United States (2002).
Berger, R., et al., "Phase I safety and pharmacokinetic study of CT-011, a humanized antibody interacting with PD-1, in patients with advanced hematologic malignancies," Clinical Cancer Research 14(10):3044-3051, American Association for Cancer-Research, United States (2008).
Blank et al "Combination of targeted therapy and immunotherapy in melanoma" Cancer Immunol Immunother (2011) vol. 60, pp. 1359-1371.
Blank, C., et al., "Interaction of PD-L1 on tumor cells with PD-1 on tumor-specific T cells as a mechanism of immune evasion: implications for tumor immunotherapy," Cancer Immunology Immunotherapy 54(4):307-314, Springer-Verlag, Germany (2005).
Blank, C., et al., "PD-L1/B7H-1 inhibits the effector phase of tumor rejection by T cell receptor (TCR) transgenic CD8+ T cells," Cancer Research 64(3):1140-1145, American Association for Cancer Research, United States (2004).
Blank, Christian, et al.; "Contribution of the PD-L1/PD-1 pathway to T-cell exhaustion: an update on implications for chronic infections and tumor evasion"; Cancer Immunol. Immunotherapy; 56(5):739-745 (2007).
Blazar, B.R., et al., "Infusion of anti-B7.1 (CD80) and anti-B7.2 (CD86) monoclenal antibodies inhibits murine graft-versus-host disease lethality in part via direct effects on CD4+ and CD8+ T cells," The Journal of Immunology 157 (8):3250-3259, TheAmerican Association of Immunologists, United States (1996).
Brahmer, J.R., et al., "Safety and activity of MDX-1106 (ONO-4538) anti-PD-1 monoclonal antibody in patients with selected refractory or relapsed malignancies," Journal of Clinical Oncology 26:Abstract No. 3006, American Society of ClinicalOncology, United States (2008).
Brahmer., J.R., et al., "Phase I study of single-agent anti-programmed death-1 (MDX-1106) in refractory solid tumors: Safety, clinical activity, pharmacodynamics, and immunologic correlates," Journal of Clinical Oncology 28 (19):3167-3175, AmericanSociety of Clinical Oncology, United States (2005).
Brown, J.A., et al., "Blockade of programmed death-1 ligands on dendritic cells enhances T cell activation and cytokine production," The Journal of Immunology 170(3):1257-1266, The American Association of Immunologists, United States (2003).
Brown, J.A., et al., "Expression and functional consequences PD-1 ligands on natural APCS and tumors," The FASEB Journal 15(4):A345 (abstract No. 275.23), Federation of American Societies for Experimental Biology, United States (2001).
Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215,Elsevier, the Netherlands (1984).
Carreno, B,M, and Collins, M., "The B7 family of ligands and its receptors: new pathways for costimulation and inhibition of immune responses," Annual Review of Immunology 20:29-53, Annual Reviews, United States (2002).
Carreno, B.M., "BTLA: a new inhibitory receptor with a B7-like ligand," TRENDS in Immunology 24(10):524-527, Elsevier, England (2003).
Carter, L.L. and Carreno, B.M., et al., "Cytotoxic T-lymphocyte antigen-4 and programmed death-1 function as negative regulators of lymphocyte activation," Immunologic Research 28(1):49-59, Humana Press, United States (2003).
Carter, L.L., et al., "PD-1:PD-L inhibitory pathway affects both CD4(+) and CD8(+) T cells and is overcome by IL-2," European Journal of Immunology 32(3):634-643, Wiley-VCH Verlag GmbH, Germany (2002).
Chen, L., "Co-inhibitory molecules of the B7-CD28 family in the control of T-cell immunity," Nature Reviews Immunology 4(5):336-347, Nature Publishing Group, England (2004).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Chervontseva A M et al: "Effect of cytarabine on expression of cell adhesion molecules and on endothelium-leukocyte interaction in vitro.", Terapevticheskii Arkhiv 2006, vol. 78, No. 7, 2006, pp. 67-72.
Christiansen et al: "Eradication of solid tumors using histone deacetylase inhibitors combined with immune-stimulating antibodies", Proceedings of the National Academy of Sciences, vol. 108 No. 10 Feb. 22, 2011 (Feb. 22, 2011), pp. 4141-4146.
Christiansson Lisa et al: "The tyrosine kinase inhibitors imatinib and dasatinib reduce myeloid suppressor cells and release effector lymphocyte responses.", Molecular Cancer Therapeutics, vol. 14, No . 5, May 2015 (May 2015), pp. 1181-1191.
ClincalTrials.gov Identifier: NCT01988896 "A Phase 1 b Study of MPDL3280A (an Engineered Anti-PDL1 Antibody) in Combination With Cobimetinib in Patients With Locally Advanced or Metastatic Solid Tumors" Clinicaltrials.gov, last updated Dec. 1, 2014.
ClinicalTrials.gov Identifier: NCT02040064 "Tolerability and Efficacy of Tremelimumab in Combination With Gefitinib in NSCLS Patients", ClinicalTrials.gov; last updated Jan. 17, 2014.
ClinicalTrials.gov Identifier: NCT02263508 "A Phase 1 b/3, Multicenter, Open-label Trial of Tafimogene Laherparepvec in Combination With Pembrolizumab (MK-3475) for Treatment of Unresected,Stage IIIB to IVM1c Melanoma (Masterkey-265)", ClinicalTrials.gov; last updated Jun. 22, 2015.
ClinicalTrials.gov Identifier: NCT02339571 "Randomized Phase II/III Study of Nivolumab Plus Ipilimumab Plus Sargramostim Versus Nivolumab Plus Ipilimumab in Patients With Unresectable Stage III or Stage IV Melanoma", ClinicalTrials.gov; last updated Apr. 9, 2015.
Cloeckaert, A., et al., "O-Polysaccharide epitopic heterogeneity at the surface of *Brucella* spp.studied by enzyme-linked immunosorbent assay and flow cytometry," Clinical and Diagnostic Laboratory Immunology 5(6):862-870, American Society forMicrobiology, United States (1998).
Collins et al., "The B7 family of immune-regulatory ligands" Genome Biology (2005) vol. 6 No. 223.
Cragg, M.S. et al., "Complement-mediated lysis by anti-CD20 mAb correlated with segregation into lipid rafts," Blood 101(3):1045-1052, American Society of Hematology, United States (2003).
Creelan, B.C., "Update on Immune Checkpoint Inhibitors in Lung Cancer," Journal of the Moffitt Cancer Center 21 (1):80-89, H. Lee Moffitt Cancer Center and Research Institute, United States (2014).
Cruse, J.M. and Lewis, Re., "Antigens and Immunogens," in Atlas of Immunology, 2nd ed., pp. 105-126, CRC Press, United States (Dec. 29, 2003).

(56) References Cited

OTHER PUBLICATIONS

Davies, D.R. and Cohen, G.H., "Interactions of protein antigens with antibodies," Proceedings of the National Academy of Sciences USA 93(1):7-12, National Academy of Sciences, United States (1996).
Davies, Julian, et al.; "Affinity improvement of single antibody VH domains: residues in all three hypervariable regions affect antigen binding"; ; 2:169-179 (1996).
Del-Rio, Maria-Luisa, et al.; "Antibody-mediated signaling through PD-1 costimulates T cells and enhances CD28-dependent proliferation"; Eur. J. Immunol.; 35(12):3545-3560 (2005).
Dey et al: "Nutl in-3 inhibits the NF[kappa]B Pathway in a p53 Dependent Manner: Implications in Lung Cancer Therapy". Cell Cycle, vol. 6, No. 17, Sep. 1, 2007 (Sep. 1, 2007), pp. 2178-2185.
Dong, H. and Chen, L., "B7-H1 pathway and its role in the evasion of tumor immunity," Journal of Molecular Medicine 81(5):281-287, Springer, Germany (2003).
Dong, H., et al., "Tumor-associated B7-H1 promotes T-cell apoptosis: a potential mechanism of immune evasion," Nature Medicine 8(8):793-800, Nature Publishing Company, United States (2002).
Dougan, D.A., et al., "Effects of subsitutions in the binding surface of an antibody on antigen affinity," Protein Engineering 11(1):65-74, Oxford University Press, England (1998).
Finger, L.R., et al., "The human PD-1 gene: complete cDNA, genomic organization, and developmentally regulated expression in B cell progenitors," Gene 197(1-2):177-187, Elsevier, United States (1997).
Fivash, M., et al., "BIAcore for macromolecular interaction," Current Opinion in Biotechnology 9(1):97-101, Current Biology, England (1998).
Fleischer, Bernhard, et al.; "T cell stimulation by staphylococcal enterotoxins"; J. Exp. Medicine; 167(5):1697-1707 (1988).
Franklin, M.C., et al., "Insights into ErbB signaling from the structure of the ErbB2-pertuzumab complex," Cancer Cell 5 (4):317-328, Cell Press, United States (Apr. 2004).
Freeman, G.J., et al., "Engagement of PD-1 immunoinhibitory receptor by a novel B7 family member leads to negative regulation of lymphocyte activation," The Journal of Experimental Medicine 192(7):1027-1034, The Rockefeller University Press, UnitedStates (2000).
Garcia et al: "The Pan-PIM Kinase Inhibitor LGH447 Shows Activity in PIM2-Dependent Multiple Myeloma and in AML Models", Blood (2013) Retrieved from the Internet: URL:http://www.bloodjournal.orgjcontent/12 Feb. 21, 1666 [retrieved on Apr. 14, 2016].
Garrison K et al: "The small molecule TGF-[beta] signaling inhibitor SM16 synergizes with agonistic OX40 antibody to suppress established mammary tumors and reduce spontaneous metastasis" Cancer Immunology, Immunotherapy (2012) vol. 61 No. 4 pp. 511-521.
Ge, X., et al., "CD134—Allodepletion Allows Selective Elimination of Alloreactive Human T Cells without Loss of Virus-Specific and Leukemia-Specific Effectors," Biology of Blood and Marrow Transplantation 14(5):518-530, American Society for Bloodand Marrow Transplantation, United States (2008).
Gettinger et al. "Safety and Response 1-98 With Nivolumab (Anti -PD-1; BMS-936558, ONO-4538) Plus Erlotinib in Patients (Pts) With Epidermal Growth Factor Receptor Mutant (EGFR MT) Advanced Non -Small Cell Lung Cancer {NSCLC} Metastatic Non-Small Cell Lung Cancer" International Journal of Radiation: Oncology Biology Physics (2014) vol. 90, No. 5, pp. S34-S35.
Greenspan, N.S., "Epitopes, paratopes and other topes: do immunologists know what they are talking about?" Bulletin de l'Institut Pasteur 90(4):267-279, Elsevier, France (1992).
Grygielewicz Paulina et al: "Epithelial-mesenchymal transition confers resistance to selective FGFR inhibitors in SNU-16 gastric cancer cells". Gastric Cancer. Springer Japan. Tokyo. vol. 19. No. 1., Nov. 19, 2014 (Nov. 19, 2014). pp. 53-62.
Hallett et al., "Immunosuppressive Effects of Multiple Myeloma Are Oversome by PD-L1 Blockade" Biol Blood Marrow Transplant (2011) vol. 17 pp. 1133-1145.
Hamid et al., "Safety and Tumor Responses with Lambrolizumab (Anti-PD-1) in Melanoma" New England Journal of Medicine (2013) vol. 369 No. 2 pp. 134-144.
Hansen, J.A., et al., "Monoclonal Antibodies Identifying a Novel T-Cell Antigen and la Antigens of Human Lymphocytes," Immunogenetics 10:247-260, Springer-Verlag (1980).
Harlow, E. and Lane, D., "Using Antibodies: A Laboratory Manual," Cold Spring Harbor Laboratory Press, Cold Spring Harbor, United States various pages (1999).
He, Y-F., et al., "Blocking programmed death-1 ligand-PD-1 interactions by local gene therapy results in enhancement of antitumor effect of secondary lymphoid tissue chemokine," The Journal of Immunology 173(8):4919-4928, The American Association ofImmunologists, United States (2004).
Hirano, F., et al., "Blockade of B7-H1 and PD-1 by monoclonal antibodies potentiates cancer therapeutic immunity," Cancer Research 65(3):1089-1096, American Association for Cancer Research, United States (2005).
Hu Yi et al: "Essential role of AKT in tumor cells addicted to FGFR.", Anti-Cancer Drugs, vol. 25, No. 2, Feb. 2014 (Feb. 2014), pp. 183-188.
Huang, Z., "Structural chemistry and therapeutic intervention of protein-protein interactions in immune response, human immunodeficiency virus entry, and apoptosis," Pharmacology & Therapeutics 86(3):201-215, Pergamon Press, England (2000).
Hutloff, A., et al.,"ICOS is an inducible T-cell co-stimulator structurally and functionally related to CD28," Nature 397 (6716):263-266, Nature Publishing Group, England (1999).
International Search Report and Written Opinion for International Application No. PCT/US2016/044547 dated Oct. 18, 2016.
International Search Report and Written Opinion for PCT/US2014/057491 dated Jan. 7, 2015.
International Search Report and Written Opinion for PCT/US2015/012754 dated May 20, 2015.
International Search Report and Written Opinion for PCT/US2015/049826 dated Dec. 16, 2015.
International Search Report and Written Opinion for PCT/U52015/053799 dated May 17, 2016.
International Search Report for International Application No. PCT/US2015/066812 dated Mar. 23, 2016.
Ishida, Yasumasa, et al.; "Induced expression of PD-1, a novel member of the immunoglobulin gene superfamily, upon programmed cell death"; The EMBO Journal; 11(11):3887-3895 (1992).
Ishima, R. and Torchia, D.A., "Protein Dynamics from NMR," Nature Structural Biology 7(9):740-743, Nature Publishing Company, United States (2000).
Iwai, Y., et al., "Microanatomical localization of PD-1 in human tonsils," Immunology Letters 83(3):215-220, Elsevier, Netherlands (2002).
Iwai, Y., et al., "PD-1 blockade inhibits hematogenous spread of poorly immunogenic tumor cells by enhanced recruitment of effector T cells," International Immunology 17(2):133-144, Oxford University Press, England (2005).
Iwai, Y., et al., "PD-1 inhibits antiviral immunity at the effector phase in the liver," The Journal of Experimental Medicine 198(1):39-50, The Rockefeller University Press, United States (2003).
Iwai, Y., et al.; "Involvement of PD-L1 on tumor cells in the escape from host immune system and tumor immunotherapy by PD-L1 blockade"; Proc. Natl. Acad. Sci.; 99(19):12293-12297 (2002).
J . Acquaviva et al: "FGFR3 Translocations in Bladder Cancer: Differential Sensitivity to HSP90 Inhibition Based on Drug Metabolism". Molecular Cancer Research. vol. 12. No. 7. Jul. 1, 2014 (Jul. 1, 2014). pp. 1042-1054.
Jason-Moller, L., et al., "Overview of Biacore Systems and Their Applications," Current Protocols in Protein Science S45:19.13.1-19.13.14, John Wiley & Sons, Inc., United States (2006).

(56) References Cited

OTHER PUBLICATIONS

Jiang et al, "mTOR Kinase Inhibitor AZD8855 Enhances the Inmunotherapeutic Activity of an Agonist CD40 Antibody in Cancer Treatment" Cancer Research (2011) vol. 71 No. 12.
Jiang X et al: "The activation of MAPK in melanoma cells resistant to BRAF inhibition promotes PD-L1 expression that is reversible by MEK and PI3K inhibition", Clinical Cancer Research, The American Association for Cancer Research, US, vol. 19, No. 3, Feb. 1, 2013 (Feb. 1, 2013). pp. 598-609.
Johne, B., "Protocol: Epitope Mapping by Surface Plasmon Resonance in the BIAcore," Molecular Biotechnology 9 (1):65-71, Humana Press, United States (1998).
Kanai, T., et al., "Blockade of B7-H1 Suppresses the Development of Chronic Intestinal Inflammation," The Journal of Immunology 171(8):4156-4163, American Association of Immunologists, Inc., United States (2003).
Kasagi, S., et al., "Anti-programmed cell death 1 antibody reduces CD4+PD-1+ T cells and relieves the lupus-like nephritis of NZB/W Fl mice," The Journal Immunology 184(5):2337-2347, The American Association of Immunologists, United States (2010).
Kaveri, S., "Epitope and idiotope mapping using monoclonal antibodies," Medthods in Molecular Biology 51:171-181, Humana Press, United States (1995).
Keytruda (pembrolizumab) Drug Label, Initial U.S. Approval: 2014, Revised Oct. 2016.
Kier et al., "PD-1 and its ligands in tolerance and immunity" Annu. Rev. Immunol. (2008) vol. 26 pp. 677-704.
Kim et al.: "Eradication of metastatic mouse cancers resistant to immune checkpoint blockade by suppression of myeloid-derived cells. (Includes Supporting Information)", Proceedings of the National Academy of Sciences of the United States of America, vol. 111, No. 32, Aug. 12, 2014 (Aug. 12, 2014), pp. 11774-11777.
Kirkwood et al, "Immunotherapy of cancer in 2012" CA: A Cancer Journal for Clinicians (2012) vol. 62 No. 5 pp. 309-335.
Klein Jan M et al: "The histone deacetylase inhibitor LBH589 (panobinostat) modulates the crosstalk of lymphocytes with Hodgkin lymphoma cell lines.", PLOS ONE, vol. 8, No. 11, E79582, 2813, pp. 1-6.
Knight et al., "Host immunity contributes to the anti-melanoma activity of BRAF inhibitors" The Journal of Clinical Investigation (2013) vol. 123 No. 3 pp. 1371-1381.
Knights et al., "Inhibitor of apoptosis protein (IAP) antagonists demonstrate divergent immunomodulatory properties in human immune subsets with implications for combination therapy" Cancer Immunology and Immunotherapy (2013) vol. 62 No. 2 pp. 321-335.
Koga, N., et al., "Blockade of the interaction between PD-1 and PD-L1 accelerates graft arterial disease in cardiac allografts," Arteriosclerosis, Thrombosis, and Vascular Biology 24(11):2057-2062, American Heart Association, Inc., United States(2004).
Konishi, J., et al., "B7-H1 expression on non-small cell lung cancer cells and its relationship with tumor-infiltrating lymphocytes and their PD-1 expression," Clinical Cancer Research 10(15):5094-5100, American Association for Cancer Research, United States (2004).
Korman et al, "Checkpoint Blockade in Cancer Immunotherapy" Adv Immunol (2006) vol. 90 pp. 297-339.
Ladner, R.C., "Mapping the epitopes of Antibodies," Biotechnology and Genetic Engineering Reviews 24(1):1-30, Taylor & Francis, England (2007).
Laricchia,Robbio, L., et al., "Mapping of Monoclonal Antibody-and Receptor-Binding Domains on Human Granulocyte-Macrophage Colony-Stimulation Factor (rhGM-CSF) Using a Surface Plasmon Resonance-Based Biosensor," Hybridoma 15(5):343-350, Mary AnnLiebert, Inc. United States (1996).
Latchman, Y., et al., "PD-L2 is a second ligand for PD-1 and inhibits T cell activation," Nature Immunology 2 (3):261-268, Nature Publishing Group, United States (2001).
Leach, D.R., et al., "Enhancement of antitumor immunity by CTLA-4 blockade," Science 271(5256):1734-1736, American Association for the Advancement of Science, United States (1996).
Lesokhin, A.M., et al., "291 Preliminary Results of a Phase I Study of Nivolumab (BMS-936558) in Patients with Relapsed of Refractory Lymphoid Malignancies," 56th ASH Annual Meeting and Exposition, Abstracts & Program, San Francisco, CA, UnitedStates, Dec. 6-9, 2014.
Lewis, D.E., et al., "Tumor Necrosis Factor-.alpha. And CD80 Modulate CD28 Expression through a Similar Mechanism of T-cell Receptor-Independent of Transcription," The Journal of Biological Chemistry 279 (28):29130-29138, The American Society forBiochemistry and Molecular Biology, Inc., United States (2004).
Li et al., "Contribution of PD-L1 to oncogenesis of lymphoma and its RNAi-based targeting therapy" Leukemia & Lymphoma (2012) vol. 53, No. 10, pp. 2015-2023.
Li, L., et al., "A pathway regulated by cell cycle inhibitor p27Kip1 and checkpoint inhibitor Smad3 is involved in the induction of T cell tolerance," Nature Immunology 7(11):1157-1165, Nature Publishing, United States (2006).
Li, L., et al., "CD4+CD25+ regulatory T-cell lines from human cord blood have functional and molecular properties and T-cell anergy," Blood 106(9):3068-3073, American Society of Hematology, United States (Nov. 2005).
Li, L., et al., "IL-1beta-Mediated Signals Preferentially Drive Conversion of Regulatory T Cells but Not Coventional T Cells into IL-17-Producing Cells," The Journal of Immunology 185(7):4148-4153, American Association of Immunologists, Inc., UnitedStates (2010).
Li, L., et al., "Rap1-GTP is a Negative Regulator of Th Cell Function and Promotes the Generation of CD4+CD103+ Regulatory T Cells in Vivo," The Journal of Immunology 175(5):3133-3139, American Association of Immunologists, Inc., United States (Sep. 2005).
Li, L., et al., "The cyclin dependent kinase inhibitor (R)-roscovitine prevents alloreactive T cell clonal expansion and protects against acute GvHD," Cell Cycle 8(11):1794-1802, Landes Bioscience, United States (2009).
Lin, David Yin-Wei, et al.; "The PD-1/PD-L1 complex resembles the antigen-binding Fv domains of antibodies and T cell receptors"; Proc. Natl. Acad. Sci. USA 105(8):3011-3016 (2008).
Linsley et al., "Intracellular Trafficking of CTLA-4 and Focal Localization Towards Sites of TCR Engagement" Immunity (1996) vol. 4 pp. 535-543.
List of clinical trials identified in ClinicalTrials.gov relating to PDR001 as of Dec. 22, 2016.
Lonberg, N., et al., "Antigen-specific human antibodies from mice comprising four distinct genetic modifications," Nature 368(6474):856-859, Nature Publishing Group, United States (1994).
Lute, K.D., et al., "Human CTLA4 knock-in mice unravel the quantitative link between tumor immunity and autoimmunity induced by anti-CTLA-4 antibodies," Blood 106(9):3127-3133, American Society of Hematology, United States (2005).
Masters et al., "Abstract 5016: Antitumor activity of anti -PD-1 in combination with tyrosine kinase inhibitors in a preclinical renal cell carcinoma model" AACR Annual Meeting (2014) vol. 74, No. 5016.
May, K.F., Jr., et al., "Anti-human CTLA-4 monoclonal antibody promotes T-cell expansion and immunity it a hu-PBL-SCID model: a new method for preclinical screening of costimulatory monoclonal antibodies," Blood 105(3):1114-1120, American Society ofHematology, United States (2005).
Menzies & Long, "Systemic treatment for BRAF-mutant melanoma: where do we go next?" The Lancet Oncology (2014) vol. 15 pp. e371-e381.
Menzies et al., "Recent advances in melanoma systemic therapy. BRAF inhibitors, CTLA antibodies and beyond" European Journal of Cancer (2013) vol. 49 No. 15 pp. 3229-3241.
Miittendorf Elizabeth A et al: "PD-L1 expression in triple-negative breast cancer." Cancer Immunology Research. vol. 2. No. 4. Apr. 2014 (Apr. 2014). pp. 361-370.
Moreira Da Silva, "Nivolumab Anti-PD-1 monoclonal antibody cancer immunotherapy" Drugs of the Future (2014) vol. 39 No. 1 pp. 15-24.

(56) References Cited

OTHER PUBLICATIONS

Naing et al. "A first-in-human phase I study of the anti-PD-1 antibody PDR001 in patients with advanced solid tumors" 2016 ASCO Annual Meeting, J Clin Oncol 34, 2016 (suppl; abstr 3060).
Nakae et al., "Mast cells enhance T cell activation: importance of mast cell costimulatory molecules and secreted TNF" The Journal of Immunology (2006) vol. 176 No. 4 pp. 2238-2248.
Nellore, A., et al., "The cyclin dependent kinase inhibitor (R)-roscovitine mediates selective suppression of alloreactive human T cells but preserves pathogen-specific and leukemia-specific effectors," Clinical Immunology 152(1-2):48-57 (May-Jun. 2014; Epub Mar. 12, 2014).
Nielsen, C., et al., "A putative regulatory polymorphism in PD-1 is associated with nephropathy in a population-based cohort of systemic lupus erythematosus patients," Lupus 13(7):510-516, SAGE, England (2004).
Nishimura, H., et al., "Autoimmune dilated cardiomyopathy Science in PD-1 receptor-deficient mice," Science 291 (5502):319-322, American Association for the Advancement of Science, United States (2001).
Nishimura, H., et al., "Development of lupus-like autoimmune diseases by disruption of the PD-1gene encoding an ITIM motif-carrying immunoreceptor," Immunity 11(2):141-151, Cell Press, United States (1999).
Nishimura, H., et al., "Immunological studies on PD-1 deficient mice: implication of PD-1 as a negative regulator for B cell responses," International Immunology 10(10):1563-1572, Oxford University Press, England (1998).
Nomi, T., et al., "Clinical significance and therapeutic potential of the programmed death-1 ligand/programmed death-1 pathway in human pancreatic cancer," Clinical Cancer Research 13(7):2151-2157, The Association, United States (2007).
Okazaki, T., et al., "New regulatory co-receptors: inducible co-stimulator and PD-1," Current Opinion in Immunology 14 (6):779-782, Elsevier, England (2002).
Okazaki, T., et al., "PD-1 immunoreceptor inhibits B cell receptor-mediated signaling by recruiting src homology 2-domain-containing tyrosine phosphatase 2 to phophotyrosine," Proceeding of the National Academy of Sciences 98 (24):13866-13871,National Academy of Sciences, United States (2001).
Oki Y et al: "Immune regulatory effects of panobinostat in patients with Hodgkin lymphoma through modulation of serum cytokine levels and T-cell PD1 expression.", Blood Cancer Journal, vol. 4, E236, 2014, pp. 1-4.
OPDIVO (nivolumab) Drug Label, Initial U.S. Approval: 2014, Revised Nov. 2016.
Ozaki, S., et al., "Immunotherapy of Multiple Myeloma with a Monoclonal Antibody Directed Against a Plasma Cell-specific Antigen, HM1.24," Blood 90(8):3179-3186, American Society of Hematology, United States (1997).
Ozkaynak, E., et al., "Programmed death-1 targeting can promote allograft survival," The Journal of Immunology 169 (11):6546-6553, The American Association of Immunologists, United States (2002).
Panka, et al.; "Variable region framework differences result in decreased or increased affinity of variant anti-digoxin antibodies"; Proc. Natl. Acad. Sci. USA; 85:3080-3084 (1988).
Pardoll, D.M., "The blockade of immune checkpoints in cancer immunotherapy," Nature Reviews Cancer 12 (4):252-264, Nature Publishing Group, England (2012).
Park, J.W. and Smolen, J., "Monoclonal antibody therapy," Advances in Protein Chemistry 56:369-421, Academic Press, United States (2001).
Parry, Richard V., et al.; "CTLA-4 and PD-1 Receptors Inhibit T-Cell Activation by Distinct Mechanisms"; Molecular and Cellular Biology; 25(21):9543-9553 (2005).
Patsoukis, N., et al., "PD-1 Increases PTEN Phosphatase Activity While Decreasing PTEN Protein Stability by Inhibiting Casein Kinase 2," Molecular and Cellular Biology 33(16):3091-3098, American Society for Microbiology, United States (Aug. 2013).
Patsoukis, N., et al., "PD-1 inhibits T cell proliferation by upregulating p. 27 and p. 15 and suppressing Cdc25A," Cell Cycle 11(23):1-5, Landes Bioscience, United States (Dec. 2012).
Patsoukis, N., et al., "Selective Effects of PD-1 on Akt and Ras Pathways Regulate Molecular Components of the Cell Cycle and Inhibit T Cell Proliferation," Science Signaling 5(230): ra46, pp. 1-14, American Association for the Advancement ofScience, United States (Jun. 2012).
Perez-Gracia et al, "Orchestrating immune check-point blockade for cancer inmunotherapy in combinations", Current Opinion in Immunology. vol. 27 pp. 89-97.

* cited by examiner

Heavy Chain (murine IgG1)

FWH1 CDRH1 FWH2 CDRH2

QVQLQQSGSE LVRPGASVKL SCKAS*GYTFT TY*WMHWVRQR PGQGLEWIGN I*YPGTGG*SNF DEKFKNRTSL

QVQLQQPGSE LVRPGASVKL SCKAS*GYTFT TY*WMHWVRQR PGQGLEWIGN I*YPGTGG*SNF DEKFKNRTSL

FWH3 CDRH3 FWH4

TVDTSSTTAY MHLASLTSED SAVYYCTR*WT TGTGAY*WGQG TLVTVSA

TVDTSSTTAY MHLASLTSED SAVYYCTR*WT TGTGAY*WGQG TLVTVSAAKT TPPSVYPLAP GSAA

Light Chain (murine κ)

FWL1 CDRL1 FWL2 CDRL2

DIVMTQSPSS LTVTAGEKVT MSCKS*SQSLL DSGNQKNF*LT WYQQKPGQPP KLLIF*WAS*TR ESGVPDRFTG

DIVMTQSPSS LTVTAGEKVT MSCKS*SQSLL DSGNQKNF*LT WYQQKPGQPP KLLIF*WAS*TR ESGVPDRFTG

FWL3 CDRL3 FWL4

SGSVTDFTLT ISSVQAEDLA VYYCQN*DYSY P*CTFGGGTKL EIK

SGSVTDFTLT ISSVQAEDLA VYYCQN*DYSY P*CTFGGGTKL EIKRAD

FIGURE 1

Heavy Chain

```
GL       QVQLQQPGSE LVRPGASVKL SCKASGYTFT SYWMHWVKQR HGQGLEWIGN IYPGSGSTNY
Mu mAb   ------S--- ---------- ---------- T-----R--  P--------- ----T-GS-F

GL       DEKFKSKGTL TVDTSSSTAY MHLSSLTSED SAVYYCTR
Mu mAb   -----NRTS- ------T--- ---A------ --------WT TGTGAYWGQG TLVTVSA
```

Light Chain

```
GL       DIVMTQSPSS LTVTAGEKVT MSCKSSQSLL NSGNQKNYLT WYQQKPGQPP KLLIYWASTR
Mu mAb   ---------- ---------- ---------- D------F-- ---------- ----F-----

GL       ESGVPDRFTG SGSGTDFTLT ISSVQAEDLA VYYCQNDYSY P
Mu mAb   ---------- ---V------ ---------- ---------- -CTFGGGTKL EIK
```

FIGURE 2A

```
mAb        C   T   F   G   G   G   T   K   L   E   I   K
mAb    g tgc acg ttc gga ggg ggg acc aag ctg gaa ata aaa
J2     - -a- --- --- --- --- --- --- --- --- --- --- ---c
J2        Y
```

FIGURE 2B

| Clone No. | Concentration µg/mL | Sequence | | | | | |
|---|---|---|---|---|---|---|---|
| | | HC | | | LC | | |
| | | FW1 | FW2 | FW3 | FW1 | FW2 | FW3 |
| | | 4 unique HC | | | 9 unique LC | | |
| 1 | 23.3 | a | a | a | b | a | c |
| 2 | 45.5 | a | a | a | e | a | b |
| 3 | 58.4 | a | b | b | e | a | b |
| 4 | 52.9 | a | b | b | b | b | d |
| 5 | 30 | a | a | a | b | b | d |
| 6 | 7.9 | a | a | a | c | a | a |
| 7 | 24.9 | a | a | a | b | b | a |
| 8 | 32.8 | a | b | b | a | a | a |
| 9 | 16.3 | a | a | a | a | a | a |
| 10 | 61.5 | a | b | b | b | a | a |
| 11 | 31.4 | a | a | a | b | a | a |
| 12 | 34.8 | a | a | a | e | c | a |
| 13 | 8.6 | a | a | a | d | b | a |
| 14 | 48.4 | b | b | b | b | a | a |
| 15 | 20.7 | b | b | b | a | a | a |
| 16 | 32.8 | a | c | b | a | a | a |

FIGURE 5

| Clone No. | Conc. μg/mL | Sequence | | | | | | Ranking | Competition Binding | | Ranking |
|---|---|---|---|---|---|---|---|---|---|---|---|
| | | HC | | | LC | | | FACS data | 1st exp. | 2nd exp.* | |
| | | FW1 | FW2 | FW3 | FW1 | FW2 | FW3 | | | | |
| Chimeric | 20.6 | 4 unique HC | | | 9 unique LC | | | | | | |
| 1 | 23.3 | a | a | a | b | a | c | 2 | 7 | 2 | A |
| 2 | 45.5 | a | a | a | e | a | b | 6 | 3 | 2 | D |
| 3 | 58.4 | a | b | b | e | a | b | 7 | 8 | 14 | E |
| 4 | 52.9 | a | b | b | b | b | d | 14 | 15 | 15 | B |
| 5 | 30 | a | a | a | b | b | d | 5 | 5 | | A |
| 6 | 7.9 | a | a | a | c | a | a | 1 | 7 | 3 | D |
| 7 | 24.9 | a | a | a | b | b | a | 4 | 7 | | D |
| 8 | 32.8 | a | b | b | a | a | a | 7 | 7 | 4 | C |
| 9 | 16.3 | a | a | a | a | a | a | 7 | 2 | 4 | B |
| 10 | 61.5 | a | b | b | b | a | a | 7 | 6 | | C |
| 11 | 31.4 | a | a | a | b | a | a | 6 | 4 | | B |
| 12 | 34.8 | a | a | a | e | c | a | 3 | 8 | 16 | D |
| 13 | 8.6 | a | a | a | d | b | a | 6 | 1 | 1 | D |
| 14 | 48.4 | b | b | b | b | a | a | 16 | 7 | 15 | C |
| 15 | 20.7 | b | b | b | a | a | a | 6 | 7 | 15 | C |
| 16 | 32.8 | a | c | b | a | a | a | 15 | 16 | 15 | C |

*empty boxes means worse than 4

FIGURE 7

```
                           10        20        30        40        50        60
                   ....|....|....|....|....|....|....|....|....|....|....|....|
BAP049-chi-HC      QVQLQQSGSELVRPGASVKLSCKASGYTFTTYWMHWVRQRPGQGLEWIGNIYPGTGGSNF
BAP049-hum01-HC    EVQLVQSGAEVKKPGESLRISCKGSGYTFTTYWMHWVRQATGQGLEWMGNIYPGTGGSNF
BAP049-hum02-HC    EVQLVQSGAEVKKPGESLRISCKGSGYTFTTYWMHWVRQATGQGLEWMGNIYPGTGGSNF
BAP049-hum05-HC    EVQLVQSGAEVKKPGESLRISCKGSGYTFTTYWMHWVRQATGQGLEWMGNIYPGTGGSNF
BAP049-hum06-HC    EVQLVQSGAEVKKPGESLRISCKGSGYTFTTYWMHWVRQATGQGLEWMGNIYPGTGGSNF
BAP049-hum07-HC    EVQLVQSGAEVKKPGESLRISCKGSGYTFTTYWMHWVRQATGQGLEWMGNIYPGTGGSNF
BAP049-hum09-HC    EVQLVQSGAEVKKPGESLRISCKGSGYTFTTYWMHWVRQATGQGLEWMGNIYPGTGGSNF
BAP049-hum11-HC    EVQLVQSGAEVKKPGESLRISCKGSGYTFTTYWMHWVRQATGQGLEWMGNIYPGTGGSNF
BAP049-hum12-HC    EVQLVQSGAEVKKPGESLRISCKGSGYTFTTYWMHWVRQATGQGLEWMGNIYPGTGGSNF
BAP049-hum13-HC    EVQLVQSGAEVKKPGESLRISCKGSGYTFTTYWMHWVRQATGQGLEWMGNIYPGTGGSNF
BAP049-hum03-HC    EVQLVQSGAEVKKPGESLRISCKGSGYTFTTYWMHWIRQSPSRGLEWLGNIYPGTGGSNF
BAP049-hum04-HC    EVQLVQSGAEVKKPGESLRISCKGSGYTFTTYWMHWIRQSPSRGLEWLGNIYPGTGGSNF
BAP049-hum08-HC    EVQLVQSGAEVKKPGESLRISCKGSGYTFTTYWMHWIRQSPSRGLEWLGNIYPGTGGSNF
BAP049-hum10-HC    EVQLVQSGAEVKKPGESLRISCKGSGYTFTTYWMHWIRQSPSRGLEWLGNIYPGTGGSNF
BAP049-hum14-HC    QVQLVQSGAEVKKPGASVKVSCKASGYTFTTYWMHWIRQSPSRGLEWLGNIYPGTGGSNF
BAP049-hum15-HC    QVQLVQSGAEVKKPGASVKVSCKASGYTFTTYWMHWIRQSPSRGLEWLGNIYPGTGGSNF
BAP049-hum16-HC    EVQLVQSGAEVKKPGESLRISCKGSGYTFTTYWMHWVRQAPGQGLEWMGNIYPGTGGSNF

                           70        80        90       100       110
                   ....|....|....|....|....|....|....|....|....|....|....|..
BAP049-chi-HC      DEKFKNRTSLTVDTSSTTAYMHLASLTSEDSAVYYCTRWTTGTGAYWGQGTTVTVSS
BAP049-hum01-HC    DEKFKNRVTITADKSTSTAYMELSSLRSEDTAVYYCTRWTTGTGAYWGQGTTVTVSS
BAP049-hum02-HC    DEKFKNRVTITADKSTSTAYMELSSLRSEDTAVYYCTRWTTGTGAYWGQGTTVTVSS
BAP049-hum05-HC    DEKFKNRVTITADKSTSTAYMELSSLRSEDTAVYYCTRWTTGTGAYWGQGTTVTVSS
BAP049-hum06-HC    DEKFKNRVTITADKSTSTAYMELSSLRSEDTAVYYCTRWTTGTGAYWGQGTTVTVSS
BAP049-hum07-HC    DEKFKNRVTITADKSTSTAYMELSSLRSEDTAVYYCTRWTTGTGAYWGQGTTVTVSS
BAP049-hum09-HC    DEKFKNRVTITADKSTSTAYMELSSLRSEDTAVYYCTRWTTGTGAYWGQGTTVTVSS
BAP049-hum11-HC    DEKFKNRVTITADKSTSTAYMELSSLRSEDTAVYYCTRWTTGTGAYWGQGTTVTVSS
BAP049-hum12-HC    DEKFKNRVTITADKSTSTAYMELSSLRSEDTAVYYCTRWTTGTGAYWGQGTTVTVSS
BAP049-hum13-HC    DEKFKNRVTITADKSTSTAYMELSSLRSEDTAVYYCTRWTTGTGAYWGQGTTVTVSS
BAP049-hum03-HC    DEKFKNRFTISRDNSKNTLYLQMNSLRAEDTAVYYCTRWTTGTGAYWGQGTTVTVSS
BAP049-hum04-HC    DEKFKNRFTISRDNSKNTLYLQMNSLRAEDTAVYYCTRWTTGTGAYWGQGTTVTVSS
BAP049-hum08-HC    DEKFKNRFTISRDNSKNTLYLQMNSLRAEDTAVYYCTRWTTGTGAYWGQGTTVTVSS
BAP049-hum10-HC    DEKFKNRFTISRDNSKNTLYLQMNSLRAEDTAVYYCTRWTTGTGAYWGQGTTVTVSS
BAP049-hum14-HC    DEKFKNRFTISRDNSKNTLYLQMNSLRAEDTAVYYCTRWTTGTGAYWGQGTTVTVSS
BAP049-hum15-HC    DEKFKNRFTISRDNSKNTLYLQMNSLRAEDTAVYYCTRWTTGTGAYWGQGTTVTVSS
BAP049-hum16-HC    DEKFKNRFTISRDNSKNTLYLQMNSLRAEDTAVYYCTRWTTGTGAYWGQGTTVTVSS
```

FIGURE 9A

```
                           10        20        30        40        50        60
                   ....|....|....|....|....|....|....|....|....|....|....|....|
BAP049-chi-HC      QVQLQQSGSELVRPGASVKLSCKASGYTFTTYWMHWVRQRPGQGLEWIGNIYPGTGGSNF
BAP049-hum01-HC    E...V...A.VKK..E.LRI...G...............AT......M............
BAP049-hum02-HC    E...V...A.VKK..E.LRI...G...............AT......M............
BAP049-hum05-HC    E...V...A.VKK..E.LRI...G...............AT......M............
BAP049-hum06-HC    E...V...A.VKK..E.LRI...G...............AT......M............
BAP049-hum07-HC    E...V...A.VKK..E.LRI...G...............AT......M............
BAP049-hum09-HC    E...V...A.VKK..E.LRI...G...............AT......M............
BAP049-hum11-HC    E...V...A.VKK..E.LRI...G...............AT......M............
BAP049-hum12-HC    E...V...A.VKK..E.LRI...G...............AT......M............
BAP049-hum13-HC    E...V...A.VKK..E.LRI...G...............AT......M............
BAP049-hum03-HC    E...V...A.VKK..E.LRI...G............I..S.SR....L............
BAP049-hum04-HC    E...V...A.VKK..E.LRI...G............I..S.SR....L............
BAP049-hum08-HC    E...V...A.VKK..E.LRI...G............I..S.SR....L............
BAP049-hum10-HC    E...V...A.VKK..E.LRI...G............I..S.SR....L............
BAP049-hum14-HC    ....V...A.VKK......V................I..S.SR....L............
BAP049-hum15-HC    ....V...A.VKK......V................I..S.SR....L............
BAP049-hum16-HC    E...V...A.VKK..E.LRI...G...............A.......M............

                           70        80        90       100       110
                   ....|....|....|....|....|....|....|....|....|....|....|..
BAP049-chi-HC      DEKFKNRTSLTVDTSSTTAYMHLASLTSEDSAVYYCTRWTTGTGAYWGQGTTVTVSS
BAP049-hum01-HC    .......VTI.A.K.TS....E.S..R...T..........................
BAP049-hum02-HC    .......VTI.A.K.TS....E.S..R...T..........................
BAP049-hum05-HC    .......VTI.A.K.TS....E.S..R...T..........................
BAP049-hum06-HC    .......VTI.A.K.TS....E.S..R...T..........................
BAP049-hum07-HC    .......VTI.A.K.TS....E.S..R...T..........................
BAP049-hum09-HC    .......VTI.A.K.TS....E.S..R...T..........................
BAP049-hum11-HC    .......VTI.A.K.TS....E.S..R...T..........................
BAP049-hum12-HC    .......VTI.A.K.TS....E.S..R...T..........................
BAP049-hum13-HC    .......VTI.A.K.TS....E.S..R...T..........................
BAP049-hum03-HC    .......FTISR.N.KN.L.LQMN..RA..T..........................
BAP049-hum04-HC    .......FTISR.N.KN.L.LQMN..RA..T..........................
BAP049-hum08-HC    .......FTISR.N.KN.L.LQMN..RA..T..........................
BAP049-hum10-HC    .......FTISR.N.KN.L.LQMN..RA..T..........................
BAP049-hum14-HC    .......FTISR.N.KN.L.LQMN..RA..T..........................
BAP049-hum15-HC    .......FTISR.N.KN.L.LQMN..RA..T..........................
BAP049-hum16-HC    .......FTISR.N.KN.L.LQMN..RA..T..........................
```

FIGURE 9B

```
                           10        20        30        40        50        60
                   ....|....|....|....|....|....|....|....|....|....|....|....|
BAP049-chi-LC      DIVMTQSPSSLTVTAGEKVTMSCKSSQSLLDSGNQKNFLTWYQQKPGQPPKLLIFWASTR
BAP049-hum08-LC    EIVLTQSPDFQSVTPKEKVTITCKSSQSLLDSGNQKNFLTWYQQKPGQAPRLLIYWASTR
BAP049-hum09-LC    EIVLTQSPDFQSVTPKEKVTITCKSSQSLLDSGNQKNFLTWYQQKPGQAPRLLIYWASTR
BAP049-hum15-LC    EIVLTQSPDFQSVTPKEKVTITCKSSQSLLDSGNQKNFLTWYQQKPGQAPRLLIYWASTR
BAP049-hum16-LC    EIVLTQSPDFQSVTPKEKVTITCKSSQSLLDSGNQKNFLTWYQQKPGQAPRLLIYWASTR
BAP049-hum10-LC    EIVLTQSPATLSLSPGERATLSCKSSQSLLDSGNQKNFLTWYQQKPGQAPRLLIYWASTR
BAP049-hum11-LC    EIVLTQSPATLSLSPGERATLSCKSSQSLLDSGNQKNFLTWYQQKPGQAPRLLIYWASTR
BAP049-hum14-LC    EIVLTQSPATLSLSPGERATLSCKSSQSLLDSGNQKNFLTWYQQKPGQAPRLLIYWASTR
BAP049-hum06-LC    DIVMTQTPLSLPVTPGEPASISCKSSQSLLDSGNQKNFLTWYQQKPGQAPRLLIYWASTR
BAP049-hum07-LC    EIVLTQSPATLSLSPGERATLSCKSSQSLLDSGNQKNFLTWYQQKPGKAPKLLIYWASTR
BAP049-hum13-LC    DVVMTQSPLSLPVTLGQPASISCKSSQSLLDSGNQKNFLTWYQQKPGKAPKLLIYWASTR
BAP049-hum12-LC    DIQMTQSPSSLSASVGDRVTITCKSSQSLLDSGNQKNFLTWYLQKPGQSPQLLIYWASTR
BAP049-hum02-LC    DIQMTQSPSSLSASVGDRVTITCKSSQSLLDSGNQKNFLTWYQQKPGQAPRLLIYWASTR
BAP049-hum03-LC    DIQMTQSPSSLSASVGDRVTITCKSSQSLLDSGNQKNFLTWYQQKPGQAPRLLIYWASTR
BAP049-hum01-LC    EIVLTQSPATLSLSPGERATLSCKSSQSLLDSGNQKNFLTWYQQKPGQAPRLLIYWASTR
BAP049-hum04-LC    EIVLTQSPATLSLSPGERATLSCKSSQSLLDSGNQKNFLTWYQQKPGKAPKLLIYWASTR
BAP049-hum05-LC    EIVLTQSPATLSLSPGERATLSCKSSQSLLDSGNQKNFLTWYQQKPGKAPKLLIYWASTR

                           70        80        90        100       110
                   ....|....|....|....|....|....|....|....|....|....|...
BAP049-chi-LC      ESGVPDRFTGSGSVTDFTLTISSVQAEDLAVYYCQNDYSYPCTFGQGTKVEIK
BAP049-hum08-LC    ESGVPSRFSGSGSGTDFTFTISSLEAEDAATYYCQNDYSYPYTFGQGTKVEIK
BAP049-hum09-LC    ESGVPSRFSGSGSGTDFTFTISSLEAEDAATYYCQNDYSYPYTFGQGTKVEIK
BAP049-hum15-LC    ESGVPSRFSGSGSGTDFTFTISSLEAEDAATYYCQNDYSYPYTFGQGTKVEIK
BAP049-hum16-LC    ESGVPSRFSGSGSGTDFTFTISSLEAEDAATYYCQNDYSYPYTFGQGTKVEIK
BAP049-hum10-LC    ESGVPSRFSGSGSGTDFTFTISSLEAEDAATYYCQNDYSYPYTFGQGTKVEIK
BAP049-hum11-LC    ESGVPSRFSGSGSGTDFTFTISSLEAEDAATYYCQNDYSYPYTFGQGTKVEIK
BAP049-hum14-LC    ESGVPSRFSGSGSGTDFTFTISSLEAEDAATYYCQNDYSYPYTFGQGTKVEIK
BAP049-hum06-LC    ESGVPSRFSGSGSGTDFTFTISSLEAEDAATYYCQNDYSYPYTFGQGTKVEIK
BAP049-hum07-LC    ESGVPSRFSGSGSGTDFTFTISSLEAEDAATYYCQNDYSYPYTFGQGTKVEIK
BAP049-hum13-LC    ESGVPSRFSGSGSGTDFTFTISSLEAEDAATYYCQNDYSYPYTFGQGTKVEIK
BAP049-hum12-LC    ESGVPSRFSGSGSGTDFTFTISSLEAEDAATYYCQNDYSYPYTFGQGTKVEIK
BAP049-hum02-LC    ESGIPPRFSGSGYGTDFTLTINNIESEDAAYYFCQNDYSYPYTFGQGTKVEIK
BAP049-hum03-LC    ESGIPPRFSGSGYGTDFTLTINNIESEDAAYYFCQNDYSYPYTFGQGTKVEIK
BAP049-hum01-LC    ESGVPSRFSGSGSGTEFTLTISSLQPDDFATYYCQNDYSYPYTFGQGTKVEIK
BAP049-hum04-LC    ESGVPSRFSGSGSGTDFTFTISSLQPEDIATYYCQNDYSYPYTFGQGTKVEIK
BAP049-hum05-LC    ESGVPSRFSGSGSGTDFTFTISSLQPEDIATYYCQNDYSYPYTFGQGTKVEIK
```

FIGURE 10A

```
                        10        20        30        40        50        60
                ....|....|....|....|....|....|....|....|....|....|....|....|
BAP049-chi-LC   DIVMTQSPSSLTVTAGEKVTMSCKSSQSLLDSGNQKNFLTWYQQKPGQPPKLLIFWASTR
BAP049-hum08-LC E..L....DFQS..PK....IT..........................A.R...Y.....
BAP049-hum09-LC E..L....DFQS..PK....IT..........................A.R...Y.....
BAP049-hum15-LC E..L....DFQS..PK....IT..........................A.R...Y.....
BAP049-hum16-LC E..L....DFQS..PK....IT..........................A.R...Y.....
BAP049-hum10-LC E..L....AT.SLSP..RA.L...........................A.R...Y.....
BAP049-hum11-LC E..L....AT.SLSP..RA.L...........................A.R...Y.....
BAP049-hum14-LC E..L....AT.SLSP..RA.L...........................A.R...Y.....
BAP049-hum06-LC ......T.L..P..P..PASI...........................A.R...Y.....
BAP049-hum07-LC E..L....AT.SLSP..RA.L..........................KA.....Y.....
BAP049-hum13-LC .V......L..P..L.QPASI..........................KA.....Y.....
BAP049-hum12-LC ..Q........SASV.DR..IT....................L.....S.Q...Y.....
BAP049-hum02-LC ..Q........SASV.DR..IT..........................A.R...Y.....
BAP049-hum03-LC ..Q........SASV.DR..IT..........................A.R...Y.....
BAP049-hum01-LC E..L....AT.SLSP..RA.L...........................A.R...Y.....
BAP049-hum04-LC E..L....AT.SLSP..RA.L..........................KA.....Y.....
BAP049-hum05-LC E..L....AT.SLSP..RA.L..........................KA.....Y.....

                        70        80        90       100       110
                ....|....|....|....|....|....|....|....|....|....|...
BAP049-chi-LC   ESGVPDRFTGSGSVTDFTLTISSVQAEDLAVYYCQNDYSYPCTFGQGTKVEIK
BAP049-hum08-LC .....S..S....G....F....LE...A.T..........Y...........
BAP049-hum09-LC .....S..S....G....F....LE...A.T..........Y...........
BAP049-hum15-LC .....S..S....G....F....LE...A.T..........Y...........
BAP049-hum16-LC .....S..S....G....F....LE...A.T..........Y...........
BAP049-hum10-LC .....S..S....G....F....LE...A.T..........Y...........
BAP049-hum11-LC .....S..S....G....F....LE...A.T..........Y...........
BAP049-hum14-LC .....S..S....G....F....LE...A.T..........Y...........
BAP049-hum06-LC .....S..S....G....F....LE...A.T..........Y...........
BAP049-hum07-LC .....S..S....G....F....LE...A.T..........Y...........
BAP049-hum13-LC .....S..S....G....F....LE...A.T..........Y...........
BAP049-hum12-LC .....S..S....G....F....LE...A.T..........Y...........
BAP049-hum02-LC ...I.P..S...YG.......NNIES..A.Y.F........Y...........
BAP049-hum03-LC ...I.P..S...YG.......NNIES..A.Y.F........Y...........
BAP049-hum01-LC .....S..S....G.E.......L.PD.F.T..........Y...........
BAP049-hum04-LC .....S..S....G....F....L.P..I.T..........Y...........
BAP049-hum05-LC .....S..S....G....F....L.P..I.T..........Y...........
```

FIGURE 10B

SEQUENCE LISTING

```
<160> NUMBER OF SEQ ID NOS: 237

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Tyr Trp Met His
1               5


<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Ile Tyr Pro Gly Thr Gly Gly Ser Asn Phe Asp Glu Lys Phe Lys
1               5                   10                  15

Asn


<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Thr Thr Gly Thr Gly Ala Tyr
1               5


<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 4

Gly Tyr Thr Phe Thr Thr Tyr
1 5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Tyr Pro Gly Thr Gly Gly
1 5

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Leu
            100                 105                 110

Val Thr Val Ser Ala
        115
```

<210> SEQ ID NO 7
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
caggtccagc tgcagcaacc tgggtctgag ctggtgaggc ctggagcttc agtgaagctg     60

tcctgcaagg cgtctggcta cacattcacc acttactgga tgcactgggt gaggcagagg    120

cctggacaag gccttgagtg gattggaaat atttatcctg gtactggtgg ttctaacttc    180

gatgagaagt tcaaaaacag gacctcactg actgtagaca catcctccac cacagcctac    240

atgcacctcg ccagcctgac atctgaggac tctgcggtct attactgtac aagatggact    300

actgggacgg gagcttattg gggccaaggg actctggtca ctgtctctgc a             351
```

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

```
Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Leu
            100                 105                 110

Val Thr Val Ser Ala
        115
```

<210> SEQ ID NO 9
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9

```
caggtccagc tgcagcagtc tgggtctgag ctggtgaggc ctggagcttc agtgaagctg      60

tcctgcaagg cgtctggcta cacattcacc acttactgga tgcactgggt gaggcagagg     120

cctggacaag gccttgagtg gattggaaat atttatcctg gtactggtgg ttctaacttc     180

gatgagaagt tcaaaaacag gacctcactg actgtagaca catcctccac cacagcctac     240

atgcacctcg ccagcctgac atctgaggac tctgcggtct attactgtac aagatggact     300

actgggacgg gagcttattg gggccaaggg actctggtca ctgtctctgc a              351
```

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

```
Lys Ser Ser Gln Ser Leu Leu Asp Ser Gly Asn Gln Lys Asn Phe Leu
1               5                   10                  15

Thr
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Trp Ala Ser Thr Arg Glu Ser
1 5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Gln Asn Asp Tyr Ser Tyr Pro Cys Thr
1 5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Ser Gln Ser Leu Leu Asp Ser Gly Asn Gln Lys Asn Phe
1 5 10

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Trp Ala Ser
1

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Asp Tyr Ser Tyr Pro Cys
1 5

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Asp Ile Val Met Thr Gln Ser Pro Ser Ser Leu Thr Val Thr Ala Gly
1 5 10 15

-continued

```
Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Cys Thr Phe Gly Gly Gly Thr Lys Leu Glu Ile
            100                 105                 110

Lys
```

<210> SEQ ID NO 17
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gacattgtga tgacccagtc tccatcctcc ctgactgtga cagcaggaga gaaggtcact      60

atgagctgca agtccagtca gagtctgtta gacagtggaa atcaaaagaa cttcttgacc     120

tggtaccagc agaaaccagg gcagcctcct aaactgttga tcttctgggc atccactagg     180

gaatctgggg tccctgatcg cttcacaggc agtggatctg taacagattt cactctcacc     240

atcagcagtg tgcaggctga agacctggca gtttattact gtcagaatga ttatagttat     300

ccgtgcacgt tcggaggggg gaccaagctg gaaataaaa                            339
```

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

<210> SEQ ID NO 19
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
caggtccagc tgcagcagcc tgggtctgag ctggtgaggc ctggagcttc agtgaagctg     60

tcctgcaagg cgtctggcta cacattcacc acttactgga tgcactgggt gaggcagagg    120

cctggacaag gccttgagtg gattggaaat atttatcctg gtactggtgg ttctaacttc    180

gatgagaagt tcaaaaacag gacctcactg actgtagaca catcctccac cacagcctac    240

atgcacctcg ccagcctgac atctgaggac tctgcggtct attactgtac aagatggact    300

actgggacgg gagcttattg gggccagggc accaccgtga ccgtgtcctc c             351
```

<210> SEQ ID NO 20
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
```

-continued

```
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 21
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

caggtccagc tgcagcagcc tgggtctgag ctggtgaggc ctggagcttc agtgaagctg      60

tcctgcaagg cgtctggcta cacattcacc acttactgga tgcactgggt gaggcagagg     120

cctggacaag gccttgagtg gattggaaat atttatcctg gtactggtgg ttctaacttc     180

gatgagaagt tcaaaaacag gacctcactg actgtagaca catcctccac cacagcctac     240

atgcacctcg ccagcctgac atctgaggac tctgcggtct attactgtac aagatggact     300

actgggacgg gagcttattg gggccagggc accaccgtga ccgtgtcctc cgcttccacc     360

aagggcccat ccgtcttccc cctggcgccc tgctccagga gcacctccga gagcacagcc     420

gccctgggct gcctggtcaa ggactacttc cccgaaccgg tgacggtgtc gtggaactca     480

ggcgccctga ccagcggcgt gcacaccttc ccggctgtcc tacagtcctc aggactctac     540

tccctcagca gcgtggtgac cgtgccctcc agcagcttgg gcacgaagac ctacacctgc     600

aacgtagatc acaagcccag caacaccaag gtggacaaga gagttgagtc caaatatggt     660

cccccatgcc caccgtgccc agcacctgag ttcctggggg gaccatcagt cttcctgttc     720

cccccaaaac ccaaggacac tctcatgatc tcccggaccc ctgaggtcac gtgcgtggtg     780

gtggacgtga gccaggaaga ccccgaggtc cagttcaact ggtacgtgga tggcgtggag     840

gtgcataatg ccaagacaaa gccgcgggag gagcagttca acagcacgta ccgtgtggtc     900
```

-continued agcgtcctca ccgtcctgca ccaggactgg ctgaacggca aggagtacaa gtgcaaggtg 960
tccaacaaag gcctcccgtc ctccatcgag aaaaccatct ccaaagccaa agggcagccc 1020
cgagagccac aggtgtacac cctgccccca tcccaggagg agatgaccaa gaaccaggtc 1080
agcctgacct gcctggtcaa aggcttctac cccagcgaca tcgccgtgga gtgggagagc 1140
aatgggcagc cggagaacaa ctacaagacc acgcctcccg tgctggactc cgacggctcc 1200
ttcttcctct acagcaggct aaccgtggac aagagcaggt ggcaggaggg gaatgtcttc 1260
tcatgctccg tgatgcatga ggctctgcac aaccactaca cacagaagag cctctccctg 1320
tctctgggta aa 1332

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 23
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
caggtccagc tgcagcagtc tgggtctgag ctggtgaggc ctggagcttc agtgaagctg 60
tcctgcaagg cgtctggcta cacattcacc acttactgga tgcactgggt gaggcagagg 120
cctggacaag gccttgagtg gattggaaat atttatcctg gtactggtgg ttctaacttc 180
gatgagaagt tcaaaaacag gacctcactg actgtagaca catcctccac cacagcctac 240
atgcacctcg ccagcctgac atctgaggac tctgcggtct attactgtac aagatggact 300
actgggacgg gagcttattg gggccagggc accaccgtga ccgtgtcctc c 351

<210> SEQ ID NO 24
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Cys Thr Phe Gly Gln Gly Thr Lys Val Glu Ile
            100                 105                 110

Lys
```

<210> SEQ ID NO 25
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
gacattgtga tgacccagtc tccatcctcc ctgactgtga cagcaggaga gaaggtcact     60

atgagctgca agtccagtca gagtctgtta gacagtggaa atcaaaagaa cttcttgacc    120

tggtaccagc agaaaccagg gcagcctcct aaactgttga tcttctgggc atccactagg    180

gaatctgggg tccctgatcg cttcacaggc agtggatctg taacagattt cactctcacc    240

atcagcagtg tgcaggctga agacctggca gtttattact gtcagaatga ttatagttat    300

ccgtgcacgt tcggccaagg gaccaaggtg gaaatcaaa                           339
```

<210> SEQ ID NO 26
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
```

-continued

```
                85                  90                  95

Asp Tyr Ser Tyr Pro Cys Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 27
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
gacattgtga tgacccagtc tccatcctcc ctgactgtga cagcaggaga gaaggtcact     60

atgagctgca agtccagtca gagtctgtta gacagtggaa atcaaaagaa cttcttgacc    120

tggtaccagc agaaaccagg gcagcctcct aaactgttga tcttctgggc atccactagg    180

gaatctgggg tccctgatcg cttcacaggc agtggatctg taacagattt cactctcacc    240

atcagcagtg tgcaggctga agacctggca gtttattact gtcagaatga ttatagttat    300

ccgtgcacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 28

<400> SEQUENCE: 28

000

<210> SEQ ID NO 29

<400> SEQUENCE: 29

000

<210> SEQ ID NO 30
<211> LENGTH: 444
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 30

```
Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400
```

Phe Phe Leu Tyr Ser Arg Leu Thr Val Asp Lys Ser Arg Trp Gln Glu
405 410 415

Gly Asn Val Phe Ser Cys Ser Val Met His Glu Ala Leu His Asn His
420 425 430

Tyr Thr Gln Lys Ser Leu Ser Leu Ser Leu Gly Lys
435 440

<210> SEQ ID NO 31
<211> LENGTH: 1332
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 31
caggtccagc tgcagcagtc tgggtctgag ctggtgaggc ctggagcttc agtgaagctg 60
tcctgcaagg cgtctggcta cacattcacc acttactgga tgcactgggt gaggcagagg 120
cctggacaag gccttgagtg gattggaaat atttatcctg gtactggtgg ttctaacttc 180
gatgagaagt tcaaaaacag gacctcactg actgtagaca catcctccac cacagcctac 240
atgcacctcg ccagcctgac atctgaggac tctgcggtct attactgtac aagatggact 300
actgggacgg gagcttattg gggccagggc accaccgtga ccgtgtcctc cgcttccacc 360
aagggcccat ccgtcttccc cctggcgccc tgctccagga gcacctccga gagcacagcc 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacgaagac ctacacctgc 600
aacgtagatc acaagcccag caacaccaag gtggacaaga gagttgagtc caaatatggt 660
cccccatgcc caccgtgccc agcacctgag ttcctggggg gaccatcagt cttcctgttc 720
cccccaaaac ccaaggacac tctcatgatc tcccggaccc ctgaggtcac gtgcgtggtg 780
gtggacgtga gccaggaaga ccccgaggtc cagttcaact ggtacgtgga tggcgtggag 840
gtgcataatg ccaagacaaa gccgcgggag gagcagttca acagcacgta ccgtgtggtc 900
agcgtcctca ccgtcctgca ccaggactgg ctgaacggca aggagtacaa gtgcaaggtg 960
tccaacaaag gcctcccgtc ctccatcgag aaaaccatct ccaaagccaa agggcagccc 1020
cgagagccac aggtgtacac cctgccccca tcccaggagg agatgaccaa gaaccaggtc 1080
agcctgacct gcctggtcaa aggcttctac cccagcgaca tcgccgtgga gtgggagagc 1140
aatgggcagc cggagaacaa ctacaagacc acgcctcccg tgctggactc cgacggctcc 1200
ttcttcctct acagcaggct aaccgtggac aagagcaggt ggcaggaggg gaatgtcttc 1260
tcatgctccg tgatgcatga ggctctgcac aaccactaca cacagaagag cctctccctg 1320
tctctgggta aa 1332

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Gln Asn Asp Tyr Ser Tyr Pro Tyr Thr 1 5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Asp Tyr Ser Tyr Pro Tyr
1 5

<210> SEQ ID NO 34
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Pro Pro Lys Leu Leu Ile Phe Trp Ala Ser Thr Arg Glu Ser Gly Val
50 55 60

Pro Asp Arg Phe Thr Gly Ser Gly Ser Val Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 35
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35
gacattgtga tgacccagtc tccatcctcc ctgactgtga cagcaggaga gaaggtcact 60
atgagctgca agtccagtca gagtctgtta gacagtggaa atcaaaagaa cttcttgacc 120
tggtaccagc agaaaccagg gcagcctcct aaactgttga tcttctgggc atccactagg 180
gaatctgggg tccctgatcg cttcacaggc agtggatctg taacagattt cactctcacc 240
atcagcagtg tgcaggctga agacctggca gtttattact gtcagaatga ttatagttat 300
ccgtacacgt tcggccaagg gaccaaggtg gaaatcaaa 339

<210> SEQ ID NO 36
<211> LENGTH: 220
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 36

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Pro Pro Lys Leu Leu Ile Phe Trp Ala Ser Thr Arg Glu Ser Gly Val
50 55 60

Pro Asp Arg Phe Thr Gly Ser Gly Ser Val Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Ser Tyr Pro Tyr Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 37
<211> LENGTH: 660
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37
gacattgtga tgacccagtc tccatcctcc ctgactgtga cagcaggaga gaaggtcact 60
atgagctgca agtccagtca gagtctgtta gacagtggaa atcaaaagaa cttcttgacc 120
tggtaccagc agaaaccagg gcagcctcct aaactgttga tcttctgggc atccactagg 180
gaatctgggg tccctgatcg cttcacaggc agtggatctg taacagattt cactctcacc 240
atcagcagtg tgcaggctga agacctggca gtttattact gtcagaatga ttatagttat 300
ccgtacacgt tcggccaagg gaccaaggtg gaaatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 39
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaagtgcagc tggtgcagtc tggagcagag gtgaaaaagc ccggggagtc tctgaggatc     60
tcctgtaagg gttctggcta cacattcacc acttactgga tgcactgggt gcgacaggcc    120
actggacaag ggcttgagtg gatgggtaat atttatcctg gtactggtgg ttctaacttc    180
gatgagaagt tcaagaacag agtcacgatt accgcggaca aatccacgag cacagcctac    240
atggagctga gcagcctgag atctgaggac acggccgtgt attactgtac aagatggact    300
actgggacgg gagcttattg gggccagggc accaccgtga ccgtgtcctc c             351

<210> SEQ ID NO 40
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

```
Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 41
<211> LENGTH: 1332
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 41
gaagtgcagc tggtgcagtc tggagcagag gtgaaaaagc ccggggagtc tctgaggatc 60
tcctgtaagg gttctggcta cacattcacc acttactgga tgcactgggt gcgacaggcc 120
actggacaag ggcttgagtg gatgggtaat atttatcctg gtactggtgg ttctaacttc 180
gatgagaagt tcaagaacag agtcacgatt accgcggaca aatccacgag cacagcctac 240
atggagctga gcagcctgag atctgaggac acggccgtgt attactgtac aagatggact 300
actgggacgg gagcttattg gggccagggc accaccgtga ccgtgtcctc cgcttccacc 360
aagggcccat ccgtcttccc cctggcgccc tgctccagga gcacctccga gagcacagcc 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacgaagac ctacacctgc 600
aacgtagatc acaagcccag caacaccaag gtggacaaga gagttgagtc caaatatggt 660
cccccatgcc caccgtgccc agcacctgag ttcctggggg gaccatcagt cttcctgttc 720
cccccaaaac ccaaggacac tctcatgatc tcccggaccc ctgaggtcac gtgcgtggtg 780
gtggacgtga gccaggaaga ccccgaggtc cagttcaact ggtacgtgga tggcgtggag 840
gtgcataatg ccaagacaaa gccgcgggag gagcagttca acagcacgta ccgtgtggtc 900
agcgtcctca ccgtcctgca ccaggactgg ctgaacggca aggagtacaa gtgcaaggtg 960
tccaacaaag gcctcccgtc ctccatcgag aaaaccatct ccaaagccaa agggcagccc 1020
cgagagccac aggtgtacac cctgccccca tcccaggagg agatgaccaa gaaccaggtc 1080
agcctgacct gcctggtcaa aggcttctac cccagcgaca tcgccgtgga gtgggagagc 1140
aatgggcagc cggagaacaa ctacaagacc acgcctcccg tgctggactc cgacggctcc 1200
ttcttcctct acagcaggct aaccgtggac aagagcaggt ggcaggaggg gaatgtcttc 1260
tcatgctccg tgatgcatga ggctctgcac aaccactaca cacagaagag cctctccctg 1320
tctctgggta aa 1332

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

Glu Ile Val Leu Thr Gln Ser Pro Ala Thr Leu Ser Leu Ser Pro Gly
1 5 10 15

Glu Arg Ala Thr Leu Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Glu Phe Thr Leu Thr
65 70 75 80

```
Ile Ser Ser Leu Gln Pro Asp Asp Phe Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 43
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
gaaattgtgt tgacacagtc tccagccacc ctgtctttgt ctccagggga aagagccacc      60

ctctcctgca agtccagtca gagtctgtta gacagtggaa atcaaaagaa cttcttgacc     120

tggtaccagc agaaacctgg ccaggctccc aggctcctca tctattgggc atccactagg     180

gaatctgggg tcccatcaag gttcagcggc agtggatctg ggacagaatt cactctcacc     240

atcagcagcc tgcagcctga tgattttgca acttattact gtcagaatga ttatagttat     300

ccgtacacgt tcggccaagg gaccaaggtg gaaatcaaa                            339
```

<210> SEQ ID NO 44
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Glu Phe Thr Leu Thr
65                  70                  75                  80

Ile Ser Ser Leu Gln Pro Asp Asp Phe Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

```
        195                 200                 205

Ser Pro Val Thr Lys Ser Phe Asn Arg Gly Glu Cys
    210                 215                 220
```

<210> SEQ ID NO 45
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gaaattgtgt tgacacagtc tccagccacc ctgtctttgt ctccagggga aagagccacc     60

ctctcctgca agtccagtca gagtctgtta gacagtggaa atcaaaagaa cttcttgacc    120

tggtaccagc agaaacctgg ccaggctccc aggctcctca tctattgggc atccactagg    180

gaatctgggg tcccatcaag gttcagcggc agtggatctg ggacagaatt cactctcacc    240

atcagcagcc tgcagcctga tgattttgca acttattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 46
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Pro Arg Phe Ser Gly Ser Gly Tyr Gly Thr Asp Phe Thr Leu Thr
65                  70                  75                  80

Ile Asn Asn Ile Glu Ser Glu Asp Ala Ala Tyr Tyr Phe Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 47
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47
gacatccaga tgacccagtc tccatcctcc ctgtctgcat ctgtaggaga cagagtcacc 60
atcacttgca agtccagtca gagtctgtta gacagtggaa atcaaaagaa cttcttgacc 120
tggtaccagc agaaacctgg ccaggctccc aggctcctca tctattgggc atccactagg 180
gaatctggga tcccacctcg attcagtggc agcgggtatg gaacagattt taccctcaca 240
attaataaca tagaatctga ggatgctgca tattacttct gtcagaatga ttatagttat 300
ccgtacacgt tcggccaagg gaccaaggtg gaaatcaaa 339

<210> SEQ ID NO 48
<211> LENGTH: 220
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 48

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Ile
50 55 60

Pro Pro Arg Phe Ser Gly Ser Gly Tyr Gly Thr Asp Phe Thr Leu Thr
65 70 75 80

Ile Asn Asn Ile Glu Ser Glu Asp Ala Ala Tyr Tyr Phe Cys Gln Asn
85 90 95

Asp Tyr Ser Tyr Pro Tyr Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 49
<211> LENGTH: 660
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
gacatccaga tgacccagtc tccatcctcc ctgtctgcat ctgtaggaga cagagtcacc 60
atcacttgca agtccagtca gagtctgtta gacagtggaa atcaaaagaa cttcttgacc 120
tggtaccagc agaaacctgg ccaggctccc aggctcctca tctattgggc atccactagg 180
gaatctggga tcccacctcg attcagtggc agcgggtatg gaacagattt taccctcaca 240
attaataaca tagaatctga ggatgctgca tattacttct gtcagaatga ttatagttat 300
ccgtacacgt tcggccaagg gaccaaggtg gaaatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 50
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Thr Tyr
20 25 30

Trp Met His Trp Ile Arg Gln Ser Pro Ser Arg Gly Leu Glu Trp Leu
35 40 45

Gly Asn Ile Tyr Pro Gly Thr Gly Gly Ser Asn Phe Asp Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Thr Arg Trp Thr Thr Gly Thr Gly Ala Tyr Trp Gly Gln Gly Thr Thr
100 105 110

Val Thr Val Ser Ser
115

<210> SEQ ID NO 51
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
gaagtgcagc tggtgcagtc tggagcagag gtgaaaaagc ccggggagtc tctgaggatc 60
tcctgtaagg gttctggcta cacattcacc acttactgga tgcactggat caggcagtcc 120
ccatcgagag gccttgagtg gctgggtaat atttatcctg gtactggtgg ttctaacttc 180
gatgagaagt tcaagaacag attcaccatc tccagagaca attccaagaa cacgctgtat 240
cttcaaatga acagcctgag agccgaggac acggccgtgt attactgtac aagatggact 300
actgggacgg gagcttattg gggccagggc accaccgtga ccgtgtcctc c 351

<210> SEQ ID NO 52
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

-continued

```
Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 53
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

gaagtgcagc tggtgcagtc tggagcagag gtgaaaaagc ccggggagtc tctgaggatc      60

tcctgtaagg gttctggcta cacattcacc acttactgga tgcactggat caggcagtcc     120

ccatcgagag gccttgagtg gctgggtaat atttatcctg gtactggtgg ttctaacttc     180

gatgagaagt tcaagaacag attcaccatc tccagagaca attccaagaa cacgctgtat     240

cttcaaatga acagcctgag agccgaggac acggccgtgt attactgtac aagatggact     300

actgggacgg gagcttattg gggccagggc accaccgtga ccgtgtcctc cgcttccacc     360

aagggcccat ccgtcttccc cctggcgccc tgctccagga gcacctccga gagcacagcc     420

gccctgggct gcctggtcaa ggactacttc cccgaaccgg tgacggtgtc gtggaactca     480

ggcgccctga ccagcggcgt gcacaccttc ccggctgtcc tacagtcctc aggactctac     540

tccctcagca gcgtggtgac cgtgccctcc agcagcttgg gcacgaagac ctacacctgc     600

aacgtagatc acaagcccag caacaccaag gtggacaaga gagttgagtc caaatatggt     660

cccccatgcc caccgtgccc agcacctgag ttcctggggg gaccatcagt cttcctgttc     720

cccccaaaac ccaaggacac tctcatgatc tcccggaccc ctgaggtcac gtgcgtggtg     780

gtggacgtga gccaggaaga ccccgaggtc cagttcaact ggtacgtgga tggcgtggag     840

gtgcataatg ccaagacaaa gccgcgggag gagcagttca acagcacgta ccgtgtggtc     900

agcgtcctca ccgtcctgca ccaggactgg ctgaacggca aggagtacaa gtgcaaggtg     960

tccaacaaag gcctcccgtc ctccatcgag aaaaccatct ccaaagccaa agggcagccc    1020

cgagagccac aggtgtacac cctgccccca tcccaggagg agatgaccaa gaaccaggtc    1080

agcctgacct gcctggtcaa aggcttctac cccagcgaca tcgccgtgga gtgggagagc    1140

aatgggcagc cggagaacaa ctacaagacc acgcctcccg tgctggactc cgacggctcc    1200

ttcttcctct acagcaggct aaccgtggac aagagcaggt ggcaggaggg gaatgtcttc    1260

tcatgctccg tgatgcatga ggctctgcac aaccactaca cacagaagag cctctccctg    1320

tctctgggta aa                                                        1332


<210> SEQ ID NO 54
<211> LENGTH: 113
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 54

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 55
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55

```
gaaattgtgt tgacacagtc tccagccacc ctgtctttgt ctccagggga aagagccacc      60

ctctcctgca agtccagtca gagtctgtta gacagtggaa atcaaaagaa cttcttgacc     120

tggtatcagc agaaaccagg gaaagctcct aagctcctga tctattgggc atccactagg     180

gaatctgggg tcccatcaag gttcagtgga agtggatctg ggacagattt tactttcacc     240

atcagcagcc tgcagcctga agatattgca acatattact gtcagaatga ttatagttat     300

ccgtacacgt tcggccaagg gaccaaggtg gaaatcaaa                            339
```

<210> SEQ ID NO 56
<211> LENGTH: 220
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80
```

-continued

```
Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 57
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

gaaattgtgt tgacacagtc tccagccacc ctgtctttgt ctccagggga aagagccacc      60

ctctcctgca agtccagtca gagtctgtta gacagtggaa atcaaaagaa cttcttgacc     120

tggtatcagc agaaaccagg gaaagctcct aagctcctga tctattgggc atccactagg     180

gaatctgggg tcccatcaag gttcagtgga agtggatctg ggacagattt tactttcacc     240

atcagcagcc tgcagcctga agatattgca acatattact gtcagaatga ttatagttat     300

ccgtacacgt tcggccaagg gaccaaggtg gaaatcaaac gtacggtggc tgcaccatct     360

gtcttcatct tcccgccatc tgatgagcag ttgaaatctg gaactgcctc tgttgtgtgc     420

ctgctgaata acttctatcc cagagaggcc aaagtacagt ggaaggtgga taacgccctc     480

caatcgggta actcccagga gagtgtcaca gagcaggaca gcaaggacag cacctacagc     540

ctcagcagca ccctgacgct gagcaaagca gactacgaga aacacaaagt ctacgcctgc     600

gaagtcaccc atcagggcct gagctcgccc gtcacaaaga gcttcaacag gggagagtgt     660


<210> SEQ ID NO 58
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45
```

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 59
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gatattgtga tgacccagac tccactctcc ctgcccgtca cccctggaga gccggcctcc      60
atctcctgca agtccagtca gagtctgtta gacagtggaa atcaaaagaa cttcttgacc     120
tggtaccagc agaaacctgg ccaggctccc aggctcctca tctattgggc atccactagg     180
gaatctgggg tcccctcgag gttcagtggc agtggatctg ggacagattt cacctttacc     240
atcagtagcc tggaagctga agatgctgca acatattact gtcagaatga ttatagttat     300
ccgtacacgt tcggccaagg gaccaaggtg gaaatcaaa                            339

<210> SEQ ID NO 60
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

```
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 61
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

gatattgtga tgacccagac tccactctcc ctgcccgtca cccctggaga gccggcctcc      60

atctcctgca agtccagtca gagtctgtta gacagtggaa atcaaaagaa cttcttgacc     120

tggtaccagc agaaacctgg ccaggctccc aggctcctca tctattgggc atccactagg     180

gaatctgggg tcccctcgag gttcagtggc agtggatctg ggacagattt cacctttacc     240

atcagtagcc tggaagctga agatgctgca acatattact gtcagaatga ttatagttat     300

ccgtacacgt tcggccaagg gaccaaggtg gaaatcaaac gtacggtggc tgcaccatct     360

gtcttcatct tcccgccatc tgatgagcag ttgaaatctg gaactgcctc tgttgtgtgc     420

ctgctgaata acttctatcc cagagaggcc aaagtacagt ggaaggtgga taacgccctc     480

caatcgggta actcccagga gagtgtcaca gagcaggaca gcaaggacag cacctacagc     540

ctcagcagca ccctgacgct gagcaaagca gactacgaga aacacaaagt ctacgcctgc     600

gaagtcaccc atcagggcct gagctcgccc gtcacaaaga gcttcaacag gggagagtgt     660


<210> SEQ ID NO 62
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 63
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63
gaaattgtgt tgacacagtc tccagccacc ctgtctttgt ctccagggga aagagccacc 60
ctctcctgca agtccagtca gagtctgtta gacagtggaa atcaaaagaa cttcttgacc 120
tggtatcagc agaaaccagg gaaagctcct aagctcctga tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaa 339

<210> SEQ ID NO 64
<211> LENGTH: 220
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

Glu Ile Val Leu Thr Gln Ser Pro Ala Thr Leu Ser Leu Ser Pro Gly
1 5 10 15

Glu Arg Ala Thr Leu Ser Cys Lys Ser Ser Gln Ser Leu Leu Asp Ser
20 25 30

Gly Asn Gln Lys Asn Phe Leu Thr Trp Tyr Gln Gln Lys Pro Gly Lys
35 40 45

Ala Pro Lys Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 65
<211> LENGTH: 660

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
gaaattgtgt tgacacagtc tccagccacc ctgtctttgt ctccagggga aagagccacc 60
ctctcctgca agtccagtca gagtctgtta gacagtggaa atcaaaagaa cttcttgacc 120
tggtatcagc agaaaccagg gaaagctcct aagctcctga tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Glu Ile Val Leu Thr Gln Ser Pro Asp Phe Gln Ser Val Thr Pro Lys
1 5 10 15

Glu Lys Val Thr Ile Thr Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 67
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67
gaaattgtgc tgactcagtc tccagacttt cagtctgtga ctccaaagga gaaagtcacc 60
atcacctgca agtccagtca gagtctgtta gacagtggaa atcaaaagaa cttcttgacc 120
tggtaccagc agaaacctgg ccaggctccc aggctcctca tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaa 339

<210> SEQ ID NO 68
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Glu Ile Val Leu Thr Gln Ser Pro Asp Phe Gln Ser Val Thr Pro Lys
1 5 10 15

Glu Lys Val Thr Ile Thr Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 69
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69
gaaattgtgc tgactcagtc tccagacttt cagtctgtga ctccaaagga gaaagtcacc 60
atcacctgca agtccagtca gagtctgtta gacagtggaa atcaaaagaa cttcttgacc 120
tggtaccagc agaaacctgg ccaggctccc aggctcctca tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 70
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 71
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71
gaaattgtgt tgacacagtc tccagccacc ctgtctttgt ctccagggga aagagccacc 60
ctctcctgca agtccagtca gagtctgtta gacagtggaa atcaaaagaa cttcttgacc 120
tggtaccagc agaaacctgg ccaggctccc aggctcctca tctattgggc atccactagg 180
gaatctgggg tccccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaa 339

<210> SEQ ID NO 72
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 73
<211> LENGTH: 660
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 73

```
gaaattgtgt tgacacagtc tccagccacc ctgtctttgt ctccagggga aagagccacc     60

ctctcctgca agtccagtca gagtctgtta gacagtggaa atcaaaagaa cttcttgacc    120

tggtaccagc agaaacctgg ccaggctccc aggctcctca tctattgggc atccactagg    180

gaatctgggg tcccctcgag gttcagtggc agtggatctg ggacagattt cacctttacc    240

atcagtagcc tggaagctga agatgctgca acatattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 75
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 75

```
gacatccaga tgacccagtc tccatcctcc ctgtctgcat ctgtaggaga cagagtcacc      60

atcacttgca agtccagtca gagtctgtta gacagtggaa atcaaaagaa cttcttgacc     120

tggtacctgc agaagccagg gcagtctcca cagctcctga tctattgggc atccactagg     180

gaatctgggg tcccctcgag gttcagtggc agtggatctg ggacagattt cacctttacc     240

atcagtagcc tggaagctga agatgctgca acatattact gtcagaatga ttatagttat     300

ccgtacacgt tcggccaagg gaccaaggtg gaaatcaaa                            339
```

<210> SEQ ID NO 76
<211> LENGTH: 220
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 76

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60
```

```
Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 77
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

gacatccaga tgacccagtc tccatcctcc ctgtctgcat ctgtaggaga cagagtcacc     60

atcacttgca agtccagtca gagtctgtta gacagtggaa atcaaaagaa cttcttgacc    120

tggtacctgc agaagccagg gcagtctcca cagctcctga tctattgggc atccactagg    180

gaatctgggg tcccctcgag gttcagtggc agtggatctg ggacagattt cacctttacc    240

atcagtagcc tggaagctga agatgctgca acatattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660


<210> SEQ ID NO 78
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
```

```
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 79
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
gatgttgtga tgactcagtc tccactctcc ctgcccgtca cccttggaca gccggcctcc      60

atctcctgca agtccagtca gagtctgtta gacagtggaa atcaaaagaa cttcttaacc     120

tggtatcagc agaaaccagg gaaagctcct aagctcctga tctattgggc atccactagg     180

gaatctgggg tcccctcgag gttcagtggc agtggatctg ggacagattt cacctttacc     240

atcagtagcc tggaagctga agatgctgca acatattact gtcagaatga ttatagttat     300

ccgtacacgt tcggccaagg gaccaaggtg gaaatcaaa                            339
```

<210> SEQ ID NO 80
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 81
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
gatgttgtga tgactcagtc tccactctcc ctgcccgtca cccttggaca gccggcctcc     60

atctcctgca agtccagtca gagtctgtta gacagtggaa atcaaaagaa cttcttaacc    120

tggtatcagc agaaaccagg gaaagctcct aagctcctga tctattgggc atccactagg    180

gaatctgggg tcccctcgag gttcagtggc agtggatctg ggacagattt cacctttacc    240

atcagtagcc tggaagctga agatgctgca acatattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
```

```
            100                 105                 110

Val Thr Val Ser Ser
        115


<210> SEQ ID NO 83
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

caggttcagc tggtgcagtc tggagctgag gtgaagaagc ctggggcctc agtgaaggtc      60

tcctgcaagg cttctggcta cacattcacc acttactgga tgcactggat caggcagtcc     120

ccatcgagag gccttgagtg gctgggtaat atttatcctg gtactggtgg ttctaacttc     180

gatgagaagt tcaagaacag attcaccatc tccagagaca attccaagaa cacgctgtat     240

cttcaaatga acagcctgag agccgaggac acggccgtgt attactgtac aagatggact     300

actgggacgg gagcttactg gggccagggc accaccgtga ccgtgtcctc c              351


<210> SEQ ID NO 84
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
```

```
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 85
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
caggttcagc tggtgcagtc tggagctgag gtgaagaagc ctggggcctc agtgaaggtc     60

tcctgcaagg cttctggcta cacattcacc acttactgga tgcactggat caggcagtcc    120

ccatcgagag gccttgagtg gctgggtaat atttatcctg gtactggtgg ttctaacttc    180

gatgagaagt tcaagaacag attcaccatc tccagagaca attccaagaa cacgctgtat    240

cttcaaatga acagcctgag agccgaggac acggccgtgt attactgtac aagatggact    300

actgggacgg gagcttactg gggccagggc accaccgtga ccgtgtcctc cgcttccacc    360

aagggcccat ccgtcttccc cctggcgccc tgctccagga gcacctccga gagcacagcc    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacgaagac ctacacctgc    600

aacgtagatc acaagcccag caacaccaag gtggacaaga gagttgagtc caaatatggt    660

cccccatgcc caccgtgccc agcacctgag ttcctggggg gaccatcagt cttcctgttc    720
```

```
cccccaaaac ccaaggacac tctcatgatc tcccggaccc ctgaggtcac gtgcgtggtg     780

gtggacgtga gccaggaaga ccccgaggtc cagttcaact ggtacgtgga tggcgtggag     840

gtgcataatg ccaagacaaa gccgcgggag gagcagttca acagcacgta ccgtgtggtc     900

agcgtcctca ccgtcctgca ccaggactgg ctgaacggca aggagtacaa gtgcaaggtg     960

tccaacaaag gcctcccgtc ctccatcgag aaaaccatct ccaaagccaa agggcagccc    1020

cgagagccac aggtgtacac cctgccccca tcccaggagg agatgaccaa gaaccaggtc    1080

agcctgacct gcctggtcaa aggcttctac cccagcgaca tcgccgtgga gtgggagagc    1140

aatgggcagc cggagaacaa ctacaagacc acgcctcccg tgctggactc cgacggctcc    1200

ttcttcctct acagcaggct aaccgtggac aagagcaggt ggcaggaggg gaatgtcttc    1260

tcatgctccg tgatgcatga ggctctgcac aaccactaca cacagaagag cctctccctg    1320

tctctgggta aa                                                        1332
```

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

<210> SEQ ID NO 87
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
gaagtgcagc tggtgcagtc tggagcagag gtgaaaaagc ccggggagtc tctgaggatc      60

tcctgtaagg gttctggcta cacattcacc acttactgga tgcactgggt gcgacaggcc     120

cctggacaag ggcttgagtg gatgggtaat atttatcctg gtactggtgg ttctaacttc     180

gatgagaagt tcaagaacag attcaccatc tccagagaca attccaagaa cacgctgtat     240

cttcaaatga acagcctgag agccgaggac acggccgtgt attactgtac aagatggact     300

actgggacgg gagcttattg gggccagggc accaccgtga ccgtgtcctc c              351
```

<210> SEQ ID NO 88
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 88

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
```

355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Val Leu Asp Ser Asp Gly Ser
385 390 395 400

Phe Phe Leu Tyr Ser Arg Leu Thr Val Asp Lys Ser Arg Trp Gln Glu
405 410 415

Gly Asn Val Phe Ser Cys Ser Val Met His Glu Ala Leu His Asn His
420 425 430

Tyr Thr Gln Lys Ser Leu Ser Leu Ser Leu Gly Lys
435 440

<210> SEQ ID NO 89
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89
gaagtgcagc tggtgcagtc tggagcagag gtgaaaaagc ccggggagtc tctgaggatc 60
tcctgtaagg gttctggcta cacattcacc acttactgga tgcactgggt gcgacaggcc 120
cctggacaag ggcttgagtg gatgggtaat atttatcctg gtactggtgg ttctaacttc 180
gatgagaagt tcaagaacag attcaccatc tccagagaca attccaagaa cacgctgtat 240
cttcaaatga acagcctgag agccgaggac acggccgtgt attactgtac aagatggact 300
actgggacgg gagcttattg gggccagggc accaccgtga ccgtgtcctc cgcttccacc 360
aagggcccat ccgtcttccc cctggcgccc tgctccagga gcacctccga gagcacagcc 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacgaagac ctacacctgc 600
aacgtagatc acaagcccag caacaccaag gtggacaaga gagttgagtc caaatatggt 660
cccccatgcc caccgtgccc agcacctgag ttcctggggg gaccatcagt cttcctgttc 720
cccccaaaac ccaaggacac tctcatgatc tcccggaccc ctgaggtcac gtgcgtggtg 780
gtggacgtga gccaggaaga ccccgaggtc cagttcaact ggtacgtgga tggcgtggag 840
gtgcataatg ccaagacaaa gccgcgggag gagcagttca acagcacgta ccgtgtggtc 900
agcgtcctca ccgtcctgca ccaggactgg ctgaacggca aggagtacaa gtgcaaggtg 960
tccaacaaag gcctcccgtc ctccatcgag aaaaccatct ccaaagccaa agggcagccc 1020
cgagagccac aggtgtacac cctgccccca tcccaggagg agatgaccaa gaaccaggtc 1080
agcctgacct gcctggtcaa aggcttctac cccagcgaca tcgccgtgga gtgggagagc 1140
aatgggcagc cggagaacaa ctacaagacc acgcctcccg tgctggactc cgacggctcc 1200
ttcttcctct acagcaggct aaccgtggac aagagcaggt ggcaggaggg gaatgtcttc 1260
tcatgctccg tgatgcatga ggctctgcac aaccactaca cacagaagag cctctccctg 1320
tctctgggta aa 1332

<210> SEQ ID NO 90
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90
gaagtgcagc tggtgcagtc tggcgccgaa gtgaagaagc ctggcgagtc cctgcggatc 60
tcctgcaagg gctctggcta caccttcacc acctactgga tgcactgggt gcgacaggct 120
accggccagg gcctggaatg gatgggcaac atctatcctg gcaccggcgg ctccaacttc 180
gacgagaagt tcaagaacag agtgaccatc accgccgaca agtccacctc caccgcctac 240
atggaactgt cctccctgag atccgaggac accgccgtgt actactgcac ccggtggaca 300
accggcacag gcgcttattg gggccagggc accacagtga ccgtgtcctc t 351

<210> SEQ ID NO 91
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Thr Tyr
20 25 30

Trp Met His Trp Val Arg Gln Ala Thr Gly Gln Gly Leu Glu Trp Met
35 40 45

Gly Asn Ile Tyr Pro Gly Thr Gly Gly Ser Asn Phe Asp Glu Lys Phe
50 55 60

Lys Asn Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Trp Thr Thr Gly Thr Gly Ala Tyr Trp Gly Gln Gly Thr Thr
100 105 110

Val Thr Val Ser Ser Ala Ser Thr Lys Gly Pro Ser Val Phe Pro Leu
115 120 125

Ala Pro Cys Ser Arg Ser Thr Ser Glu Ser Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Lys Thr Tyr Thr Cys Asn Val Asp His Lys Pro Ser Asn
195 200 205

Thr Lys Val Asp Lys Arg Val Glu Ser Lys Tyr Gly Pro Pro Cys Pro
210 215 220

Pro Cys Pro Ala Pro Glu Phe Leu Gly Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser Gln Glu Asp Pro Glu Val Gln Phe
260 265 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 92
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gaagtgcagc tggtgcagtc tggcgccgaa gtgaagaagc ctggcgagtc cctgcggatc     60
tcctgcaagg gctctggcta caccttcacc acctactgga tgcactgggt gcgacaggct    120
accggccagg gcctggaatg gatgggcaac atctatcctg gcaccggcgg ctccaacttc    180
gacgagaagt tcaagaacag agtgaccatc accgccgaca agtccacctc caccgcctac    240
atggaactgt cctccctgag atccgaggac accgccgtgt actactgcac ccggtggaca    300
accggcacag gcgcttattg gggccagggc accacagtga ccgtgtcctc tgcttctacc    360
aaggggccca gcgtgttccc cctggccccc tgctccagaa gcaccagcga gagcacagcc    420
gccctgggct gcctggtgaa ggactacttc cccgagcccg tgaccgtgtc ctggaacagc    480
ggagccctga ccagcggcgt gcacaccttc cccgccgtgc tgcagagcag cggcctgtac    540
agcctgagca gcgtggtgac cgtgcccagc agcagcctgg gcaccaagac ctacacctgt    600
aacgtggacc acaagcccag caacaccaag gtggacaaga gggtggagag caagtacggc    660
ccaccctgcc ccccctgccc agcccccgag ttcctgggcg gacccagcgt gttcctgttc    720
ccccccaagc ccaaggacac cctgatgatc agcagaaccc ccgaggtgac ctgtgtggtg    780
gtggacgtgt cccaggagga ccccgaggtc cagttcaact ggtacgtgga cggcgtggag    840
gtgcacaacg ccaagaccaa gcccagagag gagcagttta acagcaccta ccgggtggtg    900
tccgtgctga ccgtgctgca ccaggactgg ctgaacggca aagagtacaa gtgtaaggtc    960
tccaacaagg gcctgccaag cagcatcgaa aagaccatca gcaaggccaa gggccagcct   1020

-continued agagagcccc aggtctacac cctgccaccc agccaagagg agatgaccaa gaaccaggtg 1080
tccctgacct gtctggtgaa gggcttctac ccaagcgaca tcgccgtgga gtgggagagc 1140
aacggccagc ccgagaacaa ctacaagacc acccccccag tgctggacag cgacggcagc 1200
ttcttcctgt acagcaggct gaccgtggac aagtccagat ggcaggaggg caacgtcttt 1260
agctgctccg tgatgcacga ggccctgcac aaccactaca cccagaagag cctgagcctg 1320
tccctgggc 1329

<210> SEQ ID NO 93
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93
gagatcgtgc tgacccagtc ccctgccacc ctgtcactgt ctccaggcga gagagctacc 60
ctgtcctgca agtcctccca gtccctgctg gactccggca accagaagaa cttcctgacc 120
tggtatcagc agaagcccgg ccaggccccc agactgctga tctactgggc ctccacccgg 180
gaatctggcg tgccctctag attctccggc tccggctctg gcaccgagtt taccctgacc 240
atctccagcc tgcagcccga cgacttcgcc acctactact gccagaacga ctactcctac 300
ccctacacct tcggccaggg caccaaggtg gaaatcaag 339

<210> SEQ ID NO 94
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94
gagatcgtgc tgacccagtc ccctgccacc ctgtcactgt ctccaggcga gagagctacc 60
ctgtcctgca agtcctccca gtccctgctg gactccggca accagaagaa cttcctgacc 120
tggtatcagc agaagcccgg ccaggccccc agactgctga tctactgggc ctccacccgg 180
gaatctggcg tgccctctag attctccggc tccggctctg gcaccgagtt taccctgacc 240
atctccagcc tgcagcccga cgacttcgcc acctactact gccagaacga ctactcctac 300
ccctacacct tcggccaggg caccaaggtg gaaatcaagc gtacggtggc cgctcccagc 360
gtgttcatct tcccccccaag cgacgagcag ctgaagagcg gcaccgccag cgtggtgtgt 420
ctgctgaaca acttctaccc cagggaggcc aaggtgcagt ggaaggtgga caacgccctg 480
cagagcggca acagccagga gagcgtcacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaacag gggcgagtgc 660

<210> SEQ ID NO 95
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

-continued gaggtgcagc tggtgcagtc aggcgccgaa gtgaagaagc ccggcgagtc actgagaatt 60
agctgtaaag gttcaggcta caccttcact acctactgga tgcactgggt ccgccaggct 120
accggtcaag gcctcgagtg gatgggtaat atctaccccg gcaccggcgg ctctaacttc 180
gacgagaagt ttaagaatag agtgactatc accgccgata agtctactag caccgcctat 240
atggaactgt ctagcctgag atcagaggac accgccgtct actactgcac taggtggact 300
accggcacag gcgcctactg ggtcaaggc actaccgtga ccgtgtctag c 351

<210> SEQ ID NO 96
<211> LENGTH: 1329
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 96
gaggtgcagc tggtgcagtc aggcgccgaa gtgaagaagc ccggcgagtc actgagaatt 60
agctgtaaag gttcaggcta caccttcact acctactgga tgcactgggt ccgccaggct 120
accggtcaag gcctcgagtg gatgggtaat atctaccccg gcaccggcgg ctctaacttc 180
gacgagaagt ttaagaatag agtgactatc accgccgata agtctactag caccgcctat 240
atggaactgt ctagcctgag atcagaggac accgccgtct actactgcac taggtggact 300
accggcacag gcgcctactg ggtcaaggc actaccgtga ccgtgtctag cgctagcact 360
aagggcccgt ccgtgttccc cctggcacct tgtagccgga gcactagcga atccaccgct 420
gccctcggct gcctggtcaa ggattacttc ccggagcccg tgaccgtgtc ctggaacagc 480
ggagccctga cctccggagt gcacaccttc cccgctgtgc tgcagagctc cgggctgtac 540
tcgctgtcgt cggtggtcac ggtgccttca tctagcctgg gtaccaagac ctacacttgc 600
aacgtggacc acaagccttc caacactaag gtggacaagc gcgtcgaatc gaagtacggc 660
ccaccgtgcc cgccttgtcc cgcgccggag ttcctcggcg gtccctcggt ctttctgttc 720
ccaccgaagc ccaaggacac tttgatgatt tcccgcaccc ctgaagtgac atgcgtggtc 780
gtggacgtgt cacaggaaga tccggaggtg cagttcaatt ggtacgtgga tggcgtcgag 840
gtgcacaacg ccaaaaccaa gccgagggag gagcagttca actccactta ccgcgtcgtg 900
tccgtgctga cggtgctgca tcaggactgg ctgaacggga aggagtacaa gtgcaaagtg 960
tccaacaagg gacttcctag ctcaatcgaa aagaccatct cgaaagccaa gggacagccc 1020
cgggaacccc aagtgtatac cctgccaccg agccaggaag aaatgactaa gaaccaagtc 1080
tcattgactt gccttgtgaa gggcttctac ccatcggata tcgccgtgga atgggagtcc 1140
aacggccagc cggaaaacaa ctacaagacc acccctccgg tgctggactc agacggatcc 1200
ttcttcctct actcgcggct gaccgtggat aagagcagat ggcaggaggg aaatgtgttc 1260
agctgttctg tgatgcatga agccctgcac aaccactaca ctcagaagtc cctgtccctc 1320
tccctggga 1329

<210> SEQ ID NO 97
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 97
gagatcgtcc tgactcagtc acccgctacc ctgagcctga gccctggcga gcgggctaca 60
ctgagctgta aatctagtca gtcactgctg gatagcggta atcagaagaa cttcctgacc 120
tggtatcagc agaagcccgg taaagcccct aagctgctga tctactgggc ctctactaga 180
gaatcaggcg tgccctctag gtttagcggt agcggtagtg gcaccgactt caccttcact 240
atctctagcc tgcagcccga ggatatcgct acctactact gtcagaacga ctatagctac 300
ccctacacct tcggtcaagg cactaaggtc gagattaag 339

<210> SEQ ID NO 98
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98
gagatcgtcc tgactcagtc acccgctacc ctgagcctga gccctggcga gcgggctaca 60
ctgagctgta aatctagtca gtcactgctg gatagcggta atcagaagaa cttcctgacc 120
tggtatcagc agaagcccgg taaagcccct aagctgctga tctactgggc ctctactaga 180
gaatcaggcg tgccctctag gtttagcggt agcggtagtg gcaccgactt caccttcact 240
atctctagcc tgcagcccga ggatatcgct acctactact gtcagaacga ctatagctac 300
ccctacacct tcggtcaagg cactaaggtc gagattaagc gtacggtggc cgctcccagc 360
gtgttcatct tccccccag cgacgagcag ctgaagagcg gcaccgccag cgtggtgtgc 420
ctgctgaaca acttctaccc ccgggaggcc aaggtgcagt ggaaggtgga caacgccctg 480
cagagcggca acagccagga gagcgtcacc gagcaggaca gcaaggactc cacctacagc 540
ctgagcagca ccctgaccct gagcaaggcc gactacgaga agcataaggt gtacgcctgc 600
gaggtgaccc accagggcct gtccagcccc gtgaccaaga gcttcaacag gggcgagtgc 660

<210> SEQ ID NO 99
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99
gagatcgtgc tgacccagtc ccccgacttc cagtccgtga cccccaaaga aaaagtgacc 60
atcacatgca agtcctccca gtccctgctg gactccggca accagaagaa cttcctgacc 120
tggtatcagc agaagcccgg ccaggccccc agactgctga tctactgggc ctccacccgg 180
gaatctggcg tgccctctag attctccggc tccggctctg gcaccgactt taccttcacc 240
atctccagcc tggaagccga ggacgccgcc acctactact gccagaacga ctactcctac 300
ccctacacct tcggccaggg caccaaggtg gaaatcaag 339

<210> SEQ ID NO 100
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100
gagatcgtgc tgacccagtc ccccgacttc cagtccgtga cccccaaaga aaaagtgacc 60
atcacatgca agtcctccca gtccctgctg gactccggca accagaagaa cttcctgacc 120
tggtatcagc agaagcccgg ccaggccccc agactgctga tctactgggc ctccacccgg 180
gaatctggcg tgccctctag attctccggc tccggctctg gcaccgactt taccttcacc 240
atctccagcc tggaagccga ggacgccgcc acctactact gccagaacga ctactcctac 300
ccctacacct tcggccaggg caccaaggtg gaaatcaagc gtacggtggc cgctcccagc 360
gtgttcatct tcccccccaag cgacgagcag ctgaagagcg gcaccgccag cgtggtgtgt 420
ctgctgaaca acttctaccc cagggaggcc aaggtgcagt ggaaggtgga caacgccctg 480
cagagcggca acagccagga gagcgtcacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaacag gggcgagtgc 660

<210> SEQ ID NO 101
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 101
gaagtgcagc tggtgcagtc tggcgccgaa gtgaagaagc ctggcgagtc cctgcggatc 60
tcctgcaagg gctctggcta caccttcacc acctactgga tgcactggat ccggcagtcc 120
ccctctaggg gcctggaatg gctgggcaac atctaccctg gcaccggcgg ctccaacttc 180
gacgagaagt tcaagaacag gttcaccatc tcccgggaca actccaagaa caccctgtac 240
ctgcagatga actccctgcg ggccgaggac accgccgtgt actactgtac cagatggacc 300
accggaaccg gcgcctattg gggccagggc acaacagtga ccgtgtcctc c 351

<210> SEQ ID NO 102
<211> LENGTH: 443
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Thr Tyr
20 25 30

Trp Met His Trp Ile Arg Gln Ser Pro Ser Arg Gly Leu Glu Trp Leu
35 40 45

Gly Asn Ile Tyr Pro Gly Thr Gly Gly Ser Asn Phe Asp Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Thr Arg Trp Thr Thr Gly Thr Gly Ala Tyr Trp Gly Gln Gly Thr Thr
100 105 110

Val Thr Val Ser Ser Ala Ser Thr Lys Gly Pro Ser Val Phe Pro Leu

```
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 103
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
gaagtgcagc tggtgcagtc tggcgccgaa gtgaagaagc ctggcgagtc cctgcggatc      60

tcctgcaagg gctctggcta caccttcacc acctactgga tgcactggat ccggcagtcc     120

ccctctaggg gcctggaatg gctgggcaac atctaccctg gcaccggcgg ctccaacttc     180
```

```
gacgagaagt tcaagaacag gttcaccatc tcccgggaca actccaagaa caccctgtac    240

ctgcagatga actccctgcg ggccgaggac accgccgtgt actactgtac cagatggacc    300

accggaaccg gcgcctattg gggccagggc acaacagtga ccgtgtcctc cgcttctacc    360

aaggggccca gcgtgttccc cctggccccc tgctccagaa gcaccagcga gagcacagcc    420

gccctgggct gcctggtgaa ggactacttc cccgagcccg tgaccgtgtc ctggaacagc    480

ggagccctga ccagcggcgt gcacaccttc cccgccgtgc tgcagagcag cggcctgtac    540

agcctgagca gcgtggtgac cgtgcccagc agcagcctgg gcaccaagac ctacacctgt    600

aacgtggacc acaagcccag caacaccaag gtggacaaga gggtggagag caagtacggc    660

ccaccctgcc ccccctgccc agcccccgag ttcctgggcg gacccagcgt gttcctgttc    720

ccccccaagc ccaaggacac cctgatgatc agcagaaccc ccgaggtgac ctgtgtggtg    780

gtggacgtgt cccaggagga ccccgaggtc cagttcaact ggtacgtgga cggcgtggag    840

gtgcacaacg ccaagaccaa gcccagagag gagcagttta acagcaccta ccgggtggtg    900

tccgtgctga ccgtgctgca ccaggactgg ctgaacggca aagagtacaa gtgtaaggtc    960

tccaacaagg gcctgccaag cagcatcgaa aagaccatca gcaaggccaa gggccagcct   1020

agagagcccc aggtctacac cctgccaccc agccaagagg agatgaccaa gaaccaggtg   1080

tccctgacct gtctggtgaa gggcttctac cccagcgaca tcgccgtgga gtgggagagc   1140

aacggccagc ccgagaacaa ctacaagacc acccccccag tgctggacag cgacggcagc   1200

ttcttcctgt acagcaggct gaccgtggac aagtccagat ggcaggaggg caacgtcttt   1260

agctgctccg tgatgcacga ggccctgcac aaccactaca cccagaagag cctgagcctg   1320

tccctgggc                                                           1329
```

<210> SEQ ID NO 104
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104

```
gagatcgtgc tgacccagtc ccctgccacc ctgtcactgt ctccaggcga gagagctacc     60

ctgtcctgca agtcctccca gtccctgctg gactccggca accagaagaa cttcctgacc    120

tggtatcagc agaagcccgg ccaggccccc agactgctga tctactgggc ctccacccgg    180

gaatctggcg tgccctctag attctccggc tccggctctg gcaccgactt taccttcacc    240

atctccagcc tggaagccga ggacgccgcc acctactact gccagaacga ctactcctac    300

ccctacacct tcggccaggg caccaaggtg gaaatcaag                           339
```

<210> SEQ ID NO 105
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
gagatcgtgc tgacccagtc ccctgccacc ctgtcactgt ctccaggcga gagagctacc     60

ctgtcctgca agtcctccca gtccctgctg gactccggca accagaagaa cttcctgacc    120

tggtatcagc agaagcccgg ccaggccccc agactgctga tctactgggc ctccacccgg    180
```

```
gaatctggcg tgccctctag attctccggc tccggctctg gcaccgactt taccttcacc    240

atctccagcc tggaagccga ggacgccgcc acctactact gccagaacga ctactcctac    300

ccctacacct tcggccaggg caccaaggtg gaaatcaagc gtacggtggc cgctcccagc    360

gtgttcatct tcccccccaag cgacgagcag ctgaagagcg gcaccgccag cgtggtgtgt    420

ctgctgaaca acttctaccc cagggaggcc aaggtgcagt ggaaggtgga caacgccctg    480

cagagcggca acagccagga gagcgtcacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaacag gggcgagtgc    660
```

<210> SEQ ID NO 106
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
gagatcgtcc tgactcagtc acccgctacc ctgagcctga gccctggcga gcgggctaca     60

ctgagctgta aatctagtca gtcactgctg gatagcggta atcagaagaa cttcctgacc    120

tggtatcagc agaagcccgg tcaagcccct agactgctga tctactgggc ctctactaga    180

gaatcaggcg tgccctctag gtttagcggt agcggtagtg gcaccgactt caccttcact    240

atctctagcc tggaagccga ggacgccgct acctactact gtcagaacga ctatagctac    300

ccctacacct tcggtcaagg cactaaggtc gagattaag                           339
```

<210> SEQ ID NO 107
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
gagatcgtcc tgactcagtc acccgctacc ctgagcctga gccctggcga gcgggctaca     60

ctgagctgta aatctagtca gtcactgctg gatagcggta atcagaagaa cttcctgacc    120

tggtatcagc agaagcccgg tcaagcccct agactgctga tctactgggc ctctactaga    180

gaatcaggcg tgccctctag gtttagcggt agcggtagtg gcaccgactt caccttcact    240

atctctagcc tggaagccga ggacgccgct acctactact gtcagaacga ctatagctac    300

ccctacacct tcggtcaagg cactaaggtc gagattaagc gtacggtggc cgctcccagc    360

gtgttcatct tcccccccag cgacgagcag ctgaagagcg gcaccgccag cgtggtgtgc    420

ctgctgaaca acttctaccc ccgggaggcc aaggtgcagt ggaaggtgga caacgccctg    480

cagagcggca acagccagga gagcgtcacc gagcaggaca gcaaggactc cacctacagc    540

ctgagcagca ccctgaccct gagcaaggcc gactacgaga agcataaggt gtacgcctgc    600

gaggtgaccc accagggcct gtccagcccc gtgaccaaga gcttcaacag gggcgagtgc    660
```

<210> SEQ ID NO 108
<211> LENGTH: 15
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 108

acttactgga tgcac                                                        15

<210> SEQ ID NO 109
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109

aatatttatc ctggtactgg tggttctaac ttcgatgaga agttcaagaa c                 51

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110

tggactactg ggacgggagc ttat                                              24

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111

ggctacacat tcaccactta c                                                 21

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112

tatcctggta ctggtggt                                                     18

<210> SEQ ID NO 113
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

aagtccagtc agagtctgtt agacagtgga aatcaaaaga acttcttgac c                 51

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 114
tgggcatcca ctagggaatc t 21

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
cagaatgatt atagttatcc gtgcacg 27

<210> SEQ ID NO 116
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
agtcagagtc tgttagacag tggaaatcaa aagaacttc 39

<210> SEQ ID NO 117
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117 tgggcatcc 9

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
gattatagtt atccgtgc 18

<210> SEQ ID NO 119
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
cagaatgatt atagttatcc gtacacg 27

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
gattatagtt atccgtac 18

<210> SEQ ID NO 121
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
aagtccagtc agagtctgtt agacagtgga aatcaaaaga acttcttaac c 51

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
acctactgga tgcac 15

<210> SEQ ID NO 123
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
aacatctatc ctggcaccgg cggctccaac ttcgacgaga agttcaagaa c 51

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
tggacaaccg gcacaggcgc ttat 24

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
ggctacacct tcaccaccta c 21

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
tatcctggca ccggcggc 18

<210> SEQ ID NO 127
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
aagtcctccc agtccctgct ggactccggc aaccagaaga acttcctgac c 51

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
tgggcctcca cccgggaatc t 21

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
cagaacgact actcctaccc ctacacc 27

<210> SEQ ID NO 130
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
tcccagtccc tgctggactc cggcaaccag aagaacttc 39

<210> SEQ ID NO 131
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131 tgggcctcc 9

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132

```
gactactcct acccctac                                                18


<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133

acctactgga tgcac                                                   15


<210> SEQ ID NO 134
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134

aatatctacc ccggcaccgg cggctctaac ttcgacgaga agtttaagaa t           51


<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135

tggactaccg gcacaggcgc ctac                                         24


<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136

ggctacacct tcactaccta c                                            21


<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137

taccccggca ccggcggc                                                18


<210> SEQ ID NO 138
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
```

aaatctagtc agtcactgct ggatagcggt aatcagaaga acttcctgac c 51

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
tgggcctcta ctagagaatc a 21

<210> SEQ ID NO 140
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
cagaacgact atagctaccc ctacacc 27

<210> SEQ ID NO 141
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
agtcagtcac tgctggatag cggtaatcag aagaacttc 39

<210> SEQ ID NO 142
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142 tgggcctct 9

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
gactatagct acccctac 18

<210> SEQ ID NO 144
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
aacatctacc ctggcaccgg cggctccaac ttcgacgaga agttcaagaa c 51

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
tggaccaccg gaaccggcgc ctat 24

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146
taccctggca ccggcggc 18

<210> SEQ ID NO 147
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Glu Val Gln Leu Val Gln Ser Gly Ala Glu Val Lys Lys Pro Gly Glu
1 5 10 15

Ser Leu Arg Ile Ser Cys Lys Gly Ser
20 25

<210> SEQ ID NO 148
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148
gaagtgcagc tggtgcagtc tggagcagag gtgaaaaagc ccggggagtc tctgaggatc 60
tcctgtaagg gttct 75

<210> SEQ ID NO 149
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149
gaagtgcagc tggtgcagtc tggcgccgaa gtgaagaagc ctggcgagtc cctgcggatc 60
tcctgcaagg gctct 75

<210> SEQ ID NO 150
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
gaggtgcagc tggtgcagtc aggcgccgaa gtgaagaagc ccggcgagtc actgagaatt 60
agctgtaaag gttca 75

<210> SEQ ID NO 151
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 152
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
caggttcagc tggtgcagtc tggagctgag gtgaagaagc ctggggcctc agtgaaggtc 60
tcctgcaagg cttct 75

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Trp Val Arg Gln Ala Thr Gly Gln Gly Leu Glu Trp Met Gly
1 5 10

<210> SEQ ID NO 154
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 154
tgggtgcgac aggccactgg acaagggctt gagtggatgg gt 42

<210> SEQ ID NO 155
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 155
tgggtgcgac aggctaccgg ccagggcctg gaatggatgg gc 42

<210> SEQ ID NO 156
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
tgggtccgcc aggctaccgg tcaaggcctc gagtggatgg gt 42

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Trp Ile Arg Gln Ser Pro Ser Arg Gly Leu Glu Trp Leu Gly
1 5 10

<210> SEQ ID NO 158
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
tggatcaggc agtccccatc gagaggcctt gagtggctgg gt 42

<210> SEQ ID NO 159
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
tggatccggc agtccccctc taggggcctg gaatggctgg gc 42

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Trp Val Arg Gln Ala Pro Gly Gln Gly Leu Glu Trp Met Gly
1 5 10

<210> SEQ ID NO 161
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
tgggtgcgac aggcccctgg acaagggctt gagtggatgg gt 42

<210> SEQ ID NO 162
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 162

Arg Val Thr Ile Thr Ala Asp Lys Ser Thr Ser Thr Ala Tyr Met Glu
1 5 10 15

Leu Ser Ser Leu Arg Ser Glu Asp Thr Ala Val Tyr Tyr Cys Thr Arg
20 25 30

<210> SEQ ID NO 163
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 163
agagtcacga ttaccgcgga caaatccacg agcacagcct acatggagct gagcagcctg 60
agatctgagg acacggccgt gtattactgt acaaga 96

<210> SEQ ID NO 164
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 164
agagtgacca tcaccgccga caagtccacc tccaccgcct acatggaact gtcctccctg 60
agatccgagg acaccgccgt gtactactgc acccgg 96

<210> SEQ ID NO 165
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 165
agagtgacta tcaccgccga taagtctact agcaccgcct atatggaact gtctagcctg 60
agatcagagg acaccgccgt ctactactgc actagg 96

<210> SEQ ID NO 166
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 166

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Thr Arg
20 25 30

<210> SEQ ID NO 167
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
agattcacca tctccagaga caattccaag aacacgctgt atcttcaaat gaacagcctg 60
agagccgagg acacggccgt gtattactgt acaaga 96

<210> SEQ ID NO 168
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 168
aggttcacca tctcccggga caactccaag aacaccctgt acctgcagat gaactccctg 60
cgggccgagg acaccgccgt gtactactgt accaga 96

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Trp Gly Gln Gly Thr Thr Val Thr Val Ser Ser
1 5 10

<210> SEQ ID NO 170
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
tggggccagg gcaccaccgt gaccgtgtcc tcc 33

<210> SEQ ID NO 171
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
tggggccagg gcaccacagt gaccgtgtcc tct 33

<210> SEQ ID NO 172
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 172
tggggtcaag gcactaccgt gaccgtgtct agc 33

<210> SEQ ID NO 173
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 173
tggggccagg gcacaacagt gaccgtgtcc tcc 33

<210> SEQ ID NO 174
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Glu Ile Val Leu Thr Gln Ser Pro Asp Phe Gln Ser Val Thr Pro Lys
1 5 10 15

Glu Lys Val Thr Ile Thr Cys
20

<210> SEQ ID NO 175
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
gaaattgtgc tgactcagtc tccagacttt cagtctgtga ctccaaagga gaaagtcacc 60
atcacctgc 69

<210> SEQ ID NO 176
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
gagatcgtgc tgacccagtc ccccgacttc cagtccgtga cccccaaaga aaaagtgacc 60
atcacatgc 69

<210> SEQ ID NO 177
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 177

Glu Ile Val Leu Thr Gln Ser Pro Ala Thr Leu Ser Leu Ser Pro Gly
1 5 10 15

Glu Arg Ala Thr Leu Ser Cys
20

<210> SEQ ID NO 178
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 178
gaaattgtgt tgacacagtc tccagccacc ctgtctttgt ctccagggga aagagccacc 60
ctctcctgc 69

<210> SEQ ID NO 179
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 179
gagatcgtgc tgacccagtc ccctgccacc ctgtcactgt ctccaggcga gagagctacc 60
ctgtcctgc 69

<210> SEQ ID NO 180
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 180
gagatcgtcc tgactcagtc acccgctacc ctgagcctga gccctggcga gcgggctaca 60
ctgagctgt 69

<210> SEQ ID NO 181
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Asp Ile Val Met Thr Gln Thr Pro Leu Ser Leu Pro Val Thr Pro Gly
1 5 10 15

Glu Pro Ala Ser Ile Ser Cys
20

<210> SEQ ID NO 182
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 182
gatattgtga tgacccagac tccactctcc ctgcccgtca cccctggaga gccggcctcc 60
atctcctgc 69

<210> SEQ ID NO 183
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 183

Asp Val Val Met Thr Gln Ser Pro Leu Ser Leu Pro Val Thr Leu Gly
1 5 10 15

Gln Pro Ala Ser Ile Ser Cys
20

<210> SEQ ID NO 184
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 184
gatgttgtga tgactcagtc tccactctcc ctgcccgtca cccttggaca gccggcctcc 60
atctcctgc 69

<210> SEQ ID NO 185
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 185

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 186
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 186
gacatccaga tgacccagtc tccatcctcc ctgtctgcat ctgtaggaga cagagtcacc 60
atcacttgc 69

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Trp Tyr Gln Gln Lys Pro Gly Gln Ala Pro Arg Leu Leu Ile Tyr
1 5 10 15

<210> SEQ ID NO 188
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 188
tggtaccagc agaaacctgg ccaggctccc aggctcctca tctat 45

<210> SEQ ID NO 189
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 189
tggtatcagc agaagcccgg ccaggccccc agactgctga tctac 45

<210> SEQ ID NO 190
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 190
tggtatcagc agaagcccgg tcaagcccct agactgctga tctac 45

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Trp Tyr Gln Gln Lys Pro Gly Lys Ala Pro Lys Leu Leu Ile Tyr
1 5 10 15

<210> SEQ ID NO 192
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 192
tggtatcagc agaaaccagg gaaagctcct aagctcctga tctat 45

<210> SEQ ID NO 193
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 193
tggtatcagc agaagcccgg taaagcccct aagctgctga tctac 45

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Trp Tyr Leu Gln Lys Pro Gly Gln Ser Pro Gln Leu Leu Ile Tyr
1 5 10 15

<210> SEQ ID NO 195
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 195
tggtacctgc agaagccagg gcagtctcca cagctcctga tctat 45

<210> SEQ ID NO 196
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 196

Gly Val Pro Ser Arg Phe Ser Gly Ser Gly Ser Gly Thr Asp Phe Thr
1 5 10 15

Phe Thr Ile Ser Ser Leu Glu Ala Glu Asp Ala Ala Thr Tyr Tyr Cys
20 25 30

<210> SEQ ID NO 197
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 197
ggggtcccct cgaggttcag tggcagtgga tctgggacag atttcacctt taccatcagt 60
agcctggaag ctgaagatgc tgcaacatat tactgt 96

<210> SEQ ID NO 198
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 198
ggcgtgccct ctagattctc cggctccggc tctggcaccg actttacctt caccatctcc 60
agcctggaag ccgaggacgc cgccacctac tactgc 96

<210> SEQ ID NO 199

<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
ggcgtgccct ctaggtttag cggtagcggt agtggcaccg acttcacctt cactatctct 60
agcctggaag ccgaggacgc cgctacctac tactgt 96

<210> SEQ ID NO 200
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 200

Gly Ile Pro Pro Arg Phe Ser Gly Ser Gly Tyr Gly Thr Asp Phe Thr
1 5 10 15

Leu Thr Ile Asn Asn Ile Glu Ser Glu Asp Ala Ala Tyr Tyr Phe Cys
20 25 30

<210> SEQ ID NO 201
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 201
gggatcccac ctcgattcag tggcagcggg tatggaacag attttaccct cacaattaat 60
aacatagaat ctgaggatgc tgcatattac ttctgt 96

<210> SEQ ID NO 202
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 202

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 203
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 203
ggggtcccat caaggttcag cggcagtgga tctgggacag aattcactct caccatcagc 60
agcctgcagc ctgatgattt tgcaacttat tactgt 96

<210> SEQ ID NO 204

<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
ggcgtgccct ctagattctc cggctccggc tctggcaccg agtttaccct gaccatctcc 60
agcctgcagc ccgacgactt cgccacctac tactgc 96

<210> SEQ ID NO 205
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 205

Gly Val Pro Ser Arg Phe Ser Gly Ser Gly Ser Gly Thr Asp Phe Thr
1 5 10 15

Phe Thr Ile Ser Ser Leu Gln Pro Glu Asp Ile Ala Thr Tyr Tyr Cys
20 25 30

<210> SEQ ID NO 206
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 206
ggggtcccat caaggttcag tggaagtgga tctgggacag attttacttt caccatcagc 60
agcctgcagc ctgaagatat tgcaacatat tactgt 96

<210> SEQ ID NO 207
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 207
ggcgtgccct ctaggtttag cggtagcggt agtggcaccg acttcacctt cactatctct 60
agcctgcagc ccgaggatat cgctacctac tactgt 96

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 208

Phe Gly Gln Gly Thr Lys Val Glu Ile Lys
1 5 10

<210> SEQ ID NO 209
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ttcggccaag ggaccaaggt ggaaatcaaa 30

<210> SEQ ID NO 210
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ttcggccagg gcaccaaggt ggaaatcaag 30

<210> SEQ ID NO 211
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ttcggtcaag gcactaaggt cgagattaag 30

<210> SEQ ID NO 212
<211> LENGTH: 327
<212> TYPE: PRT
<213> ORGANISM: Homo sapiens

<400> SEQUENCE: 212

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 213
<211> LENGTH: 107
<212> TYPE: PRT
<213> ORGANISM: Homo sapiens

<400> SEQUENCE: 213

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 214
<211> LENGTH: 326
<212> TYPE: PRT
<213> ORGANISM: Homo sapiens

<400> SEQUENCE: 214

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
```

```
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325


<210> SEQ ID NO 215
<211> LENGTH: 330
<212> TYPE: PRT
<213> ORGANISM: Homo sapiens

<400> SEQUENCE: 215

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 216
<211> LENGTH: 330
<212> TYPE: PRT
<213> ORGANISM: Homo sapiens

<400> SEQUENCE: 216

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 217
<211> LENGTH: 330
<212> TYPE: PRT
<213> ORGANISM: Homo sapiens

<400> SEQUENCE: 217

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
```

```
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 218
<211> LENGTH: 330
<212> TYPE: PRT
<213> ORGANISM: Homo sapiens

<400> SEQUENCE: 218

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 219
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Met Glu Trp Ser Trp Val Phe Leu Phe Phe Leu Ser Val Thr Thr Gly
1               5                   10                  15

Val His Ser


<210> SEQ ID NO 220
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Met Ser Val Pro Thr Gln Val Leu Gly Leu Leu Leu Leu Trp Leu Thr
1               5                   10                  15

Asp Ala Arg Cys
            20


<210> SEQ ID NO 221
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Met Ala Trp Val Trp Thr Leu Pro Phe Leu Met Ala Ala Ala Gln Ser
1               5                   10                  15

Val Gln Ala


<210> SEQ ID NO 222
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Met Ser Val Leu Thr Gln Val Leu Ala Leu Leu Leu Leu Trp Leu Thr
1               5                   10                  15

Gly Thr Arg Cys
```

20

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 223
tggactactg ggacgggagc ttac 24

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Gly Tyr Thr Phe Thr Thr Tyr Trp Met His
1 5 10

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Cys Asn Gly Arg Cys
1 5

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
gctgacagac taacagactg ttcc 24

<210> SEQ ID NO 227
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
caaatgtggt atggctga 18

<210> SEQ ID NO 228
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala
    130

<210> SEQ ID NO 229
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Cys Thr Phe Gly Gly Gly Thr Lys Leu Glu Ile
            100                 105                 110

Lys Arg Ala Asp
        115

<210> SEQ ID NO 230
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

```
Trp Met His Trp Val Lys Gln Arg His Gly Gln Gly Leu Glu Trp Ile
        35                  40                  45

Gly Asn Ile Tyr Pro Gly Ser Gly Ser Thr Asn Tyr Asp Glu Lys Phe
    50                  55                  60

Lys Ser Lys Gly Thr Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Thr Arg


<210> SEQ ID NO 231
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro
            100


<210> SEQ ID NO 232
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(37)

<400> SEQUENCE: 232

g tgc acg ttc gga ggg ggg acc aag ctg gaa ata aaa                     37
  Cys Thr Phe Gly Gly Gly Thr Lys Leu Glu Ile Lys
  1               5                   10


<210> SEQ ID NO 233
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Cys Thr Phe Gly Gly Gly Thr Lys Leu Glu Ile Lys
1               5                   10
```

-continued

```
<210> SEQ ID NO 234
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(37)

<400> SEQUENCE: 234

g tac acg ttc gga ggg ggg acc aag ctg gaa ata aaa c                   38
  Tyr Thr Phe Gly Gly Gly Thr Lys Leu Glu Ile Lys
  1               5                   10


<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Tyr Thr Phe Gly Gly Gly Thr Lys Leu Glu Ile Lys
1               5                   10


<210> SEQ ID NO 236
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Met Tyr Pro Pro Tyr
1               5


<210> SEQ ID NO 237
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Arg Gly Asp Ser
1
```

ANTIBODY MOLECULES TO PD-1 AND USES THEREOF

CROSS REFERENCE TO RELATED APPLICATIONS

This application is a divisional application of U.S. application Ser. No. 14/604,415, filed Jan. 23, 2015, now allowed, which claims the benefit of U.S. Provisional Application No. 61/931,512, filed Jan. 24, 2014, U.S. Provisional Application No. 62/059,676, filed Oct. 3, 2014, and U.S. Provisional Application No. 62/094,834, filed Dec. 19, 2014. The contents of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jan. 12, 2015, is named C2160-700010_SL.txt and is 186,670 bytes in size.

BACKGROUND

The ability of T cells to mediate an immune response against an antigen requires two distinct signaling interactions (Viglietta, V. et al. (2007) *Neurotherapeutics* 4:666-675; Korman, A. J. et al. (2007) *Adv. Immunol.* 90:297-339). First, an antigen that has been arrayed on the surface of antigen-presenting cells (APC) is presented to an antigen-specific naive $CD4^+$ T cell. Such presentation delivers a signal via the T cell receptor (TCR) that directs the T cell to initiate an immune response specific to the presented antigen. Second, various co-stimulatory and inhibitory signals mediated through interactions between the APC and distinct T cell surface molecules trigger the activation and proliferation of the T cells and ultimately their inhibition.

The immune system is tightly controlled by a network of costimulatory and co-inhibitory ligands and receptors. These molecules provide the second signal for T cell activation and provide a balanced network of positive and negative signals to maximize immune responses against infection, while limiting immunity to self (Wang, L. et al. (Epub Mar. 7, 2011) *J. Exp. Med.* 208(3):577-92; Lepenies, B. et al. (2008) *Endocrine, Metabolic & Immune Disorders—Drug Targets* 8:279-288). Examples of costimulatory signals include the binding between the B7.1 (CD80) and B7.2 (CD86) ligands of the APC and the CD28 and CTLA-4 receptors of the $CD4^+$ T-lymphocyte (Sharpe, A. H. et al. (2002) *Nature Rev. Immunol.* 2:116-126; Lindley, P. S. et al. (2009) *Immunol. Rev.* 229:307-321). Binding of B7.1 or B7.2 to CD28 stimulates T cell activation, whereas binding of B7.1 or B7.2 to CTLA-4 inhibits such activation (Dong, C. et al. (2003) *Immunolog. Res.* 28(1):39-48; Greenwald, R. J. et al. (2005) *Ann. Rev. Immunol.* 23:515-548). CD28 is constitutively expressed on the surface of T cells (Gross, J., et al. (1992) *J. Immunol.* 149:380-388), whereas CTLA-4 expression is rapidly up-regulated following T-cell activation (Linsley, P. et al. (1996) *Immunity* 4:535-543).

Other ligands of the CD28 receptor include a group of related B7 molecules, also known as the "B7 Superfamily" (Coyle, A. J. et al. (2001) *Nature Immunol.* 2(3):203-209; Sharpe, A. H. et al. (2002) *Nature Rev. Immunol.* 2:116-126; Collins, M. et al. (2005) *Genome Biol.* 6:223.1-223.7; Korman, A. J. et al. (2007) *Adv. Immunol.* 90:297-339). Several members of the B7 Superfamily are known, including B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) *Genome Biol.* 6:223.1-223.7).

The Programmed Death 1 (PD-1) protein is an inhibitory member of the extended CD28/CTLA-4 family of T cell regulators (Okazaki et al. (2002) *Curr Opin Immunol* 14: 391779-82; Bennett et al. (2003) *J. Immunol.* 170:711-8). Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes.

The PD-1 gene encodes a 55 kDa type I transmembrane protein (Agata et al. (1996) *Int Immunol.* 8:765-72). Although structurally similar to CTLA-4, PD-1 lacks the MYPPY motif (SEQ ID NO: 236) that is important for B7-1 and B7-2 binding. Two ligands for PD-1 have been identified, PD-L1 (B7-H1) and PD-L2 (B7-DC), that have been shown to downregulate T cell activation upon binding to PD-1 (Freeman et al. (2000) *J. Exp. Med.* 192:1027-34; Carter et al. (2002) *Eur. J. Immunol.* 32:634-43). Both PD-L1 and PD-L2 are B7 homologs that bind to PD-1, but do not bind to other CD28 family members. PD-L1 is abundant in a variety of human cancers (Dong et al. (2002) *Nat. Med.* 8:787-9).

PD-1 is known as an immunoinhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci.* USA 99:12293-7; Brown et al. (2003) *J. Immunol.* 170:1257-66).

Given the importance of immune checkpoint pathways in regulating an immune response, the need exists for developing novel agents that modulate the activity of immunoinhibitory proteins, such as PD-1, thus leading to activation of the immune system. Such agents can be used, e.g., for cancer immunotherapy and treatment of other conditions, such as chronic infection.

SUMMARY

Disclosed herein are antibody molecules (e.g., humanized antibody molecules) that bind to Programmed Death 1 (PD-1) with high affinity and specificity. In one embodiment, the anti-PD-1 antibody molecules comprise a novel combination of framework regions (e.g., FW1, FW2, FW3 and/or FW4), e.g., novel combinations of a heavy chain framework regions and/or light chain framework regions. Nucleic acid molecules encoding the antibody molecules, expression vectors, host cells and methods for making the antibody molecules are also provided. Immunoconjugates, multi- or bispecific antibody molecules and pharmaceutical compositions comprising the antibody molecules are also provided. The anti-PD-1 antibody molecules disclosed herein can be used (alone or in combination with other agents or therapeutic modalities) to treat, prevent and/or diagnose disorders, such as cancerous disorders (e.g., solid and soft-tissue tumors), as well as infectious diseases (e.g., chronic infectious disorders or sepsis). Thus, compositions and methods for detecting PD-1, as well as methods for treating various disorders including cancer and/or infectious diseases, using the anti-PD-1 antibody molecules are disclosed herein.

Accordingly, in one aspect, the invention features an antibody molecule (e.g., an isolated or recombinant antibody molecule) having one or more of the following properties:

(i) binds to PD-1, e.g., human PD-1, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger;

(ii) does not substantially bind to CD28, CTLA-4, ICOS or BTLA;

(iii) inhibits or reduces binding of PD-1 to a PD-1 ligand, e.g., PD-L1 or PD-L2, or both;

(iv) binds specifically to an epitope on PD-1, e.g., the same or similar epitope as the epitope recognized by murine monoclonal antibody BAP049 or a chimeric antibody BAP049, e.g., BAP049-chi or BAP049-chi-Y;

(v) shows the same or similar binding affinity or specificity, or both, as any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(vi) shows the same or similar binding affinity or specificity, or both, as an antibody molecule (e.g., an heavy chain variable region and light chain variable region) described in Table 1;

(vii) shows the same or similar binding affinity or specificity, or both, as an antibody molecule (e.g., an heavy chain variable region and light chain variable region) having an amino acid sequence shown in Table 1;

(viii) shows the same or similar binding affinity or specificity, or both, as an antibody molecule (e.g., an heavy chain variable region and light chain variable region) encoded by the nucleotide sequence shown in Table 1;

(ix) inhibits, e.g., competitively inhibits, the binding of a second antibody molecule to PD-1, wherein the second antibody molecule is an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(x) binds the same or an overlapping epitope with a second antibody molecule to PD-1, wherein the second antibody molecule is an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xi) competes for binding, and/or binds the same epitope, with a second antibody molecule to PD-1, wherein the second antibody molecule is an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xii) has one or more biological properties of an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xiii) has one or more pharmacokinetic properties of an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xiv) inhibits one or more activities of PD-1, e.g., results in one or more of: an increase in tumor infiltrating lymphocytes, an increase in T-cell receptor mediated proliferation, or a decrease in immune evasion by cancerous cells;

(xv) binds human PD-1 and is cross-reactive with cynomolgus PD-1;

(xvi) binds to one or more residues within the C strand, CC' loop, C' strand, or FG loop of PD-1, or a combination two, three or all of the C strand, CC' loop, C' strand or FG loop of PD-1, e.g., wherein the binding is assayed using ELISA or Biacore; or (xvii) has a VL region that contributes more to binding to PD-1 than a VH region. In some embodiments, the antibody molecule binds to PD-1 with high affinity, e.g., with a $K_D$ that is about the same, or at least about 10%, 20%, 30%, 40%, 50%, 60%, 70%, 80% or 90% higher or lower than the $K_D$ of a murine or chimeric anti-PD-1 antibody molecule, e.g., a murine or chimeric anti-PD-1 antibody molecule described herein. In some embodiments, the $K_D$ of the murine or chimeric anti-PD-1 antibody molecule is less than about 0.4, 0.3, 0.2, 0.1, or 0.05 nM, e.g., measured by a Biacore method. In some embodiments, the $K_D$ of the murine or chimeric anti-PD-1 antibody molecule is less than about 0.2 nM, e.g., about 0.135 nM. In other embodiments, the $K_D$ of the murine or chimeric anti PD-1 antibody molecule is less than about 10, 5, 3, 2, or 1 nM, e.g., measured by binding on cells expressing PD-1 (e.g., 300.19 cells). In some embodiments, the $K_D$ of the murine or chimeric anti PD-1 antibody molecule is less than about 5 nM, e.g., about 4.60 nM (or about 0.69 μg/mL).

In some embodiments, the anti-PD-1 antibody molecule binds to PD-1 with a $K_{off}$ slower than $1\times10^4$, $5\times10^{-5}$, or $1\times10^{-5}$ $S^{-1}$, e.g., about $1.65\times10^{-5}$ $s^{-1}$. In some embodiments, the anti-PD-1 antibody molecule binds to PD-1 with a $K_{on}$ faster than $1\times10^4$, $5\times10^4$, $1\times10^5$, or $5\times10^5$ $M^{-1}s^{-1}$, e.g., about $1.23\times10^5$ $M^{-1}s^{-1}$.

In some embodiments, the expression level of the antibody molecule is higher, e.g., at least about 0.5, 1, 2, 3, 4, 5, 6, 7, 8, 9 or 10-fold higher, than the expression level of a murine or chimeric antibody molecule, e.g., a murine or chimeric anti-PD-1 antibody molecule described herein. In some embodiments, the antibody molecule is expressed in CHO cells.

In some embodiments, the anti-PD-1 antibody molecule reduces one or more PD-1-associated activities with an $IC_{50}$ (concentration at 50% inhibition) that is about the same or lower, e.g., at least about 10%, 20%, 30%, 40%, 50%, 60%, 70%, 80% or 90% lower, than the $IC_{50}$ of a murine or chimeric anti-PD-1 antibody molecule, e.g., a murine or chimeric anti-PD-1 antibody molecule described herein. In some embodiments, the $IC_{50}$ of the murine or chimeric anti-PD-1 antibody molecule is less than about 6, 5, 4, 3, 2, or 1 nM, e.g., measured by binding on cells expressing PD-1 (e.g., 300.19 cells). In some embodiments, the $IC_{50}$ of the murine or chimeric anti-PD-1 antibody molecule is less than about 4 nM, e.g., about 3.40 nM (or about 0.51 μg/mL). In some embodiments, the PD-1-associated activity reduced is the binding of PD-L1 and/or PD-L2 to PD-1. In some embodiments, the anti-PD-1 antibody molecule binds to peripheral blood mononucleated cells (PBMCs) activated by Staphylococcal enterotoxin B (SEB). In other embodiments, the anti-PD-1 antibody molecule increases the expression of IL-2 on whole blood activated by SEB. For example, the anti-PD-1 antibody increases the expression of IL-2 by at least about 2, 3, 4, or 5-fold, compared to the expression of IL-2 when an isotype control (e.g., IgG4) is used.

In some embodiments, the anti-PD-1 antibody molecule has improved stability, e.g., at least about 0.5, 1, 2, 3, 4, 5, 6, 7, 8, 9 or 10-fold more stable in vivo or in vitro, than a murine or chimeric anti-PD-1 antibody molecule, e.g., a murine or chimeric anti-PD-1 antibody molecule described herein.

In one embodiment, the anti PD-1 antibody molecule is a humanized antibody molecule and has a risk score based on T cell epitope analysis of 300 to 700, 400 to 650, 450 to 600, or a risk score as described herein.

In another embodiment, the anti-PD-1 antibody molecule comprises at least one antigen-binding region, e.g., a variable region or an antigen-binding fragment thereof, from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one, two, three or four variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one or two heavy chain variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one or two light chain variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes a heavy chain constant region for an IgG4, e.g., a human IgG4. In one embodiment, the human IgG4 includes a substitution at position 228 according to EU numbering (e.g., a Ser to Pro substitution). In still another embodiment, the anti-PD-1 antibody molecule includes a heavy chain constant region for an IgG1, e.g., a human IgG1. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235). In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In yet another embodiment, the anti-PD-1 antibody molecule includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In another embodiment, the anti-PD-1 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG4 includes a substitution at position 228 according to EU numbering (e.g., a Ser to Pro substitution). In yet another embodiment, the anti-PD-1 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235).

In another embodiment, the anti-PD-1 antibody molecule includes a heavy chain variable domain and a constant region, a light chain variable domain and a constant region, or both, comprising the amino acid sequence of BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as showing in Table 4; or a sequence substantially identical thereto.

In yet another embodiment, the anti-PD-1 antibody molecule includes at least one, two, or three complementarity determining regions (CDRs) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-1 antibody molecule includes at least one, two, or three CDRs from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequence.

In yet another embodiment, the anti-PD-1 antibody molecule includes at least one, two, or three CDRs (or collectively all of the CDRs) from a light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-1 antibody molecule includes all six CDRs from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions). In one embodiment, the anti-PD-1 antibody molecule may include any CDR described herein. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, or three CDRs according to Kabat et al. (e.g., at least one, two, or three CDRs according to the Kabat definition as set out in Table 1) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In another embodiment, the anti-PD-1 antibody molecule includes at least one, two, or three CDRs according to Kabat et al. (e.g., at least one, two, or three CDRs according to the Kabat definition as set out in Table 1) from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In yet another embodiment, the anti-PD-1 antibody molecule includes at least one, two, three, four, five, or six CDRs according to Kabat et al. (e.g., at least one, two, three, four, five, or six CDRs according to the Kabat definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Table 1.

In yet another embodiment, the anti-PD-1 antibody molecule includes all six CDRs according to Kabat et al. (e.g., all six CDRs according to the Kabat definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-PD-1 antibody molecule may include any CDR described herein.

In another embodiment, the anti-PD-1 antibody molecule includes at least one, two, or three Chothia hypervariable loops (e.g., at least one, two, or three hypervariable loops according to the Chothia definition as set out in Table 1) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In another embodiment, the anti-PD-1 antibody molecule includes at least one, two, or three Chothia hypervariable loops (e.g., at least one, two, or three hypervairalbe loops according to the Chothia definition as set out in Table 1) of a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In yet another embodiment, the anti-PD-1 antibody molecule includes at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Table 1.

In one embodiment, the anti-PD-1 antibody molecule includes all six hypervariable loops (e.g., all six hypervariable loops according to the Chothia definition as set out in Table 1) of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Table 1. In one embodiment, the anti-PD-1 antibody molecule may include any hypervariable loop described herein.

In still another embodiment, the anti-PD-1 antibody molecule includes at least one, two, or three hypervariable loops that have the same canonical structures as the corresponding hypervariable loop of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-PD-1 antibody molecule includes a combination of CDRs or hypervariable loops defined according to the Kabat et al. and Chothia et al.

In one embodiment, the anti-PD-1 antibody molecule includes at least one, two or three CDRs or hypervariable loops from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, according to the Kabat and Chothia definition (e.g., at least one, two, or three CDRs or hypervariable loops according to the Kabat and Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

For example, the anti-PD-1 antibody molecule can include VH CDR1 according to Kabat et al. or VH hypervariable loop 1 according to Chothia et al., or a combination thereof, e.g., as shown in Table 1. In one embodiment, the combination of Kabat and Chothia CDR of VH CDR1 comprises the amino acid sequence GYTFTTYWMH (SEQ ID NO: 224), or an amino acid sequence substantially identical thereto (e.g., having at least one amino acid alteration, but not more than two, three or four alterations (e.g., substitutions, deletions, or insertions, e.g., conservative substitutions)). The anti-PD-1 antibody molecule can further include, e.g., VH CDRs 2-3 according to Kabat et al. and VL CDRs 1-3 according to Kabat et al., e.g., as shown in Table 1. Accordingly, in some embodiments, framework regions are defined based on a combination of CDRs defined according to Kabat et al. and hypervariable loops defined according to Chothia et al. For example, the anti-PD-1 antibody molecule can include VH FR1 defined based on VH hypervariable loop 1 according to Chothia et al. and VH FR2 defined based on VH CDRs 1-2 according to Kabat et al., e.g., as shown in Table 1. The anti-PD-1 antibody molecule can further include, e.g., VH FRs 3-4 defined based on VH CDRs 2-3 according to Kabat et al. and VL FRs 1-4 defined based on VL CDRs 1-3 according to Kabat et al.

The anti-PD-1 antibody molecule can contain any combination of CDRs or hypervariable loops according to the Kabat and Chothia definitions. In one embodiment, the anti-PD-1 antibody molecule includes at least one, two or three CDRs from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, according to the Kabat and Chothia definition (e.g., at least one, two, or three CDRs according to the Kabat and Chothia definition as set out in Table 1).

In an embodiment, e.g., an embodiment comprising a variable region, a CDR (e.g., Chothia CDR or Kabat CDR), or other sequence referred to herein, e.g., in Table 1, the antibody molecule is a monospecific antibody molecule, a bispecific antibody molecule, or is an antibody molecule that comprises an antigen binding fragment of an antibody, e.g., a half antibody or antigen binding fragment of a half antibody. In certain embodiments the antibody molecule is a bispecific antibody molecule having a first binding specificity for PD-1 and a second binding specificity for TIM-3, LAG-3, CEACAM (e.g., CEACAM-1 and/or CEACAM-5), PD-L1 or PD-L2.

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the anti-PD-1 antibody molecule comprises a VH comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the anti-PD-1 antibody molecule comprises a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the antibody molecule is a humanized antibody molecule. In another embodiment, the antibody molecule is a monospecific antibody molecule. In yet another embodiment, the antibody molecule is a bispecific antibody molecule.

In one embodiment, the anti-PD-1 antibody molecule includes:

(i) a heavy chain variable region (VH) including a VHCDR1 amino acid sequence chosen from SEQ ID NO: 1, SEQ ID NO: 4 or SEQ ID NO: 224; a VHCDR2 amino acid sequence of SEQ ID NO: 2; and a VHCDR3 amino acid sequence of SEQ ID NO: 3; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 32.

In another embodiment, the anti-PD-1 antibody molecule includes:

(i) a heavy chain variable region (VH) including a VHCDR1 amino acid sequence chosen from SEQ ID NO: 1, SEQ ID NO: 4 or SEQ ID NO: 224; a VHCDR2 amino acid sequence of SEQ ID NO: 5, and a VHCDR3 amino acid sequence of SEQ ID NO: 3; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises the VHCDR1 amino acid sequence of SEQ ID NO: 1. In another embodiment, the anti-PD-1 antibody molecule comprises the VHCDR1 amino acid sequence of SEQ ID NO: 4. In yet another embodiment, the anti-PD-1 antibody molecule comprises the VHCDR1 amino acid sequence of SEQ ID NO: 224.

In one embodiment, the light or the heavy chain variable framework (e.g., the region encompassing at least FR1, FR2, FR3, and optionally FR4) of the anti-PD-1 antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-PD-1 antibody molecule comprises a heavy chain variable domain having at least one, two, three, four, five, six, seven, ten, fifteen, twenty or more changes, e.g., amino acid substitutions or deletions, from an amino acid sequence of BAP049-chi-HC, e.g., the amino acid sequence of the FR region in the entire variable region, e.g., shown in FIG. 9A-9B, or SEQ ID NO: 18, 20, 22 or 30. In one embodiment, the anti-PD-1 antibody molecule comprises a heavy chain variable domain having one or more of: E at position 1, V at position 5, A at position 9, V at position 11, K at position 12, K at position 13, E at position 16, L at position 18, R at position 19, I or V at position 20, G at position 24, I at position 37, A or S at position 40, T at position 41, S at position 42, R at position 43, M or L at position 48, V or F at position 68, T at position 69, I at position 70, S at position 71, A or R at position 72, K or N at position 74, T or K at position 76, S or N at position 77, L at position 79, L at position 81, E or Q at position 82, M at position 83, S or N at position 84, R at position 87, A at position 88, or T at position 91 of amino acid sequence of BAP049-chi-HC, e.g., the amino acid sequence of the FR in the entire variable region, e.g., shown in FIG. 9A-9B, or SEQ ID NO: 18, 20, 22 or 30.

Alternatively, or in combination with the heavy chain substitutions of BAP049-chi-HC described herein, the anti-PD-1 antibody molecule comprises a light chain variable domain having at least one, two, three, four, five, six, seven, ten, fifteen, twenty or more amino acid changes, e.g., amino acid substitutions or deletions, from an amino acid sequence of BAP049-chi-LC, e.g., the amino acid sequence shown in FIG. 10A-10B, or SEQ ID NO: 24 or 26. In one embodiment, the anti-PD-1 antibody molecule comprises a heavy chain variable domain having one or more of: E at position 1, V at position 2, Q at position 3, L at position 4, T at position 7, D or L or A at position 9, F or T at position 10, Q at position 11, S or P at position 12, L or A at position 13, S at position 14, P or L or V at position 15, K at position 16, Q or D at position 17, R at position 18, A at position 19, S at position 20, I or L at position 21, T at position 22, L at position 43, K at position 48, A or S at position 49, R or Q at position 51, Y at position 55, I at position 64, S or P at position 66, S at position 69, Y at position 73, G at position 74, E at position 76, F at position 79, N at position 82, N at position 83, L or I at position 84, E at position 85, S or P at position 86, D at position 87, A or F or I at position 89, T or Y at position 91, F at position 93, or Y at position 102 of the amino acid sequence of BAP049-chi-LC, e.g., the amino acid sequence shown in FIG. 10A-10B, or SEQ ID NO: 24 or 26.

In other embodiments, the anti-PD-1 antibody molecule includes one, two, three, or four heavy chain framework regions (e.g., a VHFW amino acid sequence shown in Table 2, or encoded by the nucleotide sequence shown in Table 2), or a sequence substantially identical thereto.

In yet other embodiments, the anti-PD-1 antibody molecule includes one, two, three, or four light chain framework regions (e.g., a VLFW amino acid sequence shown in Table 2, or encoded by the nucleotide sequence shown in Table 2), or a sequence substantially identical thereto.

In other embodiments, the anti-PD-1 antibody molecule includes one, two, three, or four heavy chain framework regions (e.g., a VHFW amino acid sequence shown in Table 2, or encoded by the nucleotide sequence shown in Table 2), or a sequence substantially identical thereto; and one, two, three, or four light chain framework regions (e.g., a VLFW amino acid sequence shown in Table 2, or encoded by the nucleotide sequence shown in Table 2), or a sequence substantially identical thereto.

In some embodiments, the anti-PD-1 antibody molecule comprises the heavy chain framework region 1 (VHFW1) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum15, BAP049-hum16, BAP049-Clone-A, BAP049-Clone-B, BAP049-Clone-C, BAP049-Clone-D, or BAP049-Clone-E (e.g., SEQ ID NO: 147). In some embodiments, the antibody molecule comprises the heavy chain framework region 1 (VHFW1) of BAP049-hum14 or BAP049-hum15 (e.g., SEQ ID NO: 151).

In some embodiments, the anti-PD-1 antibody molecule comprises the heavy chain framework region 2 (VHFW2) of BAP049-hum01, BAP049-hum02, BAP049-hum05, BAP049-hum06, BAP049-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 153). In some embodiments, the antibody molecule comprises the heavy chain framework region 2 (VHFW2) of BAP049-hum03, BAP049-hum04, BAP049-hum08, BAP049-hum10, BAP049-hum14, BAP049-hum15, or BAP049-Clone-D (e.g., SEQ ID NO: 157). In some embodiments, the antibody molecule comprises the heavy chain framework region 2 (VHFW2) of BAP049-hum16 (e.g., SEQ ID NO: 160).

In some embodiments, the anti-PD-1 antibody molecule comprises the heavy chain framework region 3 (VHFW3) of BAP049-hum01, BAP049-hum02, BAP049-hum05, BAP049-hum06, BAP049-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 162). In some embodiments, the antibody molecule comprises the heavy chain framework region 3 (VHFW3) of BAP049-hum03, BAP049-hum04, BAP049-hum08, BAP049-hum10, BAP049-hum14, BAP049-hum15, BAP049-hum16, or BAP049-Clone-D (e.g., SEQ ID NO: 166).

In some embodiments, the anti-PD-1 antibody molecule comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169).

In some embodiments, the anti-PD-1 antibody molecule comprises the light chain framework region 1 (VLFW1) of BAP049-hum08, BAP049-hum09, BAP049-hum15, BAP049-hum16, or BAP049-Clone-C (e.g., SEQ ID NO: 174). In some embodiments, the antibody molecule comprises the light chain framework region 1 (VLFW1) of BAP049-hum01, BAP049-hum04, BAP049-hum05, BAP049-hum07, BAP049-hum10, BAP049-hum11, BAP049-hum14, BAP049-Clone-A, BAP049-Clone-B, BAP049-Clone-D, or BAP049-Clone-E (e.g., SEQ ID NO: 177). In some embodiments, the antibody molecule comprises the light chain framework region 1 (VLFW1) of BAP049-hum06 (e.g., SEQ ID NO: 181). In some embodiments, the antibody molecule comprises the light chain framework region 1 (VLFW1) of BAP049-hum13 (e.g., SEQ ID NO: 183). In some embodiments, the antibody molecule comprises the light chain framework region 1 (VLFW1) of BAP049-hum02, BAP049-hum03, or BAP049-hum12 (e.g., SEQ ID NO: 185).

In some embodiments, the anti-PD-1 antibody molecule comprises the light chain framework region 2 (VLFW2) of BAP049-hum01, BAP049-hum02, BAP049-hum03, BAP049-hum06, BAP049-hum08, BAP049-hum09, BAP049-hum10, BAP049-hum11, BAP049-hum14, BAP049-hum15, BAP049-hum16, BAP049-Clone-A, BAP049-Clone-B, BAP049-Clone-D, or BAP049-Clone-E (e.g., SEQ ID NO: 187). In some embodiments, the antibody molecule comprises the light chain framework region 2 (VLFW2) of BAP049-hum04, BAP049-hum05, BAP049-hum07, BAP049-hum13, or BAP049-Clone-C (e.g., SEQ ID NO: 191). In some embodiments, the antibody molecule comprises the light chain framework region 2 (VLFW2) of BAP049-hum12 (e.g., SEQ ID NO: 194).

In some embodiments, the anti-PD-1 antibody molecule comprises the light chain framework region 3 (VLFW3) of BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-C, BAP049-Clone-D, or BAP049-Clone-E (e.g., SEQ ID NO: 196). In some embodiments, the antibody molecule comprises the light chain framework region 3 (VLFW3) of BAP049-hum02 or BAP049-hum03 (e.g., SEQ ID NO: 200). In some embodiments, the antibody molecule comprises the light chain framework region 3 (VLFW3) of BAP049-hum01 or BAP049-Clone-A (e.g., SEQ ID NO: 202). In some embodiments, the antibody molecule comprises the light chain framework region 3 (VLFW3) of BAP049-hum04, BAP049-hum05, or BAP049-Clone-B (e.g., SEQ ID NO: 205).

In some embodiments, the anti-PD-1 antibody molecule comprises the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises the heavy chain framework regions 1-3 of BAP049-hum01, BAP049-hum02, BAP049-hum05, BAP049-hum06, BAP-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 147 (VHFW1), SEQ ID NO: 153 (VHFW2), and SEQ ID NO: 162 (VHFW3)). In some embodiments, the antibody molecule comprises the heavy chain framework regions 1-3 of BAP049-hum03, BAP049-hum04, BAP049-hum08, BAP049-hum10, or BAP049-Clone-D (e.g., SEQ ID NO: 147 (VHFW1), SEQ ID NO: 157 (VHFW2), and SEQ ID NO: 166 (VHFW3)). In some embodiments, the antibody molecule comprises the heavy chain framework regions 1-3 of BAP049-hum14 or BAP049-hum15 (e.g., SEQ ID NO: 151 (VHFW1), SEQ ID NO: 157 (VHFW2), and SEQ ID NO: 166 (VHFW3)). In some embodiments, the antibody molecule comprises the heavy chain framework regions 1-3 of BAP049-hum16 (e.g., SEQ ID NO: 147 (VHFW1), SEQ ID NO: 160 (VHFW2), and SEQ ID NO: 166 (VHFW3)). In some embodiments, the antibody molecule further comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169).

In some embodiments, the anti-PD-1 antibody molecule comprises the light chain framework regions 1-3 of BAP049-hum01 or BAP049-Clone-A (e.g., SEQ ID NO: 177 (VLFW1), SEQ ID NO: 187 (VLFW2), and SEQ ID NO: 202 (VLFW3)). In some embodiments, the antibody molecule comprises the light chain framework regions 1-3 of BAP049-hum02 or BAP049-hum03 (e.g., SEQ ID NO: 185 (VLFW1), SEQ ID NO: 187 (VLFW2), and SEQ ID NO: 200 (VLFW3)). In some embodiments, the antibody molecule comprises the light chain framework regions 1-3 of BAP049-hum04, BAP049-hum05, or BAP049-Clone-B (e.g., SEQ ID NO: 177 (VLFW1), SEQ ID NO: 191 (VLFW2), and SEQ ID NO: 205 (VLFW3)). In some embodiments, the antibody molecule comprises the light chain framework regions 1-3 of BAP049-hum06 (e.g., SEQ ID NO: 181 (VLFW1), SEQ ID NO: 187 (VLFW2), and SEQ ID NO: 196 (VLFW3)). In some embodiments, the antibody molecule comprises the light chain framework regions 1-3 of BAP049-hum07 (e.g., SEQ ID NO: 177 (VLFW1), SEQ ID NO: 191 (VLFW2), and SEQ ID NO: 196 (VLFW3)). In some embodiments, the antibody molecule comprises the light chain framework regions 1-3 of BAP049-hum08, BAP049-hum09, BAP049-hum15, BAP049-hum16, or BAP049-Clone-C (e.g., SEQ ID NO: 174 (VLFW1), SEQ ID NO: 187 (VLFW2), and SEQ ID NO: 196 (VLFW3)). In some embodiments, the antibody molecule comprises the light chain framework regions 1-3 of BAP049-hum10, BAP049-hum11, BAP049-hum14, BAP049-Clone-D, or BAP049-Clone-E (e.g., SEQ ID NO: 177 (VLFW1), SEQ ID NO: 187 (VLFW2), and SEQ ID NO: 196 (VLFW3)). In some embodiments, the antibody molecule comprises the light chain framework regions 1-3 of BAP049-hum12 (e.g., SEQ ID NO: 185 (VLFW1), SEQ ID NO: 194 (VLFW2), and SEQ ID NO: 196 (VLFW3)). In some embodiments, the antibody molecule comprises the light chain framework regions 1-3 of BAP049-hum13 (e.g., SEQ ID NO: 183 (VLFW1), SEQ ID NO: 191 (VLFW2), and SEQ ID NO: 196 (VLFW3)). In some embodiments, the antibody molecule further comprises the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises the heavy chain framework regions 1-3 of BAP049-hum01 or BAP049-Clone-A (e.g., SEQ ID NO: 147 (VHFW1), SEQ ID NO: 153 (VHFW2), and SEQ ID NO: 162 (VHFW3)) and the light chain framework regions 1-3 of BAP049-hum01 or BAP049-Clone-A (e.g., SEQ ID NO: 177 (VLFW1), SEQ ID NO: 187 (VLFW2), and SEQ ID NO: 202 (VLFW3)).

In some embodiments, the anti-PD-1 antibody molecule comprises the heavy chain framework regions 1-3 of BAP049-hum02 (e.g., SEQ ID NO: 147 (VHFW1), SEQ ID NO: 153 (VHFW2), and SEQ ID NO: 162 (VHFW3)) and the light chain framework regions 1-3 of BAP049-hum02 (e.g., SEQ ID NO: 185 (VLFW1), SEQ ID NO: 187 (VLFW2), and SEQ ID NO: 200 (VLFW3)).

In some embodiments, the anti-PD-1 antibody molecule comprises the heavy chain framework regions 1-3 of BAP049-hum03 (e.g., SEQ ID NO: 147 (VHFW1), SEQ ID NO: 157 (VHFW2), and SEQ ID NO: 166 (VHFW3)) and the light chain framework regions 1-3 of BAP049-hum03

(e.g., SEQ ID NO: 185 (VLFW1), SEQ ID NO: 187 (VLFW2), and SEQ ID NO: 200 (VLFW3)).

In some embodiments, the anti-PD-1 antibody molecule comprises the heavy chain framework regions 1-3 of BAP049-hum04 (e.g., SEQ ID NO: 147 (VHFW1), SEQ ID NO: 157 (VHFW2), and SEQ ID NO: 166 (VHFW3)) and the light chain framework regions 1-3 of BAP049-hum04 (e.g., SEQ ID NO: 177 (VLFW1), SEQ ID NO: 191 (VLFW2), and SEQ ID NO: 205 (VLFW3)).

In some embodiments, the anti-PD-1 antibody molecule comprises the heavy chain framework regions 1-3 of BAP049-hum05 or BAP049-Clone-B (e.g., SEQ ID NO: 147 (VHFW1), SEQ ID NO: 153 (VHFW2), and SEQ ID NO: 162 (VHFW3)) and the light chain framework regions 1-3 of BAP049-hum05 or BAP049-Clone-B (e.g., SEQ ID NO: 177 (VLFW1), SEQ ID NO: 191 (VLFW2), and SEQ ID NO: 205 (VLFW3)).

In some embodiments, the anti-PD-1 antibody molecule comprises the heavy chain framework regions 1-3 of BAP049-hum06 (e.g., SEQ ID NO: 147 (VHFW1), SEQ ID NO: 153 (VHFW2), and SEQ ID NO: 162 (VHFW3)) and the light chain framework regions 1-3 of BAP049-hum06 (e.g., SEQ ID NO: 181 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum07 (e.g., SEQ ID NO: 147 (VHFW1), SEQ ID NO: 153 (VHFW2), and SEQ ID NO: 162 (VHFW3)) and the light chain framework regions 1-3 of BAP049-hum07 (e.g., SEQ ID NO: 177 (VLFW1), SEQ ID NO: 191 (VLFW2), and SEQ ID NO: 196 (VLFW3)).

In some embodiments, the anti-PD-1 antibody molecule comprises the heavy chain framework regions 1-3 of BAP049-hum08 (e.g., SEQ ID NO: 147 (VHFW1), SEQ ID NO: 157 (VHFW2), and SEQ ID NO: 166 (VHFW3)) and the light chain framework regions 1-3 of BAP049-hum08 (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum09 or BAP049-Clone-C (e.g., SEQ ID NO: 147 (VHFW1), SEQ ID NO: 153 (VHFW2), and SEQ ID NO: 162 (VHFW3)) and the light chain framework regions 1-3 of BAP049-hum09 or BAP049-Clone-C (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum10 or BAP049-Clone-D (e.g., SEQ ID NO: 147 (VHFW1), SEQ ID NO: 157 (VHFW2), and SEQ ID NO: 166 (VHFW3)) and the light chain framework regions 1-3 of BAP049-hum10 or BAP049-Clone-D (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum11 or BAP049-Clone-E (e.g., SEQ ID NO: 147 (VHFW1), SEQ ID NO: 153 (VHFW2), and SEQ ID NO: 162 (VHFW3)) and the light chain framework regions 1-3 of BAP049-hum11 or BAP049-Clone-E (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum12 (e.g., SEQ ID NO: 147 (VHFW1), SEQ ID NO: 153 (VHFW2), and SEQ ID NO: 162 (VHFW3)) and the light chain framework regions 1-3 of BAP049-hum12 (e.g., SEQ ID NO: 185 (VLFW1), SEQ ID NO: 194 (VLFW2), and SEQ ID NO: 196 (VLFW3)).

In some embodiments, the anti-PD-1 antibody molecule comprises the heavy chain framework regions 1-3 of BAP049-hum13 (e.g., SEQ ID NO: 147 (VHFW1), SEQ ID NO: 153 (VHFW2), and SEQ ID NO: 162 (VHFW3)) and the light chain framework regions 1-3 of BAP049-hum13 (e.g., SEQ ID NO: 183 (VLFW1), SEQ ID NO: 191 (VLFW2), and SEQ ID NO: 196 (VLFW3)).

In some embodiments, the anti-PD-1 antibody molecule comprises the heavy chain framework regions 1-3 of BAP049-hum14 (e.g., SEQ ID NO: 151 (VHFW1), SEQ ID NO: 157 (VHFW2), and SEQ ID NO: 166 (VHFW3)) and the light chain framework regions 1-3 of BAP049-hum14 (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum15 (e.g., SEQ ID NO: 151 (VHFW1), SEQ ID NO: 157 (VHFW2), and SEQ ID NO: 166 (VHFW3)) and the light chain framework regions 1-3 of BAP049-hum15 (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum16 (e.g., SEQ ID NO: 147 (VHFW1), SEQ ID NO: 160 (VHFW2), and SEQ ID NO: 166 (VHFW3)) and the light chain framework regions 1-3 of BAP049-hum16 (e.g., SEQ ID NO: 174 (VLFW1), SEQ ID NO: 187 (VLFW2), and SEQ ID NO: 196 (VLFW3)).

In some embodiments, the anti-PD-1 antibody molecule further comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169) and the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises a heavy chain framework region having a combination of framework regions FW1, FW2 and FW3 as showing in FIG. 5 or 7. In other embodiment, the antibody molecule comprises a light chain framework region having a combination of framework regions FW1, FW2 and FW3 as showing in FIG. 5 or 7. In yet other embodiments, the antibody molecule comprises a heavy chain framework region having a combination of framework regions FW1, FW2 and FW3 as showing in FIG. 5 or 7, and a light chain framework region having a combination of framework regions FW1, FW2 and FW3 as showing in FIG. 5 or 7.

In one embodiment, the heavy or light chain variable domain, or both, of the anti-PD-1 antibody molecule includes an amino acid sequence, which is substantially identical to an amino acid disclosed herein, e.g., at least 80%, 85%, 90%, 92%, 95%, 97%, 98%, 99% or higher identical to a variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-Clone-A, BAP049-Clone-B, BAP049-Clone-C, BAP049-Clone-D, or BAP049-Clone-E; or as described in Table 1, or encoded by the nucleotide sequence in Table 1; or which differs at least 1 or 5 residues, but less than 40, 30, 20, or 10 residues, from a variable region of an antibody described herein.

In one embodiment, the heavy or light chain variable region, or both, of the anti-PD-1 antibody molecule includes an amino acid sequence encoded by a nucleic acid sequence described herein or a nucleic acid that hybridizes to a nucleic acid sequence described herein (e.g., a nucleic acid sequence as shown in Tables 1 and 2) or its complement, e.g., under low stringency, medium stringency, or high stringency, or other hybridization condition described herein.

In another embodiment, the anti-PD-1 antibody molecule comprises at least one, two, three, or four antigen-binding regions, e.g., variable regions, having an amino acid sequence as set forth in Table 1, or a sequence substantially identical thereto (e.g., a sequence at least about 85%, 90%, 95%, 99% or more identical thereto, or which differs by no more than 1, 2, 5, 10, or 15 amino acid residues from the sequences shown in Table 1. In another embodiment, the anti-PD-1 antibody molecule includes a VH and/or VL domain encoded by a nucleic acid having a nucleotide sequence as set forth in Table 1, or a sequence substantially identical thereto (e.g., a sequence at least about 85%, 90%, 95%, 99% or more identical thereto, or which differs by no more than 3, 6, 15, 30, or 45 nucleotides from the sequences shown in Table 1.

In yet another embodiment, the anti-PD-1 antibody molecule comprises at least one, two, or three CDRs from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-PD-1 antibody molecule comprises at least one, two, or three CDRs from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-PD-1 antibody molecule comprises at least one, two, three, four, five or six CDRs from heavy and light chain variable regions having an amino acid sequence as set forth in Table 1), or a sequence substantially homologous thereto (e.g., a sequence at least about 85%, 90%, 95%, 99% or more identical thereto, and/or having one, two, three or more substitutions, insertions or deletions, e.g., conserved substitutions).

In one embodiment, the anti-PD-1 antibody molecule comprises at least one, two, or three CDRs and/or hypervariable loops from a heavy chain variable region having an amino acid sequence of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In another embodiment, the anti-PD-1 antibody molecule comprises at least one, two, or three CDRs and/or hypervariable loops from a light chain variable region having an amino acid sequence of of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In one embodiment, the anti-PD-1 antibody molecule comprises all six CDRs and/or hypervariable loops described herein, e.g., described in Table 1.

In one embodiment, the anti-PD-1 antibody molecule has a variable region that is identical in sequence, or which differs by 1, 2, 3, or 4 amino acids from a variable region described herein (e.g., an FR region disclosed herein).

In one embodiment, the anti-PD-1 antibody molecule is a full antibody or fragment thereof (e.g., a Fab, $F(ab')_2$, Fv, or a single chain Fv fragment (scFv)). In certain embodiments, the anti-PD-1 antibody molecule is a monoclonal antibody or an antibody with single specificity. The anti-PD-1 antibody molecule can also be a humanized, chimeric, camelid, shark, or an in vitro-generated antibody molecule. In one embodiment, the anti-PD-1 antibody molecule thereof is a humanized antibody molecule. The heavy and light chains of the anti-PD-1 antibody molecule can be full-length (e.g., an antibody can include at least one, and preferably two, complete heavy chains, and at least one, and preferably two, complete light chains) or can include an antigen-binding fragment (e.g., a Fab, $F(ab')_2$, Fv, a single chain Fv fragment, a single domain antibody, a diabody (dAb), a bivalent antibody, or bispecific antibody or fragment thereof, a single domain variant thereof, or a camelid antibody).

In certain embodiments, the anti-PD-1 antibody molecule is in the form of a bispecific or a multispecific antibody molecule. In one embodiment, the bispecific antibody molecule has a first binding specificity for PD-1 and a second binding specificity for TIM-3, LAG-3, CEACAM (e.g., CEACAM-1, CEACAM-3, and/or CEACAM-5), PD-L1 or PD-L2. In one embodiment, the bispecific antibody molecule binds to PD-1 and TIM-3. In another embodiment, the bispecific antibody molecule binds to PD-1 and LAG-3. In another embodiment, the bispecific antibody molecule binds to PD-1 and CEACAM (e.g., CEACAM-1, CEACAM-3, and/or CEACAM-5). In another embodiment, the bispecific antibody molecule binds to PD-1 and CEACAM-1. In yet another embodiment, the bispecific antibody molecule binds to PD-1 and CEACAM-5. In another embodiment, the bispecific antibody molecule binds to PD-1 and PD-L1. In yet another embodiment, the bispecific antibody molecule binds to PD-1 and PD-L2. Any combination of the aforesaid molecules can be made in a multispecific antibody molecule, e.g., a trispecific antibody that includes a first binding specificity to PD-1, and a second and third binding specificity to one or more of: TIM-3, LAG-3, CEACAM (e.g., CEACAM-1, CEACAM-3, or CEACAM-5), PD-L1 or PD-L2.

In other embodiments, the anti-PD-1 antibody molecule is used in combination with a bispecific molecule comprising one or more of: TIM-3, LAG-3, CEACAM (e.g., CEACAM-1, CEACAM-3, or CEACAM-5), PD-L1 or PD-L2. In one embodiment, the bispecific antibody molecule used in combination binds to CEACAM (e.g., CEACAM-1, CEACAM-3, and/or CEACAM-5) and LAG-3. In another embodiment, the bispecific antibody molecule used in combination binds to CEACAM (e.g., CEACAM-1, CEACAM-3, and/or CEACAM-5) and TIM-3. In another embodiment, the bispecific antibody molecule used in combination binds to LAG-3 and TIM-3.

In yet other embodiments, the anti-PD-1 antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG2 (e.g., human IgG1, IgG2 or IgG4). In one embodiment, the heavy chain constant region is human IgG1. In another embodiment, the anti-PD-1 antibody molecule has a light chain constant region chosen from, e.g., the light chain constant regions of kappa or lambda, preferably kappa (e.g., human kappa). In one embodiment, the constant region is altered, e.g., mutated, to modify the properties of the anti-PD-1 antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 212 or 214; or positions 135 (M to Y), 137 (S to T), 139 (T to E), 316 (H to K) and 317 (N to F) of SEQ ID NOs: 215, 216, 217 or 218). In another embodiment, the heavy chain constant region of an IgG4, e.g., a human IgG4, is mutated at position 228 according to EU numbering (e.g., S to P), e.g., as shown in Table 3. In certain embodiments, the anti-PD-1 antibody molecules comprises a human IgG4 mutated at position 228 according to EU numbering (e.g., S to P), e.g., as shown in Table 3; and a kappa light chain constant region, e.g., as shown in Table 3. In still another embodiment, the heavy chain constant region of an IgG1, e.g., a human IgG1, is mutated at one or more of position 297 according to EU numbering (e.g., N to A), position 265 according to EU numbering (e.g., D to A), position 329 according to EU numbering (e.g., P to A), position 234 according to EU numbering (e.g., L to A), or position 235 according to EU numbering (e.g., L to A), e.g., as shown in Table 3. In certain embodiments, the anti-PD-1 antibody molecules comprises a human IgG1 mutated at one or more of the aforesaid positions, e.g., as shown in Table 3; and a kappa light chain constant region, e.g., as shown in Table 3.

In one embodiment, the anti-PD-1 antibody molecule is isolated or recombinant.

In one embodiment, the anti-PD-1 antibody molecule is a humanized antibody molecule.

In one embodiment, the anti-PD-1 antibody molecule has a risk score based on T cell epitope analysis of less than 700, 600, 500, 400 or less.

In one embodiment, the anti-PD-1 antibody molecule is a humanized antibody molecule and has a risk score based on T cell epitope analysis of 300 to 700, 400 to 650, 450 to 600, or a risk score as described herein.

The invention also features a nucleic acid molecule that comprise one or both nucleotide sequences that encode heavy and light chain variable regions, CDRs, hypervariable loops, framework regions of the anti-PD-1 antibody molecules, as described herein. In certain embodiments, the nucleotide sequence that encodes the anti-PD-1 antibody molecule is codon optimized. For example, the invention features a first and second nucleic acid encoding heavy and light chain variable regions, respectively, of an anti-PD-1 antibody molecule chosen from one or more of, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1, or a sequence substantially identical thereto. For example, the nucleic acid can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In other embodiments, the nucleic acid molecule comprises a nucleotide sequence that encodes a heavy chain variable domain and/or a heavy chain constant region comprising the amino acid sequence of BAP049-Clone-A, BAP049-Clone-B, BAP049-Clone-C, BAP049-Clone-D, or BAP049-Clone-E; or as described in Table 1; or the nucleotide sequence in Table 1; or a sequence substantially identical (e.g., a sequence at least about 85%, 90%, 95%, 99% or more identical) to any of the aforesaid sequences.

In other embodiments, the nucleic acid molecule comprises a nucleotide sequence that encodes a light chain variable domain and/or a light chain constant region comprising the amino acid sequence of BAP049-Clone-A, BAP049-Clone-B, BAP049-Clone-C, BAP049-Clone-D, or BAP049-Clone-E; or as described in Table 1; or the nucleotide sequence in Table 1; or a sequence substantially identical (e.g., a sequence at least about 85%, 90%, 95%, 99% or more identical) to any of the aforesaid sequences.

The aforesaid nucleotide sequences encoding the anti-PD-1 heavy and light chain variable domain and constant regions can be present in a separate nucleic acid molecule, or in the same nucleic acid molecule. In certain embodiments, the nucleic acid molecules comprise a nucleotide sequence encoding a leader sequence, e.g., a leader sequence as shown in Table 4, or a sequence substantially identical thereto.

In certain embodiments, the nucleic acid molecule comprises a nucleotide sequence encoding at least one, two, or three CDRs, or hypervariable loops, from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule comprises a nucleotide sequence encoding at least one, two, or three CDRs, or hypervariable loops, from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In yet another embodiment, the nucleic acid molecule comprises a nucleotide sequence encoding at least one, two, three, four, five, or six CDRs, or hypervariable loops, from heavy and light chain variable regions having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In one embodiment, the nucleic acid molecule includes a nucleotide sequence encoding an anti-PD-1 antibody molecule that includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the nucleic acid molecule includes one or more heavy chain framework region (e.g., any of VHFW1 (type a), VHFW1 (type b), VHFW2 (type a), VHFW2 (type b), VHFW2 (type c), VHFW3 (type a), VHFW3 (type b), or VHFW4, or any combination thereof, e.g., a framework combination as described herein) for any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1 and 2, or a sequence substantially identical thereto. For example, the nucleic acid molecule can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In another embodiment, the nucleic acid molecule includes one or more light chain framework region (e.g., any of VLFW1 (type a), VLFW1 (type b), VLFW1 (type c), VLFW1 (type d), VLFW1 (type e), VLFW2 (type a), VLFW2 (type b), VLFW2 (type c), VLFW3 (type a), VLFW3 (type b), VLFW3 (type c), VLFW3 (type d), or VLFW4, or any combination thereof, e.g., a framework combination as described herein) for any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1 and 2, or a sequence substantially identical thereto. For example, the nucleic acid molecule can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In another embodiment, the nucleic acid molecule includes one or more heavy chain framework region and one or more light chain framework region as described herein. The heavy and light chain framework regions may be present in the same vector or separate vectors.

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

In one aspect, the invention features a method of providing an antibody molecule described herein. The method includes: providing a PD-1 antigen (e.g., an antigen comprising at least a portion of a PD-1 epitope); obtaining an antibody molecule that specifically binds to the PD-1 polypeptide; and evaluating if the antibody molecule specifically binds to the PD-1 polypeptide, or evaluating efficacy of the antibody molecule in modulating, e.g., inhibiting, the activity of the PD-1. The method can further include administering the antibody molecule to a subject, e.g., a human or non-human animal.

In another aspect, the invention provides, compositions, e.g., pharmaceutical compositions, which include a pharmaceutically acceptable carrier, excipient or stabilizer, and at least one of the anti-PD-1 antibody molecules described herein. In one embodiment, the composition, e.g., the pharmaceutical composition, includes a combination of the antibody molecule and one or more agents, e.g., a therapeutic agent or other antibody molecule, as described herein. In one embodiment, the antibody molecule is conjugated to a label or a therapeutic agent.

The anti-PD-1 antibody molecules disclosed herein can inhibit, reduce or neutralize one or more activities of PD-1, resulting in blockade or reduction of an immune checkpoint. In one embodiment, the antibody molecule results in one or more of: an increase in tumor infiltrating lymphocytes, an increase in T-cell receptor mediated proliferation, a decrease in immune evasion by cancerous cells, restoration of effector cell function (e.g., one or more of T cell proliferation, IFN-γ secretion or cytolytic function), inhibition of regulatory T cell function, or an effect on the activity of multiple cell types, such as regulatory T cell, effector T cells and NK cells). Thus, such antibody molecules can be used to treat or prevent disorders where enhancing an immune response in a subject is desired.

Uses of the Anti-PD-1 Antibody Molecules

Accordingly, in another aspect, a method of modulating an immune response in a subject is provided. The method comprises administering to the subject an anti-PD-1 antibody molecule disclosed herein (e.g., a therapeutically effective amount of an anti-PD-1 antibody molecule), alone or in combination with one or more agents or procedures, such that the immune response in the subject is modulated. In one embodiment, the antibody molecule enhances, stimulates or increases the immune response in the subject. The subject can be a mammal, e.g., a primate, preferably a higher primate, e.g., a human (e.g., a patient having, or at risk of having, a disorder described herein). In one embodiment, the subject is in need of enhancing an immune response. In one embodiment, the subject has, or is at risk of, having a disorder described herein, e.g., a cancer or an infectious disorder as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

In one aspect, a method of treating (e.g., one or more of reducing, inhibiting, or delaying progression) a cancer or a tumor in a subject is provided. The method comprises administering to the subject an anti-PD-1 antibody molecule described herein, e.g., a therapeutically effective amount of an anti-PD-1 antibody molecule, alone or in combination with one or more agents or procedures. In certain embodiments, the anti-PD-1 antibody molecule is administered in combination with a modulator of a costimulatory molecule (e.g., an agonist of a costimulatory molecule) or a modulator of an inhibitory molecule (e.g., an inhibitor of an immune checkpoint inhibitor), e.g., as described herein.

In certain embodiments, the cancer treated with the anti-PD-1 antibody molecule, includes but is not limited to, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, B-cell lymphoma, a non-Hogdkin lymphoma, or a leukemia (e.g., a myeloid leukemia or a lymphoid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer or small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-PD-1 antibody molecule is administered after treatment with an anti-CTLA4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma (CCRCC)).

In one embodiment, the cancer microenvironment has an elevated level of PD-L1 expression. Alternatively, or in combination, the cancer microenvironment can have increased IFNγ and/or CD8 expression.

In some embodiments, the subject has, or is identified as having, a tumor that has one or more of high PD-L1 level or expression, or as being Tumor Infiltrating Lymphocyte (TIL)+(e.g., as having an increased number of TILs), or both. In certain embodiments, the subject has, or is identified as having, a tumor that has high PD-L1 level or expression and that is TIL+. In some embodiments, the methods described herein further include identifying a subject based on having a tumor that has one or more of high PD-L1 level or expression, or as being TIL+, or both. In certain embodiments, the methods described herein further include identifying a subject based on having a tumor that has high PD-L1 level or expression and as being TIL+. In some embodiments, tumors that are TIL+ are positive for CD8 and IFNγ. In some embodiments, the subject has, or is identified as having, a high percentage of cells that are positive for one, two or more of PD-L1, CD8, and/or IFNγ. In certain embodiments, the subject has or is identified as having a high percentage of cells that are positive for all of PD-L1, CD8, and IFNγ. In some embodiments, the methods described herein further include identifying a subject based on having a high percentage of cells that are positive for one, two or more of PD-L1, CD8, and/or IFNγ. In certain embodiments, the methods described herein further include identifying a subject based on having a high percentage of cells that are positive for all of PD-L1, CD8, and IFNγ. In some embodiments, the subject has, or is identified as having, one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; an esophageal cancer; a thyroid cancer; a melanoma, and/or a nasopharyngeal cancer (NPC). In certain embodiments, the methods described herein further describe identifying a subject based on having one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; a thyroid cancer; a melanoma, and or a nasopharyngeal cancer.

Methods and compositions disclosed herein are useful for treating metastatic lesions associated with the aforementioned cancers.

In a further aspect, the invention provides a method of treating an infectious disease in a subject, comprising administering to a subject a therapeutically effective amount of an anti-PD-1 antibody molecule described herein, alone or in combination with one or more agents or procedures. In one embodiment, the infection disease is chosen from hepatitis (e.g., hepatis C infection), or sepsis.

Still further, the invention provides a method of enhancing an immune response to an antigen in a subject, comprising administering to the subject: (i) the antigen; and (ii)

an anti-PD-1 antibody molecule, such that an immune response to the antigen in the subject is enhanced. The antigen can be, for example, a tumor antigen, a viral antigen, a bacterial antigen or an antigen from a pathogen.

The anti-PD-1 antibody molecule can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week.

The antibody molecules described herein are preferred for use in the methods described herein, although other anti-PD-1 antibodies can be used instead, or in combination with an anti-PD-1 antibody molecule of the invention.

Combination Therapies

The methods and compositions described herein can be used in combination with other agents or therapeutic modalities. In one embodiment, the methods described herein include administering to the subject an anti-PD-1 antibody molecule as described herein, in combination with an agent or therapeutic procedure or modality, in an amount effective to treat or prevent a disorder. The anti-PD-1 antibody molecule and the agent or therapeutic procedure or modality can be administered simultaneously or sequentially in any order. Any combination and sequence of the anti-PD-1 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody molecule can be administered before the other treatment, concurrently with the treatment, post-treatment, or during remission of the disorder.

In certain embodiments, the methods and compositions described herein are administered in combination with one or more of other antibody molecules, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) or radiation procedures, or a combination of any of the foregoing. The additional therapy may be in the form of adjuvant or neoadjuvant therapy. In some embodiments, the additional therapy is an enzymatic inhibitor (e.g., a small molecule enzymatic inhibitor) or a metastatic inhibitor. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting one or more of PI3K/AKT/mTOR pathway, an HSP90 inhibitor, or a tubulin inhibitor.

Alternatively, or in combination with the aforesaid combinations, the methods and compositions described herein can be administered in combination with one or more of: an immunomodulator (e.g., an activator of a costimulatory molecule or an inhibitor of an inhibitory molecule, e.g., an immune checkpoint molecule); a vaccine, e.g., a therapeutic cancer vaccine; or other forms of cellular immunotherapy.

Exemplary non-limiting combinations and uses of the anti-PD-1 antibody molecules include the following.

In certain embodiments, the anti-PD-1 antibody molecule is administered in combination with a modulator of a costimulatory molecule or an inhibitory molecule, e.g., a co-inhibitory ligand or receptor.

In one embodiment, the anti-PD-1 antibody molecule is administered in combination with a modulator, e.g., agonist, of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In one embodiment, the anti-PD-1 antibody molecule is administered in combination with an inhibitor of an inhibitory (or immune checkpoint) molecule chosen from PD-L1, PD-L2, CTLA-4, TIM-3, LAG-3, CEACAM (e.g., CEACAM-1, CEACAM-3, and/or CEACAM-5), VISTA, BTLA, TIGIT, LAIR1, CD160, 2B4 and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule. In one embodiment, the inhibitor is a soluble ligand (e.g., a CTLA-4-Ig), or an antibody or antibody fragment that binds to PD-L1, PD-L2 or CTLA-4. For example, the anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). In one embodiment, the anti-PD-1 antibody molecule is administered after treatment with an anti-CTLA-4 antibody (e.g., ipilimumab) with or without a BRAF inhibitor (e.g., vemurafenib or dabrafenib).

In another embodiment, the anti-PD-1 antibody molecule is administered in combination with an anti-LAG-3 antibody or antigen-binding fragment thereof.

In another embodiment, the anti-PD-1 antibody molecule is administered in combination with an anti-TIM-3 antibody or antigen-binding fragment thereof.

In yet other embodiments, the anti-PD-1 antibody molecule is administered in combination with an anti-LAG-3 antibody and an anti-TIM-3 antibody (or antigen-binding fragments thereof).

In another embodiment, the anti-PD-1 antibody molecule is administered in combination with a CEACAM inhibitor (e.g., CEACAM-1 and/or CEACAM-5 inhibitor), e.g., an anti-CEACAM antibody molecule. In another embodiment, the anti-PD-1 antibody molecule is administered in combination with a CEACAM-1 inhibitor, e.g., an anti-CEACAM-1 antibody molecule. In another embodiment, the anti-PD-1 antibody molecule is administered in combination with a CEACAM-5 inhibitor, e.g., an anti-CEACAM-5 antibody molecule.

The combination of antibodies recited herein can be administered separately, e.g., as separate antibodies or antigen-binding fragments thereof, or linked, e.g., as a bispecific or trispecific antibody molecule. In one embodiment, a bispecific antibody that includes an anti-PD-1 antibody molecule and an anti-TIM-3, anti-CEACAM (e.g., anti-CEACAM-1, CEACAM-3, and/or anti-CEACAM-5), or anti-LAG-3 antibody, or an antigen-binding fragment thereof, is administered. In certain embodiments, the combination of antibodies recited herein is used to treat a cancer, e.g., a cancer as described herein (e.g., a solid tumor or a hematologic malignancy).

In other embodiments, the anti-PD-1 antibody molecule is administered in combination with a cytokine. The cytokine can be administered as a fusion molecule to the anti-PD-1 antibody molecule, or as separate compositions. In one embodiment, the anti-PD-1 antibody is administered in combination with one, two, three or more cytokines, e.g., as a fusion molecule or as separate compositions. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to PD-1), a second binding specificity to a second target (e.g., LAG-3 or TIM-3), and is optionally linked to an interleukin (e.g., IL-12) domain e.g., full length IL-12 or a portion thereof. In certain embodiments, the combination of anti-PD-1 antibody molecule and the cytokine described herein is used to treat a cancer, e.g., a cancer as described herein (e.g., a solid tumor).

In certain embodiments, the anti-PD-1 antibody molecule is administered in combination with an antibody specific against an HLA C, e.g., an antibody specific to Killer-cell Immunoglobulin-like Receptors (also referred to herein as an "anti-KIR antibody"). In certain embodiments, the combination of anti-PD-1 antibody molecule and anti-KIR antibody is used to treat a cancer, e.g., a cancer as described herein (e.g., a solid tumor, e.g., an advanced solid tumor).

In one embodiment, the anti-PD-1 antibody molecule is administered in combination with a cellular immunotherapy (e.g., Provenge® (e.g., Sipuleucel-T)), and optionally in combination with cyclophosphamide. In certain embodiments, the combination of anti-PD-1 antibody molecule, Provenge® and/or cyclophosphamide is used to treat a cancer, e.g., a cancer as described herein (e.g., a prostate cancer, e.g., an advanced prostate cancer).

In another embodiment, the anti-PD-1 antibody molecule is administered in combination with a vaccine, e.g., a cancer vaccine, (e.g., a dendritic cell renal carcinoma (DC-RCC) vaccine). In one embodiment, the vaccine is peptide-based, DNA-based, RNA-based, or antigen-based, or a combination thereof. In embodiments, the vaccine comprises one or more peptides, nucleic acids (e.g., DNA or RNA), antigens, or a combination thereof. In certain embodiments, the combination of anti-PD-1 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In another embodiment, the anti-PD-1 antibody molecule is administered in combination with an adjuvant.

In yet another embodiment, the anti-PD-1 antibody molecule is administered in combination with chemotherapy, and/or immunotherapy. For example, the anti-PD-1 antibody molecule can be used to treat a myeloma, alone or in combination with one or more of: chemotherapy or other anti-cancer agents (e.g., thalidomide analogs, e.g., lenalidomide), an anti-TIM-3 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-PD-1 antibody molecule is used in combination with an anti-TIM-3 antibody to treat a myeloma, e.g., a multiple myeloma.

In one embodiment, the anti-PD-1 antibody molecule is used in combination with chemotherapy to treat a lung cancer, e.g., non-small cell lung cancer. In one embodiment, the anti-PD-1 antibody molecule is used with standard lung, e.g., NSCLC, chemotherapy, e.g., platinum doublet therapy, to treat lung cancer. In yet other embodiments, the anti-PD-1 antibody molecule is used in combination with an indoleamine-pyrrole 2,3-dioxygenase (IDO) inhibitor (e.g., (4E)-4-[(3-chloro-4-fluoroanilino)-nitrosomethylidene]-1,2,5-oxadiazol-3-amine (also known as INCB24360), indoximod (1-methyl-D-tryptophan), α-cyclohexyl-5H-Imidazo[5,1-a]isoindole-5-ethanol (also known as NLG919), etc.) in a subject with advanced or metastatic cancer (e.g., a patient with metastic and recurrent NSCL cancer).

In yet other embodiments, the anti-PD-1 antibody molecule is used in combination with one or more of: an immune-based strategy (e.g., interleukin-2 or interferon-α), a targeting agent (e.g., a VEGF inhibitor such as a monoclonal antibody to VEGF); a VEGF tyrosine kinase inhibitor such as sunitinib, sorafenib, axitinib and pazopanib; an RNAi inhibitor; or an inhibitor of a downstream mediator of VEGF signaling, e.g., an inhibitor of the mammalian target of rapamycin (mTOR), e.g., everolimus and temsirolimus. Any of such combinations can be used to treat a renal cancer, e.g., renal cell carcinoma (RCC) (e.g., clear cell renal cell carcinoma (CCRCC)) or metastatic RCC.

In some embodiments, the anti-PD-1 antibody molecule, e.g., the anti-PD-1 antibody molecule described herein, is used in combination with a MEK inhibitor (e.g., a MEK inhibitor as described herein). In some embodiments, the combination of the anti-PD-1 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage.

In another embodiment, the anti-PD-1 antibody molecule is used in combination with one, two or all of oxaliplatin, leucovorin or 5-FU (e.g., a FOLFOX co-treatment). Alternatively or in combination, combination further includes a VEGF inhibitor (e.g., a VEGF inhibitor as disclosed herein). In some embodiments, the combination of the anti-PD-1 antibody, the FOLFOX co-treatment, and the VEGF inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. The cancer may be at an early, intermediate or late stage.

In other embodiments, the anti-PD-1 antibody molecule is administered with a tyrosine kinase inhibitor (e.g., axitinib) to treat renal cell carcinoma and other solid tumors.

In other embodiments, the anti-PD-1 antibody molecule is administered with a 4-1BB receptor targeting agent (e.g., an antibody that stimulates signaling through 4-1BB (CD-137), e.g., PF-2566). In one embodiment, the anti-PD-1 antibody molecule is administered in combination with a tyrosine kinase inhibitor (e.g., axitinib) and a 4-1BB receptor targeting agent.

The anti-PD-1 antibody molecule can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody can be coupled to a radioactive isotope such as an $\alpha$-, $\beta$-, or $\gamma$-emitter, or a $\beta$- and $\gamma$-emitter.

Any combination and sequence of the anti-PD-1 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody molecule can be administered before the other treatment, concurrently with the treatment, post-treatment, or during remission of the disorder.

Additional Combination Therapies

The methods and compositions described herein (e.g., PD-1 antibodies and methods of using them) can be used in combination with other agents or therapeutic modalities, e.g., a second therapeutic agent chosen from one or more of the agents listed in Table 7. In one embodiment, the methods described herein include administering to the subject an anti-PD-1 antibody molecule as described herein (optionally in combination with one or more inhibitors of PD-L1, LAG-3, TIM-3, CEACAM (e.g., CEACAM-1 and/or CEACAM-5), or CTLA-4)), further include administration of a second therapeutic agent chosen from one or more of the agents listed in Table 7, in an amount effective to treat or prevent a disorder, e.g., a disorder as described herein, e.g., a cancer. When administered in combination, the anti-PD-1 antibody molecule, the additional agent (e.g., second or third agent), or all, can be administered in an amount or dose that is higher, lower or the same than the amount or dosage of each agent used individually, e.g., as a monotherapy. In certain embodiments, the administered amount or dosage of the anti-PD-1 antibody, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the anti-PD-1 antibody, the additional agent (e.g., second or third agent), or all, that results in a desired effect (e.g., treatment of cancer) is lower (e.g., at least 20%, at least 30%, at least 40%, or at least 50% lower).

In other embodiments, the second therapeutic agent is chosen from one or more of the agents listed in Table 7. In one embodiment, the cancer is chosen from a lung cancer (e.g., a non-small cell lung cancer (NSCLC) (e.g., a NSCLC with squamous and/or non-squamous histology, or a NSCLC adenocarcinoma), or disclosed in a publication listed in Table 7. In some embodiments, the second therapeutic agent is chosen from one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11(3-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase, e.g., as described herein and in Table 7.

In one embodiment, the second therapeutic agent is chosen from one or more of: Compound A8, Compound A17, Compound A23, Compound A24, Compound A27, Compound A29, Compound A33, and Compound A13.

In other embodiments, the second therapeutic agent is chosen from one or more of: Compound A5, Compound A8, Compound A17, Compound A23, Compound A24, Compound A29, and Compound A40.

In other embodiments, the second therapeutic agent is chosen from one or more of: Compound A9, Compound A16, Compound A17, Compound A21, Compound A22, Compound A25, Compound A28, Compound A48, and Compound 49.

In embodiments, the second therapeutic agent is administered at a therapeutic or lower-than therapeutic dose. In certain embodiments, the concentration of the second therapeutic agent that is required to achieve inhibition, e.g., growth inhibition, is lower when the second therapeutic agent is administered in combination with the anti-PD-1 antibody molecule than when the second therapeutic agent is administered individually. In certain embodiments, the concentration of the anti-PD-1 antibody molecule that is required to achieve inhibition, e.g., growth inhibition, is lower when the anti-PD-1 antibody molecule is administered in combination with the second therapeutic agent than when the anti-PD-1 antibody molecule is administered individually. In certain embodiments, in a combination therapy, the concentration of the second therapeutic agent that is required to achieve inhibition, e.g., growth inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration of the anti-PD-1 antibody molecule that is required to achieve inhibition, e.g., growth inhibition, is lower than the therapeutic dose of the anti-PD-1 antibody molecule as a monotherapy, e.g., 10-20%, 20-30%, 30-40%, 40-50%, 50-60%, 60-70%, 70-80%, or 80-90% lower.

Detection

In another aspect, the invention features methods for detecting the presence of PD-1 in a sample, e.g., in vitro or in vivo (e.g., a biological sample, e.g., serum, semen or urine, or a tissue biopsy, e.g., from a hyperproliferative or cancerous lesion). The subject method can be used to evaluate (e.g., monitor treatment or progression of, diagnose and/or stage a disorder described herein, e.g., a hyperproliferative or cancerous disorder, in a subject). The method includes: (i) contacting the sample with (and optionally, a reference, e.g., a control sample), or administering to the subject, an antibody molecule as described herein, under conditions that allow interaction to occur, and (ii) detecting formation of a complex between the antibody molecule, and the sample (and optionally, the reference, e.g., control, sample). Formation of the complex is indicative of the presence of PD-1, and can indicate the suitability or need for a treatment described herein. The method can involve an immunohistochemistry, immunocytochemistry, FACS, antibody molecule complexed magnetic beads, ELISA assays, PCR-techniques (e.g., RT-PCR).

Typically, the antibody molecule used in the in vivo and in vitro diagnostic methods is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials.

Additional embodiments provide a method of treating a cancer, comprising: identifying in a subject or a sample (e.g., a subject's sample comprising cancer cells and optionally immune cells such as TILs) the presence of one, two or all of PD-L1, CD8, or IFN-γ, thereby providing a value for one, two or all of PD-L1, CD8, and IFN-γ. The method can further include comparing the PD-L1, CD8, and/or IFN-γ values to a reference value, e.g., a control value. If the PD-L1, CD8, and/or IFN-γ values are greater than the reference value, e.g., the control values, administering a therapeutically effective amount of an anti-PD-1 antibody (e.g., an anti-PD-1 antibody described herein) to the subject, optionally in combination with one or more other agents, thereby treating the cancer. The cancer may be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer, or breast cancer, e.g., TN breast cancer, e.g., IM-TN breast cancer. In some embodiments, the cancer is ER+ breast cancer or pancreatic cancer.

Also provided is a method of treating a cancer, comprising: testing a subject or a sample (e.g., a subject's sample comprising cancer cells) for the presence of PD-L1, thereby identifying a PD-L1 value, comparing the PD-L1 value to a control value, and if the PD-L1 value is greater than the control value, administering a therapeutically effective amount of an anti-PD-1 antibody (e.g., an anti-PD-1 antibody described herein) to the subject, optionally in combination with one or more other agents, thereby treating the cancer. The cancer may be, e.g., a cancer as described herein, such as cancer is non-small cell lung (NSCLC) adenocarcinoma (ACA), NSCLC squamous cell carcinoma (SCC), or hepatocellular carcinoma (HCC).

In another aspect, the invention features diagnostic or therapeutic kits that include the antibody molecules described herein and instructions for use.

All publications, patent applications, patents, and other references mentioned herein are incorporated by reference in their entirety.

Other features, objects, and advantages of the invention will be apparent from the description and drawings, and from the claims.

BRIEF DESCRIPTION OF THE DRAWINGS

FIG. 1 depicts the amino acid sequences of the light and heavy chain variable regions of murine anti-PD-1 mAb BAP049. The upper and lower sequences were from two independent analyses. The light and heavy chain CDR sequences based on Kabat numbering are underlined. The light heavy chain CDR sequences based on Chothia numbering are shown in bold italics. The unpaired Cys residue at position 102 of the light chain sequence is boxed. Sequences are disclosed as SEQ ID NOs: 8, 228, 16 and 229, respectively, in order of appearance.

FIG. 2A depicts the amino acid sequences of the light and heavy chain variable regions of murine anti-PD-1 mAb BAP049 aligned with the germline sequences. The upper and lower sequences are the germline (GL) and BAP049 (Mu mAb) sequences, respectively. The light and heavy chain CDR sequences based on Kabat numbering are underlined. The light heavy chain CDR sequences based on Chothia numbering are shown in bold italics. "-" means identical amino acid residue. Sequences disclosed as SEQ ID NOs: 230, 8, 231 and 16, respectively, in order of appearance.

FIG. 2B depicts the sequence of murine κ J2 gene and the corresponding mutation in murine anti-PD-1 mAb BAP049. "-" means identical nucleotide residue. Sequences disclosed as SEQ ID NOs: 233, 232, 234 and 235, respectively, in order of appearance.

FIG. 5 depicts the structural analysis of the humanized BAP049 clones (a, b, c, d and e represent various types of framework region sequences). The concentrations of the mAbs in the samples are also shown.

FIG. 7 depicts the ranking of humanized BAP049 clones based on FACS data, competition binding and structural analysis. The concentrations of the mAbs in the samples are also shown.

FIGS. 9A-9B depict the alignment of heavy chain variable domain sequences for the sixteen humanized BAP049 clones and BAP049 chimera (BAP049-chi). In FIG. 9A, all of the sequences are shown (SEQ ID NOs: 22, 38, 38, 38, 38, 38, 38, 38, 38, 38, 50, 50, 50, 50, 82, 82 and 86, respectively, in order of appearance). In FIG. 9B, only amino acid sequences that are different from mouse sequence are shown (SEQ ID NOs: 22, 38, 38, 38, 38, 38, 38, 38, 38, 38, 50, 50, 50, 50, 82, 82 and 86, respectively, in order of appearance).

FIGS. 10A-10B depict the alignment of light chain variable domain sequences for the sixteen humanized BAP049 clones and BAP049 chimera (BAP049-chi). In FIG. 10A, all of the sequences are shown (SEQ ID NOs: 24, 66, 66, 66, 66, 70, 70, 70, 58, 62, 78, 74, 46, 46, 42, 54 and 54, respectively, in order of appearance). In FIG. 10B, only amino acid sequences that are different from mouse sequence are shown (SEQ ID NOs: 24, 66, 66, 66, 66, 70, 70, 70, 58, 62, 78, 74, 46, 46, 42, 54 and 54, respectively, in order of appearance).

BRIEF DESCRIPTION OF THE TABLES

Figure 3A:
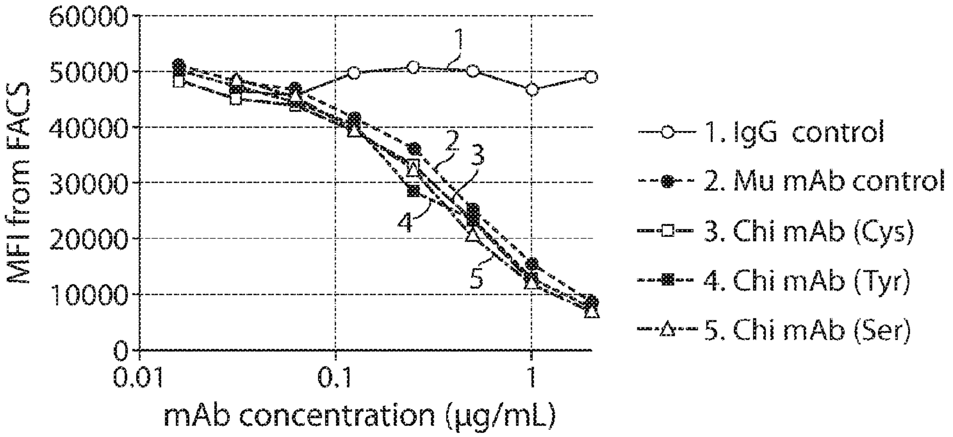
FIGS. 3A-3B depict the competition binding between fluorescently labeled murine anti-PD-1 mAb BAP049 (Mu mAb) and three chimeric versions of BAP049 (Chi mAb). Experiment was performed twice, and the results are shown in FIGS. 3A and 3B, respectively. The three chimeric BAP049 antibodies (Chi mAb (Cys), Chi mAb (Tyr) and Chi mAb (Ser)) have Cys, Tyr and Ser residue at position 102 of the light chain variable region, respectively. Chi mAb (Cys), Chi mAb (Tyr) and Chi mAb (Ser) are also known as BAP049-chi, BAP049-chi-Y, and BAP049-chi-S, respectively.

Table 1 is a summary of the amino acid and nucleotide sequences for the murine, chimeric and humanized anti-PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the amino acid and nucleotide sequences of the heavy and light chain variable regions, and the amino acid and nucleotide sequences of the heavy and light chains are shown in this Table.

Table 2 depicts the amino acid and nucleotide sequences of the heavy and light chain framework regions for humanized mAbs BAP049-hum01 to BAP049-hum16 and BAP049-Clone-A to BAP049-Clone-E.

Table 3 depicts the constant region amino acid sequences of human IgG heavy chains and human kappa light chain.

Table 4 shows the amino acid sequences of the heavy and light chain leader sequences for humanized mAbs BAP049-Clone-A to BAP049-Clone-E.

Table 5 is a summary of yield, titre, monomer content and endotoxin levels for selected humanized BAP049 mAbs expressed in CHO cells.

Table 6 shows the charge isoforms as detected by Novex IEF analysis for selected humanized BAP049 mAbs expressed in CHO cells.

Table 7 is a summary of selected therapeutic agents that can be administered in combination with the anti-PD-1 antibody molecules and other immunomodulators (e.g., one or more of: an activator of a costimulatory molecule and/or an inhibitor of an immune checkpoint molecule) described herein. Table 7 provides from left to right the following: the Compound Designation of the second therapeutic agent, the Compound structure, and Patent publication(s) disclosing the Compound.

DETAILED DESCRIPTION

Programmed Death 1 (PD-1) is a CD28/CTLA-4 family member expressed on activated $CD4^+$ and $CD8^+$ T cells, $T_{regs}$, and B cells. It negatively regulates effector T cell signaling and function. PD-1 is induced on tumor-infiltrating T cells, resulting in functional exhaustion or dysfunction (Keir et al. (2008) *Annu. Rev. Immunol.* 26:677-704; Pardoll et al. (2012) *Nat Rev Cancer* 12(4):252-64).

PD-1 delivers a coinhibitory signal upon binding to either of its two ligands, Programmed Death-Ligand 1 (PD-L1) or Programmed Death-Ligand 2 (PD-L2). PD-L1 is expressed on T cells, natural killer (NK) cells, macrophages, dendritic cells (DCs), B cells, epithelial cells, vascular endothelial cells, as well as many types of tumors. High expression of PD-L1 on murine and human tumors has been linked to poor clinical outcomes in a variety of cancers (Keir et al. (2008) *Annu. Rev. Immunol.* 26:677-704; Pardoll et al. (2012) *Nat Rev Cancer* 12(4):252-64). PD-L2 is expressed on dendritic cells, macrophages, and some tumors.

Blockade of the PD-1 pathway has been pre-clinically and clinically validated for cancer immunotherapy. Both preclinical and clinical studies have demonstrated that anti-PD-1 blockade restores activity of effector T cells and results in robust anti-tumor response. For example, blockade of PD-1 pathway restores exhausted/dysfunctional effector T cell function (e.g., proliferation, IFN-γ secretion, or cytolytic function) and inhibits $T_{reg}$ cell function (Keir et al. (2008) *Annu. Rev. Immunol.* 26:677-704; Pardoll et al. (2012) *Nat Rev Cancer* 12(4):252-64).

Accordingly, the present invention provides, at least in part, antibody molecules (e.g., humanized antibody molecules) that bind to Programmed Death 1 (PD-1) with high affinity and specificity. In one embodiment, humanized antibodies against PD-1 are disclosed, which show a surprisingly low immunogenicity. For example, humanized BAP049 antibodies were found to have a risk score of less than 650, 600, 550, or less than 500, according to the T cell epitope assays described herein. In other embodiments, selected combination of framework regions, e.g., as shown in FIGS. 5 and 7, were shown to have distinct production efficiencies and binding properties.

Additional aspects of the invention include nucleic acid molecules encoding the antibody molecules, expression vectors, host cells and methods for making the antibody molecules. Immunoconjugates, multi- or bispecific molecules and pharmaceutical compositions comprising the antibody molecules are also provided. The anti-PD-1 antibody molecules disclosed herein can be used to treat, prevent and/or diagnose cancerous or malignant disorders (e.g., solid and soft-tissue tumors; melanoma, e.g., advanced melanoma; hepatocellular carcinoma; pancreatic cancer; renal cell carcinoma (RCC), e.g., metastatic RCC or clear cell RCC; gliomas or glioblastomas; multiple myeloma; colorectal cancer; and lung cancer, e.g., non-small cell carcinoma), as well as infectious diseases (e.g., infectious disorders such as hepatitis, e.g., hepatitis C (e.g., chronic viral hepatitis); sepsis). Thus, methods for detecting PD-1, as well as methods for treating various disorders, including cancer and infectious diseases using the anti-PD-1 antibody molecules are disclosed herein.

The term "Programmed Death F1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) *Genomics* 23(3):704-6; Finger L R, et al. *Gene* (1997) 197(1-2):177-87.

Additional terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Antibody Molecules

In one embodiment, the antibody molecule binds to a mammalian, e.g., human, PD-1. For example, the antibody molecule binds specifically to an epitope, e.g., linear or conformational epitope, (e.g., an epitope as described herein) on PD-1.

As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full length antibody, or a full length immunoglobulin chain. In an embodiment, an antibody molecule comprises an antigen binding or functional fragment of a full length antibody, or a full length immunoglobulin chain.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope. In an embodiment the first epitope is located on PD-1 and the second epitope is located on a TIM-3, LAG-3, CEACAM (e.g., CEACAM-1 and/or CEACAM-5), PD-L1, or PD-L2.

In an embodiment, an antibody molecule comprises a diabody, and a single-chain molecule, as well as an antigen-binding fragment of an antibody (e.g., Fab, $F(ab')_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', $F(ab')_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibody molecules can be monoclonal or polyclonal. An antibodymolecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term “immunoglobulin” (Ig) is used interchangeably with the term “antibody” herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

The term “antibody” includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the anti-PD-1 antibody molecules can include any combination of one or more Kabat CDRs and/or Chothia hypervariable loops, e.g., described in Table 1. In one embodiment, the following definitions are used for the anti-PD-1 antibody molecules described in Table 1: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the PD-1 polypeptide, or an epitope thereof. With respect to proteins (or protein mimetics), the antigen-binding site typically includes one or more loops (of at least four amino acids or amino acid mimics) that form an interface that binds to the PD-1 polypeptide. Typically, the antigen-binding site of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-PD-1 antibody molecule, e.g., an anti-PD-1 antibody molecule provided herein, to a target, e.g., human PD-1. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-PD-1 antibody molecule is said to compete for binding to the target with a second anti-PD-1 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.,* 32:180-190 (1990)) and also because of potential allergic reactions (see, e.g., LoBuglio et al., *Hybridoma,* 5:5117-5123 (1986)).

The antibody molecule can be a polyclonal or a monoclonal antibody. In other embodiments, the antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 Year *Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to PD-1. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody molecule of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecules may be conjugated to another molecular entity, typically a label or a therapeutic (e.g., a cytotoxic or cytostatic) agent or moiety. Radioactive isotopes can be used in diagnostic or therapeutic applications. Radioactive isotopes that can be coupled to the anti-PD-1 antibodies include, but are not limited to α-, β-, or γ-emitters, or β- and γ-emitters. Such radioactive isotopes include, but are not limited to iodine ($^{131}I$ or $^{125}I$) yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), indium ($^{111}In$) technetium ($^{99}mTc$), phosphorus ($^{32}P$), rhodium ($^{188}Rh$), sulfur ($^{35}S$), carbon ($^{14}C$), tritium ($^{3}H$), chromium ($^{51}Cr$), chlorine ($^{36}Cl$), cobalt ($^{57}Co$ or $^{58}Co$), iron ($^{59}Fe$), selenium ($^{75}5e$), or gallium ($^{67}Ga$). Radioisotopes useful as therapeutic agents include yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), and rhodium ($^{188}Rh$). Radioisotopes useful as labels, e.g., for use in diagnostics, include iodine ($^{131}I$ or $^{125}I$), indium ($^{111}In$) technetium ($^{99}mTc$), phosphorus ($^{32}P$), carbon ($^{14}C$), and tritium ($^{3}H$), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In one aspect, the invention features a method of providing a target binding molecule that specifically binds to a PD-1 receptor. For example, the target binding molecule is an antibody molecule. The method includes: providing a target protein that comprises at least a portion of non-human protein, the portion being homologous to (at least 70, 75, 80, 85, 87, 90, 92, 94, 95, 96, 97, 98% identical to) a corresponding portion of a human target protein, but differing by at least one amino acid (e.g., at least one, two, three, four, five, six, seven, eight, or nine amino acids); obtaining an antibody molecule that specifically binds to the antigen; and evaluating efficacy of the binding agent in modulating activity of the target protein. The method can further include administering the binding agent (e.g., antibody molecule) or a derivative (e.g., a humanized antibody molecule) to a human subject.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also disclosed creating bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. No. 5,910,573, U.S. Pat. No. 5,932,448, U.S. Pat. No. 5,959,083, U.S. Pat. No. 5,989,830, U.S. Pat. No. 6,005,079, U.S. Pat. No. 6,239,259, U.S. Pat. No. 6,294,353, U.S. Pat. No. 6,333,396, U.S. Pat. No. 6,476,198, U.S. Pat. No. 6,511,663, U.S. Pat. No. 6,670,453, U.S. Pat. No. 6,743,896, U.S. Pat. No. 6,809,185, U.S. Pat. No. 6,833,441, U.S. Pat. No. 7,129,330, U.S. Pat. No. 7,183,076, U.S. Pat. No. 7,521,056, U.S. Pat. No. 7,527,787, U.S. Pat. No. 7,534,866, U.S. Pat. No. 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

In other embodiments, the anti-PD-1 antibody molecule (e.g., a monospecific, bispecific, or multispecific antibody molecule) is covalently linked, e.g., fused, to another partner e.g., a protein e.g., one, two or more cytokines, e.g., as a fusion molecule for example a fusion protein. In other embodiments, the fusion molecule comprises one or more proteins, e.g., one, two or more cytokines. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to PD-1), a second binding specificity to a second target (e.g., LAG-3 or TIM-3), and is optionally linked to an interleukin (e.g., IL-12) domain e.g., full length IL-12 or a portion thereof.

A "fusion protein" and a "fusion polypeptide" refer to a polypeptide having at least two portions covalently linked together, where each of the portions is a polypeptide having a different property. The property may be a biological property, such as activity in vitro or in vivo. The property can also be simple chemical or physical property, such as binding to a target molecule, catalysis of a reaction, etc. The two portions can be linked directly by a single peptide bond or through a peptide linker, but are in reading frame with each other.

This invention provides an isolated nucleic acid molecule encoding the above antibody molecule, vectors and host cells thereof. The nucleic acid molecule includes but is not limited to RNA, genomic DNA and cDNA.

Exemplary Anti-PD-1 Antibody Molecules

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In certain embodiments, the anti-PD-1 antibody molecule comprises:

(i) a heavy chain variable region (VH) comprising a VHCDR1 amino acid sequence chosen from SEQ ID NO: 1, SEQ ID NO: 4 or SEQ ID NO: 224; a VHCDR2 amino acid sequence of SEQ ID NO: 2; and a VHCDR3 amino acid sequence of SEQ ID NO: 3; and (ii) a light chain variable region (VL) comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In other embodiments, the anti-PD-1 antibody molecule comprises:

(i) a heavy chain variable region (VH) comprising a VHCDR1 amino acid sequence chosen from SEQ ID NO: 1, SEQ ID NO: 4 or SEQ ID NO: 224; a VHCDR2 amino acid sequence of SEQ ID NO: 5, and a VHCDR3 amino acid sequence of SEQ ID NO: 3; and (ii) a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In embodiments of the aforesaid antibody molecules, the VHCDR1 comprises the amino acid sequence of SEQ ID NO: 1. In other embodiments, the VHCDR1 comprises the amino acid sequence of SEQ ID NO: 4. In yet other embodiments, the VHCDR1 amino acid sequence of SEQ ID NO: 224.

In embodiments, the aforesaid antibody molecules have a heavy chain variable region comprising at least one framework (FW) region comprising the amino acid sequence of any of SEQ ID NOs: 147, 151, 153, 157, 160, 162, 166, or 169, or an amino acid sequence at least 90% identical thereto, or having no more than two amino acid substitutions, insertions or deletions compared to the amino acid sequence of any of SEQ ID NOs: 147, 151, 153, 157, 160, 162, 166, or 169.

In other embodiments, the aforesaid antibody molecules have a heavy chain variable region comprising at least one framework region comprising the amino acid sequence of any of SEQ ID NOs: 147, 151, 153, 157, 160, 162, 166, or 169.

In yet other embodiments, the aforesaid antibody molecules have a heavy chain variable region comprising at least two, three, or four framework regions comprising the amino acid sequences of any of SEQ ID NOs: 147, 151, 153, 157, 160, 162, 166, or 169.

In other embodiments, the aforesaid antibody molecules comprise a VHFW1 amino acid sequence of SEQ ID NO: 147 or 151, a VHFW2 amino acid sequence of SEQ ID NO: 153, 157, or 160, and a VHFW3 amino acid sequence of SEQ ID NO: 162 or 166, and, optionally, further comprising a VHFW4 amino acid sequence of SEQ ID NO: 169.

In other embodiments, the aforesaid antibody molecules have a light chain variable region comprising at least one framework region comprising the amino acid sequence of any of SEQ ID NOs: 174, 177, 181, 183, 185, 187, 191, 194, 196, 200, 202, 205, or 208, or an amino acid sequence at least 90% identical thereto, or having no more than two amino acid substitutions, insertions or deletions compared to the amino acid sequence of any of 174, 177, 181, 183, 185, 187, 191, 194, 196, 200, 202, 205, or 208.

In other embodiments, the aforesaid antibody molecules have a light chain variable region comprising at least one framework region comprising the amino acid sequence of any of SEQ ID NOs: 174, 177, 181, 183, 185, 187, 191, 194, 196, 200, 202, 205, or 208.

In other embodiments, the aforesaid antibody molecules have a light chain variable region comprising at least two, three, or four framework regions comprising the amino acid sequences of any of SEQ ID NOs: 174, 177, 181, 183, 185, 187, 191, 194, 196, 200, 202, 205, or 208.

In other embodiments, the aforesaid antibody molecules comprise a VLFW1 amino acid sequence of SEQ ID NO: 174, 177, 181, 183, or 185, a VLFW2 amino acid sequence of SEQ ID NO: 187, 191, or 194, and a VLFW3 amino acid sequence of SEQ ID NO: 196, 200, 202, or 205, and, optionally, further comprising a VLFW4 amino acid sequence of SEQ ID NO: 208.

In other embodiments, the aforesaid antibodies comprise a heavy chain variable domain comprising an amino acid sequence at least 85% identical to any of SEQ ID NOs: 38, 50, 82, or 86.

In other embodiments, the aforesaid antibody molecules comprise a heavy chain variable domain comprising the amino acid sequence of SEQ ID NO: 38, 50, 82, or 86.

In other embodiments, the aforesaid antibody molecules comprise a light chain variable domain comprising an amino acid sequence at least 85% identical to any of SEQ ID NOs: 42, 46, 54, 58, 62, 66, 70, 74, or 78.

In other embodiments, the aforesaid antibody molecules comprise a light chain variable domain comprising the amino acid sequence of SEQ ID NO: 42, 46, 54, 58, 62, 66, 70, 74, or 78.

In other embodiments, the aforesaid antibody molecules comprise a heavy chain variable domain comprising the amino acid sequence of SEQ ID NO: 38.

In other embodiments, the aforesaid antibody molecules comprise a heavy chain comprising the amino acid sequence of SEQ ID NO: 40.

In other embodiments, the aforesaid antibody molecules comprise a heavy chain comprising the amino acid sequence of SEQ ID NO: 91.

In other embodiments, the aforesaid antibody molecules comprise a heavy chain variable domain comprising the amino acid sequence of SEQ ID NO: 50.

In other embodiments, the aforesaid antibody molecules comprise a heavy chain comprising the amino acid sequence of SEQ ID NO: 52 or SEQ ID NO: 102.

In other embodiments, the aforesaid antibody molecules comprise a heavy chain variable domain comprising the amino acid sequence of SEQ ID NO: 82.

In other embodiments, the aforesaid antibody molecules comprise a heavy chain comprising the amino acid sequence of SEQ ID NO: 84.

In other embodiments, the aforesaid antibody molecules comprise a heavy chain variable domain comprising the amino acid sequence of SEQ ID NO: 86.

In other embodiments, the aforesaid antibody molecules comprise a heavy chain comprising the amino acid sequence of SEQ ID NO: 88.

In other embodiments, the aforesaid antibody molecules comprise a light chain variable domain comprising the amino acid sequence of SEQ ID NO: 42.

In other embodiments, the aforesaid antibody molecules comprise a light chain comprising the amino acid sequence of SEQ ID NO: 44.

In other embodiments, the aforesaid antibody molecules comprise a light chain variable domain comprising the amino acid sequence of SEQ ID NO: 46.

In other embodiments, the aforesaid antibody molecules comprise a light chain comprising the amino acid sequence of SEQ ID NO: 48.

In other embodiments, the aforesaid antibody molecules comprise a light chain variable domain comprising the amino acid sequence of SEQ ID NO: 54.

In other embodiments, the aforesaid antibody molecules comprise a light chain comprising the amino acid sequence of SEQ ID NO: 56.

In other embodiments, the aforesaid antibody molecules comprise a light chain variable domain comprising the amino acid sequence of SEQ ID NO: 58.

In other embodiments, the aforesaid antibody molecules comprise a light chain comprising the amino acid sequence of SEQ ID NO: 60.

In other embodiments, the aforesaid antibody molecules comprise a light chain variable domain comprising the amino acid sequence of SEQ ID NO: 62.

In other embodiments, the aforesaid antibodies comprise a light chain comprising the amino acid sequence of SEQ ID NO: 64.

In other embodiments, the aforesaid antibody molecules comprise a light chain variable domain comprising the amino acid sequence of SEQ ID NO: 66.

In other embodiments, the aforesaid antibody molecules comprise a light chain comprising the amino acid sequence of SEQ ID NO: 68.

In other embodiments, the aforesaid antibody molecules comprise a light chain variable domain comprising the amino acid sequence of SEQ ID NO: 70.

In other embodiments, the aforesaid antibody molecules comprise a light chain comprising the amino acid sequence of SEQ ID NO: 72.

In other embodiments, the aforesaid antibody molecules comprise a light chain variable domain comprising the amino acid sequence of SEQ ID NO: 74.

In other embodiments, the aforesaid antibody molecules comprise a light chain comprising the amino acid sequence of SEQ ID NO: 76.

In other embodiments, the aforesaid antibody molecules comprise a light chain variable domain comprising the amino acid sequence of SEQ ID NO: 78.

In other embodiments, the aforesaid antibody molecules comprise a light chain comprising the amino acid sequence of SEQ ID NO: 80.

In other embodiments, the aforesaid antibody molecules comprise a heavy chain variable domain comprising the amino acid sequence of SEQ ID NO: 38 and a light chain variable domain comprising the amino acid sequence of SEQ ID NO: 42.

In other embodiments, the aforesaid antibody molecules comprise a heavy chain variable domain comprising the amino acid sequence of SEQ ID NO: 38 and a light chain variable domain comprising the amino acid sequence of SEQ ID NO: 66.

In other embodiments, the aforesaid antibody molecules comprise a heavy chain variable domain comprising the amino acid sequence of SEQ ID NO: 38 and a light chain variable domain comprising the amino acid sequence of SEQ ID NO: 70.

In other embodiments, the aforesaid antibody molecules comprise a heavy chain variable domain comprising the amino acid sequence of SEQ ID NO: 50 and a light chain variable domain comprising the amino acid sequence of SEQ ID NO: 70.

In other embodiments, the aforesaid antibody molecules comprise a heavy chain variable domain comprising the amino acid sequence of SEQ ID NO: 38 and a light chain variable domain comprising the amino acid sequence of SEQ ID NO: 46.

In other embodiments, the aforesaid antibody molecules comprise a heavy chain variable domain comprising the amino acid sequence of SEQ ID NO: 50 and a light chain variable domain comprising the amino acid sequence of SEQ ID NO: 46.

In other embodiments, the aforesaid antibody molecules comprise a heavy chain variable domain comprising the amino acid sequence of SEQ ID NO: 50 and a light chain variable domain comprising the amino acid sequence of SEQ ID NO: 54.

In other embodiments, the aforesaid antibody molecules comprise a heavy chain variable domain comprising the amino acid sequence of SEQ ID NO: 38 and a light chain variable domain comprising the amino acid sequence of SEQ ID NO: 54.

In other embodiments, the aforesaid antibody molecules comprise a heavy chain variable domain comprising the amino acid sequence of SEQ ID NO: 38 and a light chain variable domain comprising the amino acid sequence of SEQ ID NO: 58.

In other embodiments, the aforesaid antibody molecules comprise a heavy chain variable domain comprising the amino acid sequence of SEQ ID NO: 38 and a light chain variable domain comprising the amino acid sequence of SEQ ID NO: 62.

In other embodiments, the aforesaid antibody molecules comprise a heavy chain variable domain comprising the amino acid sequence of SEQ ID NO: 50 and a light chain variable domain comprising the amino acid sequence of SEQ ID NO: 66.

In other embodiments, the aforesaid antibody molecules comprise a heavy chain variable domain comprising the amino acid sequence of SEQ ID NO: 38 and a light chain variable domain comprising the amino acid sequence of SEQ ID NO: 74.

In other embodiments, the aforesaid antibody molecules comprise a heavy chain variable domain comprising the amino acid sequence of SEQ ID NO: 38 and a light chain variable domain comprising the amino acid sequence of SEQ ID NO: 78.

In other embodiments, the aforesaid antibody molecules comprise a heavy chain variable domain comprising the amino acid sequence of SEQ ID NO: 82 and a light chain variable domain comprising the amino acid sequence of SEQ ID NO: 70.

In other embodiments, the aforesaid antibody molecules comprise a heavy chain variable domain comprising the amino acid sequence of SEQ ID NO: 82 and a light chain variable domain comprising the amino acid sequence of SEQ ID NO: 66.

In other embodiments, the aforesaid antibody molecules comprise a heavy chain variable domain comprising the amino acid sequence of SEQ ID NO: 86 and a light chain variable domain comprising the amino acid sequence of SEQ ID NO: 66.

In other embodiments, the aforesaid antibody molecules comprise a heavy chain comprising the amino acid sequence of SEQ ID NO: 91 and a light chain comprising the amino acid sequence of SEQ ID NO: 44.

In other embodiments, the aforesaid antibody molecules comprise a heavy chain comprising the amino acid sequence of SEQ ID NO: 91 and a light chain comprising the amino acid sequence of SEQ ID NO: 56.

In other embodiments, the aforesaid antibody molecules comprise a heavy chain comprising the amino acid sequence of SEQ ID NO: 91 and a light chain comprising the amino acid sequence of SEQ ID NO: 68.

In other embodiments, the aforesaid antibody molecules comprise a heavy chain comprising the amino acid sequence of SEQ ID NO: 91 and a light chain comprising the amino acid sequence of SEQ ID NO: 72.

In other embodiments, the aforesaid antibody molecules comprise a heavy chain comprising the amino acid sequence of SEQ ID NO: 102 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 44.

In other embodiments, the aforesaid antibody molecules comprise a heavy chain comprising the amino acid sequence of SEQ ID NO: 40 and a light chain comprising the amino acid sequence of SEQ ID NO: 48.

In other embodiments, the aforesaid antibody molecules comprise a heavy chain comprising the amino acid sequence of SEQ ID NO: 52 and a light chain comprising the amino acid sequence of SEQ ID NO: 48.

In other embodiments, the aforesaid antibody molecules comprise a heavy chain comprising the amino acid sequence of SEQ ID NO: 52 and a light chain comprising the amino acid sequence of SEQ ID NO: 56.

In other embodiments, the aforesaid antibody molecules comprise a heavy chain comprising the amino acid sequence of SEQ ID NO: 40 and a light chain comprising the amino acid sequence of SEQ ID NO: 56.

In other embodiments, the aforesaid antibodies comprise a heavy chain comprising the amino acid sequence of SEQ ID NO: 40 and a light chain comprising the amino acid sequence of SEQ ID NO: 60.

In other embodiments, the aforesaid antibody molecules comprise a heavy chain comprising the amino acid sequence of SEQ ID NO: 40 and a light chain comprising the amino acid sequence of SEQ ID NO: 64.

In other embodiments, the aforesaid antibody molecules comprise a heavy chain comprising the amino acid sequence of SEQ ID NO: 52 and a light chain comprising the amino acid sequence of SEQ ID NO: 68.

In other embodiments, the aforesaid antibody molecules comprise a heavy chain comprising the amino acid sequence of SEQ ID NO: 40 and a light chain comprising the amino acid sequence of SEQ ID NO: 68.

In other embodiments, the aforesaid antibody molecules comprise a heavy chain comprising the amino acid sequence of SEQ ID NO: 52 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 76.

In other embodiments, the aforesaid antibody molecules comprise a heavy chain comprising the amino acid sequence of SEQ ID NO: 40 and a light chain comprising the amino acid sequence of SEQ ID NO: 80.

In other embodiments, the aforesaid antibody molecules comprise a heavy chain comprising the amino acid sequence of SEQ ID NO: 84 and a light chain comprising the amino acid sequence of SEQ ID NO: 72.

In other embodiments, the aforesaid antibodies comprise a heavy chain comprising the amino acid sequence of SEQ ID NO: 84 and a light chain comprising the amino acid sequence of SEQ ID NO: 68.

In other embodiments, the aforesaid antibody molecules comprise a heavy chain comprising the amino acid sequence of SEQ ID NO: 88 and a light chain comprising the amino acid sequence of SEQ ID NO: 68.

In other embodiments, the aforesaid antibody molecules are chosen from a Fab, F(ab')2, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules comprise a light chain constant region chosen from the light chain constant regions of kappa or lambda.

In other embodiments, the aforesaid antibody molecules comprise a human IgG4 heavy chain constant region with a mutation at position 228 according to EU numbering or position 108 of SEQ ID NO: 212 or 214 and a kappa light chain constant region.

In other embodiments, the aforesaid antibody molecules comprise a human IgG4 heavy chain constant region with a Serine to Proline mutation at position 228 according to EU numbering or position 108 of SEQ ID NO: 212 or 214 and a kappa light chain constant region.

In other embodiments, the aforesaid antibody molecules comprise a human IgG1 heavy chain constant region with an Asparagine to Alanine mutation at position 297 according to EU numbering or position 180 of SEQ ID NO: 216 and a kappa light chain constant region.

In other embodiments, the aforesaid antibody molecules comprise a human IgG1 heavy chain constant region with an Aspartate to Alanine mutation at position 265 according to EU numbering or position 148 of SEQ ID NO: 217, and Proline to Alanine mutation at position 329 according to EU numbering or position 212 of SEQ ID NO: 217 and a kappa light chain constant region.

In other embodiments, the aforesaid antibody molecules comprise a human IgG1 heavy chain constant region with a Leucine to Alanine mutation at position 234 according to EU numbering or position 117 of SEQ ID NO: 218, and Leucine to Alanine mutation at position 235 according to EU numbering or position 118 of SEQ ID NO: 218 and a kappa light chain constant region.

In other embodiments, the aforesaid antibody molecules are capable of binding to human PD-1 with a dissociation constant ($K_D$) of less than about 0.2 nM.

In some embodiments, the aforesaid antibody molecules bind to human PD-1 with a $K_D$ of less than about 0.2 nM, 0.15 nM, 0.1 nM, 0.05 nM, or 0.02 nM, e.g., about 0.13 nM to 0.03 nM, e.g., about 0.077 nM to 0.088 nM, e.g., about 0.083 nM, e.g., as measured by a Biacore method.

In other embodiments, the aforesaid antibody molecules bind to cynomolgus PD-1 with a $K_D$ of less than about 0.2 nM, 0.15 nM, 0.1 nM, 0.05 nM, or 0.02 nM, e.g., about 0.11 nM to 0.08 nM, e.g., about 0.093 nM, e.g., as measured by a Biacore method.

In certain embodiments, the aforesaid antibody molecules bind to both human PD-1 and cynomolgus PD-1 with similar $K_D$, e.g., in the nM range, e.g., as measured by a Biacore method. In some embodiments, the aforesaid antibody molecules bind to a human PD-1-Ig fusion protein with a $K_D$ of less than about 0.1 nM, 0.075 nM, 0.05 nM, 0.025 nM, or 0.01 nM, e.g., about 0.04 nM, e.g., as measured by ELISA.

In some embodiments, the aforesaid antibody molecules bind to Jurkat cells that express human PD-1 (e.g., human PD-1-transfected Jurkat cells) with a $K_D$ of less than about 0.1 nM, 0.075 nM, 0.05 nM, 0.025 nM, or 0.01 nM, e.g., about 0.06 nM, e.g., as measured by FACS analysis.

In some embodiments, the aforesaid antibody molecules bind to cynomolgus T cells with a $K_D$ of less than about 1 nM, 0.75 nM, 0.5 nM, 0.25 nM, or 0.1 nM, e.g., about 0.4 nM, e.g., as measured by FACS analysis.

In some embodiments, the aforesaid antibody molecules bind to cells that express cynomolgus PD-1 (e.g., cells transfected with cynomolgus PD-1) with a $K_D$ of less than about 1 nM, 0.75 nM, 0.5 nM, 0.25 nM, or 0.01 nM, e.g., about 0.6 nM, e.g., as measured by FACS analysis.

In certain embodiments, the aforesaid antibody molecules are not cross-reactive with mouse or rat PD-1. In other embodiments, the aforesaid antibodies are cross-reactive with rhesus PD-1. For example, the cross-reactivity can be measured by a Biacore method or a binding assay using cells that expresses PD-1 (e.g., human PD-1-expressing 300.19 cells). In other embodiments, the aforesaid antibody molecules bind an extracellular Ig-like domain of PD-1.

In other embodiments, the aforesaid antibody molecules are capable of reducing binding of PD-1 to PD-L1, PD-L2, or both, or a cell that expresses PD-L1, PD-L2, or both. In some embodiments, the aforesaid antibody molecules reduce (e.g., block) PD-L1 binding to a cell that expresses PD-1 (e.g., human PD-1-expressing 300.19 cells) with an IC50 of less than about 1.5 nM, 1 nM, 0.8 nM, 0.6 nM, 0.4 nM, 0.2 nM, or 0.1 nM, e.g., between about 0.79 nM and about 1.09 nM, e.g., about 0.94 nM, or about 0.78 nM or less, e.g., about 0.3 nM. In some embodiments, the aforesaid antibodies reduce (e.g., block) PD-L2 binding to a cell that expresses PD-1 (e.g., human PD-1-expressing 300.19 cells) with an IC50 of less than about 2 nM, 1.5 nM, 1 nM, 0.5 nM, or 0.2 nM, e.g., between about 1.05 nM and about 1.55 nM, or about 1.3 nM or less, e.g., about 0.9 nM.

In other embodiments, the aforesaid antibody molecules are capable of enhancing an antigen-specific T cell response.

In embodiments, the antibody molecule is a monospecific antibody molecule or a bispecific antibody molecule. In embodiments, the antibody molecule has a first binding specificity for PD-1 and a second binding specificity for TIM-3, LAG-3, CEACAM (e.g., CEACAM-1, CEACAM-3, and/or CEACAM-5), PD-L1 or PD-L2. In embodiments, the antibody molecule comprises an antigen binding fragment of an antibody, e.g., a half antibody or antigen binding fragment of a half antibody.

In some embodiments, the aforesaid antibody molecules increase the expression of IL-2 from cells activated by Staphylococcal enterotoxin B (SEB) (e.g., at 25 μg/mL) by at least about 2, 3, 4, 5-fold, e.g., about 2 to 3-fold, e.g., about 2 to 2.6-fold, e.g., about 2.3-fold, compared to the expression of IL-2 when an isotype control (e.g., IgG4) is used, e.g., as measured in a SEB T cell activation assay or a human whole blood ex vivo assay.

In some embodiments, the aforesaid antibody molecules increase the expression of IFN-γ from T cells stimulated by anti-CD3 (e.g., at 0.1 μg/mL) by at least about 2, 3, 4, 5-fold, e.g., about 1.2 to 3.4-fold, e.g., about 2.3-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated by SEB (e.g., at 3 μg/mL) by at least about 2, 3, 4, 5-fold, e.g., about 0.5 to 4.5-fold, e.g., about 2.5-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated with an CMV peptide by at least about 2, 3, 4, 5-fold, e.g., about 2 to 3.6-fold, e.g., about 2.8-fold, compared to the expression of IFN-γ when an isotype control (e.g., IgG4) is used, e.g., as measured in an IFN-γ activity assay.

In some embodiments, the aforesaid antibody molecules increase the proliferation of $CD8^+$ T cells activated with an CMV peptide by at least about 1, 2, 3, 4, 5-fold, e.g., about 1.5-fold, compared to the proliferation of $CD8^+$ T cells when an isotype control (e.g., IgG4) is used, e.g., as measured by the percentage of CD8+ T cells that passed through at least n (e.g., n=2 or 4) cell divisions.

In certain embodiments, the aforesaid antibody molecules has a Cmax between about 100 μg/mL and about 500 μg/mL, between about 150 μg/mL and about 450 μg/mL, between about 250 μg/mL and about 350 μg/mL, or between about 200 μg/mL and about 400 μg/mL, e.g., about 292.5 μg/mL, e.g., as measured in monkey.

In certain embodiments, the aforesaid antibody molecules has a $T_{1/2}$ between about 250 hours and about 650 hours, between about 300 hours and about 600 hours, between about 350 hours and about 550 hours, or between about 400 hours and about 500 hours, e.g., about 465.5 hours, e.g., as measured in monkey.

In some embodiments, the aforesaid antibody molecules bind to PD-1 with a Kd slower than $5\times10^{-4}$, $1\times10^{-4}$, $5\times10^{-5}$, or $1\times10^{-5}$ $s^{-1}$, e.g., about $2.13\times10^{-4}$ $s^{-1}$, e.g., as measured by a Biacore method. In some embodiments, the aforesaid antibody molecules bind to PD-1 with a Ka faster than $1\times10^{4}$, $5\times10^{4}$, $1\times10^{5}$, or $5\times10^{5}$ $M^{-1}s^{-1}$, e.g., about $2.78\times10^{5}$ $M^{-1}s^{-1}$, e.g., as measured by a Biacore method.

In some embodiments, the aforesaid anti-PD-1 antibody molecules bind to one or more residues within the C strand, CC' loop, C' strand and FG loop of PD-1. The domain structure of PD-1 is described, e.g., in Cheng et al., "Structure and Interactions of the Human Programmed Cell Death 1 Receptor" *J. Biol. Chem.* 2013, 288:11771-11785. As described in Cheng et. al., the C strand comprises residues F43-M50, the CC' loop comprises S51-N54, the C' strand comprises residues Q55-F62, and the FG loop comprises residues L108-I114 (amino acid numbering according to Chang et al. supra). Accordingly, in some embodiments, an anti-PD-1 antibody as described herein binds to at least one residue in one or more of the ranges F43-M50, S51-N54, Q55-F62, and L108-I114 of PD-1. In some embodiments, an anti-PD-1 antibody as described herein binds to at least one residue in two, three, or all four of the ranges F43-M50, S51-N54, Q55-F62, and L108-I114 of PD-1. In some embodiments, the anti-PD-1 antibody binds to a residue in PD-1 that is also part of a binding site for one or both of PD-L1 and PD-L2.

In another aspect, the invention provides an isolated nucleic acid molecule encoding any of the aforesaid antibody molecules, vectors and host cells thereof.

An isolated nucleic acid encoding the antibody heavy chain variable region or light chain variable region, or both, of any the aforesaid antibody molecules is also provided.

In one embodiment, the isolated nucleic acid encodes heavy chain CDRs 1-3, wherein said nucleic acid comprises a nucleotide sequence of SEQ ID NO: 108-112, 223, 122-126, 133-137, or 144-146.

In another embodiment, the isolated nucleic acid encodes light chain CDRs 1-3, wherein said nucleic acid comprises a nucleotide sequence of SEQ ID NO: 113-120, 127-132, or 138-143.

In other embodiments, the aforesaid nucleic acid further comprises a nucleotide sequence encoding a heavy chain variable domain, wherein said nucleotide sequence is at least 85% identical to any of SEQ ID NO: 39, 51, 83, 87, 90, 95, or 101.

In other embodiments, the aforesaid nucleic acid further comprises a nucleotide sequence encoding a heavy chain variable domain, wherein said nucleotide sequence comprises any of SEQ ID NO: 39, 51, 83, 87, 90, 95, or 101.

In other embodiments, the aforesaid nucleic acid further comprises a nucleotide sequence encoding a heavy chain, wherein said nucleotide sequence is at least 85% identical to any of SEQ ID NO: 41, 53, 85, 89, 92, 96, or 103.

In other embodiments, the aforesaid nucleic acid further comprises a nucleotide sequence encoding a heavy chain, wherein said nucleotide sequence comprises any of SEQ ID NO: 41, 53, 85, 89, 92, 96, or 103.

In other embodiments, the aforesaid nucleic acid further comprises a nucleotide sequence encoding a light chain variable domain, wherein said nucleotide sequence is at least 85% identical to any of SEQ ID NO: 45, 49, 57, 61, 65, 69, 73, 77, 81, 94, 98, 100, 105, or 107.

In other embodiments, the aforesaid nucleic acid further comprises a nucleotide sequence encoding a light chain variable domain, wherein said nucleotide sequence comprises any of SEQ ID NO: 45, 49, 57, 61, 65, 69, 73, 77, 81, 94, 98, 100, 105, or 107.

In other embodiments, the aforesaid nucleic acid further comprises a nucleotide sequence encoding a light chain, wherein said nucleotide sequence is at least 85% identical to any of SEQ ID NO: 45, 49, 57, 61, 65, 69, 73, 77, 81, 94, 98, 100, 105 or 107.

In other embodiments, the aforesaid nucleic acid further comprises a nucleotide sequence encoding a light chain, wherein said nucleotide sequence comprises any of SEQ ID NO: 45, 49, 57, 61, 65, 69, 73, 77, 81, 94, 98, 100, 105 or 107.

In certain embodiments, one or more expression vectors and host cells comprising the aforesaid nucleic acids are provided.

A method of producing an antibody molecule or fragment thereof, comprising culturing the host cell as described herein under conditions suitable for gene expression is also provided.

Pharmaceutical Compositions and Kits

In another aspect, the present invention provides compositions, e.g., pharmaceutically acceptable compositions, which include an antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules can be administered by a variety of methods known in the art, although for many therapeutic applications, the preferred route/mode of administration is intravenous injection or infusion. For example, the antibody molecules can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody molecule is 0.1-30 mg/kg, more preferably 1-25 mg/kg. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week. The antibody molecule can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the infusion rate of about 110 to 130 mg/m$^2$ achieves a level of about 3 mg/kg. In other embodiments, the antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the antibody is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising an antibody molecule described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

Uses of Anti-PD-1 Antibody Molecules

The anti-PD-1 antibody molecules disclosed herein have in vitro and in vivo diagnostic, as well as therapeutic and prophylactic utilities. For example, these molecules can be administered to cells in culture, in vitro or ex vivo, or to a subject, e.g., a human subject, to treat, prevent, and/or diagnose a variety of disorders, such as cancers and infectious disorders.

Accordingly, in one aspect, the invention provides a method of modifying an immune response in a subject comprising administering to the subject the antibody molecule described herein, such that the immune response in the subject is modified. In one embodiment, the immune response is enhanced, stimulated or up-regulated. In one embodiment, the antibody molecules enhance an immune response in a subject by blockade of PD-1.

As used herein, the term "subject" is intended to include human and non-human animals. In one embodiment, the subject is a human subject, e.g., a human patient having a disorder or condition characterized by abnormal PD-1 functioning. The term "non-human animals" includes mammals and non-mammals, such as non-human primates. In one embodiment, the subject is a human. In one embodiment, the subject is a human patient in need of enhancement of an immune response. In one embodiment, the subject is immunocompromised, e.g., the subject is undergoing, or has undergone a chemotherapeutic or radiation therapy. Alternatively, or in combination, the subject is, or is at risk of being, immunocompromised as a result of an infection. The methods and compositions described herein are suitable for treating human patients having a disorder that can be treated by augmenting the T-cell mediated immune response. For example, the methods and compositions described herein can enhance a number of immune activities. In one embodiment, the subject has increased number or activity of tumour-infiltrating T lymphocytes (TILs). In another embodiment, the subject has increased expression or activity of interferon-gamma (IFN-γ). In yet another embodiment, the subject has decreased PD-L1 expression or activity.

Therapeutic Uses

Cancer

Blockade of PD-1 can enhance an immune response to cancerous cells in a subject. The ligand for PD-1, PD-L1, is not expressed in normal human cells, but is abundant in a variety of human cancers (Dong et al. (2002) *Nat Med* 8:787-9). The interaction between PD-1 and PD-L1 can result in a decrease in tumor infiltrating lymphocytes, a decrease in T-cell receptor mediated proliferation, and/or immune evasion by the cancerous cells (Dong et al. (2003) *J Mol Med* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 to PD-L1; the effect is additive when the interaction of PD-1 to PD-L2 is blocked as well (Iwai et al. (2002) *PNAS* 99:12293-7; Brown et al. (2003) *J. Immunol.* 170:1257-66). Thus, inhibition of PD-1 can result in augmenting an immune response.

In one aspect, the invention relates to treatment of a subject in vivo using an anti-PD-1 antibody molecule such that growth of cancerous tumors is inhibited or reduced. An anti-PD-1 antibody may be used alone to inhibit the growth of cancerous tumors. Alternatively, an anti-PD-1 antibody may be used in combination with one or more of: a standard of care treatment (e.g., for cancers or infectious disorders), another antibody or antigen-binding fragment thereof, an immunomodulator (e.g., an activator of a costimulatory molecule or an inhibitor of an inhibitory molecule); a vaccine, e.g., a therapeutic cancer vaccine; or other forms of cellular immunotherapy, as described below.

Accordingly, in one embodiment, the invention provides a method of inhibiting growth of tumor cells in a subject, comprising administering to the subject a therapeutically effective amount of an anti-PD-1 antibody molecule described herein.

In one embodiment, the methods are suitable for the treatment of cancer in vivo. To achieve antigen-specific enhancement of immunity, the anti-PD-1 antibody molecule can be administered together with an antigen of interest. When antibodies to PD-1 are administered in combination with one or more agents, the combination can be administered in either order or simultaneously.

Types of Cancer; Theranostic Methods

In another aspect, a method of treating a subject, e.g., reducing or ameliorating, a hyperproliferative condition or disorder (e.g., a cancer), e.g., solid tumor, a hematological cancer, soft tissue tumor, or a metastatic lesion, in a subject is provided. The method includes administering to the subject one or more anti-PD-1 antibody molecules described herein, alone or in combination with other agents or therapeutic modalities.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated or prevented using the methods and compositions of the invention.

Exemplary cancers whose growth can be inhibited using the antibodies molecules disclosed herein include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, colon cancer and lung cancer (e.g., non-small cell lung cancer). Additionally, refractory or recurrent malignancies can be treated using the antibody molecules described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, testicular cancer, uterine cancer, carcinoma of the fallopian tubes, carcinoma of the endometrium, carcinoma of the cervix, carcinoma of the vagina, carcinoma of the vulva, Merkel cell cancer, Hodgkin lymphoma, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, multiple myeloma, myelodisplastic syndromes, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos (e.g., mesothelioma), and combinations of said cancers.

Treatment of metastatic cancers, e.g., metastatic cancers that express PD-L1 (Iwai et al. (2005) *Int. Immunol.* 17:133-144) can be effected using the antibody molecules described herein. In one embodiment, the cancer expresses an elevated level of PD-L1, IFNγ and/or CD8.

While not wishing to be bound by theory, in some embodiments, a patient is more likely to respond to treatment with an immunomodulator (optionally in combination with one or more agents as described herein) if the patient has a cancer that highly expresses PD-L1, and/or the cancer is infiltrated by anti-tumor immune cells, e.g., TILs. The anti-tumor immunce cells may be positive for CD8, PD-L1, and/or IFN-γ; thus levels of CD8, PD-L1, and/or IFN-γ can serve as a readout for levels of TILs in the microenvironment. In certain embodiments, the cancer microenvironment is referred to as triple-positive for PD-L1/CD8/IFN-γ.

Accordingly, in certain aspects, this application provides methods of determining whether a tumor sample is positive for one or more of PD-L1, CD8, and IFN-γ, and if the tumor sample is positive for one or more, e.g., two, or all three, of the markers, then administering to the patient a therapeutically effective amount of an anti-PD-1 antibody molecule, optionally in combination with one or more other immunomodulators or anti-cancer agents.

In the following indications, a large fraction of patients are triple-positive for PD-L1/CD8/IFN-γ: Lung cancer (squamous); lung cancer (adenocarcinoma); head and neck cancer; stomach cancer; NSCLC; HNSCC; gastric cancers (e.g., MSIhi and/or EBV+); CRC (e.g., MSIhi); nasopharyngeal cancer (NPC); cervical cancer (e.g., squamous); thyroid cancer e.g., papillary thyroid; melanoma; TN breast cancer; and DLBCL (Diffuse Large B-Cell Lymphoma). In breast cancer generally and in colon cancer generally, a moderate fraction of patients is triple-positive for PD-L1/CD8/IFN-γ. In the following indications, a small fraction of patients are triple-positive for PD-L1/CD8/1FN-γ: ER+ breast cancer, and pancreatic cancer. These findings are discussed further in Example 4. Regardless of whether a large or small fraction of patients is triple-positive for these markers, screening the patients for these markers allows one to identify a fraction of patients that has an especially high likelihood of responding favorably to therapy with a PD-1 antibody (e.g., a blocking PD-1 antibody), optionally in combination with one or more other immunomodulators (e.g., an anti-TIM-3 antibody molecule, an anti-LAG-3 antibody molecule, or an anti-PD-L1 antibody molecule) and/or anti-cancer agents, e.g., those listed in Table 7 and disclosed in the publications listed in Table 7.

In some embodiments, the cancer sample is classified as triple-positive for PD-L1/CD8/IFN-γ. This measurement can roughly be broken down into two thresholds: whether an individual cell is classified as positive, and whether the sample as a whole is classified as positive. First, one can measure, within an individual cell, the level of PD-L1, CD8, and/or IFN-γ. In some embodiments, a cell that is positive for one or more of these markers is a cell that has a higher level of the marker compared to a control cell or a reference value. For example, in some embodiments, a high level of PD-L1 in a given cell is a level higher than the level of PD-L1 in a corresponding non-cancerous tissue in the patient. As another example, in some embodiments, a high level of CD8 or IFN-γ in a given cell is a level of that protein typically seen in a TIL. Second, one can also measure the percentage of cells in the sample that are positive for PD-L1, CD8, and/or IFN-γ. (It is not necessary for a single cell to express all three markers.) In some embodiments, a triple positive sample is one that has a high percentage of cells, e.g., higher than a reference value or higher than a control sample, that are positive for these markers.

In other embodiments, one can measure the levels of PD-L1, CD8, and/or IFN-γ overall in the sample. In this case, a high level of CD8 or IFN-γ in the sample can be the level of that protein typically seen in a tumor infiltrated with TIL. Similarly, a high level of PD-L1 can be the level of that protein typically seen in a tumor sample, e.g., a tumor microenvironment.

The identification of subsets of patients that are triple-positive for PD-L1/CD8/IFN-γ, as shown in Example 4 herein, reveals certain sub-populations of patients that are likely to be responsive to PD-1 antibody therapy. For instance, many IM-TN (immunomodulatory, triple negative) breast cancer patients are triple-positive for PD-L1/CD8/IFN-γ. IM-TN breast cancer is described in, e.g., Brian D. Lehmann et al., "Identification of human triple-negative breast cancer subtypes and preclinical models for selection of targeted therapies", *J Clin Invest. Jul.* 1, 2011; 121(7): 2750-2767. Triple-negative breast cancers are those that do not express estrogen receptor (ER), progesterone receptor (PR) and Her2/neu. These cancers are difficult to treat because they are typically not responsive to agents that target ER, PR, and Her2/neu. Triple-negative breast cancers can be further subdivided into different classes, one of which is immunomodulatory. As described in Lehmann et al., IM-TN breast cancer is enriched for factors involved in immune cell processes, for example, one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing. Accordingly, in some embodiments, the cancer treated is a cancer that is, or is determined to be, positive for one or more marker of IM-TN breast cancer, e.g., a factor that promotes one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing.

As another example, it is shown herein that a subset of colon cancer patients having high MSI (microsatellite instability) is also triple-positive for PD-L1/CD8/IFN-γ. Accordingly, in some embodiments, a PD-1 antibody, e.g., a PD-1 antibody as described herein, (optionally in combination with one or more immunomodulators such as a LAG-3 antibody, TIM-3 antibody, or PD-L1 antibody, and one or more anti-cancer agents, e.g., an anti-cancer agent described in Table 7 or in a publication in Table 7) is administered to a patient who has, or who is identified as having, colon cancer with high MSI, thereby treating the cancer. In some embodiments, a cell with high MSI is a cell having MSI at a level higher than a reference value or a control cell, e.g., a non-cancerous cell of the same tissue type as the cancer.

As another example, it is shown herein that a subset of gastric cancer patients having high MSI, and/or which is EBV+, is also triple-positive for PD-L1/CD8/IFN-γ. Accordingly, in some embodiments, a PD-1 antibody, e.g., a PD-1 antibody as described herein, (optionally in combination with one or more immunomodulators such as a LAG-3 antibody, TIM-3 antibody, or PD-L1 antibody, and one or more anti-cancer agents, e.g., an anti-cancer agent described in Table 7 or in a publication in Table 7) is administered to a patient who has, or who is identified as having, gastric cancer with high MSI and/or EBV+, thereby treating the cancer. In some embodiments, a cell with high MSI is a cell having MSI at a level higher than a reference value or a control cell, e.g., a non-cancerous cell of the same tissue type as the cancer.

Additionally disclosed herein are methods of assaying a cancer for PD-L1, and then treating the cancer with a PD-1 antibody. As described in Example 5 herein, a cancer sample can be assayed for PD-L1 protein levels or mRNA levels. A sample having levels of PD-L1 (protein or mRNA) higher than a reference value or a control cell (e.g., a non-cancerous cell) can be classified as PD-L1 positive. Accordingly, in some embodiments, a PD-1 antibody, e.g., a PD-1 antibody as described herein, (optionally in combination with one or more anti-cancer agents) is administered to a patient who has, or who is identified as having, a cancer that is PD-L1 positive. The cancer may be, e.g., non-small cell lung (NSCLC) adenocarcinoma (ACA), NSCLC squamous cell carcinoma (SCC), or hepatocellular carcinoma (HCC).

In some embodiments, the methods herein involve using a PD-1 antibody, e.g., a PD-1 antibody as described herein, e.g., as a monotherapy, for treating a cancer that is (or is identified as being) positive for PD-L1. In some embodiments, the cancer is colorectal cancer (e.g., MSI-high), gastric cancer (e.g., MSI-high and/or EBV+), NPC, cervical cancer, breast cancer (e.g., TN breast cancer), and ovarian cancer. In some embodiments, the cancer is NSCLC, melanoma, or HNSCC. In some embodiments, the PD-1 antibody is administered at a dose of, e.g., 1, 3, 10, or 20 mg/kg.

Based on, e.g, Example 4 herein, it was found that certain gastric cancers that are triple-positive for PD-L1/CD8/IFN-γ are also positive for PIK3CA. Accordingly, in some embodiments, a cancer can be treated with an anti-PD-1 antibody molecule (optionally in combination with one or more immunomodulators, e.g., an anti-LAG-3 antibody molecule, an anti-TIM-3 antibody molecule, or an anti-PD-L1 antibody molecule) and an agent that inhibits PIK3CA. Exemplary agents in this category are described in Stein RC (September 2001). "Prospects for phosphoinositide 3-kinase inhibition as a cancer treatment". *Endocrine-related Cancer* 8 (3): 237-48 and Marone R, Cmiljanovic V, Giese B, Wymann M P (January 2008). "Targeting phosphoinositide 3-kinase: moving towards therapy". *Biochimica et Biophysica Acta* 1784 (1): 159-85.

Based on, e.g, Example 4 herein, CRC, e.g., a patient that has (or is identified as having) MSI-high CRC may be treated with a PD-1 antibody, optionally in combination with a therapeutic that targets one or more of LAG-3, RNF43, and BRAF. For instance, these cancers may be treated with a PD-1 antibody, optionally in combination with one or more therapeutics that target one or more of LAG-3, PD-1, RNF43, and BRAF. In embodiments, the one or more therapeutics include an immunomodulators such as an anti-LAG-3 antibody molecule, and an anti-cancer agent described in Table 7 or a publication listed in Table 7. LAG-3 inhibitors, e.g., antibodies, are described herein. RNF43 can be inhibited, e.g., with an antibody, small molecule (e.g., 2-(2',3-dimethyl-[2,4'-bipyridin]-5-yl)-N-(5-(pyrazin-2-yl)pyridin-2-yl)acetamide (Compound A28)), siRNA, or a Rspo ligand or derivative thereof. BRAF inhibitors (e.g., vemurafenib or dabrafenib) are described herein.

Based on, e.g, Example 4 herein, a patient that has (or is identified as having) a squamous cell lung cancer may be treated with a PD-1 antibody molecule in combination with a therapeutic that targets LAG-3, e.g., a LAG-3 antibody molecule, and optionally with one or more anti-cancer agents, e.g., an anti-cancer agent described in Table 7 or in a publication in Table 7.

In some embodiments, a subject that has (or is identified as having) a squamous cell lung cancer may be treated with a PD-1 antibody, optionally in combination with a therapeutic that targets TIM-3, e.g., a TIM-3 antibody. TIM-3 inhibitors, e.g., antibodies, are described herein.

Based on, e.g, Example 4 herein, a patient that has (or is identified as having) a thyroid cancer may be treated with a PD-1 antibody molecule, optionally in combination with a therapeutic that targets BRAF, and optionally in combination with one or more immunomodulators, e.g., an anti-LAG-3 antibody molecule, an anti-TIM-3 antibody molecule, and an anti-PD-L1 antibody molecule. BRAF inhibitors (e.g., vemurafenib or dabrafenib) are described herein, e.g., in Table 7 and the publications listed in Table 7.

In some embodiments, the therapies here can be used to treat a patient that has (or is identified as having) a cancer associated with an infection, e.g., a viral or bacterial infection. Exemplary cancers include cervical cancer, anal cancer, HPV-associated head and neck squamous cell cancer, HPV-associated esophageal papillomas, HHV6-associated lymphomas, EBV-associated lymphomas (including Burkitt lymphoma), Gastric MALT lymphoma, other infection-associated MALT lymphomas, HCC, and Kaposi's sarcoma.

In other embodiments, the cancer is a hematological malignancy or cancer including but is not limited to a leukemia or a lymphoma. For example, the anti-PD-1 antibody molecule can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, a non-Hogdkin's lymphoma, or a leukemia (e.g., a myeloid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer.

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma).

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-PD-1 antibody molecule is administered after treatment with an anti-CTLA-4 antibody (e.g., ipilimumab) with or without a BRAF inhibitor (e.g., vemurafenib or dabrafenib).

Methods and compositions disclosed herein are useful for treating metastatic lesions associated with the aforementioned cancers.

Combination of Anti-PD-1 Antibodies with Cancer Vaccines

Antibody molecules to PD-1 can be combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, tumor cells transfected to express the cytokine GM-CSF, DNA-based vaccines, RNA-based vaccines, and viral transduction-based vaccines. The cancer vaccine may be prophylactic or therapeutic.

PD-1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, *Cancer:* Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

PD-1 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV), Kaposi's Herpes Sarcoma Virus (KHSV), and Epstein-Barr virus (EBV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269: 1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with PD-1 blockade to activate more potent anti-tumor responses.

In embodiments, the combination further includes an inhibitor or activator of an immune checkpoint modulator (e.g., a LAG-3 inhibitor (e.g., an anti-LAG-3 antibody molecule), a PD-L1 inhibitor (e.g., an anti-PD-L1 antibody molecule), a TIM-3 modulator (e.g., a TIM-3 activator or inhibitor, e.g., an anti-TIM-3 antibody molecule), or a CTLA-4 inhibitor (e.g., an anti-CTLA-4 antibody), or any combination thereof.

PD-1 blockade may also be combined with a standard cancer treatment. PD-1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include anti-microtubule agents, topoisomerase inhibitors, anti-metabolites, mitotic inhibitors, alkylating agents, anthracyclines, *vinca* alkaloids, intercalating agents, agents capable of interfering with a signal transduction pathway, agents that promote apoptosis, proteosome inhibitors, and radiation (e.g., local or whole body irradiation).

Alternatively, or in combination with the aforesaid combinations, the methods and compositions described herein can be administered in combination with one or more of: an immunomodulator (e.g., an activator of a costimulatory molecule or an inhibitor of an inhibitory molecule); a vaccine, e.g., a therapeutic cancer vaccine; or other forms of cellular immunotherapy.

Exemplary non-limiting combinations and uses of the anti-PD-1 antibody molecules include the following.

In certain embodiments, the anti-PD-1 antibody molecule is administered in combination with a modulator of a costimulatory molecule or an inhibitory molecule, e.g., a co-inhibitory ligand or receptor.

In one embodiment, the anti-PD-1 antibody molecule is administered in combination with a modulator, e.g., agonist, of a costimulatory molecule. In one embodiment, the agonist of the costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the anti-PD-1 antibody molecule is used in combination with a costimulatory molecule, e.g., an agonist associated with a positive signal that includes a costimulatory domain of CD28, CD27, ICOS and GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No. 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B1, U.S. Pat. No. 7,812,135, U.S. Pat. No. 8,388,967, U.S. Pat. No. 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726.

In one embodiment, the anti-PD-1 antibody molecule is administered in combination with an inhibitor of an inhibitory molecule of an immune checkpoint molecule. It will be understood by those of ordinary skill in the art, that the term "immune checkpoints" means a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, LAG-3 and TIM-3, which directly inhibit immune cells. Immunotherapeutic agents which can act as immune checkpoint inhibitors useful in the methods of the present invention, include, but are not limited to, inhibitors of PD-L1, PD-L2, CTLA4, TIM-3, LAG-3, VISTA, BTLA, TIGIT, LAIR1, CD160, 2B4, CEACAM (e.g., CEACAM-1 and/or CEACAM-5), and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule.

In one embodiment, the inhibitor is a soluble ligand (e.g., a CTLA-4-Ig or a TIM-3-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9). In one embodiment, the anti-PD-1 antibody molecule is administered after treatment, e.g., after treatment of a melanoma, with an anti-CTLA4 antibody (e.g., ipilimumab) with or without a BRAF inhibitor (e.g., vemurafenib or dabrafenib). Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Immune inhibitory molecules, e.g., PD-1 and LAG-3, can regulate, e.g., synergistically regulate, T-cell function to promote tumoral immune escape. In another embodiment, the anti-PD-1 antibody molecule is administered in combination with an anti-LAG-3 antibody or an antigen-binding fragment thereof. In another embodiment, the anti-PD-1 antibody molecule is administered in combination with an anti-TIM-3 antibody or antigen-binding fragment thereof. In yet other embodiments, the anti-PD-1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In another embodiment, the anti-PD-1 antibody molecule is administered in combination with a CEACAM inhibitor (e.g., CEACAM-1, CEACAM-3, and/or CEACAM-5 inhibitor), e.g., an anti-CEACAM antibody molecule. In another embodiment, the anti-PD-1 antibody molecule is administered in combination with a CEACAM-1 inhibitor, e.g., an anti-CEACAM-1 antibody molecule. In another embodiment, the anti-PD-1 antibody molecule is administered in combination with a CEACAM-5 inhibitor, e.g., an anti-CEACAM-5 antibody molecule. In one embodiment, a bispecific antibody that includes an anti-PD-1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) *Cancer Res.* 72(4):917-27).

In one embodiment, the inhibitor of CEACAM (e.g., CEACAM-1 and/or CEACAM-5) is an anti-CEACAM antibody molecule. Without wishing to be bound by theory, CEACAM-1 has been described as a ligand and partner of TIM-3 (see e.g., WO 2014/022332). Synergistic in vivo effect of the combination of anti-TIM-3 and anti-CEACAM-1 antibodies have been detected in xenograft cancer models (see e.g., WO 2014/022332). Tumors are believed to use CEACAM-1 or CEACAM-5 to inhibit the immune system, as described in, e.g., Markel et al. *J Immunol.* 2002 Mar. 15; 168(6):2803-10; Markel et al. *J Immunol.* 2006 Nov. 1; 177(9):6062-71; Markel et al. *Immunology.* 2009 February; 126(2):186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529. Thus, CEACAM inhibitors can be used with the other immunomodulators described herein (e.g., anti-PD-1 or anti-TIM-3 inhibitors) to enhance an immune response against a cancer, e.g., melanoma, lung cancer (e.g., NSCLC), bladder, colon or ovarian cancer, or other cancers as described herein. In one embodiment, the inhibitor of CEACAM is an anti-CEACAM-1 antibody as described in WO 2010/125571, WO 2013/82366 and WO 2014/022332, e.g., a monoclonal antibody 34B1, 26H7, and 5F4 or a recombinant form thereof, as described in, e.g., US 2004/0047858, U.S. Pat. No. 7,132,255 and WO 99/52552. In other embodiments, the anti-CEACAM antibody is an anti-CEACAM-1 and/or anti-CEACAM-5 antibody molecule as described in, e.g., WO 2010/125571, WO 2013/054331 and US 2014/0271618.

In some embodiments, the PD-1 and LAG-3 immune inhibitory molecules (e.g., antibody molecules) are administered in combination with each other, e.g., to treat cancer. In some embodiments, the patient is a patient who progressed (e.g., experienced tumor growth) during therapy with a PD-1 inhibitor (e.g., an antibody molecule as described herein) and/or a PD-L1 inhibitor (e.g., antibody molecule). In some embodiments, therapy with the PD-1 antibody molecule and/or PD-L1 antibody molecule is continued, and a LAG-3 immune inhibitory molecule (e.g., antibody) is added to the therapy.

In some embodiments, the PD-1 and TIM-3 immune inhibitory molecules (e.g., antibody molecules) are administered in combination with each other, e.g., to treat cancer. In some embodiments, the patient is a patient who progressed (e.g., experienced tumor growth) during therapy with a PD-1 inhibitor (e.g., an antibody molecule as described herein) and/or a PD-L1 inhibitor (e.g., antibody molecule). In some embodiments, therapy with the PD-1 antibody molecule and/or PD-L1 antibody molecule is continued, and a TIM-3 immune inhibitory molecule (e.g., antibody) is added to the therapy.

In other embodiments, the anti-PD-1 antibody molecule is administered in combination with a cytokine, e.g., interleukin-21, interleukin-2, interleukin-12, or interleukin-15. In certain embodiments, the combination of anti-PD-1 antibody molecule and cytokine described herein is used to treat a cancer, e.g., a cancer as described herein (e.g., a solid tumor or melanoma).

Exemplary immunomodulators that can be used in combination with anti-PD-1 antibody molecules include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

In yet other embodiments, the anti-PD-1 antibody molecule is used in combination with an indoleamme-pyrrole 2,3-dioxygenase (IDO) inhibitor (e.g., INCB24360) in a subject with advanced or metastatic cancer (e.g., a patient with metastic and recurrent NSCL cancer).

In other embodiments, the anti-PD-1 antibody molecules are administered to a subject in conjunction with (e.g., before, simultaneously or following) one or more of: bone marrow transplantation, T cell ablative therapy using chemotherapy agents such as, fludarabine, external-beam radiation therapy (XRT), cyclophosphamide, and/or antibodies such as OKT3 or CAMPATH. In one embodiment, the anti-PD-1 antibody molecules are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive the anti-PD-1 antibody molecules. In an additional embodiment, the anti-PD-1 antibody molecules are administered before or following surgery.

Another example of a combination is an anti-PD-1 antibody in combination with decarbazine for the treatment of melanoma. Without being bound by theory, the combined use of PD-1 blockade and chemotherapy is believed to be facilitated by cell death, that is a consequence of the cytotoxic action of most chemotherapeutic compounds, which can result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors may also be combined with PD-1 blockade. Inhibition of angiogenesis leads to tumor cell death which may feed tumor antigen into host antigen presentation pathways.

PD-1 blocking antibodies can also be used in combination with bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of PD-1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies or antigen-binding fragments thereof to each of these entities may be used in combination with anti-PD-1 to counteract the effects of the immunosuppressive agent and favor tumor immune responses by the host.

Other antibodies which may be used to activate host immune responsiveness can be used in combination with anti-PD-1. These include molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjunction with PD-1 antibodies (Ito, N. et al. (2000) *Immunobiology* 201 (5) 527-40). Antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Additional exemplary standard of care treatments are described in the section entitled "Combination Therapies" below.

In all of the methods described herein, PD-1 blockade can be combined with other forms of immunotherapy such as cytokine treatment (e.g., interferons, GM-CSF, G-CSF, IL-2, IL-21), or bispecific antibody therapy, which provides for enhanced presentation of tumor antigens (see e.g., Holliger (1993) *Proc. Natl. Acad. Sci.* USA 90:6444-6448; Poljak (1994) *Structure* 2:1121-1123).

Methods of administering the antibody molecules are known in the art and are described below. Suitable dosages of the molecules used will depend on the age and weight of the subject and the particular drug used. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. In some embodiments, the anti-PD-1 antibody molecule is administered at a dose of about 1 mg/kg, about 3 mg/kg, or 10 mg/kg, about 20 mg/kg, about 30 mg/kg, or about 40 mg/kg. In some embodiments, the anti-PD-1 antibody molecule is administered at a dose of about 1-3 mg/kg, or about 3-10 mg/kg. In some embodiments, the anti-PD-1 antibody molecule is administered at a dose of about 0.5-2, 2-4, 2-5, 5-15, or 5-20 mg/kg. The dosing schedule can vary from e.g., once a week to once every 2, 3, or 4 weeks. In one embodiment, the anti-PD-1 antibody molecule is administered at a dose from about 10 to 20 mg/kg every other week.

The antibody molecules can be used in unconjugated forms or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Additional Combination Therapies

The anti-PD-1 antibody molecule can be used in combination with other therapies. For example, the combination therapy can include a composition of the present invention co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

By "in combination with," it is not intended to imply that the therapy or the therapeutic agents must be administered at the same time and/or formulated for delivery together, although these methods of delivery are within the scope described herein. The anti-PD-1 antibody molecules can be administered concurrently with, prior to, or subsequent to, one or more other additional therapies or therapeutic agents. The anti-PD-1 antibody molecule and the other agent or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In certain embodiments, the anti-PD-1 molecules described herein are administered in combination with one or more other inhibitors of PD-1, PD-L1 and/or PD-L2 known in the art. The antagonist may be an antibody, an antigen binding fragment thereof, an immunoadhesin, a fusion protein, or oligopeptide. In some embodiments, the other anti-PD-1 antibody is chosen from MDX-1106, Merck 3475 or CT-011. In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224. In some embodiments, the PD-L1 inhibitor is anti-PD-L1 antibody. In some embodiments, the anti-PD-L1 binding antagonist is chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634.

MDX-1106, also known as MDX-1106-04, ONO-4538 or BMS-936558, is an anti-PD-1 antibody described in WO2006/121168. Merck 3745, also known as MK-3475 or SCH-900475, is an anti-PD-1 antibody described in WO2009/114335. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. In other embodiments, the anti-PD-1 antibody is pembrolizumab. Pembrolizumab (Trade name Keytruda formerly lambrolizumab also known as MK-3475) disclosed, e.g., in Hamid, O. et al. (2013) *New England Journal of Medicine* 369 (2): 134-44. AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

In some embodiments, the other anti-PD-1 antibody is MDX-1106. Alternative names for MDX-1106 include MDX-1106-04, ONO-4538, BMS-936558 or Nivolumab. In some embodiments, the anti-PD-1 antibody is Nivolumab (CAS Registry Number: 946414-94-4). Nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Lambrolizumab (also referred to as pembrolizumab or MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No. 20120039906. Other anti-PD-L1 binding agents include YW243.55.570 (heavy and light chain variable regions are shown in SEQ ID NOs 20 and 21 in WO2010/077634) and MDX-1105 (also referred to as BMS-936559, and, e.g., anti-PD-L1 binding agents disclosed in WO2007/005874).

Cancer Therapies

Exemplary combinations of anti-PD-1 antibody molecules (alone or in combination with other stimulatory agents) and standard of care for cancer, include at least the following. In certain embodiments, the anti-PD-1 antibody molecule, e.g., the anti-PD-1 antibody molecule described herein, is used in combination with a standard of cancer care chemotherapeutic agent including, but not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids that can be used in combination with the anti-PD-1 antibody molecules, alone or in combination with another immunomodulator (e.g., an anti-LAG-3, anti-PD-L1 or anti-TIM-3 antibody molecule), include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors that can be used in combination with the anti-PD-1 antibody molecules, alone or in combination with another immunomodulator (e.g., an anti-LAG-3, anti-PD-L1 or anti-TIM-3 antibody molecule), include, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl) amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In some embodiments, the anti-PD-1 antibody molecule, e.g., the anti-PD-1 antibody molecule described herein, is used, alone or in combination with another immunomodulator (e.g., an anti-LAG-3, anti-PD-L1 or anti-TIM-3 antibody molecule), in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the hedgehog inhibitor is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951(tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68(SU6668), vatalanib, XL880 (GSK1363089, EXEL-2880). Selected tyrosine kinase inhibitors are chosen from sunitinib, erlotinib, gefitinib, or sorafenib.

In certain embodiments, the anti-PD-1 antibody molecule, e.g., the anti-PD-1 antibody molecule described herein, is used, alone or in combination with another immunomodulator (e.g., an anti-LAG-3, anti-PD-L1 or anti-TIM-3 antibody molecule), in combination with a Vascular Endothelial Growth Factor (VEGF) receptor inhibitors, including but not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2, 3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) *Cancer Res.* 57:4593-4599. In one embodiment, the anti-VEGF antibody is Bevacizumab (BV), also known as rhuMAb VEGF or AVASTIN®. It comprises mutated human IgG1 framework regions and antigen-binding complementarity-determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies see U.S. Pat. Nos. 7,060,269, 6,582,959, 6,703,020, 6,054,297, WO98/45332, WO 96/30046, WO94/10202, EP 0666868B1, U.S. Patent Application Publication Nos. 2006009360, 20050186208, 20030206899, 20030190317, 20030203409, and 20050112126; and Popkov et al, Journal of Immunological Methods 288: 149-164 (2004). Other antibodies include those that bind to a functional epitope on human VEGF comprising of residues F17, Ml 8, D19, Y21, Y25, Q89, 191, Kl 01, El 03, and C104 or, alternatively, comprising residues F17, Y21, Q22, Y25, D63, 183 and Q89.

In some embodiments, the anti-PD-1 antibody molecule, e.g., the anti-PD-1 antibody molecule described herein, is used, alone or in combination with another immunomodulator (e.g., an anti-LAG-3, anti-PD-L1 or anti-TIM-3 antibody molecule), in combination with a PI3K inhibitor. In one embodiment, the PI3K inhibitor is an inhibitor of delta and gamma isoforms of PI3K. Exemplary PI3K inhibitors that can be used in combination are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments, the anti-PD-1 antibody molecules described herein is used, alone or in combination with another immunomodulator (e.g., an anti-LAG-3, anti-PD-L1 or anti-TIM-3 antibody molecule), in combination with a mTOR inhibitor, e.g., one or more mTOR inhibitors chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.$0^{4,9}$] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and $N^2$-[1,4-dioxo-4-[[4-(4-oxo-8-phenyl-4H-1-benzopyran-2-yl)morpholinium-4-yl[methoxy]butyl]-L-arginylglycyl-L-α-aspartylL-serine-(SEQ ID NO: 237), inner salt (SF1126, CAS 936487-67-1), and XL765.

In some embodiments, the anti-PD-1 antibody molecule, e.g., the anti-PD-1 antibody molecule described herein, is used, alone or in combination with another immunomodulator (e.g., an anti-LAG-3, anti-PD-L1 or anti-TIM-3 antibody molecule), in combination with a BRAF inhibitor, e.g., GSK2118436, RG7204, PLX4032, GDC-0879, PLX4720, and sorafenib tosylate (Bay 43-9006).

In some embodiments, the anti-PD-1 antibody molecule, e.g., the anti-PD-1 antibody molecule described herein, is used, alone or in combination with another immunomodulator (e.g., an anti-LAG-3, anti-PD-L1 or anti-TIM-3 antibody molecule), in combination with a MEK inhibitor. In some embodiments, the combination of the anti-PD-1 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage. Any MEK inhibitor can be used in combination including, but not limited to, ARRY-142886, G02442104 (also known as GSK1120212), RDEA436, RDEA119/BAY 869766, AS703026, G00039805 (also known as AZD-6244 or selumetinib), BIX 02188, BIX 02189, CI-1040 (PD-184352), PD0325901, PD98059, U0126, GDC-0973 (Methanone, [3,4-difluoro-2-[(2-fluoro-4-iodophenyl)amino]phenyl][3-hydroxy-3-(25)-2-piperidinyl-1-azetidinyl]-), G-38963, G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983, the contents of which are incorporated herein by reference.

In some embodiments, the anti-PD-1 antibody molecule, e.g., the anti-PD-1 antibody molecule described herein, is used, alone or in combination with another immunomodulator (e.g., an anti-LAG-3, anti-PD-L1 or anti-TIM-3 antibody molecule), in combination with a JAK2 inhibitor, e.g., CEP-701, INCB18424, CP-690550 (tasocitinib).

In some embodiments, the pharmaceutical composition described herein is used, alone or in combination with another immunomodulator (e.g., an anti-LAG-3, anti-PD-L1 or anti-TIM-3 antibody molecule), in combination with paclitaxel or a paclitaxel agent, e.g., TAXOL®, protein-bound paclitaxel (e.g., ABRAXANE®). Exemplary paclitaxel agents include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term “brachytherapy,” refers to radiation therapy delivered by a spatially confined radioactive material inserted into the body at or near a tumor or other proliferative tissue disease site. The term is intended without limitation to include exposure to radioactive isotopes (e.g., At-211, O-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide (s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Anti-PD-1 antibody molecules, alone or in combination with another immunomodulator (e.g., an anti-LAG-3, anti-PD-L1 or anti-TIM-3 antibody molecule), can be administered in combination with one or more of the existing modalities for treating cancers, including, but not limited to: surgery; radiation therapy (e.g., external-beam therapy which involves three dimensional, conformal radiation therapy where the field of radiation is designed, local radiation (e.g., radiation directed to a preselected target or organ), or focused radiation). Focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray), e.g., as described in WO 2012/177624.

In certain embodiments, the anti-PD-1 antibody molecule, alone or in combination with another immunomodulator (e.g., an anti-LAG-3, anti-PD-L1 or anti-TIM-3 antibody molecule), is administered in combination with an antibody against a Killer-cell Immunoglobulin-like Receptors (also referred to herein as an "anti-KIR antibody"), a pan-KIR antibody, an anti-NKG2D antibody, and an anti-MICA antibody. In certain embodiments, the combination of anti-PD-1 antibody molecule and anti-KIR antibody, pan-KIR antibody, or an anti-NKG2D antibody described herein is used to treat a cancer, e.g., a cancer as described herein (e.g., a solid tumor, e.g., an advanced solid tumor).

In one embodiment, the anti-PD-1 antibody molecule, alone or in combination with another immunomodulator (e.g., an anti-LAG-3, anti-PD-L1 or anti-TIM-3 antibody molecule), is administered in combination with a cellular immunotherapy (e.g., Provenge (e.g., Sipuleucel)), and optionally in combination with cyclophosphamide. In certain embodiments, the combination of anti-PD-1 antibody molecule, Provenge and/or cyclophosphamide is used to treat a cancer, e.g., a cancer as described herein (e.g., a prostate cancer, e.g., an advanced prostate cancer).

In another embodiment, the anti-PD-1 antibody molecule, alone or in combination with another immunomodulator (e.g., an anti-LAG-3, anti-PD-L1 or anti-TIM-3 antibody molecule), is administered in combination with a vaccine, e.g., a dendritic cell renal carcinoma (DC-RCC) vaccine. In certain embodiments, the combination of anti-PD-1 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In yet another embodiment, the anti-PD-1 antibody molecule, alone or in combination with another immunomodulator (e.g., an anti-LAG-3, anti-PD-L1 or anti-TIM-3 antibody molecule), is administered in combination with chemotherapy, and/or immunotherapy. For example, the anti-PD-1 antibody molecule can be used to treat a myeloma, alone or in combination with one or more of: chemotherapy or other anti-cancer agents (e.g., thalidomide analogs, e.g., lenalidomide), an anti-TIM-3 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-PD-1 antibody molecule is used in combination with an anti-TIM-3 antibody to treat a myeloma, e.g., a multiple myeloma.

In one embodiment, the anti-PD-1 antibody molecule, alone or in combination with another immunomodulator (e.g., an anti-LAG-3, anti-PD-L1 or anti-TIM-3 antibody molecule), is used in combination with chemotherapy to treat a lung cancer, e.g., non-small cell lung cancer. In one embodiment, the anti-PD-1 antibody molecule is used with platinum doublet therapy to treat lung cancer.

In yet another embodiment, the anti-PD-1 antibody molecule, alone or in combination with another immunomodulator (e.g., an anti-LAG-3, anti-PD-L1 or anti-TIM-3 antibody molecule), is used to treat a renal cancer, e.g., renal cell carcinoma (RCC) (e.g., clear cell renal cell carcinoma (CCRCC) or metastatic RCC. The anti-PD-1 antibody molecule can be administered in combination with one or more of: an immune-based strategy (e.g., interleukin-2 or interferon-α), a targeted agent (e.g., a VEGF inhibitor such as a monoclonal antibody to VEGF); a VEGF tyrosine kinase inhibitor such as sunitinib, sorafenib, axitinib and pazopanib; an RNAi inhibitor), or an inhibitor of a downstream mediator of VEGF signaling, e.g., an inhibitor of the mammalian target of rapamycin (mTOR), e.g., everolimus and temsirolimus.

An example of suitable therapeutics for use in combination with the anti-PD-1 antibody molecules described herein, alone or in combination with another immunomodulator (e.g., an anti-LAG-3, anti-PD-L1 or anti-TIM-3 antibody molecule), for treatment of pancreatic cancer includes, but is not limited to, a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., R05126766); Notch signaling inhibitor (e.g., MK0752); monoclonal antibody-antibody fusion protein (e.g., L191L2); curcumin; HSP90 inhibitor (e.g., tanespimycin, STA-9090); rIL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., R04929097); ribonucleotide reductase inhibitor (e.g., 3-AP); immunotoxin (e.g., HuC242-DM4); PARP inhibitor (e.g., KU-0059436, veliparib); CTLA-4 inhbitor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the anti-PD-1 antibody molecules described herein.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of small cell lung cancer includes, but is not limited to, a chemotherapeutic agent, e.g., etoposide, carboplatin, cisplatin, oxaliplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of non-small cell lung cancer includes, but is not limited to, a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, R05083945), MET inhibitor (e.g., PF-02341066, ARQ 197), PI3K kinase inhibitor (e.g., XL147, GDC-0941), Raf/MEK dual kinase inhibitor (e.g., R05126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide (SEQ ID NO: 225)-TNF alpha conjugate, dichloroacetate (DCA), HGF inhibitor (e.g., SCH 900105), SAR240550, PPAR-gamma agonist (e.g., CS-7017), gamma-secretase inhibitor (e.g., R04929097), epigenetic therapy (e.g., 5-azacitidine), nitroglycerin, MEK inhibitor (e g, AZD6244), cyclin-dependent kinase inhibitor (e.g., UCN-01), cholesterol-Fusl, antitubulin agent (e.g., E7389), farnesyl-OH-transferase inhibitor (e.g., lonafarnib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of ovarian cancer includes, but is not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e g, AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., R04929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

In one exemplary embodiment, the anti-PD-1 antibody molecule, alone or in combination with another immunomodulator (e.g., an anti-LAG-3, anti-PD-L1 or anti-TIM-3 antibody molecule), is used to treat a myeloma, alone or in combination with one or more of: chemotherapy or other anti-cancer agents (e.g., thalidomide analogs, e.g., lenalidomide), HSCT (Cook, R. (2008) *J Manag Care Pharm.* 14(7 Suppl):19-25), an anti-TIM-3 antibody (Hallett, W H D et al.

(2011) *J of American Society for Blood and Marrow Transplantation* 17(8):1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) *Cancer J.* 15(6):502-10).

In yet another embodiment, the anti-PD-1 antibody molecule, alone or in combination with another immunomodulator (e.g., an anti-LAG-3, anti-PD-L1 or anti-TIM-3 antibody molecule), is used to treat a renal cancer, e.g., renal cell carcinoma (RCC) or metastatic RCC. The anti-PD-1 antibody molecule can be administered in combination with one or more of: an immune-based strategy (e.g., interleukin-2 or interferon-$\alpha$), a targeted agent (e.g., a VEGF inhibitor such as a monoclonal antibody to VEGF, e.g., bevacizumab (Rini, B. I. et al. (2010) *J. Clin. Oncol.* 28(13):2137-2143)); a VEGF tyrosine kinase inhibitor such as sunitinib, sorafenib, axitinib and pazopanib (reviewed in Pal. S. K. et al. (2014) *Clin. Advances in Hematology & Oncology* 12(2):90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) *N. Engl. J. Med.* 356(22): 2271-2281, Motzer, R. J. et al. (2008) *Lancet* 372: 449-456).

An example of suitable therapeutics for use in combination with the anti-PD-1 antibody molecules described herein, alone or in combination with another immunomodulator (e.g., an anti-LAG-3, anti-PD-L1 or anti-TIM-3 antibody molecule), for treatment of chronic myelogenous leukemia (AML) according to the invention includes, but is not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), ON 01910.Na, dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), Hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., R05045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of chronic lymphocytic leukemia (CLL) includes, but is not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, R05072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., R05045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG186, radiation therapy, bone marrow transplantation, stem cell transplantation, and a combination thereof.

An example of suitable therapeutics for use in combination with the anti-PD-1 antibody molecules described herein, alone or in combination with another immunomodulator (e.g., an anti-LAG-3, anti-PD-L1 or anti-TIM-3 antibody molecule), for treatment of acute lymphocytic leukemia (ALL) includes, but is not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., R05045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

An example of suitable therapeutics for use in combination with the anti-PD-1 antibody molecules described herein, alone or in combination with another immunomodulator (e.g., an anti-LAG-3, anti-PD-L1 or anti-TIM-3 antibody molecule), for treatment of acute myeloid leukemia (AML) includes, but is not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT3881L3 fusion protein, HDAC inhibitor (e.g., vorinostat, LBH589), plerixafor, mTOR inhibitor (e.g., everolimus), SRC inhibitor (e.g., dasatinib), HSP90 inhbitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., R05045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

An example of suitable therapeutics for use in combination with the anti-PD-1 antibody molecules described herein, alone or in combination with another immunomodulator (e.g., an anti-LAG-3, anti-PD-L1 or anti-TIM-3 antibody molecule), for treatment of multiple myeloma (MM) includes, but is not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), radiation therapy, bone marrow transplantation, stem cell transplantation, and a combination thereof.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of prostate cancer includes, but is not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of HNSCC includes, but is not limited to, one or both of Compound A8 as described herein (or a compound described in PCT Publication No. WO2010/029082) and cetuximab (e.g., Erbitux, marketed by BMS). In some embodiments, the therapeutic (e.g., the Compound A8 or compound related to A8) is a PI3K modulator, e.g., a PI3K inhibitor. In some embodiments, the therapeutic (e.g., cetuximab) modulates, e.g., inhibits, EGFR. In some embodiments, the cancer has, or is identified as having, elevated levels or activity of PI3K or EGFR compared to a control cell or reference value.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of gastric cancer, e.g., MSI-high and/or EBV+ gastric cancer, includes, but is not limited to, Compound A8 as described herein (or a compound described in PCT Publication No. WO2010/029082). In some embodiments, the therapeutic (e.g., the Compound A8 or compound related to A8) is a PI3K modulator, e.g., a PI3K inhibitor. In some embodiments, the cancer has, or is identified as having, elevated levels or activity of PI3K compared to a control cell or reference value.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of gastric cancer, e.g., MSI-high and/or RNF43-inactivated gastric cancer, includes, but is not limited to, Compound A28 as described herein (or a compound described in PCT Publication No. WO2010/101849). In some embodiments, the therapeutic (e.g., the Compound A28 or compound related to A28) is a modulator, e.g., inhibitor, of porcupine. In some embodiments, the cancer has, or is identified as having, elevated levels or activity of porcupine compared to a control cell or reference value.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of GI stromal tumor (GIST), includes, but is not limited to, Compound A16 as described herein (or a compound described in PCT Publication No. WO1999/003854). In some embodiments, the therapeutic (e.g., the Compound A16 or compound related to A16) is a modulator, e.g., inhibitor, of a tyrosine kinase. In some embodiments, the cancer has, or is determined to have, elevated levels or activity of a tyrosine kinase compared to a control cell or reference value.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of NSCLC, e.g., squamous or adenocarcinoma, includes, but is not limited to, one or both of Compound A17 as described herein (or a compound described in U.S. Pat. Nos. 7,767,675 and 8,420,645) and Compound A23 as described herein (or a compound described in PCT Publication No. WO2003/077914). In some embodiments, the compound (e.g., the Compound A17 or compound related to A17) modulates, e.g., inhibits, c-MET. In some embodiments, the compound (e.g., the Compound A23 or compound related to A23) modulates, e.g., inhibits, Alk. In some embodiments, the cancer has, or is determined to have, elevated levels or activity of one or both of c-MET or Alk compared to a control cell or reference value. In some embodiments, the cancer has, or is identified as having, a mutation in EGFR.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of melanoma (e.g., NRAS melanoma) includes, but is not limited to, one or both of Compound A24 as described herein (or a compound described in U.S. Pat. Nos. 8,415,355 and 8,685,980) and Compound A34 as described herein (or a compound described in PCT Publication No. WO2003/077914). In some embodiments, the compound (e.g., the Compound A24 or compound related to A24) modulates, e.g., inhibits, one or more of JAK and CDK4/6. In some embodiments, the compound (e.g., the Compound A34 or compound related to A34) modulates, e.g., inhibits, MEK. In some embodiments, the cancer has, or is identified as having, elevated levels or activity of one or more of JAK, CDK4/6, and MEK compared to a control cell or reference value.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of melanoma (e.g., NRAS melanoma) includes, but is not limited to, one or both of Compound A29 as described herein (or a compound described in PCT Publication No. WO2011/025927) and Compound A34 as described herein (or a compound described in PCT Publication No. WO2003/077914). In some embodiments, the compound (e.g., the Compound A29 or compound related to A29) modulates, e.g., inhibits, BRAF. In some embodiments, the compound (e.g., the Compound A34 or compound related to A34) modulates, e.g., inhibits, MEK. In some embodiments, the cancer has, or is identified as having, elevated levels or activity of one or both of BRAF and MEK compared to a control cell or reference value.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of squamous NSCLC includes, but is not limited to, Compound A5 as described herein (or a compound described in U.S. Pat. No. 8,552,002). In some embodiments, the compound (e.g., the Compound A5 or compound related to A5) modulates, e.g., inhibits, FGFR. In some embodiments, the cancer has, or is identified as having, elevated levels or activity of FGFR compared to a control cell or reference value.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of colorectal cancer includes, but is not limited to, one or both of Compound A29 as described herein (or a compound PCT Publication No. WO2011/025927) and cetuximab (e.g., Erbitux, marketed by BMS). In some embodiments, the therapeutic (e.g., the Compound A29 or compound related to A29) modulates, e.g., inhibits, BRAF. In some embodiments, the therapeutic (e.g., cetuximab) modulates, e.g., inhibits EGFR. In some embodiments, the cancer has, or is identified as having, elevated levels or activity of BRAF or EGFR compared to a control cell or reference value.

This disclosure also provides a method of treating cancer with Compound A8, cetuximab, and a PD-1 antibody molecule (optionally in combination with a TIM-3 antibody molecule or LAG-3 antibody molecule). In some embodiments, the patient is first treated with Compound A8 and cetuximab. This treatment continues for an amount of time, e.g., a predetermined amount of time, e.g., about 1, 2, 4, 6, 8, 10, or 12 months. Next, the PD-1 antibody molecule (optionally in combination with a TIM-3 antibody molecule or LAG-3 antibody molecule) is administered. The PD-1 antibody can optionally be administered in combination with cetuximab.

In some embodiments, the patient is first treated with all three of Compound A8, cetuximab, and a PD-1 antibody molecule (optionally in combination with a TIM-3 antibody molecule or LAG-3 antibody molecule). This treatment continues for an amount of time, e.g., a predetermined amount of time, e.g., about 6, 8, 10, or 12 months. Next, the Compound A8 and/or cetuximab can be tapered off, so that the maintenance phase involves treatment with the PD-1 antibody molecule (e.g., as a monotherapy, or in combination with a TIM-3 antibody molecule or LAG-3 antibody molecule) but not Compound A8 or cetuximab.

In other embodiments, the three compounds (Compound A8, cetuximab, and a PD-1 antibody molecule, optionally in combination with a TIM-3 antibody molecule or LAG-3 antibody molecule) are given sequentially at the outset of the treatment. For instance, Compound A8 and cetuximab can be given first, as described above. Next, the PD-1 antibody molecule (optionally in combination with a TIM-3 antibody molecule or LAG-3 antibody molecule) is added to the regimen. Next, the Compound A8 and/or cetuximab can be tapered off as described above.

Exemplary doses for the three (or more) agent regimens are as follows. The PD-1 antibody molecule can be administered, e.g., at a dose of about 1 to 40 mg/kg, e.g., 1 to 30 mg/kg, e.g., about 5 to 25 mg/kg, about 10 to 20 mg/kg, about 1 to 5 mg/kg, or about 3 mg/kg. In some embodiments, the Compound A8 is administered at a dose of approximately 200-300, 300-400, or 200-400 mg. In some embodiments, the cetuximab is administered at a 400 mg/m2 initial dose as a 120-minute intravenous infusion followed by 250 mg/m2 weekly infused over 60 minutes. In embodiments, one or more of the Compound A8, cetuximab, and PD-1 antibody molecule is administered at a dose that is lower than the dose at which that agent is typically administered as a monotherapy, e.g., about 0-10%, 10-20%, 20-30%, 30-40%, 40-50%, 50-60%, 60-70%, 70-80%, or 80-90% lower than the dose at which that agent is typically administered as a monotherapy. In embodiments, the one or more of the Compound A8, cetuximab, and PD-1 antibody molecule is administered at a dose that is lower than the dose of that agent recited in this paragraph, e.g., about 0-10%, 10-20%, 20-30%, 30-40%, 40-50%, 50-60%, 60-70%, 70-80%, or 80-90% lower than the dose of that agent recited in this paragraph. In certain embodiments, the concentration of the Compound A8 that is required to achieve inhibition, e.g., growth inhibition, is lower when the Compound A8 is administered in combination with one or both of the cetuximab and PD-1 antibody molecule than when the Compound A8 is administered individually. In certain embodiments, the concentration of the cetuximab that is required to achieve inhibition, e.g., growth inhibition, is lower when the cetuximab is administered in combination with one or both of the Compound A8 and PD-1 antibody molecule than when the cetuximab is administered individually. In certain embodiments, the concentration of the PD-1 antibody molecule that is required to achieve inhibition, e.g., growth inhibition, is lower when the PD-1 antibody molecule is administered in combination with one or both of the cetuximab and Compound A8 than when the PD-1 antibody molecule is administered individually.

Additionally disclosed herein is a method of treating cancer with the anti-PD-1 antibody molecules, alone or in combination with another immunomodulator (e.g., an anti-LAG-3, anti-PD-L1 or anti-TIM-3 antibody molecule), and a targeted anti-cancer agent, e.g., an agent that targets one or more proteins. In some embodiments, the anti-PD-1 antibody molecule (and optionally other immunomodulator(s)) are administered first, and the targeted anti-cancer agent is administered second. The length of time between administration of the anti-PD-1 antibody molecule and the targeted anti-cancer agent can be, e.g., 10, 20, or 30 minutes, 1, 2, 4, 6, or 12 hours, or 1, 2, 3, 4, 5, 6, or 7 days, or any span of time within this range. In certain embodiments, the anti-PD-1 antibody molecule is administered repeatedly over a period of time (e.g., 1, 2, 3, 4, 5, or 6 days, or 1, 2, 4, 8, 12, 16, or 20 weeks, or any span of time within this range) before the targeted anti-cancer agent is administered. In other embodiments, the anti-PD-1 antibody molecule and the targeted anti-cancer agent are administered at substantially the same time.

Infectious Diseases

Other methods of the invention are used to treat patients that have been exposed to particular toxins or pathogens. Accordingly, another aspect of the invention provides a method of treating an infectious disease in a subject comprising administering to the subject an anti-PD-1 antibody molecule, such that the subject is treated for the infectious disease.

In the treatment of infection (e.g., acute and/or chronic), administration of the anti-PD-1 antibody molecules can be combined with conventional treatments in addition to or in lieu of stimulating natural host immune defenses to infection. Natural host immune defenses to infection include, but are not limited to inflammation, fever, antibody-mediated host defense, T-lymphocyte-mediated host defenses, including lymphokine secretion and cytotoxic T-cells (especially during viral infection), complement mediated lysis and opsonization (facilitated phagocytosis), and phagocytosis. The ability of the anti-PD-1 antibody molecules to reactivate dysfunctional T-cells would be useful to treat chronic infections, in particular those in which cell-mediated immunity is important for complete recovery.

Similar to its application to tumors as discussed above, antibody mediated PD-1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas Aeruginosa*. PD-1 blockade is particularly useful against established infections by agents such as HIV that present altered antigens over the course of the infections. These novel epitopes are recognized as foreign at the time of anti-human PD-1 administration, thus provoking a strong T cell response that is not dampened by negative signals through PD-1.

Viruses

For infections resulting from viral causes, the anti-PD-1 antibody molecules can be combined by application simultaneous with, prior to or subsequent to application of standard therapies for treating viral infections. Such standard therapies vary depending upon type of virus, although in almost all cases, administration of human serum containing antibodies (e.g., IgA, IgG) specific to the virus can be effective.

Some examples of pathogenic viruses causing infections treatable by methods include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In one embodiment, the infection is an influenza infection. Influenza infection can result in fever, cough, myalgia, headache and malaise, which often occur in seasonal epidemics. Influenza is also associated with a number of postinfectious disorders, such as encephalitis, myopericarditis, Goodpasture's syndrome, and Reye's syndrome. Influenza infection also suppresses normal pulmonary antibacterial defenses, such that patient's recovering from influenza have an increased risk of developing bacterial pneumonia. Influenza viral surface proteins show marked antigenic variation, resulting from mutation and recombination. Thus, cytolytic T lymphocytes are the host's primary vehicle for the elimination of virus after infection. Influenza is classified into three primary types: A, B and C. Influenza A is unique in that it infects both humans and many other animals (e.g., pigs, horses, birds and seals) and is the principal cause of pandemic influenza. Also, when a cell is infected by two different influenza A strains, the segmented RNA genomes of two parental virus types mix during replication to create a hybrid replicant, resulting in new epidemic strains. Influenza B does not replicate in animals and thus has less genetic variation and influenza C has only a single serotype.

Most conventional therapies are palliatives of the symptoms resulting from infection, while the host's immune response actually clears the disease. However, certain strains (e.g., influenza A) can cause more serious illness and death. Influenza A may be treated both clinically and prophylactically by the administration of the cyclic amines inhibitors amantadine and rimantadine, which inhibit viral replication. However, the clinical utility of these drugs is limited due to the relatively high incidence of adverse reactions, their narrow anti-viral spectrum (influenza A only), and the propensity of the virus to become resistant. The administration of serum IgG antibody to the major influenza surface proteins, hemagglutinin and neuraminidase can prevent pulmonary infection, whereas mucosal IgA is required to prevent infection of the upper respiratory tract and trachea. The most effective current treatment for influenza is vaccination with the administration of virus inactivated with formalin or β-propiolactone.

In another embodiment, the infection is a hepatitis infection, e.g., a Hepatitis B or C infection.

Hepatitis B virus (HB-V) is the most infectious known bloodborne pathogen. It is a major cause of acute and chronic heptatis and hepatic carcinoma, as well as life-long, chronic infection. Following infection, the virus replicates in hepatocytes, which also then shed the surface antigen HBsAg. The detection of excessive levels of HBsAg in serum is used a standard method for diagnosing a hepatitis B infection. An acute infection may resolve or it can develop into a chronic persistent infection. Current treatments for chronic HBV include α-interferon, which increases the expression of class I human leukocyte antigen (HLA) on the surface of hepatocytes, thereby facilitating their recognition by cytotoxic T lymphocytes. Additionally, the nucleoside analogs ganciclovir, famciclovir and lamivudine have also shown some efficacy in the treatment of HBV infection in clinical trials. Additional treatments for HBV include pegylated α-interferon, adenfovir, entecavir and telbivudine. While passive immunity can be conferred through parental administration of anti-HBsAg serum antibodies, vaccination with inactivated or recombinant HBsAg also confers resistance to infection. The anti-PD-1 antibody molecules may be combined with conventional treatments for hepatitis B infections for therapeutic advantage.

Hepatitis C virus (HC-V) infection may lead to a chronic form of hepatitis, resulting in cirrosis. While symptoms are similar to infections resulting from Hepatitis B, in distinct contrast to HB-V, infected hosts can be asymptomatic for 10-20 years. The anti-PD-1 antibody molecule can be administered as a monotherapy, or combined with the standard of care for hepatitis C infection. For example, the anti-PD-1 antibody molecule can be administered with one or more of Sovaldi (sofosbuvir) Olysio (simeprevir), plus ribavirin or pegylated interferon. Although regimens that include Incivek (telaprevir) or Victrelis (boceprevir) plus ribavirin and pegylated interferon are also approved, they are associated with increased side effects and longer duration of treatment and are therefore not considered preferred regimens.

Conventional treatment for HC-V infection includes the administration of a combination of α-interferon and ribavirin. A promising potential therapy for HC-V infection is the protease inhibitor telaprevir (VX-960). Additional treatments include: anti-PD-1 antibody (MDX-1106, Medarex), bavituximab (an antibody that binds anionic phospholipid phosphatidylserine in a B2-glycoprotein I dependent manner, Peregrine Pharmaceuticals), anti-HPV viral coat protein E2 antibod(y)(ies) (e.g., ATL 6865-Ab68+Ab65, XTL Pharmaceuticals) and Civacir® (polyclonal anti-HCV human immune globulin). The anti-PD-L1 antibodies of the invention may be combined with one or more of these treatments for hepatitis C infections for therapeutic advantage. Protease, polymerase and NS5A inhibitors which may be used in combination with the anti-PD-1 antibody molecules to specifically treat Hepatitis C infection include those described in US 2013/0045202, incorporated herein by reference.

In another embodiment, the infection is a measles virus. After an incubation of 9-11 days, hosts infected with the measles virus develop fever, cough, coryza and conjunctivitis. Within 1-2 days, an erythematous, maculopapular rash develop, which quickly spreads over the entire body. Because infection also suppresses cellular immunity, the host is at greater risk for developing bacterial superinfections, including otitis media, pneumonia and postinfectious encephalomyelitis. Acute infection is associated with significant morbidity and mortality, especially in malnourished adolescents.

Treatment for measles includes the passive administration of pooled human IgG, which can prevent infection in non-immune subjects, even if given up to one week after exposure. However, prior immunization with live, attenuated virus is the most effective treatment and prevents disease in more than 95% of those immunized. As there is one serotype of this virus, a single immunization or infection typically results in protection for life from subsequent infection.

In a small proportion of infected hosts, measles can develop into SSPE, which is a chronic progressive neurologic disorder resulting from a persistent infection of the central nervous system. SSPE is caused by clonal variants of measles virus with defects that interfere with virion assembly and budding. For these patients, reactivation of T-cells with the anti-PD-1 antibody molecules so as to facilitate viral clearance would be desirable.

In another embodiment, the infection is HIV. HIV attacks $CD4^+$ cells, including T-lymphocytes, monocyte-macrophages, follicular dendritic cells and Langerhan's cells, and $CD4^+$ helper/inducer cells are depleted. As a result, the host acquires a severe defect in cell-mediated immunity. Infection with HIV results in AIDS in at least 50% of individuals, and is transmitted via sexual contact, administration of infected blood or blood products, artificial insemination with infected semen, exposure to blood-containing needles or syringes and transmission from an infected mother to infant during childbirth.

A host infected with HIV may be asymptomatic, or may develop an acute illness that resembling mononucleosis—fever, headache, sore throat, malaise and rash. Symptoms can progress to progressive immune dysfunction, including persistent fever, night sweats, weight loss, unexplained diarrhea, eczema, psoriasis, seborrheic dermatitis, herpes zoster, oral candidiasis and oral hairy leukoplakia. Opportunistic infections by a host of parasites are common in patients whose infections develop into AIDS.

Treatments for HIV include antiviral therapies including nucleoside analogs, zidovudine (AST) either alone or in combination with didanosine or zalcitabine, dideoxyinosine, dideoxycytidine, lamidvudine, stavudine; reverse transcriptive inhibitors such as delavirdine, nevirapine, loviride, and proteinase inhibitors such as saquinavir, ritonavir, indinavir and nelfinavir. The anti-PD-1 antibody molecules may be combined with conventional treatments for HIV infections for therapeutic advantage.

In another embodiment, the infection is a Cytomegalovirus (CMV). CMV infection is often associated with persistent, latent and recurrent infection. CMV infects and remains latent in monocytes and granulocyte-monocyte progenitor cells. The clinical symptoms of CMV include mononucleosis-like symptoms (i.e., fever, swollen glands, malaise), and a tendancy to develop allergic skin rashes to antibiotics. The virus is spread by direct contact. The virus is shed in the urine, saliva, semen and to a lesser extent in other body fluids. Transmission can also occur from an infected mother to her fetus or newborn and by blood transfusion and organ transplants. CMV infection results in general impairment of cellular immunity, characterized by impaired blastogenic responses to nonspecific mitogens and specific CMV antigens, diminished cytotoxic ability and elevation of CD8 lymphocyte number of $CD4^+$ lymphocytes.

Treatments of CMV infection include the anti-virals ganciclovir, foscarnet and cidovir, but these druges are typically only prescribed in immunocompromised patients. The anti-PD-1 antibody molecules may be combined with conventional treatments for cytomegalovirus infections for therapeutic advantage.

In another embodiment, the infection is Epstein-Barr virus (EBV). EBV can establish persistent and latent infections and primarily attacks B cells. Infection with EBV results in the clinical condition of infectious mononucleosis, which includes fever, sore throat, often with exudate, generalized lymphadenopathy and splenomegaly. Hepatitis is also present, which can develop into jaundice.

While typical treatments for EBV infections are palliative of symptoms, EBV is associated with the development of certain cancers such as Burkitt's lymphoma and nasopharyngeal cancer. Thus, clearance of viral infection before these complications result would be of great benefit. The anti-PD-1 antibody molecules may be combined with conventional treatments for Epstein-Ban virus infections for therapeutic advantage.

In another embodiment, the infection is Herpes simplex virus (HSV). HSV is transmitted by direct contact with an infected host. A direct infection may be asymptomatic, but typically result in blisters containing infectious particles. The disease manifests as cycles of active periods of disease, in which lesions appear and disappear as the viral latently infect the nerve ganglion for subsequent outbreaks. Lesions may be on the face, genitals, eyes and/or hands. In some case, an infection can also cause encephalitis.

Treatments for herpes infections are directed primarily to resolving the symptomatic outbreaks, and include systemic antiviral medicines such as: acyclovir (e.g., Zovirax®), valaciclovir, famciclovir, penciclovir, and topical medications such as docosanol (Abreva®), tromantadine and zilactin. The clearance of latent infections of herpes would be of great clinical benefit. The anti-PD-1 antibody molecules may be combined with conventional treatments for herpes virus infections for therapeutic advantage.

In another embodiment, the infection is Human T-lymphotrophic virus (HTLV-1, HTLV-2). HTLV is transmitted via sexual contact, breast feeding or exposure to contaminated blood. The virus activates a subset of $T_H$ cells called Th1 cells, resulting in their overproliferation and overproduction of Th1 related cytokines (e.g., IFN-γ and TNF-α). This in turn results in a suppression of Th2 lymphocytes and reduction of Th2 cytokine production (e.g., IL-4, IL-5, IL-10 and IL-13), causing a reduction in the ability of an infected host to mount an adequate immune response to invading organisms requiring a Th2-dependent response for clearance (e.g., parasitic infections, production of mucosal and humoral antibodies).

HTLV infections cause lead to opportunistic infections resulting in bronchiectasis, dermatitis and superinfections with *Staphylococcus* spp. and *Strongyloides* spp. resulting in death from polymicrobial sepsis. HTLV infection can also lead directly to adult T-cell leukemia/lymphoma and progressive demyelinating upper motor neuron disease known as HAM/TSP. The clearance of HTLV latent infections would be of great clinical benefit. The anti-PD-1 antibody molecules may be combined with conventional treatments for HTLV infections for therapeutic advantage.

In another embodiment, the infection is Human papilloma virus (HPV). HPV primarily affects keratinocytes and occurs in two forms: cutaneous and genital. Transmission is believed to occur through direct contact and/or sexual activity. Both cutaneous and genital HPV infection, can result in warts and latent infections and sometimes recurring infections, which are controlled by host immunity which controls the symptoms and blocks the appearance of warts, but leaves the host capable of transmitting the infection to others.

Infection with HPV can also lead to certain cancers, such as cervical, anal, vulvar, penile and oropharynial cancer. There are no known cures for HPV infection, but current treatment is topical application of Imiquimod, which stimulates the immune system to attack the affected area. The clearance of HPV latent infections would be of great clinical benefit. The anti-PD-L1 antibodies of the invention may be combined with conventional treatments for HPV infections for therapeutic advantage.

Bacterial Infections

Some examples of pathogenic bacteria causing infections treatable by methods of the invention include syphilis, *chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis*, and *Lymes* disease bacteria. The anti-PD-1 antibody molecules can be used in combination with existing treatment modalities for the aforesaid infections. For example, Treatments for syphilis include penicillin (e.g., penicillin G.), tetracycline, doxycycline, ceftriaxone and azithromycin.

Lyme disease, caused by *Borrelia burgdorferi* is transmitted into humans through tick bites. The disease manifests initially as a localized rash, followed by flu-like symptoms including malaise, fever, headache, stiff neck and arthralgias. Later manifestations can include migratory and polyarticular arthritis, neurologic and cardiac involvement with cranial nerve palsies and radiculopathy, myocarditis and arrhythmias. Some cases of Lyme disease become persistent, resulting in irreversible damage analogous to tertiary syphilis. Current therapy for Lyme disease includes primarily the administration of antibiotics. Antibiotic-resistant strains may be treated with hydroxychloroquine or methotrexate. Antibiotic refractory patients with neuropathic pain can be treated with gabapentin. Minocycline may be helpful in late/chronic Lyme disease with neurological or other inflammatory manifestations.

Other forms of borreliois, such as those resulting from *B. recurentis, B. hermsii, B. turicatae, B. parikeri., B. hispanica, B. duttonii* and *B. persica*, as well leptospirosis (E.g., *L. interrogans*), typically resolve spontaneously unless blood titers reach concentrations to cause intrahepatic obstruction.

Fungi and Parasites

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), *Genus Mucorales* (*mucor, absidia, rhizophus*), *Sporothrix schenkii, Blastomyces dermatitidis, Paracoccidioides brasiliensis, Coccidioides immitis* and *Histoplasma capsulatum.*

Some examples of pathogenic parasites causing infections treatable by methods described herein include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

Additional Combination Therapies

Combinations of PD-1 antibody molecules with one or more second therapeutics are provided herein. Many of the combinations in this section are useful in treating cancer, but other indications are also described. This section focuses on combinations of anti-PD-1 antibody molecules, optionally in combination with one or more immunomodulators (e.g., an anti-TIM-3 antibody molecule, an anti-LAG-3 antibody molecule, or an anti-PD-L1 antibody molecule), with one or more of the agents described in Table 7. In the combinations herein below, in one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In the combinations herein below, in another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33.

In one embodiment, the anti-PD-1 antibody molecule, e.g., an anti-PD-1 antibody molecule as described herein, alone or in combination with one or more other immunomodulators, is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, a PD-1 antibody molecule is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis.

In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the anti-PD-1 antibody molecule, e.g., an anti-PD-1 antibody molecule as described herein, alone or in combination with one or more other immunomodulators, is used in combination with a BCR-ABL inhibitor, TASIGNA (Compound A2), or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, a PD-1 antibody molecule is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension.

In one embodiment, the BCR-ABL inhibitor or TASIGNA is administered at a dose of about 300 mg (e.g., twice daily, e.g., for newly diagnosed Ph+ CML-CP), or about 400 mg, e.g., twice daily, e.g., for resistant or intolerant Ph+ CML-CP and CML-AP). BCR-ABL inhibitor or a Compound A2 is administered at a dose of about 300-400 mg.

In another embodiment, the anti-PD-1 antibody molecule, e.g., an anti-PD-1 antibody molecule as described herein, alone or in combination with one or more other immunomodulators, is used in combination with an HSP90 inhibitor, such as 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051. In one embodiment, a PD-1 antibody molecule is used in combination with 5-(2,4-dihydroxy-5-isopropylphenyl)-N-ethyl-4-(4-(morpholinomethyl)phenyl) isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the anti-PD-1 antibody molecule, e.g., an anti-PD-1 antibody molecule as described herein, alone or in combination with one or more other immunomodulators, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, a PD-1 antibody molecule is used in combination with Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the anti-PD-1 antibody molecule, e.g., an anti-PD-1 antibody molecule as described herein, alone or in combination with one or more other immunomodulators, is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, a PD-1 antibody molecule is used in combination with Compound A5, or a compound as described in U.S. Pat. No. 8,552,002, to treat a disorder such as a digestive/gastrointestinal cancer, a hematological cancer, or a solid tumor.

In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurea (Compound A5) is administered at a dose of about 100-125 mg (e.g., per day), e.g., about 100 mg or about 125 mg.

In another embodiment, the anti-PD-1 antibody molecule, e.g., an anti-PD-1 antibody molecule as described herein, alone or in combination with one or more other immunomodulators, is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, a PD-1 antibody molecule is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer.

In one embodiment, the PI3K inhibitor or Buparlisib (Compound A6) is administered at a dose of about 100 mg (e.g., per day).

In another embodiment, the anti-PD-1 antibody molecule, e.g., an anti-PD-1 antibody molecule as described herein, alone or in combination with one or more other immunomodulators, is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386 to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide(Compound A7) or a compound disclosed in a PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide(Compound A7). In one embodiment, a PD-1 antibody molecule is used in combination with 8-(2,6-difluoro-3,5-dimethoxyphenyl)-N-(4-((dimethylamino)methyl)-1H-imidazol-2-yl)quinoxaline-5-carboxamide(Compound A7), or a compound disclosed in PCT Publication No. WO 2009/141386, to treat a disorder such as a cancer characterized by angiogenesis.

In one embodiment, the FGFR inhibitor or 8-(2,6-difluoro-3,5-dimethoxyphenyl)-N-(4-((dimethylamino)methyl)-1H-imidazol-2-yl)quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment, the anti-PD-1 antibody molecule, e.g., an anti-PD-1 antibody molecule as described herein, alone or in combination with one or more other immunomodulators, is used in combination with a PI3K inhibitor, (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082 to treat a disorder, e.g., a disorder described herein. In one embodiment, the PI3K inhibitor is (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, a PD-1 antibody molecule is used in combination with (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer.

In one embodiment, the PI3K inhibitor or (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the anti-PD-1 antibody molecule, e.g., an anti-PD-1 antibody molecule as described herein, alone or in combination with one or more other immunomodulators, is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, a PD-1 antibody molecule is used in combination with a compound disclosed in PCT Publication No. WO 2010/149755, to treat prostate cancer.

In another embodiment, the anti-PD-1 antibody molecule, e.g., an anti-PD-1 antibody molecule as described herein, alone or in combination with one or more other immunomodulators, is used in combination with an HDM2 inhibitor, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one(Compound A10) or a compound disclosed in PCT Publication No. WO 2011/076786 to treat a disorder, e.g., a disorder described herein). In one embodiment, the HDM2 inhibitor is (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, a PD-1 antibody molecule is used in combination with (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10), or a compound disclosed in PCTPublication No. WO 2011/076786, to treat a disorder such as a solid tumor.

In one embodiment, the HDM2 inhibitor or (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the anti-PD-1 antibody molecule, e.g., an anti-PD-1 antibody molecule as described herein, alone or in combination with one or more other immunomodulators, is used in combination with an iron chelating agent, Deferasirox (also known as EXJADE; Compound A11), or a compound disclosed in PCT Publication No. WO 1997/049395 to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, a PD-1 antibody molecule is used in combination with Deferasirox (Compound A11), or a compound disclosed in PCT Publication No. WO 1997/049395, to treat iron overload, hemochromatosis, or myelodysplasia.

In another embodiment, the anti-PD-1 antibody molecule, e.g., an anti-PD-1 antibody molecule as described herein, alone or in combination with one or more other immunomodulators, is used in combination with an aromatase inhibitor, Letrozole (also known as FEMARA; Compound A12), or a compound disclosed in U.S. Pat. No. 4,978,672 to treat a disorder, e.g., a disorder described herein. In one embodiment, the aromatase inhibitor is Letrozole (Compound A12) or a compound disclosed in U.S. Pat. No. 4,978,672. In one embodiment, a PD-1 antibody molecule is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the anti-PD-1 antibody molecule, e.g., an anti-PD-1 antibody molecule as described herein, alone or in combination with one or more other immunomodulators, is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826 to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, a PD-1 antibody molecule is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the anti-PD-1 antibody molecule, e.g., an anti-PD-1 antibody molecule as described herein, alone or in combination with one or more other immunomodulators, is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105 to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, a PD-1 antibody molecule is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, the anti-PD-1 antibody molecule, e.g., an anti-PD-1 antibody molecule as described herein, alone or in combination with one or more other immunomodulators, is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224 to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, a PD-1 antibody molecule is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In another embodiment, the anti-PD-1 antibody molecule, e.g., an anti-PD-1 antibody molecule as described herein, alone or in combination with one or more other immunomodulators, is used in combination with an apoptosis inducer and/or an angiogenesis inhibitor, such as Imatinib mesylate (also known as GLEEVEC; Compound A16) or a compound disclosed in PCT Publication No. WO1999/003854 to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, a PD-1 antibody molecule is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis.

In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the anti-PD-1 antibody molecule, e.g., an anti-PD-1 antibody molecule as described herein, alone or in combination with one or more other immunomodulators, is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, a PD-1 antibody molecule is used in combination with 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia.

In one embodiment, the JAK inhibitor or a 2-fluoro-N-methyl-4-(7-(quinolin-6-ylmethyl)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the anti-PD-1 antibody molecule, e.g., an anti-PD-1 antibody molecule as described herein, alone or in combination with one or more other immunomodulators, is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, a PD-1 antibody molecule is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia.

In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the anti-PD-1 antibody molecule, e.g., an anti-PD-1 antibody molecule as described herein, alone or in combination with one or more other immunomodulators, is used in combination with a deacetylase (DAC) inhibitor, Panobinostat (Compound A19), or a compound disclosed in PCT Publication No. WO 2014/072493 to treat a disorder, e.g., a disorder described herein. In one embodiment, the DAC inhibitor is Panobinostat (Compound A19) or a compound disclosed in PCT Publication No. WO 2014/072493. In one embodiment, a PD-1 antibody molecule is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer.

In one embodiment, the DAC inhibitor or Panobinostat (Compound A19) is administered at a dose of about 20 mg (e.g., per day).

In another embodiment, the anti-PD-1 antibody molecule, e.g., an anti-PD-1 antibody molecule as described herein, alone or in combination with one or more other immunomodulators, is used in combination with an inhibitor of one or more of cytochrome P450 (e.g., 11B2), aldosterone or angiogenesis, Osilodrostat (Compound A20), or a compound disclosed in PCT Publication No. WO2007/024945 to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, a PD-1 antibody molecule is used in combination with Osilodrostat (Compound A20), or a compound disclosed in PCT Publication No. WO2007/024945, to treat a disorder such as Cushing's syndrome, hypertension, or heart failure therapy.

In another embodiment, the anti-PD-1 antibody molecule, e.g., an anti-PD-1 antibody molecule as described herein, alone or in combination with one or more other immunomodulators, is used in combination with a IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 to treat a disorder, e.g., a disorder described herein. In one embodiment, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003. In one embodiment, a PD-1 antibody molecule is used in combination with (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder.

In one embodiment, the IAP inhibitor or (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg, e.g., once weekly.

In another embodiment, the anti-PD-1 antibody molecule, e.g., an anti-PD-1 antibody molecule as described herein, alone or in combination with one or more other immunomodulators, is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, a PD-1 antibody molecule is used in combination with Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation.

In certain embodiments, Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the anti-PD-1 antibody molecule, e.g., an anti-PD-1 antibody molecule as described herein, alone or in combination with one or more other immunomodulators, is used in combination with an Alk inhibitor, ceritinib (also known as ZYKADIA: Compound A23) or a compound disclosed in PCT Publication No. WO 2007/131201 to treat a disorder, e.g., a disorder described herein. In one embodiment, the Alk inhibitor is ceritinib (Compound A23) or a compound disclosed in PCT Publication No. WO 2007/131201. In one embodiment, a PD-1 antibody molecule is used in combination with ceritinib (Compound A23), or a compound disclosed in PCT Publication No. WO 2007/131201, to treat a disorder such as non-small cell lung cancer or solid tumors.

In one embodiment, the Alk inhibitor or ceritinib (Compound A23) is administered at a dose of approximately 750 mg, e.g., once daily.

In another embodiment, the anti-PD-1 antibody molecule, e.g., an anti-PD-1 antibody molecule as described herein, alone or in combination with one or more other immunomodulators, is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or U.S. Pat. No. 8,685,980 to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. No. 8,415,355 or U.S. Pat. No. 8,685,980. In one embodiment, a PD-1 antibody molecule is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or U.S. Pat. No. 8,685,980, to treat a disorder such as a lymphoma, a neurologic cancer, a melanoma, a breast cancer, or a solid tumor.

In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the antibody molecule, e.g., an anti-PD-1 antibody molecule as described herein, alone or in combination with one or more other immunomodulators, is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, a PD-1 antibody molecule is used in combination with human monoclonal antibody molecule (Compound A26) described in U.S. Pat. No. 7,867,493 to treat a disorder such as, a cancer, a prostate cancer, or a breast cancer.

In another embodiment, the anti-PD-1 antibody molecule, e.g., an anti-PD-1 antibody molecule as described herein, alone or in combination with one or more other immunomodulators, is used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124 to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, a PD-1 antibody molecule is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the anti-PD-1 antibody molecule, e.g., an anti-PD-1 antibody molecule as described herein, alone or in combination with one or more other immunomodulators, is used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849 to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, a PD-1 antibody molecule is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer).

In certain embodiments, 2-(2',3-dimethyl-[2,4'-bipyridin]-5-yl)-N-(5-(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg, 5 mg, 10 mg, 20 mg, 30 mg, or 40 mg. The dosing schedule can vary from e.g., every other day to daily, twice or three times a day.

In another embodiment, the anti-PD-1 antibody molecule, e.g., an anti-PD-1 antibody molecule as described herein, alone or in combination with one or more other immunomodulators, is used in combination with a BRAF inhibitor, Encorafenib (Compound A29), or a compound disclosed in PCT Publication No. WO 2011/025927 to treat a disorder, e.g., a disorder described herein. In one embodiment, the BRAF inhibitor is Encorafenib (Compound A29) or a compound disclosed in PCT Publication No. WO 2011/025927. In one embodiment, a PD-1 antibody molecule is used in combination with Encorafenib (Compound A29), or a compound disclosed in PCT Publication No. WO 2011/025927, to treat a disorder such as a non-small cell lung cancer, a melanoma, or a colorectal cancer.

In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the anti-PD-1 antibody molecule, e.g., an anti-PD-1 antibody molecule as described herein, alone or in combination with one or more other immunomodulators, is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409 to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, a PD-1 antibody molecule is used in combination with 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the anti-PD-1 antibody molecule, e.g., an anti-PD-1 antibody molecule as described herein, alone or in combination with one or more other immunomodulators, is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, a PD-1 antibody molecule is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer.

In some embodiments, Compound A31 is a human monoclonal antibody molecule.

In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the anti-PD-1 antibody molecule, e.g., an anti-PD-1 antibody molecule as described herein, alone or in combination with one or more other immunomodulators, is used in combination an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, a PD-1 antibody molecule is used in combination with Compound A32, or a compound as described in Table 7, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer.

In some embodiments, Compound A32 is an antibody molecule drug conjugate against an FGFR2 and/or FGFR4, e.g., mAb 12425.

In another embodiment, the anti-PD-1 antibody molecule, e.g., an anti-PD-1 antibody molecule as described herein, alone or in combination with one or more other immunomodulators, is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, a PD-1 antibody molecule is used in combination with Compound A33, or a compound as described in PCT Publication No. WO 2004/045532, to treat a disorder such as a cancer, a prostate cancer, a breast cancer, or pigmented villonodular synovitis (PVNS).

In embodiments, Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

In another embodiment, the anti-PD-1 antibody molecule, e.g., an anti-PD-1 antibody molecule as described herein, alone or in combination with one or more other immunomodulators, is used in combination with a MEK inhibitor, Binimetinib (Compound A34), or a compound disclosed in PCT Publication No. WO 2003/077914 to treat a disorder, e.g., a disorder described herein. In one embodiment, the MEK inhibitor is Binimetinib (Compound A34), or a compound disclosed in PCT Publication No. WO 2003/077914. In one embodiment, a PD-1 antibody molecule is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer.

In one embodiment, the MEK inhibitor or Binimetinib (Compound A34) is administered at a dose of about 45 mg, e.g., twice daily.

In another embodiment, the anti-PD-1 antibody molecule, e.g., an anti-PD-1 antibody molecule as described herein, alone or in combination with one or more other immunomodulators, is used in combination an inhibitor of one or more of c-KIT, histamine release, Flt3 (e.g., FLK2/STK1) or PKC, Midostaurin (Compound A35) or a compound disclosed in PCT Publication No. WO 2003/037347 to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, a PD-1 antibody molecule is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related mascular degeration, a diabetic complication, or a dermatologic disorder.

In another embodiment, the anti-PD-1 antibody molecule, e.g., an anti-PD-1 antibody molecule as described herein, alone or in combination with one or more other immunomodulators, is used in combination with a TOR inhibitor (e.g., mTOR inhibitor), Everolimus (also known as AFINITOR; Compound A36) or a Compound disclosed in PCT Publication No. WO 2014/085318 to treat a disorder, e.g., a disorder described herein). In one embodiment, the TOR inhibitor is Everolimus (Compound A36) or a Compound disclosed in PCT Publication No. WO 2014/085318. In one embodiment, a PD-1 antibody molecule is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer.

In one embodiment, the TOR inhibitor or Everolimusis (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the anti-PD-1 antibody molecule, e.g., an anti-PD-1 antibody molecule as described herein, alone or in combination with one or more other immunomodulators, is used in combination an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377 to treat a disorder, e.g., a disorder described herein. In one embodiment, the inhibitor of one or more of VEGFR-2, PDGFRbeta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, a PD-1 antibody molecule is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the anti-PD-1 antibody molecule, e.g., an anti-PD-1 antibody molecule as described herein, alone or in combination with one or more other immunomodulators, is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761 to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, a PD-1 antibody molecule is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a nurologic cancer, a skin cancer (e.g., a melanoma), a pancreatic cancer, a liver cancer, Cushing's syndrome, a gastrointestinal disorder, acromegaly, a liver and biliary tract disorder, or liver cirrhosis.

In another embodiment, the anti-PD-1 antibody molecule, e.g., an anti-PD-1 antibody molecule as described herein, alone or in combination with one or more other immunomodulators, is used in combination a signal transduction modulator and/or angiogenesis inhibitor, Dovitinib (Compound A39) or a compound disclosed in PCT Publication No. WO 2009/115562 to treat a disorder, e.g., a disorder described herein. In one embodiment, the signal transduction modulator and/or angiogenesis inhibitor is Dovitinib (Compound A39) or a compound disclosed in PCT Publication No. WO 2009/115562. In one embodiment, a PD-1 antibody molecule is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the anti-PD-1 antibody molecule, e.g., an anti-PD-1 antibody molecule as described herein, alone or in combination with one or more other immunomodulators, is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757 to treat a disorder, e.g., a disorder described herein. In one embodiment, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, a PD-1 antibody molecule is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor.

In one embodiment, the EGFR inhibitor or (R,E)-N-(7-chloro-1-(1-(4-(dimethylamino)but-2-enoyl)azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In another embodiment, the anti-PD-1 antibody molecule, e.g., an anti-PD-1 antibody molecule as described herein, alone or in combination with one or more other immunomodulators, is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687 to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, a PD-1 antibody molecule is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the anti-PD-1 antibody molecule, e.g., an anti-PD-1 antibody molecule as described herein, alone or in combination with one or more other immunomodulators, is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655 to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655. In one embodiment, a PD-1 antibody molecule is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the anti-PD-1 antibody molecule, e.g., an anti-PD-1 antibody molecule as described herein, alone or in combination with one or more other immunomodulators, is used in combination a P-Glycoprotein 1 inhibitor, Valspodar (also known as AMDRAY; Compound A46) or a compound disclosed in EP 296122 to treat a disorder, e.g., a disorder described herein. In one embodiment, the P-Glycoprotein 1 inhibitor is Valspodar (Compound A46) or a compound disclosed in EP 296122. In one embodiment, a PD-1 antibody molecule is used in combination with Valspodar (Compound A46), or a compound disclosed in EP 296122, to treat a disorder such as a cancer or a drug-resistant tumor.

In another embodiment, the anti-PD-1 antibody molecule, e.g., an anti-PD-1 antibody molecule as described herein, alone or in combination with one or more other immunomodulators, is used in combination one or more of a VEGFR inhibitor, Vatalanib succinate (Compound A47) or a compound disclosed in EP 296122 to treat a disorder, e.g., a disorder described herein. In one embodiment, the VEGFR inhibitor is Vatalanib succinate (Compound A47) or a compound disclosed in EP 296122. In one embodiment, a PD-1 antibody molecule is used in combination with Vatalanib succinate (Compound A47), or a compound disclosed in EP 296122, to treat cancer.

In another embodiment, the anti-PD-1 antibody molecule, e.g., an anti-PD-1 antibody molecule as described herein, alone or in combination with one or more other immunomodulators, is used in combination with an IDH inhibitor or a compound disclosed in WO2014/141104 to treat a disorder, e.g., a disorder described herein. In one embodiment, the IDH inhibitor is a compound disclosed in PCT Publication No. WO2014/141104. In one embodiment, a PD-1 antibody molecule is used in combination with a compound disclosed in WO2014/141104 to treat a disorder such as a cancer.

In another embodiment, the anti-PD-1 antibody molecule, e.g., an anti-PD-1 antibody molecule as described herein, alone or in combination with one or more other immunomodulators, is used in combination with a BCL-ABL inhibitor or a compound disclosed in PCT Publication No. WO2013/171639, WO2013/171640, WO2013/171641, or WO2013/171642 to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, a PD-1 antibody molecule is used in combination with a compound disclosed in PCT Publication No. WO2013/171639, WO2013/171640, WO2013/171641, or WO2013/171642 to treat a disorder such as a cancer.

In another embodiment, the anti-PD-1 antibody molecule, e.g., an anti-PD-1 antibody molecule as described herein, alone or in combination with one or more other immunomodulators, is used in combination with a c-RAF inhibitor or a compound disclosed in PCT Publication No. WO2014/151616 to treat a disorder, e.g., a disorder described herein. In one embodiment, the c-RAF inhibitor is Compound A50 or a compound disclosed in PCT Publication No. WO2014/151616. In one embodiment, a PD-1 antibody molecule is used in combination with a compound disclosed in PCT Publication No. WO2014/151616 to treat a disorder such as a cancer.

In another embodiment, the anti-PD-1 antibody molecule, e.g., an anti-PD-1 antibody molecule as described herein, alone or in combination with one or more other immunomodulators, is used in combination with an ERK1/2 ATP competitive inhibitor or a compound disclosed in International Patent Application No. PCT/US2014/062913 to treat a disorder, e.g., a disorder described herein. In one embodiment, the ERK1/2 ATP competitive inhibitor is a compound disclosed in International Patent Application No. PCT/US2014/062913. In one embodiment, a PD-1 antibody molecule is used in combination with Compound A51 or a compound disclosed in International Patent Application No. PCT/US2014/062913 to treat a disorder such as a cancer.

In some embodiments, the PD-1 antibody molecule is administerd in combination with one or more agents selected from, Compound A8, Compound A17, Compound A23, Compound A24, Compound A27, Compound A29, and Compound A33.

In some embodiments, a PD-1 antibody molecule is administered in combination with an anti-cancer agent having a known activity in an immune cell assay, e.g., in one or more of a huMLR assay, a T cell proliferation assay, and a B-cell proliferation assay. Exemplary assays are described below. Based on the assay, an IC50 for can be calculated for each test agent. In embodiments, the anti-cancer agent has an IC50 of, e.g., 0-1 μM, 1-4 μM, or greater than 4 μM, e.g., 4-10 μM or 4-20 μM. In embodiments, the second therapeutic agent is chosen from one or more of: Compound A9, Compound A16, Compound A17, Compound A21, Compound A22, Compound A25, Compound A28, Compound A48, and Compound 49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg. In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In embodiments, the Compound A10 (or compound related to Compound A10) is administered at a dose of approximately 400 to 700 mg, e.g., administered three times weekly, 2 weeks on and one week off. In embodiments, the BCR-ABL inhibitor is administered at a dose of approximately 20 mg bid-80 mg bid.

Exemplary huMLR assay and B or T cell proliferation assays are provided below.

Human Mixed Lymphocyte Reaction

The Mixed Lymphocyte Reaction (MLR) is a functional assay which measures the proliferative response of lymphocytes from one individual (the responder) to lymphocytes from another individual (the stimulator). To perform an allogeneic MLR, peripheral blood mononuclear cells (PBMC) from three donors were isolated from buffy-coats of unknown HLA type (Kantonspital Blutspendezentrum from Bern and Aarau, Switzerland). The cells were prepared at 2.105 in 0.2 mL of culture medium containing RPMI 1640 GlutaMAX™ with 10% fetal calf serum (FCS), 100 U penicillin/100 μg streptomycin, 50 μM 2-Mercaptoethanol. Individual 2-way reactions were set up by mixing PBMC from two different donors at a 1:1 ratio and co-cultures were done in triplicates in flat-bottomed 96-well tissue culture plates for 6 days at 37° C., 5% CO2, in presence or not of an 8-point concentration range of test compounds. Cells were pulsed with 3H-TdR (1 μCi/0.2 mL) for the last 16 h of culture and incorporated radioactivity was used as a measure of cell proliferation. The concentration that inhibited 50% of the maximal huMLR response (IC50) was calculated for each compound. Cyclosporine was used as a positive control of huMLR inhibition.

Human B Cell Proliferation Assay

PBMC were freshly isolated by Ficoll-Paque density gradient from human blood and subjected to negative B-cell isolation. B cells were resuspended in culture medium (RPMI 1640, HEPES, 10% FCS, 50 m/mL gentamicine, 50 μM 2-Mercaptoethanol, 1×ITS (Insulin, Transferrin and Sodium Selenite), 1× Non-Essential Amino-Acids) at a concentration of 9.104 per well in a flat-bottom 96-well culture plate. B cell stimulation was performed by human anti-IgM antibody molecule (30 ug/mL) and IL-4 (75 ng/mL) or by CD40 ligand (3 ug/mL) and IL-4 (75 ng/mL) in presence or not of a 7-point concentration range of test compounds. After 72 h of culture at 37° C., 10% CO2, cells were pulsed with 3H-TdR (1 μCi/well) for the last 6 h of culture. B cells were then harvested and the incorporation of thymidine was measured using a scintillation counter. Of each duplicate treatment, the mean was calculated and these data were plotted in XLfit 4 to determine the respective IC50 values.

Human T Cell Proliferation Assay

PBMC were freshly isolated by Ficoll-Paque density gradient from human blood and subjected to negative isolation of T cells. T cells were prepared in culture medium (RPMI 1640, HEPES, 10% FCS, 50 m/mL gentamicine, 50 μM 2-Mercaptoethanol, 1×ITS (Insulin, Transferrin and Sodium Selenite), 1× Non-Essential Amino-Acids) at a concentration of 8.104 per well in a flat-bottom 96-well culture plate. T cell stimulation was performed by human anti-CD3 antibody molecule (10 ug/mL) or by human anti-CD3 antibody molecule (5 m/mL) and anti-CD28 antibody molecule (1 m/mL) in presence or not of a 7-point concentration range of test compounds. After 72 h of culture at 37° C., 10% CO2, cells were pulsed with 3H-TdR (1 μCi/well) for the last 6 h of culture. Cell proliferation was measured by the incorporation of thymidine allowing IC50 determination for each tested compound.

Down-Modulators of the Immune System

In an alternative embodiment, the anti-PD-1 antibody molecules disclosed herein are used to produce anti-idiotypic peptides or antibodies (Wallmann, J. et al. (2010) "Anti-Ids in Allergy: Timeliness of a Classic Concept," *World Allergy Organiz. J.* 3(6):195-201; Nardi, M. et al. (2000) "Antiidiotype Antibody Against Platelet Anti-Gpiiia Contributes To The Regulation Of Thrombocytopenia In HIV-1-ITP Patients," *J. Exp. Med.* 191(12):2093-2100) or mimetics (Zang, Y. C. et al. (2003) "Human Anti-Idiotypic T Cells Induced By TCR Peptides Corresponding To A Common CDR3Sequence Motif In Myelin Basic Protein-Reactive T Cells," *Int. Immunol.* 15(9):1073-1080; Loiarro, M. et al. (Epub 2010 Apr. 8) "Targeting TLR/IL-1R Signalling In Human Diseases," *Mediators Inflamm.* 2010:674363) of B7-H1 or PD-1. Such molecules serve as surrogates for PD-1, and thus their administration to a subject down-modulates the immune system of such subject by mimicking or facilitating B7-H1-PD-1 binding. Such molecules have utility in the treatment of graft vs. host disease. Similarly, agonist antibodies that i) enhance binding between such antibodies and such receptor/ligand or ii) trigger signal transduction when bound directly to B7-H1 or PD-1, have utility as agonists of B7-H1-PD-1 signaling and thus have utility in the treatment of inflammation and autoimmune disease, by directly or indirectly agonizing receptor activity.

Bispecific antibodies, exhibiting immunospecific binding to both PD-1 and B7-H1 are capable of binding to both APC and T-cells, and thus facilitate the co-localization of APCs and T-cells. Such co-localization facilitates the ability of such cells to bind together via B7-H1 and PD-1 molecules that are not complexed with antibody, or by co-inhibitory molecules. Such binding provides down modulation of the immune system of the recipient.

Down-modulation of the immune system is desirable in the treatment of inflammatory and auto-immune diseases, and graft vs. host disease (GvHD). Examples of autoimmune disorders that may be treated by administering the antibodies of the present invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, transverse myelitis, ulcerative colitis, uveitis, vasculitides such as dermatitis herpetiformis vasculitis, vitiligo, and Wegener's granulomatosis.

Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

Thus, the antibodies and antigen-binding fragments of the present invention have utility in the treatment of inflammatory and autoimmune diseases.

Diagnostic Uses

In one aspect, the present invention provides a diagnostic method for detecting the presence of a PD-1 protein in vitro (e.g., in a biological sample, such as a tissue biopsy, e.g., from a cancerous tissue) or in vivo (e.g., in vivo imaging in a subject). The method includes: (i) contacting the sample with an antibody molecule described herein, or administering to the subject, the antibody molecule; (optionally) (ii) contacting a reference sample, e.g., a control sample (e.g., a control biological sample, such as plasma, tissue, biopsy) or a control subject)); and (iii) detecting formation of a complex between the antibody molecule, and the sample or subject, or the control sample or subject, wherein a change, e.g., a statistically significant change, in the formation of the complex in the sample or subject relative to the control sample or subject is indicative of the presence of PD-1 in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids, or tissue samples.

Complex formation between the antibody molecule and PD-1 can be detected by measuring or visualizing either the binding molecule bound to the PD-1 antigen or unbound binding molecule. Conventional detection assays can be used, e.g., an enzyme-linked immunosorbent assays (ELISA), a radioimmunoassay (RIA) or tissue immunohistochemistry. Alternative to labeling the antibody molecule, the presence of PD-1 can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of PD-1 in the sample is inversely proportional to the amount of labeled standard bound to the antibody molecule.

Nucleic Acids

The invention also features nucleic acids comprising nucleotide sequences that encode heavy and light chain variable regions and CDRs or hypervariable loops of the anti-PD-1 antibody molecules, as described herein. For example, the invention features a first and second nucleic acid encoding heavy and light chain variable regions, respectively, of an anti-PD-1 antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Table 1.

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

TABLE 1

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 6 | VH | QVQLQQPGSELVRPGASVKLSCKASGYTFTTYW<br>MHWVRQRPGQGLEWIGNIYPGTGGSNFDEKFKN<br>RTSLTVDTSSTTAYMHLASLTSEDSAVYYCTRW<br>TTGTGAYWGQGTLVTVSA |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 7 | DNA VH | CAGGTCCAGCTGCAGCAACCTGGGTCTGAGCTG<br>GTGAGGCCTGGAGCTTCAGTGAAGCTGTCCTGC<br>AAGGCGTCTGGCTACACATTCACCACTTACTGG<br>ATGCACTGGGTGAGGCAGAGGCCTGGACAAGGC<br>CTTGAGTGGATTGGAAATATTTATCCTGGTACT<br>GGTGGTTCTAACTTCGATGAGAAGTTCAAAAAC<br>AGGACCTCACTGACTGTAGACACATCCTCCACC<br>ACAGCCTACATGCACCTCGCCAGCCTGACATCT<br>GAGGACTCTGCGGTCTATTACTGTACAAGATGG<br>ACTACTGGGACGGGAGCTTATTGGGGCCAAGGG<br>ACTCTGGTCACTGTCTCTGCA |
| --- | --- | --- |
| SEQ ID NO: 8 | VH | QVQLQQSGSELVRPGASVKLSCKASGYTFTTYW<br>MHWVRQRPGQGLEWIGNIYPGTGGSNFDEKFKN<br>RTSLTVDTSSTTAYMHLASLTSEDSAVYYCTRW<br>TTGTGAYWGQGTLVTVSA<br>CAGGTCCAGCTGCAGCAGTCTGGGTCTGAGCTG<br>GTGAGGCCTGGAGCTTCAGTGAAGCTGTCCTGC<br>AAGGCGTCTGGCTACACATTCACCACTTACTGG<br>ATGCACTGGGTGAGGCAGAGGCCTGGACAAGGC<br>CTTGAGTGGATTGGAAATATTTATCCTGGTACT<br>GGTGGTTCTAACTTCGATGAGAAGTTCAAAAAC<br>AGGACCTCACTGACTGTAGACACATCCTCCACC<br>ACAGCCTACATGCACCTCGCCAGCCTGACATCT<br>GAGGACTCTGCGGTCTATTACTGTACAAGATGG<br>ACTACTGGGACGGGAGCTTATTGGGGCCAAGGG |
| SEQ ID NO: 9 | DNA VH | ACTCTGGTCACTGTCTCTGCA |

BAP049 LC

| SEQ ID NO: 10 (Kabat) | LCDR1 | KSSQSLLDSGNQKNFLT |
| --- | --- | --- |
| SEQ ID NO: 11 (Kabat) | LCDR2 | WASTRES |
| SEQ ID NO: 12 (Kabat) | LCDR3 | QNDYSYPCT |
| SEQ ID NO: 13 (Chothia) | LCDR1 | SQSLLDSGNQKNF |
| SEQ ID NO: 14 (Chothia) | LCDR2 | WAS |
| SEQ ID NO: 15 (Chothia) | LCDR3 | DYSYPC |
| SEQ ID NO: 16 | VL | DIVMTQSPSSLTVTAGEKVTMSCKSSQSLLDSG<br>NQKNFLTWYQQKPGQPPKLLIFWASTRESGVPD<br>RFTGSGSVTDFTLTISSVQAEDLAVYYCQNDYS<br>YPCTFGGGTKLEIK |
| SEQ ID NO: 17 | DNA VL | GACATTGTGATGACCCAGTCTCCATCCTCCCTG<br>ACTGTGACAGCAGGAGAGAAGGTCACTATGAGC<br>TGCAAGTCCAGTCAGAGTCTGTTAGACAGTGGA<br>AATCAAAAGAACTTCTTGACCTGGTACCAGCAG<br>AAACCAGGGCAGCCTCCTAAACTGTTGATCTTC<br>TGGGCATCCACTAGGGAATCTGGGGTCCCTGAT<br>CGCTTCACAGGCAGTGGATCTGTAACAGATTTC<br>ACTCTCACCATCAGCAGTGTGCAGGCTGAAGAC<br>CTGGCAGTTTATTACTGTCAGAATGATTATAGT<br>TATCCGTGCACGTTCGGAGGGGGGACCAAGCTG<br>GAAATAAAA |

BAP049-chi HC

| SEQ ID NO: 1 (Kabat) | HCDR1 | TYWMH |
| --- | --- | --- |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 3 (Chothia) | HCDR3 | WTTGTGAY |
| SEQ ID NO: 18 | VH | QVQLQQPGSELVRPGASVKLSCKASGYTFTTYW<br>MHWVRQRPGQGLEWIGNIYPGTGGSNFDEKFKN<br>RTSLTVDTSSTTAYMHLASLTSEDSAVYYCTRW<br>TTGTGAYWGQGTTVTVSS |
| SEQ ID NO: 19 | DNA VH | CAGGTCCAGCTGCAGCAGCCTGGGTCTGAGCTG<br>GTGAGGCCTGGAGCTTCAGTGAAGCTGTCCTGC<br>AAGGCGTCTGGCTACACATTCACCACTTACTGG<br>ATGCACTGGGTGAGGCAGAGGCCTGGACAAGGC<br>CTTGAGTGGATTGGAAATATTTATCCTGGTACT<br>GGTGGTTCTAACTTCGATGAGAAGTTCAAAAAC<br>AGGACCTCACTGACTGTAGACACATCCTCCACC<br>ACAGCCTACATGCACCTCGCCAGCCTGACATCT<br>GAGGACTCTGCGGTCTATTACTGTACAAGATGG<br>ACTACTGGGACGGGAGCTTATTGGGGCCAGGGC<br>ACCACCGTGACCGTGTCCTCC |
| SEQ ID NO: 20 | HC | QVQLQQPGSELVRPGASVKLSCKASGYTFTTYW<br>MHWVRQRPGQGLEWIGNIYPGTGGSNFDEKFKN<br>RTSLTVDTSSTTAYMHLASLTSEDSAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 21 | DNA HC | CAGGTCCAGCTGCAGCAGCCTGGGTCTGAGCTG<br>GTGAGGCCTGGAGCTTCAGTGAAGCTGTCCTGC<br>AAGGCGTCTGGCTACACATTCACCACTTACTGG<br>ATGCACTGGGTGAGGCAGAGGCCTGGACAAGGC<br>CTTGAGTGGATTGGAAATATTTATCCTGGTACT<br>GGTGGTTCTAACTTCGATGAGAAGTTCAAAAAC<br>AGGACCTCACTGACTGTAGACACATCCTCCACC<br>ACAGCCTACATGCACCTCGCCAGCCTGACATCT<br>GAGGACTCTGCGGTCTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC<br>GTGGATGGCGTGGAGGTGCATAATGCCAAGACA<br>AAGCCGCGGGAGGAGCAGTTCAACAGCACGTAC<br>CGTGTGGTCAGCGTCCTCACCGTCCTGCACCAG<br>GACTGGCTGAACGGCAAGGAGTACAAGTGCAAG<br>GTGTCCAACAAAGGCCTCCCGTCCTCCATCGAG<br>AAAACCATCTCCAAAGCCAAAGGGCAGCCCCGA<br>GAGCCACAGGTGTACACCCTGCCCCCATCCCAG<br>GAGGAGATGACCAAGAACCAGGTCAGCCTGACC<br>TGCCTGGTCAAAGGCTTCTACCCCAGCGACATC<br>GCCGTGGAGTGGGAGAGCAATGGGCAGCCGGAG |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | AACAACTACAAGACCACGCCTCCCGTGCTGGACTCCGACGGCTCCTTCTTCCTCTACAGCAGGCTAACCGTGGACAAGAGCAGGTGGCAGGAGGGGAATGTCTTCTCATGCTCCGTGATGCATGAGGCTCTGCACAACCACTACACACAGAAGAGCCTCTCCCTGTCTCTGGGTAAA |
| SEQ ID NO: 22 | VH | QVQLQQSGSELVRPGASVKLSCKASGYTFTTYWMHWVRQRPGQGLEWIGNIYPGTGGSNFDEKFKNRTSLTVDTSSTTAYMHLASLTSEDSAVYYCTRWTTGTGAYWGQGTTVTVSS |
| SEQ ID NO: 23 | DNA VH | CAGGTCCAGCTGCAGCAGTCTGGGTCTGAGCTGGTGAGGCCTGGAGCTTCAGTGAAGCTGTCCTGCAAGGCGTCTGGCTACACATTCACCACTTACTGGATGCACTGGGTGAGGCAGAGGCCTGGACAAGGCCTTGAGTGGATTGGAAATATTTATCCTGGTACTGGTGGTTCTAACTTCGATGAGAAGTTCAAAAACAGGACCTCACTGACTGTAGACACATCCTCCACCACAGCCTACATGCACCTCGCCAGCCTGACATCTGAGGACTCTGCGGTCTATTACTGTACAAGATGGACTACTGGGACGGGAGCTTATTGGGGCCAGGGCACCACCGTGACCGTGTCCTCC |
| SEQ ID NO: 30 | HC | QVQLQQSGSELVRPGASVKLSCKASGYTFTTYWMHWVRQRPGQGLEWIGNIYPGTGGSNFDEKFKNRTSLTVDTSSTTAYMHLASLTSEDSAVYYCTRWTTGTGAYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| SEQ ID NO: 31 | DNA HC | CAGGTCCAGCTGCAGCAGTCTGGGTCTGAGCTGGTGAGGCCTGGAGCTTCAGTGAAGCTGTCCTGCAAGGCGTCTGGCTACACATTCACCACTTACTGGATGCACTGGGTGAGGCAGAGGCCTGGACAAGGCCTTGAGTGGATTGGAAATATTTATCCTGGTACTGGTGGTTCTAACTTCGATGAGAAGTTCAAAAACAGGACCTCACTGACTGTAGACACATCCTCCACCACAGCCTACATGCACCTCGCCAGCCTGACATCTGAGGACTCTGCGGTCTATTACTGTACAAGATGGACTACTGGGACGGGAGCTTATTGGGGCCAGGGCACCACCGTGACCGTGTCCTCCGCTTCCACCAAGGGCCCATCCGTCTTCCCCCTGGCGCCCTGCTCCAGGAGCACCTCCGAGAGCACAGCCGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACGAAGACCTACACCTGCAACGTAGATCACAAGCCCAGCAACACCAAGGTGGACAAGAGAGTTGAGTCCAAATATGGTCCCCCATGCCCACCGTGCCCAGCACCTGAGTTCCTGGGGGGACCATCAGTCTTCCTGTTCCCCCCAAAACCCAAGGACACTCTCATGATCTCCCGGACCCCTGAGGTCACGTGCGTGGTGGTGGACGTGAGCCAGGAAGACCCCGAGGTCCAGTTCAACTGGTACGTGGATGGCGTGGAGGTGCATAATGCCAAGACAAAGCCGCGGGAGGAGCAGTTCAACAGCACGTACCGTGTGGTCAGCGTCCTCACCGTCCTGCACCAGGACTGGCTGAACGGCAAGGAGTACAAGTGCAAGGTGTCCAACAAAGGCCTCCCGTCCTCCATCGAGAAAACCATCTCCAAAGCCAAAGGGCAGCCCCGA |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-chi LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 12 (Kabat) | LCDR3 | QNDYSYPCT |
| SEQ ID NO: 13 (Chothia) | LCDR1 | SQSLLDSGNQKNF |
| SEQ ID NO: 14 (Chothia) | LCDR2 | WAS |
| SEQ ID NO: 15 (Chothia) | LCDR3 | DYSYPC |
| SEQ ID NO: 24 | VL | DIVMTQSPSSLTVTAGEKVTMSCKSSQSLLDSG NQKNFLTWYQQKPGQPPKLLIFWASTRESGVPD RFTGSGSVTDFTLTISSVQAEDLAVYYCQNDYS YPCTFGQGTKVEIK |
| SEQ ID NO: 25 | DNA VL | GACATTGTGATGACCCAGTCTCCATCCTCCCTG ACTGTGACAGCAGGAGAGAAGGTCACTATGAGC TGCAAGTCCAGTCAGAGTCTGTTAGACAGTGGA AATCAAAAGAACTTCTTGACCTGGTACCAGCAG AAACCAGGGCAGCCTCCTAAACTGTTGATCTTC TGGGCATCCACTAGGGAATCTGGGGTCCCTGAT CGCTTCACAGGCAGTGGATCTGTAACAGATTTC ACTCTCACCATCAGCAGTGTGCAGGCTGAAGAC CTGGCAGTTTATTACTGTCAGAATGATTATAGT TATCCGTGCACGTTCGGCCAAGGGACCAAGGTG GAAATCAAA |
| SEQ ID NO: 26 | LC | DIVMTQSPSSLTVTAGEKVTMSCKSSQSLLDSG NQKNFLTWYQQKPGQPPKLLIFWASTRESGVPD RFTGSGSVTDFTLTISSVQAEDLAVYYCQNDYS YPCTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 27 | DNA LC | GACATTGTGATGACCCAGTCTCCATCCTCCCTG ACTGTGACAGCAGGAGAGAAGGTCACTATGAGC TGCAAGTCCAGTCAGAGTCTGTTAGACAGTGGA AATCAAAAGAACTTCTTGACCTGGTACCAGCAG AAACCAGGGCAGCCTCCTAAACTGTTGATCTTC TGGGCATCCACTAGGGAATCTGGGGTCCCTGAT CGCTTCACAGGCAGTGGATCTGTAACAGATTTC ACTCTCACCATCAGCAGTGTGCAGGCTGAAGAC CTGGCAGTTTATTACTGTCAGAATGATTATAGT TATCCGTGCACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049-chi-Y HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothya) | HCDR1 | GYTFTTY |
| SEQ ID NO: 5 (Chothya) | HCDR2 | YPGTGG |
| SEQ ID NO: 3 (Chothya) | HCDR3 | WTTGTGAY |
| SEQ ID NO: 18 | VH | QVQLQQPGSELVRPGASVKLSCKASGYTFTTYW<br>MHWVRQRPGQGLEWIGNIYPGTGGSNFDEKFKN<br>RTSLTVDTSSTTAYMHLASLTSEDSAVYYCTRW<br>TTGTGAYWGQGTTVTVSS |
| SEQ ID NO: 19 | DNA VH | CAGGTCCAGCTGCAGCAGCCTGGGTCTGAGCTG<br>GTGAGGCCTGGAGCTTCAGTGAAGCTGTCCTGC<br>AAGGCGTCTGGCTACACATTCACCACTTACTGG<br>ATGCACTGGGTGAGGCAGAGGCCTGGACAAGGC<br>CTTGAGTGGATTGGAAATATTTATCCTGGTACT<br>GGTGGTTCTAACTTCGATGAGAAGTTCAAAAAC<br>AGGACCTCACTGACTGTAGACACATCCTCCACC<br>ACAGCCTACATGCACCTCGCCAGCCTGACATCT<br>GAGGACTCTGCGGTCTATTACTGTACAAGATGG<br>ACTACTGGGACGGGAGCTTATTGGGGCCAGGGC<br>ACCACCGTGACCGTGTCCTCC |
| SEQ ID NO: 20 | HC | QVQLQQPGSELVRPGASVKLSCKASGYTFTTYW<br>MHWVRQRPGQGLEWIGNIYPGTGGSNFDEKFKN<br>RTSLTVDTSSTTAYMHLASLTSEDSAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 21 | DNA HC | CAGGTCCAGCTGCAGCAGCCTGGGTCTGAGCTG<br>GTGAGGCCTGGAGCTTCAGTGAAGCTGTCCTGC<br>AAGGCGTCTGGCTACACATTCACCACTTACTGG<br>ATGCACTGGGTGAGGCAGAGGCCTGGACAAGGC<br>CTTGAGTGGATTGGAAATATTTATCCTGGTACT<br>GGTGGTTCTAACTTCGATGAGAAGTTCAAAAAC<br>AGGACCTCACTGACTGTAGACACATCCTCCACC<br>ACAGCCTACATGCACCTCGCCAGCCTGACATCT<br>GAGGACTCTGCGGTCTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| SEQ ID NO: 22 | VH | QVQLQQSGSELVRPGASVKLSCKASGYTFTTYW MHWVRQRPGQGLEWIGNIYPGTGGSNFDEKFKN RTSLTVDTSSTTAYMHLASLTSEDSAVYYCTRW TTGTGAYWGQGTTVTVSS |
| SEQ ID NO: 23 | DNA VH | CAGGTCCAGCTGCAGCAGTCTGGGTCTGAGCTG GTGAGGCCTGGAGCTTCAGTGAAGCTGTCCTGC AAGGCGTCTGGCTACACATTCACCACTTACTGG ATGCACTGGGTGAGGCAGAGGCCTGGACAAGGC CTTGAGTGGATTGGAAATATTTATCCTGGTACT GGTGGTTCTAACTTCGATGAGAAGTTCAAAAAC AGGACCTCACTGACTGTAGACACATCCTCCACC ACAGCCTACATGCACCTCGCCAGCCTGACATCT GAGGACTCTGCGGTCTATTACTGTACAAGATGG ACTACTGGGACGGGAGCTTATTGGGGCCAGGGC ACCACCGTGACCGTGTCCTCC |
| SEQ ID NO: 30 | HC | QVQLQQSGSELVRPGASVKLSCKASGYTFTTYW MHWVRQRPGQGLEWIGNIYPGTGGSNFDEKFKN RTSLTVDTSSTTAYMHLASLTSEDSAVYYCTRW TTGTGAYWGQGTTVTVSSASTKGPSVFPLAPCS RSTSESTAALGCLVKDYFPEPVTVSWNSGALTS GVHTFPAVLQSSGLYSLSSVVTVPSSSLGTKTY TCNVDHKPSNTKVDKRVESKYGPPCPPCPAPEF LGGPSVFLFPPKPKDTLMISRTPEVTCVVVDVS QEDPEVQFNWYVDGVEVHNAKTKPREEQFNSTY RVVSVLTVLHQDWLNGKEYKCKVSNKGLPSSIE KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLGK |
| SEQ ID NO: 31 | DNA HC | CAGGTCCAGCTGCAGCAGTCTGGGTCTGAGCTG GTGAGGCCTGGAGCTTCAGTGAAGCTGTCCTGC AAGGCGTCTGGCTACACATTCACCACTTACTGG ATGCACTGGGTGAGGCAGAGGCCTGGACAAGGC CTTGAGTGGATTGGAAATATTTATCCTGGTACT GGTGGTTCTAACTTCGATGAGAAGTTCAAAAAC AGGACCTCACTGACTGTAGACACATCCTCCACC ACAGCCTACATGCACCTCGCCAGCCTGACATCT GAGGACTCTGCGGTCTATTACTGTACAAGATGG ACTACTGGGACGGGAGCTTATTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC GGCGTGCACACCTTCCCGGCTGTCCTACAGTCC TCAGGACTCTACTCCCTCAGCAGCGTGGTGACC GTGCCCTCCAGCAGCTTGGGCACGAAGACCTAC ACCTGCAACGTAGATCACAAGCCCAGCAACACC AAGGTGGACAAGAGAGTTGAGTCCAAATATGGT CCCCCATGCCCACCGTGCCCAGCACCTGAGTTC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-chi-Y LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 34 | VL | DIVMTQSPSSLTVTAGEKVTMSCKSSQSLLDSG NQKNFLTWYQQKPGQPPKLLIFWASTRESGVPD RFTGSGSVTDFTLTISSVQAEDLAVYYCQNDYS YPYTFGQGTKVEIK |
| SEQ ID NO: 35 | DNA VL | GACATTGTGATGACCCAGTCTCCATCCTCCCTG ACTGTGACAGCAGGAGAGAAGGTCACTATGAGC TGCAAGTCCAGTCAGAGTCTGTTAGACAGTGGA AATCAAAAGAACTTCTTGACCTGGTACCAGCAG AAACCAGGGCAGCCTCCTAAACTGTTGATCTTC TGGGCATCCACTAGGGAATCTGGGGTCCCTGAT CGCTTCACAGGCAGTGGATCTGTAACAGATTTC ACTCTCACCATCAGCAGTGTGCAGGCTGAAGAC CTGGCAGTTTATTACTGTCAGAATGATTATAGT TATCCGTACACGTTCGGCCAAGGGACCAAGGTG GAAATCAAA |
| SEQ ID NO: 36 | LC | DIVMTQSPSSLTVTAGEKVTMSCKSSQSLLDSG NQKNFLTWYQQKPGQPPKLLIFWASTRESGVPD RFTGSGSVTDFTLTISSVQAEDLAVYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 37 | DNA LC | GACATTGTGATGACCCAGTCTCCATCCTCCCTG ACTGTGACAGCAGGAGAGAAGGTCACTATGAGC TGCAAGTCCAGTCAGAGTCTGTTAGACAGTGGA AATCAAAAGAACTTCTTGACCTGGTACCAGCAG AAACCAGGGCAGCCTCCTAAACTGTTGATCTTC TGGGCATCCACTAGGGAATCTGGGGTCCCTGAT CGCTTCACAGGCAGTGGATCTGTAACAGATTTC ACTCTCACCATCAGCAGTGTGCAGGCTGAAGAC CTGGCAGTTTATTACTGTCAGAATGATTATAGT TATCCGTACACGTTCGGCCAAGGGACCAAGGTG GAAATCAAACGTACGGTGGCTGCACCATCTGTC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |
| **BAP049-hum01 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSS |
| SEQ ID NO: 39 | DNA VH | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGGTGCGACAGGCCACTGGACAAGGG CTTGAGTGGATGGGTAATATTTATCCTGGTACT GGTGGTTCTAACTTCGATGAGAAGTTCAAGAAC AGAGTCACGATTACCGCGGACAAATCCACGAGC ACAGCCTACATGGAGCTGAGCAGCCTGAGATCT GAGGACACGGCCGTGTATTACTGTACAAGATGG ACTACTGGGACGGGAGCTTATTGGGGCCAGGGC ACCACCGTGACCGTGTCCTCC |
| SEQ ID NO: 40 | HC | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSSASTKGPSVFPLAPCS RSTSESTAALGCLVKDYFPEPVTVSWNSGALTS GVHTFPAVLQSSGLYSLSSVVTVPSSSLGTKTY TCNVDHKPSNTKVDKRVESKYGPPCPPCPAPEF LGGPSVFLFPPKPKDTLMISRTPEVTCVVVDVS QEDPEVQFNWYVDGVEVHNAKTKPREEQFNSTY RVVSVLTVLHQDWLNGKEYKCKVSNKGLPSSIE KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLGK |
| SEQ ID NO: 41 | DNA HC | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGGTGCGACAGGCCACTGGACAAGGG CTTGAGTGGATGGGTAATATTTATCCTGGTACT GGTGGTTCTAACTTCGATGAGAAGTTCAAGAAC AGAGTCACGATTACCGCGGACAAATCCACGAGC ACAGCCTACATGGAGCTGAGCAGCCTGAGATCT GAGGACACGGCCGTGTATTACTGTACAAGATGG ACTACTGGGACGGGAGCTTATTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC<br>GTGGATGGCGTGGAGGTGCATAATGCCAAGACA<br>AAGCCGCGGGAGGAGCAGTTCAACAGCACGTAC<br>CGTGTGGTCAGCGTCCTCACCGTCCTGCACCAG<br>GACTGGCTGAACGGCAAGGAGTACAAGTGCAAG<br>GTGTCCAACAAAGGCCTCCCGTCCTCCATCGAG<br>AAAACCATCTCCAAAGCCAAAGGGCAGCCCCGA<br>GAGCCACAGGTGTACACCCTGCCCCCATCCCAG<br>GAGGAGATGACCAAGAACCAGGTCAGCCTGACC<br>TGCCTGGTCAAAGGCTTCTACCCCAGCGACATC<br>GCCGTGGAGTGGGAGAGCAATGGGCAGCCGGAG<br>AACAACTACAAGACCACGCCTCCCGTGCTGGAC<br>TCCGACGGCTCCTTCTTCCTCTACAGCAGGCTA<br>ACCGTGGACAAGAGCAGGTGGCAGGAGGGGAAT<br>GTCTTCTCATGCTCCGTGATGCATGAGGCTCTG<br>CACAACCACTACACACAGAAGAGCCTCTCCCTG<br>TCTCTGGGTAAA |
| **BAP049-hum01 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 42 | VL | EIVLTQSPATLSLSPGERATLSCKSSQSLLDSG<br>NQKNFLTWYQQKPGQAPRLLIYWASTRESGVPS<br>RFSGSGSGTEFTLTISSLQPDDFATYYCQNDYS<br>YPYTFGQGTKVEIK |
| SEQ ID NO: 43 | DNA VL | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGGTCCCATCA<br>AGGTTCAGCGGCAGTGGATCTGGGACAGAATTC<br>ACTCTCACCATCAGCAGCCTGCAGCCTGATGAT<br>TTTGCAACTTATTACTGTCAGAATGATTATAGT<br>TATCCGTACACGTTCGGCCAAGGGACCAAGGTG<br>GAAATCAAA |
| SEQ ID NO: 44 | LC | EIVLTQSPATLSLSPGERATLSCKSSQSLLDSG<br>NQKNFLTWYQQKPGQAPRLLIYWASTRESGVPS<br>RFSGSGSGTEFTLTISSLQPDDFATYYCQNDYS<br>YPYTFGQGTKVEIKRTVAAPSVFIFPPSDEQLK<br>SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 45 | DNA LC | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | TGGGCATCCACTAGGGAATCTGGGGTCCCATCA AGGTTCAGCGGCAGTGGATCTGGGACAGAATTC ACTCTCACCATCAGCAGCCTGCAGCCTGATGAT TTTGCAACTTATTACTGTCAGAATGATTATAGT TATCCGTACACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |
| **BAP049-hum02 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSS |
| SEQ ID NO: 39 | DNA VH | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGGTGCGACAGGCCACTGGACAAGGG CTTGAGTGGATGGGTAATATTTATCCTGGTACT GGTGGTTCTAACTTCGATGAGAAGTTCAAGAAC AGAGTCACGATTACCGCGGACAAATCCACGAGC ACAGCCTACATGGAGCTGAGCAGCCTGAGATCT GAGGACACGGCCGTGTATTACTGTACAAGATGG ACTACTGGGACGGGAGCTTATTGGGGCCAGGGC ACCACCGTGACCGTGTCCTCC |
| SEQ ID NO: 40 | HC | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSSASTKGPSVFPLAPCS RSTSESTAALGCLVKDYFPEPVTVSWNSGALTS GVHTFPAVLQSSGLYSLSSVVTVPSSSLGTKTY TCNVDHKPSNTKVDKRVESKYGPPCPPCPAPEF LGGPSVFLFPPKPKDTLMISRTPEVTCVVVDVS QEDPEVQFNWYVDGVEVHNAKTKPREEQFNSTY RVVSVLTVLHQDWLNGKEYKCKVSNKGLPSSIE KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLGK |
| SEQ ID NO: 41 | DNA HC | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGGTGCGACAGGCCACTGGACAAGGG CTTGAGTGGATGGGTAATATTTATCCTGGTACT GGTGGTTCTAACTTCGATGAGAAGTTCAAGAAC AGAGTCACGATTACCGCGGACAAATCCACGAGC ACAGCCTACATGGAGCTGAGCAGCCTGAGATCT GAGGACACGGCCGTGTATTACTGTACAAGATGG |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | | |
|---|---|---|---|
| | | | ACTACTGGGACGGGAGCTTATTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC GGCGTGCACACCTTCCCGGCTGTCCTACAGTCC TCAGGACTCTACTCCCTCAGCAGCGTGGTGACC GTGCCCTCCAGCAGCTTGGGCACGAAGACCTAC ACCTGCAACGTAGATCACAAGCCCAGCAACACC AAGGTGGACAAGAGAGTTGAGTCCAAATATGGT CCCCCATGCCCACCGTGCCCAGCACCTGAGTTC CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum02 LC** | | | |
| SEQ ID NO: 10 | (Kabat) | LCDR1 | KSSQSLLDSGNQKNFLT |
| SEQ ID NO: 11 | (Kabat) | LCDR2 | WASTRES |
| SEQ ID NO: 32 | (Kabat) | LCDR3 | QNDYSYPYT |
| SEQ ID NO: 13 | (Chothia) | LCDR1 | SQSLLDSGNQKNF |
| SEQ ID NO: 14 | (Chothia) | LCDR2 | WAS |
| SEQ ID NO: 33 | (Chothia) | LCDR3 | DYSYPY |
| SEQ ID NO: 46 | | VL | DIQMTQSPSSLSASVGDRVTITCKSSQSLLDSG NQKNFLTWYQQKPGQAPRLLIYWASTRESGIPP RFSGSGYGTDFTLTINNIESEDAAYYFCQNDYS YPYTFGQGTKVEIK |
| SEQ ID NO: 47 | | DNA VL | GACATCCAGATGACCCAGTCTCCATCCTCCCTG TCTGCATCTGTAGGAGACAGAGTCACCATCACT TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGATCCCACCT CGATTCAGTGGCAGCGGGTATGGAACAGATTTT ACCCTCACAATTAATAACATAGAATCTGAGGAT GCTGCATATTACTTCTGTCAGAATGATTATAGT TATCCGTACACGTTCGGCCAAGGGACCAAGGTG GAAATCAAA |
| SEQ ID NO: 48 | | LC | DIQMTQSPSSLSASVGDRVTITCKSSQSLLDSG NQKNFLTWYQQKPGQAPRLLIYWASTRESGIPP RFSGSGYGTDFTLTINNIESEDAAYYFCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 49 | DNA LC | GACATCCAGATGACCCAGTCTCCATCCTCCCTG<br>TCTGCATCTGTAGGAGACAGAGTCACCATCACT<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGATCCCACCT<br>CGATTCAGTGGCAGCGGGTATGGAACAGATTTT<br>ACCCTCACAATTAATAACATAGAATCTGAGGAT<br>GCTGCATATTACTTCTGTCAGAATGATTATAGT<br>TATCCGTACACGTTCGGCCAAGGGACCAAGGTG<br>GAAATCAAACGTACGGTGGCTGCACCATCTGTC<br>TTCATCTTCCCGCCATCTGATGAGCAGTTGAAA<br>TCTGGAACTGCCTCTGTTGTGTGCCTGCTGAAT<br>AACTTCTATCCCAGAGAGGCCAAAGTACAGTGG<br>AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum03 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSS |
| SEQ ID NO: 51 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGATCAGGCAGTCCCCATCGAGAGGC<br>CTTGAGTGGCTGGGTAATATTTATCCTGGTACT<br>GGTGGTTCTAACTTCGATGAGAAGTTCAAGAAC<br>AGATTCACCATCTCCAGAGACAATTCCAAGAAC<br>ACGCTGTATCTTCAAATGAACAGCCTGAGAGCC<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 52 | HC | EVQLVQSGAEVKKPGESLRISCKGSGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 53 | DNA HC | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | ATGCACTGGATCAGGCAGTCCCCATCGAGAGGC<br>CTTGAGTGGCTGGGTAATATTTATCCTGGTACT<br>GGTGGTTCTAACTTCGATGAGAAGTTCAAGAAC<br>AGATTCACCATCTCCAGAGACAATTCCAAGAAC<br>ACGCTGTATCTTCAAATGAACAGCCTGAGAGCC<br>GAGGACACGGCCGTGTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC<br>GTGGATGGCGTGGAGGTGCATAATGCCAAGACA<br>AAGCCGCGGGAGGAGCAGTTCAACAGCACGTAC<br>CGTGTGGTCAGCGTCCTCACCGTCCTGCACCAG<br>GACTGGCTGAACGGCAAGGAGTACAAGTGCAAG<br>GTGTCCAACAAAGGCCTCCCGTCCTCCATCGAG<br>AAAACCATCTCCAAAGCCAAAGGGCAGCCCCGA<br>GAGCCACAGGTGTACACCCTGCCCCCATCCCAG<br>GAGGAGATGACCAAGAACCAGGTCAGCCTGACC<br>TGCCTGGTCAAAGGCTTCTACCCCAGCGACATC<br>GCCGTGGAGTGGGAGAGCAATGGGCAGCCGGAG<br>AACAACTACAAGACCACGCCTCCCGTGCTGGAC<br>TCCGACGGCTCCTTCTTCCTCTACAGCAGGCTA<br>ACCGTGGACAAGAGCAGGTGGCAGGAGGGGAAT<br>GTCTTCTCATGCTCCGTGATGCATGAGGCTCTG<br>CACAACCACTACACACAGAAGAGCCTCTCCCTG<br>TCTCTGGGTAAA |
| **BAP049-hum03 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 46 | VL | DIQMTQSPSSLSASVGDRVTITCKSSQSLLDSG<br>NQKNFLTWYQQKPGQAPRLLIYWASTRESGIPP<br>RFSGSGYGTDFTLTINNIESEDAAYYFCQNDYS<br>YPYTFGQGTKVEIK |
| SEQ ID NO: 47 | DNA VL | GACATCCAGATGACCCAGTCTCCATCCTCCCTG<br>TCTGCATCTGTAGGAGACAGAGTCACCATCACT<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGATCCCACCT<br>CGATTCAGTGGCAGCGGGTATGGAACAGATTTT<br>ACCCTCACAATTAATAACATAGAATCTGAGGAT<br>GCTGCATATTACTTCTGTCAGAATGATTATAGT<br>TATCCGTACACGTTCGGCCAAGGGACCAAGGTG<br>GAAATCAAA |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 48 | LC | DIQMTQSPSSLSASVGDRVTITCKSSQSLLDSG<br>NQKNFLTWYQQKPGQAPRLLIYWASTRESGIPP<br>RFSGSGYGTDFTLTINNIESEDAAYYFCQNDYS<br>YPYTFGQGTKVEIKRTVAAPSVFIFPPSDEQLK<br>SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 49 | DNA LC | GACATCCAGATGACCCAGTCTCCATCCTCCCTG<br>TCTGCATCTGTAGGAGACAGAGTCACCATCACT<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGATCCCACCT<br>CGATTCAGTGGCAGCGGGTATGGAACAGATTTT<br>ACCCTCACAATTAATAACATAGAATCTGAGGAT<br>GCTGCATATTACTTCTGTCAGAATGATTATAGT<br>TATCCGTACACGTTCGGCCAAGGGACCAAGGTG<br>GAAATCAAACGTACGGTGGCTGCACCATCTGTC<br>TTCATCTTCCCGCCATCTGATGAGCAGTTGAAA<br>TCTGGAACTGCCTCTGTTGTGTGCCTGCTGAAT<br>AACTTCTATCCCAGAGAGGCCAAAGTACAGTGG<br>AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum04 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSS |
| SEQ ID NO: 51 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGATCAGGCAGTCCCCATCGAGAGGC<br>CTTGAGTGGCTGGGTAATATTTATCCTGGTACT<br>GGTGGTTCTAACTTCGATGAGAAGTTCAAGAAC<br>AGATTCACCATCTCCAGAGACAATTCCAAGAAC<br>ACGCTGTATCTTCAAATGAACAGCCTGAGAGCC<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 52 | HC | EVQLVQSGAEVKKPGESLRISCKGSGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLGK |
| SEQ ID NO: 53 | DNA HC | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGATCAGGCAGTCCCCATCGAGAGGC CTTGAGTGGCTGGGTAATATTTATCCTGGTACT GGTGGTTCTAACTTCGATGAGAAGTTCAAGAAC AGATTCACCATCTCCAGAGACAATTCCAAGAAC ACGCTGTATCTTCAAATGAACAGCCTGAGAGCC GAGGACACGGCCGTGTATTACTGTACAAGATGG ACTACTGGGACGGGAGCTTATTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC GGCGTGCACACCTTCCCGGCTGTCCTACAGTCC TCAGGACTCTACTCCCTCAGCAGCGTGGTGACC GTGCCCTCCAGCAGCTTGGGCACGAAGACCTAC ACCTGCAACGTAGATCACAAGCCCAGCAACACC AAGGTGGACAAGAGAGTTGAGTCCAAATATGGT CCCCCATGCCCACCGTGCCCAGCACCTGAGTTC CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum04 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 54 | VL | EIVLTQSPATLSLSPGERATLSCKSSQSLLDSG NQKNFLTWYQQKPGKAPKLLIYWASTRESGVPS RFSGSGSGTDFTFTISSLQPEDIATYYCQNDYS YPYTFGQGTKVEIK |
| SEQ ID NO: 55 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTATCAGCAG AAACCAGGGAAAGCTCCTAAGCTCCTGATCTAT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | TGGGCATCCACTAGGGAATCTGGGGTCCCATCA<br>AGGTTCAGTGGAAGTGGATCTGGGACAGATTTT<br>ACTTTCACCATCAGCAGCCTGCAGCCTGAAGAT<br>ATTGCAACATATTACTGTCAGAATGATTATAGT<br>TATCCGTACACGTTCGGCCAAGGGACCAAGGTG<br>GAAATCAAA |
| SEQ ID NO: 56 | LC | EIVLTQSPATLSLSPGERATLSCKSSQSLLDSG<br>NQKNFLTWYQQKPGKAPKLLIYWASTRESGVPS<br>RFSGSGSGTDFTFTISSLQPEDIATYYCQNDYS<br>YPYTFGQGTKVEIKRTVAAPSVFIFPPSDEQLK<br>SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 57 | DNA LC | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGGA<br>AATCAAAAGAACTTCTTGACCTGGTATCAGCAG<br>AAACCAGGGAAAGCTCCTAAGCTCCTGATCTAT<br>TGGGCATCCACTAGGGAATCTGGGGTCCCATCA<br>AGGTTCAGTGGAAGTGGATCTGGGACAGATTTT<br>ACTTTCACCATCAGCAGCCTGCAGCCTGAAGAT<br>ATTGCAACATATTACTGTCAGAATGATTATAGT<br>TATCCGTACACGTTCGGCCAAGGGACCAAGGTG<br>GAAATCAAACGTACGGTGGCTGCACCATCTGTC<br>TTCATCTTCCCGCCATCTGATGAGCAGTTGAAA<br>TCTGGAACTGCCTCTGTTGTGTGCCTGCTGAAT<br>AACTTCTATCCCAGAGAGGCCAAAGTACAGTGG<br>AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum05 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSS |
| SEQ ID NO: 39 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 40 | HC | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSSASTKGPSVFPLAPCS |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | RSTSESTAALGCLVKDYFPEPVTVSWNSGALTS GVHTFPAVLQSSGLYSLSSVVTVPSSSLGTKTY TCNVDHKPSNTKVDKRVESKYGPPCPPCPAPEF LGGPSVFLFPPKPKDTLMISRTPEVTCVVVDVS QEDPEVQFNWYVDGVEVHNAKTKPREEQFNSTY RVVSVLTVLHQDWLNGKEYKCKVSNKGLPSSIE KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLGK |
| SEQ ID NO: 41 | DNA HC | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGGTGCGACAGGCCACTGGACAAGGG CTTGAGTGGATGGGTAATATTTATCCTGGTACT GGTGGTTCTAACTTCGATGAGAAGTTCAAGAAC AGAGTCACGATTACCGCGGACAAATCCACGAGC ACAGCCTACATGGAGCTGAGCAGCCTGAGATCT GAGGACACGGCCGTGTATTACTGTACAAGATGG ACTACTGGGACGGGAGCTTATTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC GGCGTGCACACCTTCCCGGCTGTCCTACAGTCC TCAGGACTCTACTCCCTCAGCAGCGTGGTGACC GTGCCCTCCAGCAGCTTGGGCACGAAGACCTAC ACCTGCAACGTAGATCACAAGCCCAGCAACACC AAGGTGGACAAGAGAGTTGAGTCCAAATATGGT CCCCCATGCCCACCGTGCCCAGCACCTGAGTTC CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum05 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 54 | VL | EIVLTQSPATLSLSPGERATLSCKSSQSLLDSG NQKNFLTWYQQKPGKAPKLLIYWASTRESGVPS RFSGSGSGTDFTFTISSLQPEDIATYYCQNDYS YPYTFGQGTKVEIK |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 55 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTATCAGCAG AAACCAGGGAAAGCTCCTAAGCTCCTGATCTAT TGGGCATCCACTAGGGAATCTGGGGTCCCATCA AGGTTCAGTGGAAGTGGATCTGGGACAGATTTT ACTTTCACCATCAGCAGCCTGCAGCCTGAAGAT ATTGCAACATATTACTGTCAGAATGATTATAGT TATCCGTACACGTTCGGCCAAGGGACCAAGGTG GAAATCAAA |
| SEQ ID NO: 56 | LC | EIVLTQSPATLSLSPGERATLSCKSSQSLLDSG NQKNFLTWYQQKPGKAPKLLIYWASTRESGVPS RFSGSGSGTDFTFTISSLQPEDIATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 57 | DNA LC | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTATCAGCAG AAACCAGGGAAAGCTCCTAAGCTCCTGATCTAT TGGGCATCCACTAGGGAATCTGGGGTCCCATCA AGGTTCAGTGGAAGTGGATCTGGGACAGATTTT ACTTTCACCATCAGCAGCCTGCAGCCTGAAGAT ATTGCAACATATTACTGTCAGAATGATTATAGT TATCCGTACACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |
| **BAP049-hum06 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSS |
| SEQ ID NO: 39 | DNA VH | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGGTGCGACAGGCCACTGGACAAGGG CTTGAGTGGATGGGTAATATTTATCCTGGTACT GGTGGTTCTAACTTCGATGAGAAGTTCAAGAAC AGAGTCACGATTACCGCGGACAAATCCACGAGC ACAGCCTACATGGAGCTGAGCAGCCTGAGATCT GAGGACACGGCCGTGTATTACTGTACAAGATGG ACTACTGGGACGGGAGCTTATTGGGGCCAGGGC ACCACCGTGACCGTGTCCTCC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 40 | HC | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSSASTKGPSVFPLAPCS RSTSESTAALGCLVKDYFPEPVTVSWNSGALTS GVHTFPAVLQSSGLYSLSSVVTVPSSSLGTKTY TCNVDHKPSNTKVDKRVESKYGPPCPPCPAPEF LGGPSVFLFPPKPKDTLMISRTPEVTCVVVDVS QEDPEVQFNWYVDGVEVHNAKTKPREEQFNSTY RVVSVLTVLHQDWLNGKEYKCKVSNKGLPSSIE KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLGK |
| SEQ ID NO: 41 | DNA HC | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGGTGCGACAGGCCACTGGACAAGGG CTTGAGTGGATGGGTAATATTTATCCTGGTACT GGTGGTTCTAACTTCGATGAGAAGTTCAAGAAC AGAGTCACGATTACCGCGGACAAATCCACGAGC ACAGCCTACATGGAGCTGAGCAGCCTGAGATCT GAGGACACGGCCGTGTATTACTGTACAAGATGG ACTACTGGGACGGGAGCTTATTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC GGCGTGCACACCTTCCCGGCTGTCCTACAGTCC TCAGGACTCTACTCCCTCAGCAGCGTGGTGACC GTGCCCTCCAGCAGCTTGGGCACGAAGACCTAC ACCTGCAACGTAGATCACAAGCCCAGCAACACC AAGGTGGACAAGAGAGTTGAGTCCAAATATGGT CCCCCATGCCCACCGTGCCCAGCACCTGAGTTC CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum06 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 58 | VL | DIVMTQTPLSLPVTPGEPASISCKSSQSLLDSG<br>NQKNFLTWYQQKPGQAPRLLIYWASTRESGVPS<br>RFSGSGSGTDFTFTISSLEAEDAATYYCQNDYS<br>YPYTFGQGTKVEIK |
| SEQ ID NO: 59 | DNA VL | GATATTGTGATGACCCAGACTCCACTCTCCCTG<br>CCCGTCACCCCTGGAGAGCCGGCCTCCATCTCC<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGGTCCCCTCG<br>AGGTTCAGTGGCAGTGGATCTGGGACAGATTTC<br>ACCTTTACCATCAGTAGCCTGGAAGCTGAAGAT<br>GCTGCAACATATTACTGTCAGAATGATTATAGT<br>TATCCGTACACGTTCGGCCAAGGGACCAAGGTG<br>GAAATCAAA |
| SEQ ID NO: 60 | LC | DIVMTQTPLSLPVTPGEPASISCKSSQSLLDSG<br>NQKNFLTWYQQKPGQAPRLLIYWASTRESGVPS<br>RFSGSGSGTDFTFTISSLEAEDAATYYCQNDYS<br>YPYTFGQGTKVEIKRTVAAPSVFIFPPSDEQLK<br>SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 61 | DNA LC | GATATTGTGATGACCCAGACTCCACTCTCCCTG<br>CCCGTCACCCCTGGAGAGCCGGCCTCCATCTCC<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGGTCCCCTCG<br>AGGTTCAGTGGCAGTGGATCTGGGACAGATTTC<br>ACCTTTACCATCAGTAGCCTGGAAGCTGAAGAT<br>GCTGCAACATATTACTGTCAGAATGATTATAGT<br>TATCCGTACACGTTCGGCCAAGGGACCAAGGTG<br>GAAATCAAACGTACGGTGGCTGCACCATCTGTC<br>TTCATCTTCCCGCCATCTGATGAGCAGTTGAAA<br>TCTGGAACTGCCTCTGTTGTGTGCCTGCTGAAT<br>AACTTCTATCCCAGAGAGGCCAAAGTACAGTGG<br>AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum07 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSS |
| SEQ ID NO: 39 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 40 | HC | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 41 | DNA HC | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC<br>GTGGATGGCGTGGAGGTGCATAATGCCAAGACA<br>AAGCCGCGGGAGGAGCAGTTCAACAGCACGTAC<br>CGTGTGGTCAGCGTCCTCACCGTCCTGCACCAG<br>GACTGGCTGAACGGCAAGGAGTACAAGTGCAAG<br>GTGTCCAACAAAGGCCTCCCGTCCTCCATCGAG<br>AAAACCATCTCCAAAGCCAAAGGGCAGCCCCGA<br>GAGCCACAGGTGTACACCCTGCCCCCATCCCAG<br>GAGGAGATGACCAAGAACCAGGTCAGCCTGACC<br>TGCCTGGTCAAAGGCTTCTACCCCAGCGACATC<br>GCCGTGGAGTGGGAGAGCAATGGGCAGCCGGAG<br>AACAACTACAAGACCACGCCTCCCGTGCTGGAC<br>TCCGACGGCTCCTTCTTCCTCTACAGCAGGCTA<br>ACCGTGGACAAGAGCAGGTGGCAGGAGGGGAAT<br>GTCTTCTCATGCTCCGTGATGCATGAGGCTCTG<br>CACAACCACTACACACAGAAGAGCCTCTCCCTG<br>TCTCTGGGTAAA |
| **BAP049-hum07 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 62 | VL | EIVLTQSPATLSLSPGERATLSCKSSQSLLDSG NQKNFLTWYQQKPGKAPKLLIYWASTRESGVPS RFSGSGSGTDFTFTISSLEAEDAATYYCQNDYS YPYTFGQGTKVEIK |
| SEQ ID NO: 63 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTATCAGCAG AAACCAGGGAAAGCTCCTAAGCTCCTGATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAA |
| SEQ ID NO: 64 | LC | EIVLTQSPATLSLSPGERATLSCKSSQSLLDSG NQKNFLTWYQQKPGKAPKLLIYWASTRESGVPS RFSGSGSGTDFTFTISSLEAEDAATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 65 | DNA LC | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTATCAGCAG AAACCAGGGAAAGCTCCTAAGCTCCTGATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |
| **BAP049-hum08 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYW MHWIRQSPSRGLEWLGNIYPGTGGSNFDEKFKN RFTISRDNSKNTLYLQMNSLRAEDTAVYYCTRW TTGTGAYWGQGTTVTVSS |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 51 | DNA VH | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGATCAGGCAGTCCCCATCGAGAGGC CTTGAGTGGCTGGGTAATATTTATCCTGGTACT GGTGGTTCTAACTTCGATGAGAAGTTCAAGAAC AGATTCACCATCTCCAGAGACAATTCCAAGAAC ACGCTGTATCTTCAAATGAACAGCCTGAGAGCC GAGGACACGGCCGTGTATTACTGTACAAGATGG ACTACTGGGACGGGAGCTTATTGGGGCCAGGGC ACCACCGTGACCGTGTCCTCC |
| SEQ ID NO: 52 | HC | EVQLVQSGAEVKKPGESLRISCKGSGYTFTTYW MHWIRQSPSRGLEWLGNIYPGTGGSNFDEKFKN RFTISRDNSKNTLYLQMNSLRAEDTAVYYCTRW TTGTGAYWGQGTTVTVSSASTKGPSVFPLAPCS RSTSESTAALGCLVKDYFPEPVTVSWNSGALTS GVHTFPAVLQSSGLYSLSSVVTVPSSSLGTKTY TCNVDHKPSNTKVDKRVESKYGPPCPPCPAPEF LGGPSVFLFPPKPKDTLMISRTPEVTCVVVDVS QEDPEVQFNWYVDGVEVHNAKTKPREEQFNSTY RVVSVLTVLHQDWLNGKEYKCKVSNKGLPSSIE KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLGK |
| SEQ ID NO: 53 | DNA HC | GAAGTGCAGCTGGTGCAGTCTGGAGCAGAGGTG AAAAAGCCCGGGGAGTCTCTGAGGATCTCCTGT AAGGGTTCTGGCTACACATTCACCACTTACTGG ATGCACTGGATCAGGCAGTCCCCATCGAGAGGC CTTGAGTGGCTGGGTAATATTTATCCTGGTACT GGTGGTTCTAACTTCGATGAGAAGTTCAAGAAC AGATTCACCATCTCCAGAGACAATTCCAAGAAC ACGCTGTATCTTCAAATGAACAGCCTGAGAGCC GAGGACACGGCCGTGTATTACTGTACAAGATGG ACTACTGGGACGGGAGCTTATTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC GGCGTGCACACCTTCCCGGCTGTCCTACAGTCC TCAGGACTCTACTCCCTCAGCAGCGTGGTGACC GTGCCCTCCAGCAGCTTGGGCACGAAGACCTAC ACCTGCAACGTAGATCACAAGCCCAGCAACACC AAGGTGGACAAGAGAGTTGAGTCCAAATATGGT CCCCCATGCCCACCGTGCCCAGCACCTGAGTTC CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049-hum08 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSG<br>NQKNFLTWYQQKPGQAPRLLIYWASTRESGVPS<br>RFSGSGSGTDFTFTISSLEAEDAATYYCQNDYS<br>YPYTFGQGTKVEIK |
| SEQ ID NO: 67 | DNA VL | GAAATTGTGCTGACTCAGTCTCCAGACTTTCAG<br>TCTGTGACTCCAAAGGAGAAAGTCACCATCACC<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGGTCCCCTCG<br>AGGTTCAGTGGCAGTGGATCTGGGACAGATTTC<br>ACCTTTACCATCAGTAGCCTGGAAGCTGAAGAT<br>GCTGCAACATATTACTGTCAGAATGATTATAGT<br>TATCCGTACACGTTCGGCCAAGGGACCAAGGTG<br>GAAATCAAA |
| SEQ ID NO: 68 | LC | EIVLTQSPDFQSVTPKEKVTITCKSSQSLLDSG<br>NQKNFLTWYQQKPGQAPRLLIYWASTRESGVPS<br>RFSGSGSGTDFTFTISSLEAEDAATYYCQNDYS<br>YPYTFGQGTKVEIKRTVAAPSVFIFPPSDEQLK<br>SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 69 | DNA LC | GAAATTGTGCTGACTCAGTCTCCAGACTTTCAG<br>TCTGTGACTCCAAAGGAGAAAGTCACCATCACC<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGGTCCCCTCG<br>AGGTTCAGTGGCAGTGGATCTGGGACAGATTTC<br>ACCTTTACCATCAGTAGCCTGGAAGCTGAAGAT<br>GCTGCAACATATTACTGTCAGAATGATTATAGT<br>TATCCGTACACGTTCGGCCAAGGGACCAAGGTG<br>GAAATCAAACGTACGGTGGCTGCACCATCTGTC<br>TTCATCTTCCCGCCATCTGATGAGCAGTTGAAA<br>TCTGGAACTGCCTCTGTTGTGTGCCTGCTGAAT<br>AACTTCTATCCCAGAGAGGCCAAAGTACAGTGG<br>AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum09 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 3 (Chothia) | HCDR3 | WTTGTGAY |
| SEQ ID NO: 38 | VH | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSS |
| SEQ ID NO: 39 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 40 | HC | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 41 | DNA HC | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC<br>GTGGATGGCGTGGAGGTGCATAATGCCAAGACA<br>AAGCCGCGGGAGGAGCAGTTCAACAGCACGTAC<br>CGTGTGGTCAGCGTCCTCACCGTCCTGCACCAG<br>GACTGGCTGAACGGCAAGGAGTACAAGTGCAAG<br>GTGTCCAACAAAGGCCTCCCGTCCTCCATCGAG<br>AAAACCATCTCCAAAGCCAAAGGGCAGCCCCGA<br>GAGCCACAGGTGTACACCCTGCCCCCATCCCAG<br>GAGGAGATGACCAAGAACCAGGTCAGCCTGACC<br>TGCCTGGTCAAAGGCTTCTACCCCAGCGACATC<br>GCCGTGGAGTGGGAGAGCAATGGGCAGCCGGAG<br>AACAACTACAAGACCACGCCTCCCGTGCTGGAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum09 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSG NQKNFLTWYQQKPGQAPRLLIYWASTRESGVPS RFSGSGSGTDFTFTISSLEAEDAATYYCQNDYS YPYTFGQGTKVEIK |
| SEQ ID NO: 67 | DNA VL | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAA |
| SEQ ID NO: 68 | LC | EIVLTQSPDFQSVTPKEKVTITCKSSQSLLDSG NQKNFLTWYQQKPGQAPRLLIYWASTRESGVPS RFSGSGSGTDFTFTISSLEAEDAATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 69 | DNA LC | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |
| **BAP049-hum10 HC** | | |
| SEQ ID NO: 1 (Kabat) | HCDR1 | TYWMH |
| SEQ ID NO: 2 (Kabat) | HCDR2 | NIYPGTGGSNFDEKFKN |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 50 | VH | EVQLVQSGAEVKKPGESLRISCKGSGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSS |
| SEQ ID NO: 51 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGATCAGGCAGTCCCCATCGAGAGGC<br>CTTGAGTGGCTGGGTAATATTTATCCTGGTACT<br>GGTGGTTCTAACTTCGATGAGAAGTTCAAGAAC<br>AGATTCACCATCTCCAGAGACAATTCCAAGAAC<br>ACGCTGTATCTTCAAATGAACAGCCTGAGAGCC<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 52 | HC | EVQLVQSGAEVKKPGESLRISCKGSGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 53 | DNA HC | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGATCAGGCAGTCCCCATCGAGAGGC<br>CTTGAGTGGCTGGGTAATATTTATCCTGGTACT<br>GGTGGTTCTAACTTCGATGAGAAGTTCAAGAAC<br>AGATTCACCATCTCCAGAGACAATTCCAAGAAC<br>ACGCTGTATCTTCAAATGAACAGCCTGAGAGCC<br>GAGGACACGGCCGTGTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC<br>GTGGATGGCGTGGAGGTGCATAATGCCAAGACA<br>AAGCCGCGGGAGGAGCAGTTCAACAGCACGTAC<br>CGTGTGGTCAGCGTCCTCACCGTCCTGCACCAG<br>GACTGGCTGAACGGCAAGGAGTACAAGTGCAAG<br>GTGTCCAACAAAGGCCTCCCGTCCTCCATCGAG |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | | |
|---|---|---|---|
| | | | AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum10 LC** | | | |
| SEQ ID NO: 10 | (Kabat) | LCDR1 | KSSQSLLDSGNQKNFLT |
| SEQ ID NO: 11 | (Kabat) | LCDR2 | WASTRES |
| SEQ ID NO: 32 | (Kabat) | LCDR3 | QNDYSYPYT |
| SEQ ID NO: 13 | (Chothia) | LCDR1 | SQSLLDSGNQKNF |
| SEQ ID NO: 14 | (Chothia) | LCDR2 | WAS |
| SEQ ID NO: 33 | (Chothia) | LCDR3 | DYSYPY |
| SEQ ID NO: 70 | | VL | EIVLTQSPATLSLSPGERATLSCKSSQSLLDSG NQKNFLTWYQQKPGQAPRLLIYWASTRESGVPS RFSGSGSGTDFTFTISSLEAEDAATYYCQNDYS YPYTFGQGTKVEIK |
| SEQ ID NO: 71 | | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAA |
| SEQ ID NO: 72 | | LC | EIVLTQSPATLSLSPGERATLSCKSSQSLLDSG NQKNFLTWYQQKPGQAPRLLIYWASTRESGVPS RFSGSGSGTDFTFTISSLEAEDAATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 73 | | DNA LC | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049-hum11 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSS |
| SEQ ID NO: 39 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 40 | HC | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 41 | DNA HC | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum11 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSG NQKNFLTWYQQKPGQAPRLLIYWASTRESGVPS RFSGSGSGTDFTFTISSLEAEDAATYYCQNDYS YPYTFGQGTKVEIK |
| SEQ ID NO: 71 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAA |
| SEQ ID NO: 72 | LC | EIVLTQSPATLSLSPGERATLSCKSSQSLLDSG NQKNFLTWYQQKPGQAPRLLIYWASTRESGVPS RFSGSGSGTDFTFTISSLEAEDAATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 73 | DNA LC | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum12 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSS |
| SEQ ID NO: 39 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 40 | HC | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 41 | DNA HC | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | ACCTGCAACGTAGATCACAAGCCCAGCAACACC AAGGTGGACAAGAGAGTTGAGTCCAAATATGGT CCCCCATGCCCACCGTGCCCAGCACCTGAGTTC CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum12 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 74 | VL | DIQMTQSPSSLSASVGDRVTITCKSSQSLLDSG NQKNFLTWYLQKPGQSPQLLIYWASTRESGVPS RFSGSGSGTDFTFTISSLEAEDAATYYCQNDYS YPYTFGQGTKVEIK |
| SEQ ID NO: 75 | DNA VL | GACATCCAGATGACCCAGTCTCCATCCTCCCTG TCTGCATCTGTAGGAGACAGAGTCACCATCACT TGCAAGTCCAGTCAGAGTCTGTTAGACAGTGGA AATCAAAAGAACTTCTTGACCTGGTACCTGCAG AAGCCAGGGCAGTCTCCACAGCTCCTGATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAA |
| SEQ ID NO: 76 | LC | DIQMTQSPSSLSASVGDRVTITCKSSQSLLDSG NQKNFLTWYLQKPGQSPQLLIYWASTRESGVPS RFSGSGSGTDFTFTISSLEAEDAATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 77 | DNA LC | GACATCCAGATGACCCAGTCTCCATCCTCCCTG TCTGCATCTGTAGGAGACAGAGTCACCATCACT TGCAAGTCCAGTCAGAGTCTGTTAGACAGTGGA AATCAAAAGAACTTCTTGACCTGGTACCTGCAG AAGCCAGGGCAGTCTCCACAGCTCCTGATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GCTGCAACATATTACTGTCAGAATGATTATAGT<br>TATCCGTACACGTTCGGCCAAGGGACCAAGGTG<br>GAAATCAAACGTACGGTGGCTGCACCATCTGTC<br>TTCATCTTCCCGCCATCTGATGAGCAGTTGAAA<br>TCTGGAACTGCCTCTGTTGTGTGCCTGCTGAAT<br>AACTTCTATCCCAGAGAGGCCAAAGTACAGTGG<br>AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum13 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSS |
| SEQ ID NO: 39 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 40 | HC | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 41 | DNA HC | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCACTGGACAAGGG<br>CTTGAGTGGATGGGTAATATTTATCCTGGTACT<br>GGTGGTTCTAACTTCGATGAGAAGTTCAAGAAC<br>AGAGTCACGATTACCGCGGACAAATCCACGAGC<br>ACAGCCTACATGGAGCTGAGCAGCCTGAGATCT<br>GAGGACACGGCCGTGTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | | |
|---|---|---|---|
| | | | AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC<br>GTGGATGGCGTGGAGGTGCATAATGCCAAGACA<br>AAGCCGCGGGAGGAGCAGTTCAACAGCACGTAC<br>CGTGTGGTCAGCGTCCTCACCGTCCTGCACCAG<br>GACTGGCTGAACGGCAAGGAGTACAAGTGCAAG<br>GTGTCCAACAAAGGCCTCCCGTCCTCCATCGAG<br>AAAACCATCTCCAAAGCCAAAGGGCAGCCCCGA<br>GAGCCACAGGTGTACACCCTGCCCCCATCCCAG<br>GAGGAGATGACCAAGAACCAGGTCAGCCTGACC<br>TGCCTGGTCAAAGGCTTCTACCCCAGCGACATC<br>GCCGTGGAGTGGGAGAGCAATGGGCAGCCGGAG<br>AACAACTACAAGACCACGCCTCCCGTGCTGGAC<br>TCCGACGGCTCCTTCTTCCTCTACAGCAGGCTA<br>ACCGTGGACAAGAGCAGGTGGCAGGAGGGGAAT<br>GTCTTCTCATGCTCCGTGATGCATGAGGCTCTG<br>CACAACCACTACACACAGAAGAGCCTCTCCCTG<br>TCTCTGGGTAAA |
| **BAP049-hum13 LC** | | | |
| SEQ ID NO: 10 | (Kabat) | LCDR1 | KSSQSLLDSGNQKNFLT |
| SEQ ID NO: 11 | (Kabat) | LCDR2 | WASTRES |
| SEQ ID NO: 32 | (Kabat) | LCDR3 | QNDYSYPYT |
| SEQ ID NO: 13 | (Chothia) | LCDR1 | SQSLLDSGNQKNF |
| SEQ ID NO: 14 | (Chothia) | LCDR2 | WAS |
| SEQ ID NO: 33 | (Chothia) | LCDR3 | DYSYPY |
| SEQ ID NO: 78 | | VL | DVVMTQSPLSLPVTLGQPASISCKSSQSLLDSG<br>NQKNFLTWYQQKPGKAPKLLIYWASTRESGVPS<br>RFSGSGSGTDFTFTISSLEAEDAATYYCQNDYS<br>YPYTFGQGTKVEIK |
| SEQ ID NO: 79 | | DNA VL | GATGTTGTGATGACTCAGTCTCCACTCTCCCTG<br>CCCGTCACCCTTGGACAGCCGGCCTCCATCTCC<br>TGCAAGTCCAGTCAGAGTCTGTTAGACAGTGGA<br>AATCAAAAGAACTTCTTAACCTGGTATCAGCAG<br>AAACCAGGGAAAGCTCCTAAGCTCCTGATCTAT<br>TGGGCATCCACTAGGGAATCTGGGGTCCCCTCG<br>AGGTTCAGTGGCAGTGGATCTGGGACAGATTTC<br>ACCTTTACCATCAGTAGCCTGGAAGCTGAAGAT<br>GCTGCAACATATTACTGTCAGAATGATTATAGT<br>TATCCGTACACGTTCGGCCAAGGGACCAAGGTG<br>GAAATCAAA |
| SEQ ID NO: 80 | | LC | DVVMTQSPLSLPVTLGQPASISCKSSQSLLDSG<br>NQKNFLTWYQQKPGKAPKLLIYWASTRESGVPS<br>RFSGSGSGTDFTFTISSLEAEDAATYYCQNDYS<br>YPYTFGQGTKVEIKRTVAAPSVFIFPPSDEQLK<br>SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 81 | | DNA LC | GATGTTGTGATGACTCAGTCTCCACTCTCCCTG<br>CCCGTCACCCTTGGACAGCCGGCCTCCATCTCC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | TGCAAGTCCAGTCAGAGTCTGTTAGACAGTGGA AATCAAAAGAACTTCTTAACCTGGTATCAGCAG AAACCAGGGAAAGCTCCTAAGCTCCTGATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |
| **BAP049-hum14 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 82 | VH | QVQLVQSGAEVKKPGASVKVSCKASGYTFTTYW MHWIRQSPSRGLEWLGNIYPGTGGSNFDEKFKN RFTISRDNSKNTLYLQMNSLRAEDTAVYYCTRW TTGTGAYWGQGTTVTVSS |
| SEQ ID NO: 83 | DNA VH | CAGGTTCAGCTGGTGCAGTCTGGAGCTGAGGTG AAGAAGCCTGGGGCCTCAGTGAAGGTCTCCTGC AAGGCTTCTGGCTACACATTCACCACTTACTGG ATGCACTGGATCAGGCAGTCCCCATCGAGAGGC CTTGAGTGGCTGGGTAATATTTATCCTGGTACT GGTGGTTCTAACTTCGATGAGAAGTTCAAGAAC AGATTCACCATCTCCAGAGACAATTCCAAGAAC ACGCTGTATCTTCAAATGAACAGCCTGAGAGCC GAGGACACGGCCGTGTATTACTGTACAAGATGG ACTACTGGGACGGGAGCTTACTGGGGCCAGGGC ACCACCGTGACCGTGTCCTCC |
| SEQ ID NO: 84 | HC | QVQLVQSGAEVKKPGASVKVSCKASGYTFTTYW MHWIRQSPSRGLEWLGNIYPGTGGSNFDEKFKN RFTISRDNSKNTLYLQMNSLRAEDTAVYYCTRW TTGTGAYWGQGTTVTVSSASTKGPSVFPLAPCS RSTSESTAALGCLVKDYFPEPVTVSWNSGALTS GVHTFPAVLQSSGLYSLSSVVTVPSSSLGTKTY TCNVDHKPSNTKVDKRVESKYGPPCPPCPAPEF LGGPSVFLFPPKPKDTLMISRTPEVTCVVVDVS QEDPEVQFNWYVDGVEVHNAKTKPREEQFNSTY RVVSVLTVLHQDWLNGKEYKCKVSNKGLPSSIE KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLGK |
| SEQ ID NO: 85 | DNA HC | CAGGTTCAGCTGGTGCAGTCTGGAGCTGAGGTG AAGAAGCCTGGGGCCTCAGTGAAGGTCTCCTGC AAGGCTTCTGGCTACACATTCACCACTTACTGG ATGCACTGGATCAGGCAGTCCCCATCGAGAGGC CTTGAGTGGCTGGGTAATATTTATCCTGGTACT GGTGGTTCTAACTTCGATGAGAAGTTCAAGAAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | AGATTCACCATCTCCAGAGACAATTCCAAGAAC ACGCTGTATCTTCAAATGAACAGCCTGAGAGCC GAGGACACGGCCGTGTATTACTGTACAAGATGG ACTACTGGGACGGGAGCTTACTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC GGCGTGCACACCTTCCCGGCTGTCCTACAGTCC TCAGGACTCTACTCCCTCAGCAGCGTGGTGACC GTGCCCTCCAGCAGCTTGGGCACGAAGACCTAC ACCTGCAACGTAGATCACAAGCCCAGCAACACC AAGGTGGACAAGAGAGTTGAGTCCAAATATGGT CCCCCATGCCCACCGTGCCCAGCACCTGAGTTC CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum14 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSG NQKNFLTWYQQKPGQAPRLLIYWASTRESGVPS RFSGSGSGTDFTFTISSLEAEDAATYYCQNDYS YPYTFGQGTKVEIK |
| SEQ ID NO: 71 | DNA VL | GAAATTGTGTTGACACAGTCTCCAGCCACCCTG TCTTTGTCTCCAGGGGAAAGAGCCACCCTCTCC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAA |
| SEQ ID NO: 72 | LC | EIVLTQSPATLSLSPGERATLSCKSSQSLLDSG NQKNFLTWYQQKPGQAPRLLIYWASTRESGVPS RFSGSGSGTDFTFTISSLEAEDAATYYCQNDYS YPYTFGQGTKVEIKRTVAAPSVFIFPPSDEQLK |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 73 | DNA LC | GAAATTGTGTTGACACAGTCTCCAGCCACCCTG<br>TCTTTGTCTCCAGGGGAAAGAGCCACCCTCTCC<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGGTCCCCTCG<br>AGGTTCAGTGGCAGTGGATCTGGGACAGATTTC<br>ACCTTTACCATCAGTAGCCTGGAAGCTGAAGAT<br>GCTGCAACATATTACTGTCAGAATGATTATAGT<br>TATCCGTACACGTTCGGCCAAGGGACCAAGGTG<br>GAAATCAAACGTACGGTGGCTGCACCATCTGTC<br>TTCATCTTCCCGCCATCTGATGAGCAGTTGAAA<br>TCTGGAACTGCCTCTGTTGTGTGCCTGCTGAAT<br>AACTTCTATCCCAGAGAGGCCAAAGTACAGTGG<br>AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum15 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 82 | VH | QVQLVQSGAEVKKPGASVKVSCKASGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSS |
| SEQ ID NO: 83 | DNA VH | CAGGTTCAGCTGGTGCAGTCTGGAGCTGAGGTG<br>AAGAAGCCTGGGGCCTCAGTGAAGGTCTCCTGC<br>AAGGCTTCTGGCTACACATTCACCACTTACTGG<br>ATGCACTGGATCAGGCAGTCCCCATCGAGAGGC<br>CTTGAGTGGCTGGGTAATATTTATCCTGGTACT<br>GGTGGTTCTAACTTCGATGAGAAGTTCAAGAAC<br>AGATTCACCATCTCCAGAGACAATTCCAAGAAC<br>ACGCTGTATCTTCAAATGAACAGCCTGAGAGCC<br>GAGGACACGGCCGTGTATTACTGTACAAGATGG<br>ACTACTGGGACGGGAGCTTACTGGGGCCAGGGC<br>ACCACCGTGACCGTGTCCTCC |
| SEQ ID NO: 84 | HC | QVQLVQSGAEVKKPGASVKVSCKASGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 85 | DNA HC | CAGGTTCAGCTGGTGCAGTCTGGAGCTGAGGTG AAGAAGCCTGGGGCCTCAGTGAAGGTCTCCTGC AAGGCTTCTGGCTACACATTCACCACTTACTGG ATGCACTGGATCAGGCAGTCCCCATCGAGAGGC CTTGAGTGGCTGGGTAATATTTATCCTGGTACT GGTGGTTCTAACTTCGATGAGAAGTTCAAGAAC AGATTCACCATCTCCAGAGACAATTCCAAGAAC ACGCTGTATCTTCAAATGAACAGCCTGAGAGCC GAGGACACGGCCGTGTATTACTGTACAAGATGG ACTACTGGGACGGGAGCTTACTGGGGCCAGGGC ACCACCGTGACCGTGTCCTCCGCTTCCACCAAG GGCCCATCCGTCTTCCCCCTGGCGCCCTGCTCC AGGAGCACCTCCGAGAGCACAGCCGCCCTGGGC TGCCTGGTCAAGGACTACTTCCCCGAACCGGTG ACGGTGTCGTGGAACTCAGGCGCCCTGACCAGC GGCGTGCACACCTTCCCGGCTGTCCTACAGTCC TCAGGACTCTACTCCCTCAGCAGCGTGGTGACC GTGCCCTCCAGCAGCTTGGGCACGAAGACCTAC ACCTGCAACGTAGATCACAAGCCCAGCAACACC AAGGTGGACAAGAGAGTTGAGTCCAAATATGGT CCCCCATGCCCACCGTGCCCAGCACCTGAGTTC CTGGGGGGACCATCAGTCTTCCTGTTCCCCCCA AAACCCAAGGACACTCTCATGATCTCCCGGACC CCTGAGGTCACGTGCGTGGTGGTGGACGTGAGC CAGGAAGACCCCGAGGTCCAGTTCAACTGGTAC GTGGATGGCGTGGAGGTGCATAATGCCAAGACA AAGCCGCGGGAGGAGCAGTTCAACAGCACGTAC CGTGTGGTCAGCGTCCTCACCGTCCTGCACCAG GACTGGCTGAACGGCAAGGAGTACAAGTGCAAG GTGTCCAACAAAGGCCTCCCGTCCTCCATCGAG AAAACCATCTCCAAAGCCAAAGGGCAGCCCCGA GAGCCACAGGTGTACACCCTGCCCCCATCCCAG GAGGAGATGACCAAGAACCAGGTCAGCCTGACC TGCCTGGTCAAAGGCTTCTACCCCAGCGACATC GCCGTGGAGTGGGAGAGCAATGGGCAGCCGGAG AACAACTACAAGACCACGCCTCCCGTGCTGGAC TCCGACGGCTCCTTCTTCCTCTACAGCAGGCTA ACCGTGGACAAGAGCAGGTGGCAGGAGGGGAAT GTCTTCTCATGCTCCGTGATGCATGAGGCTCTG CACAACCACTACACACAGAAGAGCCTCTCCCTG TCTCTGGGTAAA |
| **BAP049-hum15 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSG NQKNFLTWYQQKPGQAPRLLIYWASTRESGVPS RFSGSGSGTDFTFTISSLEAEDAATYYCQNDYS YPYTFGQGTKVEIK |
| SEQ ID NO: 67 | DNA VL | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GCTGCAACATATTACTGTCAGAATGATTATAGT<br>TATCCGTACACGTTCGGCCAAGGGACCAAGGTG<br>GAAATCAAA |
| SEQ ID NO: 68 | LC | EIVLTQSPDFQSVTPKEKVTITCKSSQSLLDSG<br>NQKNFLTWYQQKPGQAPRLLIYWASTRESGVPS<br>RFSGSGSGTDFTFTISSLEAEDAATYYCQNDYS<br>YPYTFGQGTKVEIKRTVAAPSVFIFPPSDEQLK<br>SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 69 | DNA LC | GAAATTGTGCTGACTCAGTCTCCAGACTTTCAG<br>TCTGTGACTCCAAAGGAGAAAGTCACCATCACC<br>TGCAAGTCCAGTCAGAGTCTGTTAGACAGTGGA<br>AATCAAAAGAACTTCTTGACCTGGTACCAGCAG<br>AAACCTGGCCAGGCTCCCAGGCTCCTCATCTAT<br>TGGGCATCCACTAGGGAATCTGGGGTCCCCTCG<br>AGGTTCAGTGGCAGTGGATCTGGGACAGATTTC<br>ACCTTTACCATCAGTAGCCTGGAAGCTGAAGAT<br>GCTGCAACATATTACTGTCAGAATGATTATAGT<br>TATCCGTACACGTTCGGCCAAGGGACCAAGGTG<br>GAAATCAAACGTACGGTGGCTGCACCATCTGTC<br>TTCATCTTCCCGCCATCTGATGAGCAGTTGAAA<br>TCTGGAACTGCCTCTGTTGTGTGCCTGCTGAAT<br>AACTTCTATCCCAGAGAGGCCAAAGTACAGTGG<br>AAGGTGGATAACGCCCTCCAATCGGGTAACTCC<br>CAGGAGAGTGTCACAGAGCAGGACAGCAAGGAC<br>AGCACCTACAGCCTCAGCAGCACCCTGACGCTG<br>AGCAAAGCAGACTACGAGAAACACAAAGTCTAC<br>GCCTGCGAAGTCACCCATCAGGGCCTGAGCTCG<br>CCCGTCACAAAGAGCTTCAACAGGGGAGAGTGT |
| **BAP049-hum16 HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 86 | VH | EVQLVQSGAEVKKPGESLRISCKGSGYTFTTYW<br>MHWVRQAPGQGLEWMGNIYPGTGGSNFDEKFKN<br>RFTISRDNSKNTLYLQMNSLRAEDTAVYYCTRW<br>TTGTGAYWGQGTTVTVSS |
| SEQ ID NO: 87 | DNA VH | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCCCTGGACAAGGG<br>CTTGAGTGGATGGGTAATATTTATCCTGGTACT<br>GGTGGTTCTAACTTCGATGAGAAGTTCAAGAAC<br>AGATTCACCATCTCCAGAGACAATTCCAAGAAC<br>ACGCTGTATCTTCAAATGAACAGCCTGAGAGCC<br>GAGGACACGGCCGTGTATTACTGTACAAGATGG<br>ACTACTGGGACGGGAGCTTATTGGGGCCAGGGC<br>ACCACCGTGACCGTGTCCTCC |
| SEQ ID NO: 88 | HC | EVQLVQSGAEVKKPGESLRISCKGSGYTFTTYW<br>MHWVRQAPGQGLEWMGNIYPGTGGSNFDEKFKN<br>RFTISRDNSKNTLYLQMNSLRAEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLGK |
| SEQ ID NO: 89 | DNA HC | GAAGTGCAGCTGGTGCAGTCTGGAGCAGAGGTG<br>AAAAAGCCCGGGGAGTCTCTGAGGATCTCCTGT<br>AAGGGTTCTGGCTACACATTCACCACTTACTGG<br>ATGCACTGGGTGCGACAGGCCCCTGGACAAGGG<br>CTTGAGTGGATGGGTAATATTTATCCTGGTACT<br>GGTGGTTCTAACTTCGATGAGAAGTTCAAGAAC<br>AGATTCACCATCTCCAGAGACAATTCCAAGAAC<br>ACGCTGTATCTTCAAATGAACAGCCTGAGAGCC<br>GAGGACACGGCCGTGTATTACTGTACAAGATGG<br>ACTACTGGGACGGGAGCTTATTGGGGCCAGGGC<br>ACCACCGTGACCGTGTCCTCCGCTTCCACCAAG<br>GGCCCATCCGTCTTCCCCCTGGCGCCCTGCTCC<br>AGGAGCACCTCCGAGAGCACAGCCGCCCTGGGC<br>TGCCTGGTCAAGGACTACTTCCCCGAACCGGTG<br>ACGGTGTCGTGGAACTCAGGCGCCCTGACCAGC<br>GGCGTGCACACCTTCCCGGCTGTCCTACAGTCC<br>TCAGGACTCTACTCCCTCAGCAGCGTGGTGACC<br>GTGCCCTCCAGCAGCTTGGGCACGAAGACCTAC<br>ACCTGCAACGTAGATCACAAGCCCAGCAACACC<br>AAGGTGGACAAGAGAGTTGAGTCCAAATATGGT<br>CCCCCATGCCCACCGTGCCCAGCACCTGAGTTC<br>CTGGGGGGACCATCAGTCTTCCTGTTCCCCCCA<br>AAACCCAAGGACACTCTCATGATCTCCCGGACC<br>CCTGAGGTCACGTGCGTGGTGGTGGACGTGAGC<br>CAGGAAGACCCCGAGGTCCAGTTCAACTGGTAC<br>GTGGATGGCGTGGAGGTGCATAATGCCAAGACA<br>AAGCCGCGGGAGGAGCAGTTCAACAGCACGTAC<br>CGTGTGGTCAGCGTCCTCACCGTCCTGCACCAG<br>GACTGGCTGAACGGCAAGGAGTACAAGTGCAAG<br>GTGTCCAACAAAGGCCTCCCGTCCTCCATCGAG<br>AAAACCATCTCCAAAGCCAAAGGGCAGCCCCGA<br>GAGCCACAGGTGTACACCCTGCCCCCATCCCAG<br>GAGGAGATGACCAAGAACCAGGTCAGCCTGACC<br>TGCCTGGTCAAAGGCTTCTACCCCAGCGACATC<br>GCCGTGGAGTGGGAGAGCAATGGGCAGCCGGAG<br>AACAACTACAAGACCACGCCTCCCGTGCTGGAC<br>TCCGACGGCTCCTTCTTCCTCTACAGCAGGCTA<br>ACCGTGGACAAGAGCAGGTGGCAGGAGGGGAAT<br>GTCTTCTCATGCTCCGTGATGCATGAGGCTCTG<br>CACAACCACTACACACAGAAGAGCCTCTCCCTG<br>TCTCTGGGTAAA |
| **BAP049-hum16 LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSG<br>NQKNFLTWYQQKPGQAPRLLIYWASTRESGVPS<br>RFSGSGSGTDFTFTISSLEAEDAATYYCQNDYS<br>YPYTFGQGTKVEIK |
| SEQ ID NO: 67 | DNA VL | GAAATTGTGCTGACTCAGTCTCCAGACTTTCAG<br>TCTGTGACTCCAAAGGAGAAAGTCACCATCACC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAA |
| SEQ ID NO: 68 | LC | EIVLTQSPDFQSVTPKEKVTITCKSSQSLLDSG NQKNFLTWYQQKPGQAPRLLIYWASTRESGVPS RFSGSGSGTDFTFTISSLEAEDAATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 69 | DNA LC | GAAATTGTGCTGACTCAGTCTCCAGACTTTCAG TCTGTGACTCCAAAGGAGAAAGTCACCATCACC TGCAAGTCCAGTCAGAGTCTGTTAGACAGTGGA AATCAAAAGAACTTCTTGACCTGGTACCAGCAG AAACCTGGCCAGGCTCCCAGGCTCCTCATCTAT TGGGCATCCACTAGGGAATCTGGGGTCCCCTCG AGGTTCAGTGGCAGTGGATCTGGGACAGATTTC ACCTTTACCATCAGTAGCCTGGAAGCTGAAGAT GCTGCAACATATTACTGTCAGAATGATTATAGT TATCCGTACACGTTCGGCCAAGGGACCAAGGTG GAAATCAAACGTACGGTGGCTGCACCATCTGTC TTCATCTTCCCGCCATCTGATGAGCAGTTGAAA TCTGGAACTGCCTCTGTTGTGTGCCTGCTGAAT AACTTCTATCCCAGAGAGGCCAAAGTACAGTGG AAGGTGGATAACGCCCTCCAATCGGGTAACTCC CAGGAGAGTGTCACAGAGCAGGACAGCAAGGAC AGCACCTACAGCCTCAGCAGCACCCTGACGCTG AGCAAAGCAGACTACGAGAAACACAAAGTCTAC GCCTGCGAAGTCACCCATCAGGGCCTGAGCTCG CCCGTCACAAAGAGCTTCAACAGGGGAGAGTGT |
| **BAP049-Clone-A HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSS |
| SEQ ID NO: 90 | DNA VH | GAAGTGCAGCTGGTGCAGTCTGGCGCCGAAGTG AAGAAGCCTGGCGAGTCCCTGCGGATCTCCTGC AAGGGCTCTGGCTACACCTTCACCACCTACTGG ATGCACTGGGTGCGACAGGCTACCGGCCAGGGC CTGGAATGGATGGGCAACATCTATCCTGGCACC GGCGGCTCCAACTTCGACGAGAAGTTCAAGAAC AGAGTGACCATCACCGCCGACAAGTCCACCTCC ACCGCCTACATGGAACTGTCCTCCCTGAGATCC GAGGACACCGCCGTGTACTACTGCACCCGGTGG ACAACCGGCACAGGCGCTTATTGGGGCCAGGGC ACCACAGTGACCGTGTCCTCT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 91 | HC | EVQLVQSGAEVKKPGESLRISCKGSGYTFTTYWMHWVRQATGQGLEWMGNIYPGTGGSNFDEKFKNRVTITADKSTSTAYMELSSLRSEDTAVYYCTRWTTGTGAYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| SEQ ID NO: 92 | DNA HC | GAAGTGCAGCTGGTGCAGTCTGGCGCCGAAGTGAAGAAGCCTGGCGAGTCCCTGCGGATCTCCTGCAAGGGCTCTGGCTACACCTTCACCACCTACTGGATGCACTGGGTGCGACAGGCTACCGGCCAGGGCCTGGAATGGATGGGCAACATCTATCCTGGCACCGGCGGCTCCAACTTCGACGAGAAGTTCAAGAACAGAGTGACCATCACCGCCGACAAGTCCACCTCCACCGCCTACATGGAACTGTCCTCCCTGAGATCCGAGGACACCGCCGTGTACTACTGCACCCGGTGGACAACCGGCACAGGCGCTTATTGGGGCCAGGGCACCACAGTGACCGTGTCCTCTGCTTCTACCAAGGGGCCCAGCGTGTTCCCCCTGGCCCCCTGCTCCAGAAGCACCAGCGAGAGCACAGCCGCCCTGGGCTGCCTGGTGAAGGACTACTTCCCCGAGCCCGTGACCGTGTCCTGGAACAGCGGAGCCCTGACCAGCGGCGTGCACACCTTCCCCGCCGTGCTGCAGAGCAGCGGCCTGTACAGCCTGAGCAGCGTGGTGACCGTGCCCAGCAGCAGCCTGGGCACCAAGACCTACACCTGTAACGTGGACCACAAGCCCAGCAACACCAAGGTGGACAAGAGGGTGGAGAGCAAGTACGGCCCACCCTGCCCCCCCTGCCCAGCCCCCGAGTTCCTGGGCGGACCCAGCGTGTTCCTGTTCCCCCCCAAGCCCAAGGACACCCTGATGATCAGCAGAACCCCCGAGGTGACCTGTGTGGTGGTGGACGTGTCCCAGGAGGACCCCGAGGTCCAGTTCAACTGGTACGTGGACGGCGTGGAGGTGCACAACGCCAAGACCAAGCCCAGAGAGGAGCAGTTTAACAGCACCTACCGGGTGGTGTCCGTGCTGACCGTGCTGCACCAGGACTGGCTGAACGGCAAAGAGTACAAGTGTAAGGTCTCCAACAAGGGCCTGCCAAGCAGCATCGAAAAGACCATCAGCAAGGCCAAGGGCCAGCCTAGAGAGCCCCAGGTCTACACCCTGCCACCCAGCCAAGAGGAGATGACCAAGAACCAGGTGTCCCTGACCTGTCTGGTGAAGGGCTTCTACCCAAGCGACATCGCCGTGGAGTGGGAGAGCAACGGCCAGCCCGAGAACAACTACAAGACCACCCCCCCAGTGCTGGACAGCGACGGCAGCTTCTTCCTGTACAGCAGGCTGACCGTGGACAAGTCCAGATGGCAGGAGGGCAACGTCTTTAGCTGCTCCGTGATGCACGAGGCCCTGCACAACCACTACACCCAGAAGAGCCTGAGCCTGTCCCTGGGC |
| **BAP049-Clone-A LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 42 | VL | EIVLTQSPATLSLSPGERATLSCKSSQSLLDSG NQKNFLTWYQQKPGQAPRLLIYWASTRESGVPS RFSGSGSGTEFTLTISSLQPDDFATYYCQNDYS YPYTFGQGTKVEIK |
| SEQ ID NO: 93 | DNA VL | GAGATCGTGCTGACCCAGTCCCCTGCCACCCTG TCACTGTCTCCAGGCGAGAGAGCTACCCTGTCC TGCAAGTCCTCCCAGTCCCTGCTGGACTCCGGC AACCAGAAGAACTTCCTGACCTGGTATCAGCAG AAGCCCGGCCAGGCCCCCAGACTGCTGATCTAC TGGGCCTCCACCCGGGAATCTGGCGTGCCCTCT AGATTCTCCGGCTCCGGCTCTGGCACCGAGTTT ACCCTGACCATCTCCAGCCTGCAGCCCGACGAC TTCGCCACCTACTACTGCCAGAACGACTACTCC TACCCCTACACCTTCGGCCAGGGCACCAAGGTG GAAATCAAG |
| SEQ ID NO: 44 | LC | EIVLTQSPATLSLSPGERATLSCKSSQSLLDSG NQKNFLTWYQQKPGQAPRLLIYWASTRESGVPS RFSGSGSGTEFTLTISSLQPDDFATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 94 | DNA LC | GAGATCGTGCTGACCCAGTCCCCTGCCACCCTG TCACTGTCTCCAGGCGAGAGAGCTACCCTGTCC TGCAAGTCCTCCCAGTCCCTGCTGGACTCCGGC AACCAGAAGAACTTCCTGACCTGGTATCAGCAG AAGCCCGGCCAGGCCCCCAGACTGCTGATCTAC TGGGCCTCCACCCGGGAATCTGGCGTGCCCTCT AGATTCTCCGGCTCCGGCTCTGGCACCGAGTTT ACCCTGACCATCTCCAGCCTGCAGCCCGACGAC TTCGCCACCTACTACTGCCAGAACGACTACTCC TACCCCTACACCTTCGGCCAGGGCACCAAGGTG GAAATCAAGCGTACGGTGGCCGCTCCCAGCGTG TTCATCTTCCCCCCAAGCGACGAGCAGCTGAAG AGCGGCACCGCCAGCGTGGTGTGTCTGCTGAAC AACTTCTACCCCAGGGAGGCCAAGGTGCAGTGG AAGGTGGACAACGCCCTGCAGAGCGGCAACAGC CAGGAGAGCGTCACCGAGCAGGACAGCAAGGAC TCCACCTACAGCCTGAGCAGCACCCTGACCCTG AGCAAGGCCGACTACGAGAAGCACAAGGTGTAC GCCTGTGAGGTGACCCACCAGGGCCTGTCCAGC CCCGTGACCAAGAGCTTCAACAGGGGCGAGTGC |
| **BAP049-Clone-B HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSS |
| SEQ ID NO: 95 | DNA VH | GAGGTGCAGCTGGTGCAGTCAGGCGCCGAAGTG AAGAAGCCCGGCGAGTCACTGAGAATTAGCTGT AAAGGTTCAGGCTACACCTTCACTACCTACTGG ATGCACTGGGTCCGCCAGGCTACCGGTCAAGGC CTCGAGTGGATGGGTAATATCTACCCCGGCACC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | GGCGGCTCTAACTTCGACGAGAAGTTTAAGAAT<br>AGAGTGACTATCACCGCCGATAAGTCTACTAGC<br>ACCGCCTATATGGAACTGTCTAGCCTGAGATCA<br>GAGGACACCGCCGTCTACTACTGCACTAGGTGG<br>ACTACCGGCACAGGCGCCTACTGGGGTCAAGGC<br>ACTACCGTGACCGTGTCTAGC |
| SEQ ID NO: 91 | HC | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLG |
| SEQ ID NO: 96 | DNA HC | GAGGTGCAGCTGGTGCAGTCAGGCGCCGAAGTG<br>AAGAAGCCCGGCGAGTCACTGAGAATTAGCTGT<br>AAAGGTTCAGGCTACACCTTCACTACCTACTGG<br>ATGCACTGGGTCCGCCAGGCTACCGGTCAAGGC<br>CTCGAGTGGATGGGTAATATCTACCCCGGCACC<br>GGCGGCTCTAACTTCGACGAGAAGTTTAAGAAT<br>AGAGTGACTATCACCGCCGATAAGTCTACTAGC<br>ACCGCCTATATGGAACTGTCTAGCCTGAGATCA<br>GAGGACACCGCCGTCTACTACTGCACTAGGTGG<br>ACTACCGGCACAGGCGCCTACTGGGGTCAAGGC<br>ACTACCGTGACCGTGTCTAGCGCTAGCACTAAG<br>GGCCCGTCCGTGTTCCCCCTGGCACCTTGTAGC<br>CGGAGCACTAGCGAATCCACCGCTGCCCTCGGC<br>TGCCTGGTCAAGGATTACTTCCCGGAGCCCGTG<br>ACCGTGTCCTGGAACAGCGGAGCCCTGACCTCC<br>GGAGTGCACACCTTCCCCGCTGTGCTGCAGAGC<br>TCCGGGCTGTACTCGCTGTCGTCGGTGGTCACG<br>GTGCCTTCATCTAGCCTGGGTACCAAGACCTAC<br>ACTTGCAACGTGGACCACAAGCCTTCCAACACT<br>AAGGTGGACAAGCGCGTCGAATCGAAGTACGGC<br>CCACCGTGCCCGCCTTGTCCCGCGCCGGAGTTC<br>CTCGGCGGTCCCTCGGTCTTTCTGTTCCCACCG<br>AAGCCCAAGGACACTTTGATGATTTCCCGCACC<br>CCTGAAGTGACATGCGTGGTCGTGGACGTGTCA<br>CAGGAAGATCCGGAGGTGCAGTTCAATTGGTAC<br>GTGGATGGCGTCGAGGTGCACAACGCCAAAACC<br>AAGCCGAGGGAGGAGCAGTTCAACTCCACTTAC<br>CGCGTCGTGTCCGTGCTGACGGTGCTGCATCAG<br>GACTGGCTGAACGGGAAGGAGTACAAGTGCAAA<br>GTGTCCAACAAGGGACTTCCTAGCTCAATCGAA<br>AAGACCATCTCGAAAGCCAAGGGACAGCCCCGG<br>GAACCCCAAGTGTATACCCTGCCACCGAGCCAG<br>GAAGAAATGACTAAGAACCAAGTCTCATTGACT<br>TGCCTTGTGAAGGGCTTCTACCCATCGGATATC<br>GCCGTGGAATGGGAGTCCAACGGCCAGCCGGAA<br>AACAACTACAAGACCACCCCTCCGGTGCTGGAC<br>TCAGACGGATCCTTCTTCCTCTACTCGCGGCTG<br>ACCGTGGATAAGAGCAGATGGCAGGAGGGAAAT<br>GTGTTCAGCTGTTCTGTGATGCATGAAGCCCTG<br>CACAACCACTACACTCAGAAGTCCCTGTCCCTC<br>TCCCTGGGA |
| **BAP049-Clone-B LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 54 | VL | EIVLTQSPATLSLSPGERATLSCKSSQSLLDSG NQKNFLTWYQQKPGKAPKLLIYWASTRESGVPS RFSGSGSGTDFTFTISSLQPEDIATYYCQNDYS YPYTFGQGTKVEIK |
| SEQ ID NO: 97 | DNA VL | GAGATCGTCCTGACTCAGTCACCCGCTACCCTG AGCCTGAGCCCTGGCGAGCGGGCTACACTGAGC TGTAAATCTAGTCAGTCACTGCTGGATAGCGGT AATCAGAAGAACTTCCTGACCTGGTATCAGCAG AAGCCCGGTAAAGCCCCTAAGCTGCTGATCTAC TGGGCCTCTACTAGAGAATCAGGCGTGCCCTCT AGGTTTAGCGGTAGCGGTAGTGGCACCGACTTC ACCTTCACTATCTCTAGCCTGCAGCCCGAGGAT ATCGCTACCTACTACTGTCAGAACGACTATAGC TACCCCTACACCTTCGGTCAAGGCACTAAGGTC GAGATTAAG |
| SEQ ID NO: 56 | LC | EIVLTQSPATLSLSPGERATLSCKSSQSLLDSG NQKNFLTWYQQKPGKAPKLLIYWASTRESGVPS RFSGSGSGTDFTFTISSLQPEDIATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 98 | DNA LC | GAGATCGTCCTGACTCAGTCACCCGCTACCCTG AGCCTGAGCCCTGGCGAGCGGGCTACACTGAGC TGTAAATCTAGTCAGTCACTGCTGGATAGCGGT AATCAGAAGAACTTCCTGACCTGGTATCAGCAG AAGCCCGGTAAAGCCCCTAAGCTGCTGATCTAC TGGGCCTCTACTAGAGAATCAGGCGTGCCCTCT AGGTTTAGCGGTAGCGGTAGTGGCACCGACTTC ACCTTCACTATCTCTAGCCTGCAGCCCGAGGAT ATCGCTACCTACTACTGTCAGAACGACTATAGC TACCCCTACACCTTCGGTCAAGGCACTAAGGTC GAGATTAAGCGTACGGTGGCCGCTCCCAGCGTG TTCATCTTCCCCCCCAGCGACGAGCAGCTGAAG AGCGGCACCGCCAGCGTGGTGTGCCTGCTGAAC AACTTCTACCCCCGGGAGGCCAAGGTGCAGTGG AAGGTGGACAACGCCCTGCAGAGCGGCAACAGC CAGGAGAGCGTCACCGAGCAGGACAGCAAGGAC TCCACCTACAGCCTGAGCAGCACCCTGACCCTG AGCAAGGCCGACTACGAGAAGCATAAGGTGTAC GCCTGCGAGGTGACCCACCAGGGCCTGTCCAGC CCCGTGACCAAGAGCTTCAACAGGGGCGAGTGC |
| **BAP049-Clone-C HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSS |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 90 | DNA VH | GAAGTGCAGCTGGTGCAGTCTGGCGCCGAAGTG AAGAAGCCTGGCGAGTCCCTGCGGATCTCCTGC AAGGGCTCTGGCTACACCTTCACCACCTACTGG ATGCACTGGGTGCGACAGGCTACCGGCCAGGGC CTGGAATGGATGGGCAACATCTATCCTGGCACC GGCGGCTCCAACTTCGACGAGAAGTTCAAGAAC AGAGTGACCATCACCGCCGACAAGTCCACCTCC ACCGCCTACATGGAACTGTCCTCCCTGAGATCC GAGGACACCGCCGTGTACTACTGCACCCGGTGG ACAACCGGCACAGGCGCTTATTGGGGCCAGGGC ACCACAGTGACCGTGTCCTCT |
| SEQ ID NO: 91 | HC | EVQLVQSGAEVKKPGESLRISCKGSGYTFTTYW MHWVRQATGQGLEWMGNIYPGTGGSNFDEKFKN RVTITADKSTSTAYMELSSLRSEDTAVYYCTRW TTGTGAYWGQGTTVTVSSASTKGPSVFPLAPCS RSTSESTAALGCLVKDYFPEPVTVSWNSGALTS GVHTFPAVLQSSGLYSLSSVVTVPSSSLGTKTY TCNVDHKPSNTKVDKRVESKYGPPCPPCPAPEF LGGPSVFLFPPKPKDTLMISRTPEVTCVVVDVS QEDPEVQFNWYVDGVEVHNAKTKPREEQFNSTY RVVSVLTVLHQDWLNGKEYKCKVSNKGLPSSIE KTISKAKGQPREPQVYTLPPSQEEMTKNQVSLT CLVKGFYPSDIAVEWESNGQPENNYKTTPPVLD SDGSFFLYSRLTVDKSRWQEGNVFSCSVMHEAL HNHYTQKSLSLSLG |
| SEQ ID NO: 92 | DNA HC | GAAGTGCAGCTGGTGCAGTCTGGCGCCGAAGTG AAGAAGCCTGGCGAGTCCCTGCGGATCTCCTGC AAGGGCTCTGGCTACACCTTCACCACCTACTGG ATGCACTGGGTGCGACAGGCTACCGGCCAGGGC CTGGAATGGATGGGCAACATCTATCCTGGCACC GGCGGCTCCAACTTCGACGAGAAGTTCAAGAAC AGAGTGACCATCACCGCCGACAAGTCCACCTCC ACCGCCTACATGGAACTGTCCTCCCTGAGATCC GAGGACACCGCCGTGTACTACTGCACCCGGTGG ACAACCGGCACAGGCGCTTATTGGGGCCAGGGC ACCACAGTGACCGTGTCCTCTGCTTCTACCAAG GGGCCCAGCGTGTTCCCCCTGGCCCCCTGCTCC AGAAGCACCAGCGAGAGCACAGCCGCCCTGGGC TGCCTGGTGAAGGACTACTTCCCCGAGCCCGTG ACCGTGTCCTGGAACAGCGGAGCCCTGACCAGC GGCGTGCACACCTTCCCCGCCGTGCTGCAGAGC AGCGGCCTGTACAGCCTGAGCAGCGTGGTGACC GTGCCCAGCAGCAGCCTGGGCACCAAGACCTAC ACCTGTAACGTGGACCACAAGCCCAGCAACACC AAGGTGGACAAGAGGGTGGAGAGCAAGTACGGC CCACCCTGCCCCCCCTGCCCAGCCCCCGAGTTC CTGGGCGGACCCAGCGTGTTCCTGTTCCCCCCC AAGCCCAAGGACACCCTGATGATCAGCAGAACC CCCGAGGTGACCTGTGTGGTGGTGGACGTGTCC CAGGAGGACCCCGAGGTCCAGTTCAACTGGTAC GTGGACGGCGTGGAGGTGCACAACGCCAAGACC AAGCCCAGAGAGGAGCAGTTTAACAGCACCTAC CGGGTGGTGTCCGTGCTGACCGTGCTGCACCAG GACTGGCTGAACGGCAAAGAGTACAAGTGTAAG GTCTCCAACAAGGGCCTGCCAAGCAGCATCGAA AAGACCATCAGCAAGGCCAAGGGCCAGCCTAGA GAGCCCCAGGTCTACACCCTGCCACCCAGCCAA GAGGAGATGACCAAGAACCAGGTGTCCCTGACC TGTCTGGTGAAGGGCTTCTACCCAAGCGACATC GCCGTGGAGTGGGAGAGCAACGGCCAGCCCGAG AACAACTACAAGACCACCCCCCCAGTGCTGGAC AGCGACGGCAGCTTCTTCCTGTACAGCAGGCTG ACCGTGGACAAGTCCAGATGGCAGGAGGGCAAC GTCTTTAGCTGCTCCGTGATGCACGAGGCCCTG CACAACCACTACACCCAGAAGAGCCTGAGCCTG TCCCTGGGC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049-Clone-C LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 66 | VL | EIVLTQSPDFQSVTPKEKVTITCKSSQSLLDSG<br>NQKNFLTWYQQKPGQAPRLLIYWASTRESGVPS<br>RFSGSGSGTDFTFTISSLEAEDAATYYCQNDYS<br>YPYTFGQGTKVEIK |
| SEQ ID NO: 99 | DNA VL | GAGATCGTGCTGACCCAGTCCCCCGACTTCCAG<br>TCCGTGACCCCCAAAGAAAAAGTGACCATCACA<br>TGCAAGTCCTCCCAGTCCCTGCTGGACTCCGGC<br>AACCAGAAGAACTTCCTGACCTGGTATCAGCAG<br>AAGCCCGGCCAGGCCCCCAGACTGCTGATCTAC<br>TGGGCCTCCACCCGGGAATCTGGCGTGCCCTCT<br>AGATTCTCCGGCTCCGGCTCTGGCACCGACTTT<br>ACCTTCACCATCTCCAGCCTGGAAGCCGAGGAC<br>GCCGCCACCTACTACTGCCAGAACGACTACTCC<br>TACCCCTACACCTTCGGCCAGGGCACCAAGGTG<br>GAAATCAAG |
| SEQ ID NO: 68 | LC | EIVLTQSPDFQSVTPKEKVTITCKSSQSLLDSG<br>NQKNFLTWYQQKPGQAPRLLIYWASTRESGVPS<br>RFSGSGSGTDFTFTISSLEAEDAATYYCQNDYS<br>YPYTFGQGTKVEIKRTVAAPSVFIFPPSDEQLK<br>SGTASVVCLLNNFYPREAKVQWKVDNALQSGNS<br>QESVTEQDSKDSTYSLSSTLTLSKADYEKHKVY<br>ACEVTHQGLSSPVTKSFNRGEC |
| SEQ ID NO: 100 | DNA LC | GAGATCGTGCTGACCCAGTCCCCCGACTTCCAG<br>TCCGTGACCCCCAAAGAAAAAGTGACCATCACA<br>TGCAAGTCCTCCCAGTCCCTGCTGGACTCCGGC<br>AACCAGAAGAACTTCCTGACCTGGTATCAGCAG<br>AAGCCCGGCCAGGCCCCCAGACTGCTGATCTAC<br>TGGGCCTCCACCCGGGAATCTGGCGTGCCCTCT<br>AGATTCTCCGGCTCCGGCTCTGGCACCGACTTT<br>ACCTTCACCATCTCCAGCCTGGAAGCCGAGGAC<br>GCCGCCACCTACTACTGCCAGAACGACTACTCC<br>TACCCCTACACCTTCGGCCAGGGCACCAAGGTG<br>GAAATCAAGCGTACGGTGGCCGCTCCCAGCGTG<br>TTCATCTTCCCCCCAAGCGACGAGCAGCTGAAG<br>AGCGGCACCGCCAGCGTGGTGTGTCTGCTGAAC<br>AACTTCTACCCCAGGGAGGCCAAGGTGCAGTGG<br>AAGGTGGACAACGCCCTGCAGAGCGGCAACAGC<br>CAGGAGAGCGTCACCGAGCAGGACAGCAAGGAC<br>TCCACCTACAGCCTGAGCAGCACCCTGACCCTG<br>AGCAAGGCCGACTACGAGAAGCACAAGGTGTAC<br>GCCTGTGAGGTGACCCACCAGGGCCTGTCCAGC<br>CCCGTGACCAAGAGCTTCAACAGGGGCGAGTGC |
| **BAP049-Clone-D HC** | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 3 (Chothia) | HCDR3 | WTTGTGAY |
| SEQ ID NO: 50 | VH | EVQLVQSGAEVKKPGESLRISCKGSGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSS |
| SEQ ID NO: 101 | DNA VH | GAAGTGCAGCTGGTGCAGTCTGGCGCCGAAGTG<br>AAGAAGCCTGGCGAGTCCCTGCGGATCTCCTGC<br>AAGGGCTCTGGCTACACCTTCACCACCTACTGG<br>ATGCACTGGATCCGGCAGTCCCCCTCTAGGGGC<br>CTGGAATGGCTGGGCAACATCTACCCTGGCACC<br>GGCGGCTCCAACTTCGACGAGAAGTTCAAGAAC<br>AGGTTCACCATCTCCCGGGACAACTCCAAGAAC<br>ACCCTGTACCTGCAGATGAACTCCCTGCGGGCC<br>GAGGACACCGCCGTGTACTACTGTACCAGATGG<br>ACCACCGGAACCGGCGCCTATTGGGGCCAGGGC<br>ACAACAGTGACCGTGTCCTCC |
| SEQ ID NO: 102 | HC | EVQLVQSGAEVKKPGESLRISCKGSGYTFTTYW<br>MHWIRQSPSRGLEWLGNIYPGTGGSNFDEKFKN<br>RFTISRDNSKNTLYLQMNSLRAEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLG |
| SEQ ID NO: 103 | DNA HC | GAAGTGCAGCTGGTGCAGTCTGGCGCCGAAGTG<br>AAGAAGCCTGGCGAGTCCCTGCGGATCTCCTGC<br>AAGGGCTCTGGCTACACCTTCACCACCTACTGG<br>ATGCACTGGATCCGGCAGTCCCCCTCTAGGGGC<br>CTGGAATGGCTGGGCAACATCTACCCTGGCACC<br>GGCGGCTCCAACTTCGACGAGAAGTTCAAGAAC<br>AGGTTCACCATCTCCCGGGACAACTCCAAGAAC<br>ACCCTGTACCTGCAGATGAACTCCCTGCGGGCC<br>GAGGACACCGCCGTGTACTACTGTACCAGATGG<br>ACCACCGGAACCGGCGCCTATTGGGGCCAGGGC<br>ACAACAGTGACCGTGTCCTCCGCTTCTACCAAG<br>GGGCCCAGCGTGTTCCCCCTGGCCCCCTGCTCC<br>AGAAGCACCAGCGAGAGCACAGCCGCCCTGGGC<br>TGCCTGGTGAAGGACTACTTCCCCGAGCCCGTG<br>ACCGTGTCCTGGAACAGCGGAGCCCTGACCAGC<br>GGCGTGCACACCTTCCCCGCCGTGCTGCAGAGC<br>AGCGGCCTGTACAGCCTGAGCAGCGTGGTGACC<br>GTGCCCAGCAGCAGCCTGGGCACCAAGACCTAC<br>ACCTGTAACGTGGACCACAAGCCCAGCAACACC<br>AAGGTGGACAAGAGGGTGGAGAGCAAGTACGGC<br>CCACCCTGCCCCCCCTGCCCAGCCCCCGAGTTC<br>CTGGGCGGACCCAGCGTGTTCCTGTTCCCCCCC<br>AAGCCCAAGGACACCCTGATGATCAGCAGAACC<br>CCCGAGGTGACCTGTGTGGTGGTGGACGTGTCC<br>CAGGAGGACCCCGAGGTCCAGTTCAACTGGTAC<br>GTGGACGGCGTGGAGGTGCACAACGCCAAGACC<br>AAGCCCAGAGAGGAGCAGTTTAACAGCACCTAC<br>CGGGTGGTGTCCGTGCTGACCGTGCTGCACCAG<br>GACTGGCTGAACGGCAAAGAGTACAAGTGTAAG<br>GTCTCCAACAAGGGCCTGCCAAGCAGCATCGAA<br>AAGACCATCAGCAAGGCCAAGGGCCAGCCTAGA<br>GAGCCCCAGGTCTACACCCTGCCACCCAGCCAA<br>GAGGAGATGACCAAGAACCAGGTGTCCCTGACC<br>TGTCTGGTGAAGGGCTTCTACCCAAGCGACATC<br>GCCGTGGAGTGGGAGAGCAACGGCCAGCCCGAG<br>AACAACTACAAGACCACCCCCCCAGTGCTGGAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
                                  AGCGACGGCAGCTTCTTCCTGTACAGCAGGCTG
                                  ACCGTGGACAAGTCCAGATGGCAGGAGGGCAAC
                                  GTCTTTAGCTGCTCCGTGATGCACGAGGCCCTG
                                  CACAACCACTACACCCAGAAGAGCCTGAGCCTG
                                  TCCCTGGGC
```

BAP049-Clone-D LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSGNQKNFLTWYQQKPGQAPRLLIYWASTRESGVPSRFSGSGSGTDFTFTISSLEAEDAATYYCQNDYSYPYTFGQGTKVEIK |
| SEQ ID NO: 104 | DNA VL | GAGATCGTGCTGACCCAGTCCCCTGCCACCCTGTCACTGTCTCCAGGCGAGAGAGCTACCCTGTCCTGCAAGTCCTCCCAGTCCCTGCTGGACTCCGGCAACCAGAAGAACTTCCTGACCTGGTATCAGCAGAAGCCCGGCCAGGCCCCCAGACTGCTGATCTACTGGGCCTCCACCCGGGAATCTGGCGTGCCCTCTAGATTCTCCGGCTCCGGCTCTGGCACCGACTTTACCTTCACCATCTCCAGCCTGGAAGCCGAGGACGCCGCCACCTACTACTGCCAGAACGACTACTCCTACCCCTACACCTTCGGCCAGGGCACCAAGGTGGAAATCAAG |
| SEQ ID NO: 72 | LC | EIVLTQSPATLSLSPGERATLSCKSSQSLLDSGNQKNFLTWYQQKPGQAPRLLIYWASTRESGVPSRFSGSGSGTDFTFTISSLEAEDAATYYCQNDYSYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 105 | DNA LC | GAGATCGTGCTGACCCAGTCCCCTGCCACCCTGTCACTGTCTCCAGGCGAGAGAGCTACCCTGTCCTGCAAGTCCTCCCAGTCCCTGCTGGACTCCGGCAACCAGAAGAACTTCCTGACCTGGTATCAGCAGAAGCCCGGCCAGGCCCCCAGACTGCTGATCTACTGGGCCTCCACCCGGGAATCTGGCGTGCCCTCTAGATTCTCCGGCTCCGGCTCTGGCACCGACTTTACCTTCACCATCTCCAGCCTGGAAGCCGAGGACGCCGCCACCTACTACTGCCAGAACGACTACTCCTACCCCTACACCTTCGGCCAGGGCACCAAGGTGGAAATCAAGCGTACGGTGGCCGCTCCCAGCGTGTTCATCTTCCCCCCAAGCGACGAGCAGCTGAAGAGCGGCACCGCCAGCGTGGTGTGTCTGCTGAACAACTTCTACCCCAGGGAGGCCAAGGTGCAGTGGAAGGTGGACAACGCCCTGCAGAGCGGCAACAGCCAGGAGAGCGTCACCGAGCAGGACAGCAAGGACTCCACCTACAGCCTGAGCAGCACCCTGACCCTGAGCAAGGCCGACTACGAGAAGCACAAGGTGTACGCCTGTGAGGTGACCCACCAGGGCCTGTCCAGCCCCGTGACCAAGAGCTTCAACAGGGGCGAGTGC |

BAP049-Clone-E HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSS |
| SEQ ID NO: 95 | DNA VH | GAGGTGCAGCTGGTGCAGTCAGGCGCCGAAGTG<br>AAGAAGCCCGGCGAGTCACTGAGAATTAGCTGT<br>AAAGGTTCAGGCTACACCTTCACTACCTACTGG<br>ATGCACTGGGTCCGCCAGGCTACCGGTCAAGGC<br>CTCGAGTGGATGGGTAATATCTACCCCGGCACC<br>GGCGGCTCTAACTTCGACGAGAAGTTTAAGAAT<br>AGAGTGACTATCACCGCCGATAAGTCTACTAGC<br>ACCGCCTATATGGAACTGTCTAGCCTGAGATCA<br>GAGGACACCGCCGTCTACTACTGCACTAGGTGG<br>ACTACCGGCACAGGCGCCTACTGGGGTCAAGGC<br>ACTACCGTGACCGTGTCTAGC |
| SEQ ID NO: 91 | HC | EVQLVQSGAEVKKPGESLRISCKGSGYTFTTYW<br>MHWVRQATGQGLEWMGNIYPGTGGSNFDEKFKN<br>RVTITADKSTSTAYMELSSLRSEDTAVYYCTRW<br>TTGTGAYWGQGTTVTVSSASTKGPSVFPLAPCS<br>RSTSESTAALGCLVKDYFPEPVTVSWNSGALTS<br>GVHTFPAVLQSSGLYSLSSVVTVPSSSLGTKTY<br>TCNVDHKPSNTKVDKRVESKYGPPCPPCPAPEF<br>LGGPSVFLFPPKPKDTLMISRTPEVTCVVVDVS<br>QEDPEVQFNWYVDGVEVHNAKTKPREEQFNSTY<br>RVVSVLTVLHQDWLNGKEYKCKVSNKGLPSSIE<br>KTISKAKGQPREPQVYTLPPSQEEMTKNQVSLT<br>CLVKGFYPSDIAVEWESNGQPENNYKTTPPVLD<br>SDGSFFLYSRLTVDKSRWQEGNVFSCSVMHEAL<br>HNHYTQKSLSLSLG |
| SEQ ID NO: 96 | DNA HC | GAGGTGCAGCTGGTGCAGTCAGGCGCCGAAGTG<br>AAGAAGCCCGGCGAGTCACTGAGAATTAGCTGT<br>AAAGGTTCAGGCTACACCTTCACTACCTACTGG<br>ATGCACTGGGTCCGCCAGGCTACCGGTCAAGGC<br>CTCGAGTGGATGGGTAATATCTACCCCGGCACC<br>GGCGGCTCTAACTTCGACGAGAAGTTTAAGAAT<br>AGAGTGACTATCACCGCCGATAAGTCTACTAGC<br>ACCGCCTATATGGAACTGTCTAGCCTGAGATCA<br>GAGGACACCGCCGTCTACTACTGCACTAGGTGG<br>ACTACCGGCACAGGCGCCTACTGGGGTCAAGGC<br>ACTACCGTGACCGTGTCTAGCGCTAGCACTAAG<br>GGCCCGTCCGTGTTCCCCCTGGCACCTTGTAGC<br>CGGAGCACTAGCGAATCCACCGCTGCCCTCGGC<br>TGCCTGGTCAAGGATTACTTCCCGGAGCCCGTG<br>ACCGTGTCCTGGAACAGCGGAGCCCTGACCTCC<br>GGAGTGCACACCTTCCCCGCTGTGCTGCAGAGC<br>TCCGGGCTGTACTCGCTGTCGTCGGTGGTCACG<br>GTGCCTTCATCTAGCCTGGGTACCAAGACCTAC<br>ACTTGCAACGTGGACCACAAGCCTTCCAACACT<br>AAGGTGGACAAGCGCGTCGAATCGAAGTACGGC<br>CCACCGTGCCCGCCTTGTCCCGCGCCGGAGTTC<br>CTCGGCGGTCCCTCGGTCTTTCTGTTCCCACCG<br>AAGCCCAAGGACACTTTGATGATTTCCCGCACC<br>CCTGAAGTGACATGCGTGGTCGTGGACGTGTCA<br>CAGGAAGATCCGGAGGTGCAGTTCAATTGGTAC<br>GTGGATGGCGTCGAGGTGCACAACGCCAAAACC<br>AAGCCGAGGGAGGAGCAGTTCAACTCCACTTAC<br>CGCGTCGTGTCCGTGCTGACGGTGCTGCATCAG<br>GACTGGCTGAACGGGAAGGAGTACAAGTGCAAA<br>GTGTCCAACAAGGGACTTCCTAGCTCAATCGAA |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| | | AAGACCATCTCGAAAGCCAAGGGACAGCCCCGG GAACCCCAAGTGTATACCCTGCCACCGAGCCAG GAAGAAATGACTAAGAACCAAGTCTCATTGACT TGCCTTGTGAAGGGCTTCTACCCATCGGATATC GCCGTGGAATGGGAGTCCAACGGCCAGCCGGAA AACAACTACAAGACCACCCCTCCGGTGCTGGAC TCAGACGGATCCTTCTTCCTCTACTCGCGGCTG ACCGTGGATAAGAGCAGATGGCAGGAGGGAAAT GTGTTCAGCTGTTCTGTGATGCATGAAGCCCTG CACAACCACTACACTCAGAAGTCCCTGTCCCTC TCCCTGGGA |
| **BAP049-Clone-E LC** | | |
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLLDSG NQKNFLTWYQQKPGQAPRLLIYWASTRESGVPS RFSGSGSGTDFTFTISSLEAEDAATYYCQNDYS YPYTFGQGTKVEIK |
| SEQ ID NO: 106 | DNA VL | GAGATCGTCCTGACTCAGTCACCCGCTACCCTG AGCCTGAGCCCTGGCGAGCGGGCTACACTGAGC TGTAAATCTAGTCAGTCACTGCTGGATAGCGGT AATCAGAAGAACTTCCTGACCTGGTATCAGCAG AAGCCCGGTCAAGCCCCTAGACTGCTGATCTAC TGGGCCTCTACTAGAGAATCAGGCGTGCCCTCT AGGTTTAGCGGTAGCGGTAGTGGCACCGACTTC ACCTTCACTATCTCTAGCCTGGAAGCCGAGGAC GCCGCTACCTACTACTGTCAGAACGACTATAGC TACCCCTACACCTTCGGTCAAGGCACTAAGGTC GAGATTAAG |
| SEQ ID NO: 72 | LC | EIVLTQSPATLSLSPGERATLSCKSSQSLLDSG NQKNFLTWYQQKPGQAPRLLIYWASTRESGVPS RFSGSGSGTDFTFTISSLEAEDAATYYCQNDYS YPYTFGQGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| SEQ ID NO: 107 | DNA LC | GAGATCGTCCTGACTCAGTCACCCGCTACCCTG AGCCTGAGCCCTGGCGAGCGGGCTACACTGAGC TGTAAATCTAGTCAGTCACTGCTGGATAGCGGT AATCAGAAGAACTTCCTGACCTGGTATCAGCAG AAGCCCGGTCAAGCCCCTAGACTGCTGATCTAC TGGGCCTCTACTAGAGAATCAGGCGTGCCCTCT AGGTTTAGCGGTAGCGGTAGTGGCACCGACTTC ACCTTCACTATCTCTAGCCTGGAAGCCGAGGAC GCCGCTACCTACTACTGTCAGAACGACTATAGC TACCCCTACACCTTCGGTCAAGGCACTAAGGTC GAGATTAAGCGTACGGTGGCCGCTCCCAGCGTG TTCATCTTCCCCCCCAGCGACGAGCAGCTGAAG AGCGGCACCGCCAGCGTGGTGTGCCTGCTGAAC AACTTCTACCCCCGGGAGGCCAAGGTGCAGTGG AAGGTGGACAACGCCCTGCAGAGCGGCAACAGC CAGGAGAGCGTCACCGAGCAGGACAGCAAGGAC TCCACCTACAGCCTGAGCAGCACCCTGACCCTG AGCAAGGCCGACTACGAGAAGCATAAGGTGTAC GCCTGCGAGGTGACCCACCAGGGCCTGTCCAGC CCCGTGACCAAGAGCTTCAACAGGGGCGAGTGC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 115 (Kabat) | LCDR3 | CAGAATGATTATAGTTATCCGTGCACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 118 (Chothia) | LCDR3 | GATTATAGTTATCCGTGC |
| **BAP049-chi HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-chi LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 115 (Kabat) | LCDR3 | CAGAATGATTATAGTTATCCGTGCACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 118 (Chothia) | LCDR3 | GATTATAGTTATCCGTGC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049-chi Y HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-chi Y LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum01 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum01 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049-hum02 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum02 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum03 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum03 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049-hum04 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum04 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum05 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum05 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum06 HC** | | |
| SEQ ID NO: 108 (Kabat) | HCDR1 | ACTTACTGGATGCAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum06 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum07 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum07 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum08 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum08 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum09 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum09 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum10 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum10 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum11 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum11 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum12 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum12 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum13 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum13 LC** | | |
| SEQ ID NO: 121 (Kabat) | LCDR1 | AAGTCCAGTCAGAGTCTGTTAGACAGTGGAAAT CAAAAGAACTTCTTAACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum14 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 223 (Kabat) | HCDR3 | TGGACTACTGGGACGGGAGCTTAC |
| SEQ ID NO: 111 (Chothia) | HCDR1 | GGCTACACATTCACCACTTAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 112 (Chothia) | HCDR2 | TATCCTGGTACTGGTGGT |
| SEQ ID NO: 223 (Chothia) | HCDR3 | TGGACTACTGGGACGGGAGCTTAC |
| **BAP049-hum14 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum15 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 223 (Kabat) | HCDR3 | TGGACTACTGGGACGGGAGCTTAC |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 223 (Chothia) | HCDR3 | TGGACTACTGGGACGGGAGCTTAC |
| **BAP049-hum15 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-hum16 HC** | | |
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAACTTC GATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |
| **BAP049-hum16 LC** | | |
| SEQ ID NO: 113 (Kabat) | LCDR1 | AAGTCCAGTCAGAGTCTGTTAGACAGTGGAAAT CAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAAAAG AACTTC |
| SEQ ID NO: 117 (Chothia) | LCDR2 | TGGGCATCC |
| SEQ ID NO: 120 (Chothia) | LCDR3 | GATTATAGTTATCCGTAC |
| **BAP049-Clone-A HC** | | |
| SEQ ID NO: 122 (Kabat) | HCDR1 | ACCTACTGGATGCAC |
| SEQ ID NO: 123 (Kabat) | HCDR2 | AACATCTATCCTGGCACCGGCGGCTCCAACTTC GACGAGAAGTTCAAGAAC |
| SEQ ID NO: 124 (Kabat) | HCDR3 | TGGACAACCGGCACAGGCGCTTAT |
| SEQ ID NO: 125 (Chothia) | HCDR1 | GGCTACACCTTCACCACCTAC |
| SEQ ID NO: 126 (Chothia) | HCDR2 | TATCCTGGCACCGGCGGC |
| SEQ ID NO: 124 (Chothia) | HCDR3 | TGGACAACCGGCACAGGCGCTTAT |
| **BAP049-Clone-A LC** | | |
| SEQ ID NO: 127 (Kabat) | LCDR1 | AAGTCCTCCCAGTCCCTGCTGGACTCCGGCAAC CAGAAGAACTTCCTGACC |
| SEQ ID NO: 128 (Kabat) | LCDR2 | TGGGCCTCCACCCGGGAATCT |
| SEQ ID NO: 129 (Kabat) | LCDR3 | CAGAACGACTACTCCTACCCCTACACC |
| SEQ ID NO: 130 (Chothia) | LCDR1 | TCCCAGTCCCTGCTGGACTCCGGCAACCAGAAG AACTTC |
| SEQ ID NO: 131 (Chothia) | LCDR2 | TGGGCCTCC |
| SEQ ID NO: 132 (Chothia) | LCDR3 | GACTACTCCTACCCCTAC |
| **BAP049-Clone-B HC** | | |
| SEQ ID NO: 133 (Kabat) | HCDR1 | ACCTACTGGATGCAC |
| SEQ ID NO: 134 (Kabat) | HCDR2 | AATATCTACCCCGGCACCGGCGGCTCTAACTTC GACGAGAAGTTTAAGAAT |
| SEQ ID NO: 135 (Kabat) | HCDR3 | TGGACTACCGGCACAGGCGCCTAC |
| SEQ ID NO: 136 (Chothia) | HCDR1 | GGCTACACCTTCACTACCTAC |
| SEQ ID NO: 137 (Chothia) | HCDR2 | TACCCCGGCACCGGCGGC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| SEQ ID NO: 135 (Chothia) | HCDR3 | TGGACTACCGGCACAGGCGCCTAC |
| **BAP049-Clone-B LC** | | |
| SEQ ID NO: 138 (Kabat) | LCDR1 | AAATCTAGTCAGTCACTGCTGGATAGCGGTAAT CAGAAGAACTTCCTGACC |
| SEQ ID NO: 139 (Kabat) | LCDR2 | TGGGCCTCTACTAGAGAATCA |
| SEQ ID NO: 140 (Kabat) | LCDR3 | CAGAACGACTATAGCTACCCCTACACC |
| SEQ ID NO: 141 (Chothia) | LCDR1 | AGTCAGTCACTGCTGGATAGCGGTAATCAGAAG AACTTC |
| SEQ ID NO: 142 (Chothia) | LCDR2 | TGGGCCTCT |
| SEQ ID NO: 143 (Chothia) | LCDR3 | GACTATAGCTACCCCTAC |
| **BAP049-Clone-C HC** | | |
| SEQ ID NO: 122 (Kabat) | HCDR1 | ACCTACTGGATGCAC |
| SEQ ID NO: 123 (Kabat) | HCDR2 | AACATCTATCCTGGCACCGGCGGCTCCAACTTC GACGAGAAGTTCAAGAAC |
| SEQ ID NO: 124 (Kabat) | HCDR3 | TGGACAACCGGCACAGGCGCTTAT |
| SEQ ID NO: 125 (Chothia) | HCDR1 | GGCTACACCTTCACCACCTAC |
| SEQ ID NO: 126 (Chothia) | HCDR2 | TATCCTGGCACCGGCGGC |
| SEQ ID NO: 124 (Chothia) | HCDR3 | TGGACAACCGGCACAGGCGCTTAT |
| **BAP049-Clone-C LC** | | |
| SEQ ID NO: 127 (Kabat) | LCDR1 | AAGTCCTCCCAGTCCCTGCTGGACTCCGGCAAC CAGAAGAACTTCCTGACC |
| SEQ ID NO: 128 (Kabat) | LCDR2 | TGGGCCTCCACCCGGGAATCT |
| SEQ ID NO: 129 (Kabat) | LCDR3 | CAGAACGACTACTCCTACCCCTACACC |
| SEQ ID NO: 130 (Chothia) | LCDR1 | TCCCAGTCCCTGCTGGACTCCGGCAACCAGAAG AACTTC |
| SEQ ID NO: 131 (Chothia) | LCDR2 | TGGGCCTCC |
| SEQ ID NO: 132 (Chothia) | LCDR3 | GACTACTCCTACCCCTAC |
| **BAP049-Clone-D HC** | | |
| SEQ ID NO: 122 (Kabat) | HCDR1 | ACCTACTGGATGCAC |
| SEQ ID NO: 144 (Kabat) | HCDR2 | AACATCTACCCTGGCACCGGCGGCTCCAACTTC GACGAGAAGTTCAAGAAC |
| SEQ ID NO: 145 (Kabat) | HCDR3 | TGGACCACCGGAACCGGCGCCTAT |
| SEQ ID NO: 125 (Chothia) | HCDR1 | GGCTACACCTTCACCACCTAC |
| SEQ ID NO: 146 (Chothia) | HCDR2 | TACCCTGGCACCGGCGGC |
| SEQ ID NO: 145 (Chothia) | HCDR3 | TGGACCACCGGAACCGGCGCCTAT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| | | |
|---|---|---|
| **BAP049-Clone-D LC** | | |
| SEQ ID NO: 127 (Kabat) | LCDR1 | AAGTCCTCCCAGTCCCTGCTGGACTCCGGCAAC CAGAAGAACTTCCTGACC |
| SEQ ID NO: 128 (Kabat) | LCDR2 | TGGGCCTCCACCCGGGAATCT |
| SEQ ID NO: 129 (Kabat) | LCDR3 | CAGAACGACTACTCCTACCCCTACACC |
| SEQ ID NO: 130 (Chothia) | LCDR1 | TCCCAGTCCCTGCTGGACTCCGGCAACCAGAAG AACTTC |
| SEQ ID NO: 131 (Chothia) | LCDR2 | TGGGCCTCC |
| SEQ ID NO: 132 (Chothia) | LCDR3 | GACTACTCCTACCCCTAC |
| **BAP049-Clone-E HC** | | |
| SEQ ID NO: 133 (Kabat) | HCDR1 | ACCTACTGGATGCAC |
| SEQ ID NO: 134 (Kabat) | HCDR2 | AATATCTACCCCGGCACCGGCGGCTCTAACTTC GACGAGAAGTTTAAGAAT |
| SEQ ID NO: 135 (Kabat) | HCDR3 | TGGACTACCGGCACAGGCGCCTAC |
| SEQ ID NO: 136 (Chothia) | HCDR1 | GGCTACACCTTCACTACCTAC |
| SEQ ID NO: 137 (Chothia) | HCDR2 | TACCCCGGCACCGGCGGC |
| SEQ ID NO: 135 (Chothia) | HCDR3 | TGGACTACCGGCACAGGCGCCTAC |
| **BAP049-Clone-E LC** | | |
| SEQ ID NO: 138 (Kabat) | LCDR1 | AAATCTAGTCAGTCACTGCTGGATAGCGGTAAT CAGAAGAACTTCCTGACC |
| SEQ ID NO: 139 (Kabat) | LCDR2 | TGGGCCTCTACTAGAGAATCA |
| SEQ ID NO: 140 (Kabat) | LCDR3 | CAGAACGACTATAGCTACCCCTACACC |
| SEQ ID NO: 141 (Chothia) | LCDR1 | AGTCAGTCACTGCTGGATAGCGGTAATCAGAAG AACTTC |
| SEQ ID NO: 142 (Chothia) | LCDR2 | TGGGCCTCT |
| SEQ ID NO: 143 (Chothia) | LCDR3 | GACTATAGCTACCCCTAC |

Table 2.

Amino acid and nucleotide sequences of the heavy and light chain framework regions for humanized mAbs BAP049-hum01 to BAP049-hum16 and BAP049-Clone-A to BAP049-Clone-E Table 3.

Constant region amino acid sequences of human IgG heavy chains and human kappa light chain

TABLE 3

Constant region amino acid sequences of human IgG heavy chains and human kappa light chain

| | |
|---|---|
| HC | IgG4 (S228P) mutant constant region amino acid sequence (EU Numbering)<br>ASTKGPSVFP LAPCSRSTSE STAALGCLVK DYFPEPVTVS WNSGALTSGV HTFPAVLQSS<br>GLYSLSSVVT VPSSSLGTKT YTCNVDHKPS NTKVDKRVES KYGPPCPPCP APEFLGGPSV<br>FLFPPKPKDT LMISRTPEVT CVVVDVSQED PEVQFNWYVD GVEVHNAKTK PREEQFNSTY |

TABLE 3-continued

| Constant region amino acid sequences of human IgG heavy chains and human kappa light chain | |
|---|---|
| | RVVSVLTVLH QDWLNGKEYK CKVSNKGLPS SIEKTISKAK GQPREPQVYT LPPSQEEMTK<br>NQVSLTCLVK GFYPSDIAVE WESNGQPENN YKTTPPVLDS DGSFFLYSRL TVDKSRWQEG<br>NVFSCSVMHE ALHNHYTQKS LSLSLGK (SEQ ID NO: 212) |
| LC | Human kappa constant region amino acid sequence<br>RTVAAPSVFI FPPSDEQLKS GTASVVCLLN NFYPREAKVQ WKVDNALQSG NSQESVTEQD<br>SKDSTYSLSS TLTLSKADYE KHKVYACEVT HQGLSSPVTK<br>SFNRGEC (SEQ ID NO: 213) |
| HC | IgG4 (S228P) mutant constant region amino acid sequence lacing C-terminal lysine (K) (EU Numbering)<br>ASTKGPSVFP LAPCSRSTSE STAALGCLVK DYFPEPVTVS WNSGALTSGV HTFPAVLQSS<br>GLYSLSSVVT VPSSSLGTKT YTCNVDHKPS NTKVDKRVES KYGPPCPPCP APEFLGGPSV<br>FLFPPKPKDT LMISRTPEVT CVVVDVSQED PEVQFNWYVD GVEVHNAKTK PREEQFNSTY<br>RVVSVLTVLH QDWLNGKEYK CKVSNKGLPS SIEKTISKAK GQPREPQVYT LPPSQEEMTK<br>NQVSLTCLVK GFYPSDIAVE WESNGQPENN YKTTPPVLDS DGSFFLYSRL TVDKSRWQEG<br>NVFSCSVMHE ALHNHYTQKS LSLSLG (SEQ ID NO: 214) |
| HC | IgG1 wild type<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKRVEP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSREE<br>MTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK (SEQ ID NO: 215) |
| HC | IgG1 (N297A) mutant constant region amino acid sequence (EU Numbering)<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKRVEP KSCDKTHTCP PCPAPELLGG<br>PSVFLFPPKP KDTLMISRTP EVTCVVVDVS HEDPEVKFNW YVDGVEVHNA KTKPREEQYA<br>STYRVVSVLT VLHQDWLNGK EYKCKVSNKA LPAPIEKTIS KAKGQPREPQ VYTLPPSREE<br>MTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK (SEQ ID NO: 216) |
| HC | IgG1 (D265A, P329A) mutant constant region amino acid sequence (EU Numbering)<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKRVEP KSCDKTHTCP PCPAPELLGG<br>PSVFLFPPKP KDTLMISRTP EVTCVVVAVS HEDPEVKFNW YVDGVEVHNA KTKPREEQYN<br>STYRVVSVLT VLHQDWLNGK EYKCKVSNKA LAAPIEKTIS KAKGQPREPQ VYTLPPSREE<br>MTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK (SEQ ID NO: 217) |
| HC | IgG1 (L234A, L235A) mutant constant region amino acid sequence (EU Numbering)<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKRVEP KSCDKTHTCP PCPAPEAAGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSREE<br>MTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK (SEQ ID NO: 218) |

Table 4.

Amino acid sequences of the heavy and light chain leader sequences for humanized mAbs BAP049-Clone-A to BAP049-Clone-E

TABLE 4

| Amino acid sequences of the heavy and light chain leader sequences for humanized mAbs BAP049-Clone-A to BAP049-Clone-E | | |
|---|---|---|
| BAP049-Clone-A | HC | MEWSWVFLFFLSVTTGVHS (SEQ ID NO: 219) |
| | LC | MSVPTQVLGLLLLWLTDARC (SEQ ID NO: 220) |
| BAP049-Clone-B | HC | MAWVWTLPFLMAAAQSVQA (SEQ ID NO: 221) |
| | LC | MSVLTQVLALLLLWLTGTRC (SEQ ID NO: 222) |
| BAP049-Clone-C | HC | MEWSWVFLFFLSVTTGVHS (SEQ ID NO: 219) |
| | LC | MSVPTQVLGLLLLWLTDARC (SEQ ID NO: 220) |
| BAP049-Clone-D | HC | MEWSWVFLFFLSVTTGVHS (SEQ ID NO: 219) |
| | LC | MSVPTQVLGLLLLWLTDARC (SEQ ID NO: 220) |

TABLE 4-continued

| Amino acid sequences of the heavy and light chain leader sequences for humanized mAbs BAP049-Clone-A to BAP049-Clone-E | | |
|---|---|---|
| BAP049-Clone-E | HC | MAWVWTLPFLMAAAQSVQA (SEQ ID NO: 221) |
| | LC | MSVLTQVLALLLLWLTGTRC (SEQ ID NO: 222) |

Table 5.

See Examples.

Table 6.

See Examples.

Table 7.

Selected therapeutic agents that can be administered in combination with the anti-PD-1 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A1 | Sotrastaurin | 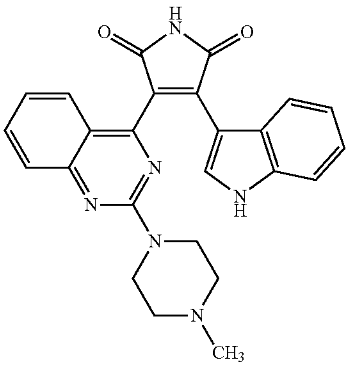 [SMILES: CN1CCN(c2nc(C3=C(c4c[nH]c5ccccc45)C(=O)NC3=O)c3ccccc3n2)CC1] | EP 1682103<br>US 2007/142401<br>WO 2005/039549 |
| A2 | Nilotinib HCl monohydrate<br>TASIGNA ® | 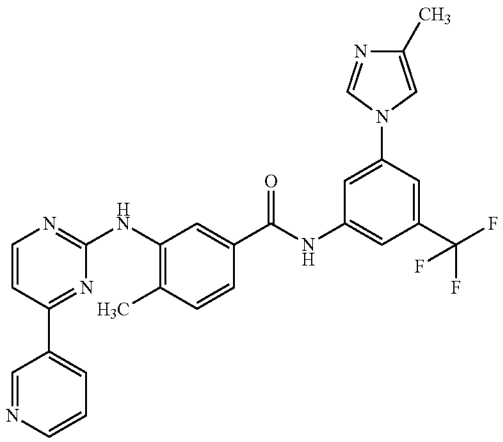<br>HCl•$H_2O$ | WO 2004/005281<br>U.S. Pat. No. 7,169,791 |
| A3 | | 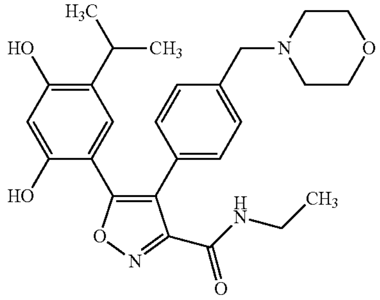 [SMILES: CCNC(=O)c1noc(-c2cc(C(C)C)c(O)cc2O)c1-c1ccc(CN2CCOCC2)cc1] | WO 2010/060937<br>WO 2004/072051<br>EP 1611112<br>U.S. Pat. No. 8,450,310 |
| A4 | Dactolisib | 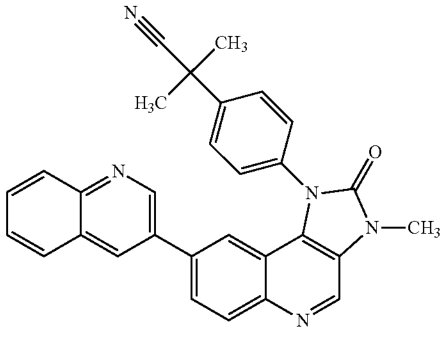 [SMILES: Cn1c(=O)n(-c2ccc(C(C)(C)C#N)cc2)c2c3cc(-c4cnc5ccccc5c4)ccc3ncc21] | WO 2006/122806 |

-continued
| Compound Designation | Generic Name Tradename | Compound Structure | Patents/Patent Application Publications |
|---|---|---|---|
| A5 | | 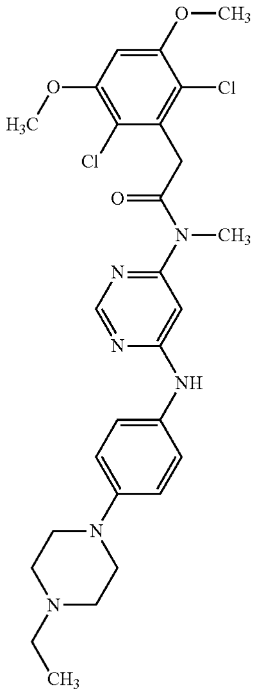 | U.S. Pat. No. 8,552,002 |
| A6 | Buparlisib | 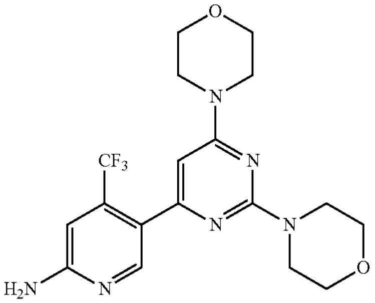 [SMILES: Nc1cc(C(F)(F)F)c(-c2cc(N3CCOCC3)nc(N3CCOCC3)n2)cn1] | WO 2007/084786 |
| A7 | | 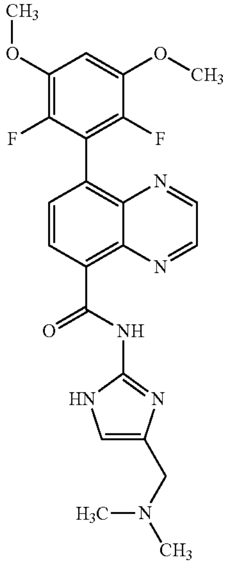 [SMILES: COc1cc(OC)c(F)c(-c2ccc(C(=O)Nc3nc(CN(C)C)c[nH]3)c3nccnc23)c1F] | WO 2009/141386<br>US 2010/0105667 |

-continued
| Compound Designation | Generic Name Tradename | Compound Structure | Patents/Patent Application Publications |
| --- | --- | --- | --- |
| A8 | | 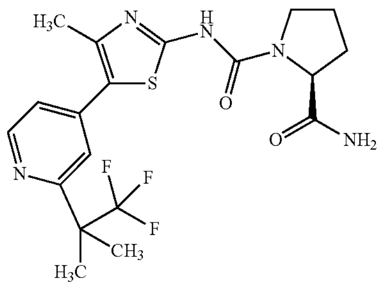 [SMILES: Cc1nc(NC(=O)N2CCC[C@H]2C(N)=O)sc1-c1ccnc(C(C)(C)C(F)(F)F)c1] | WO 2010/029082 |
| A9 | | CYP17 inhibitor | WO 2010/149755<br>U.S. Pat. No. 8,263,635 B2<br>EP 2445903 B1 |
| A10 | | 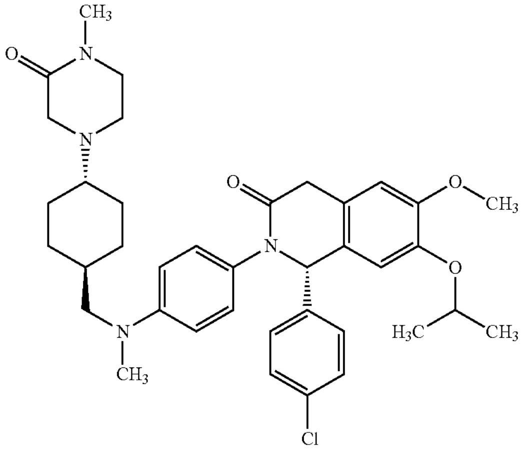 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] | WO 2011/076786 |
| A11 | Deferasirox<br>EXJADE ® | 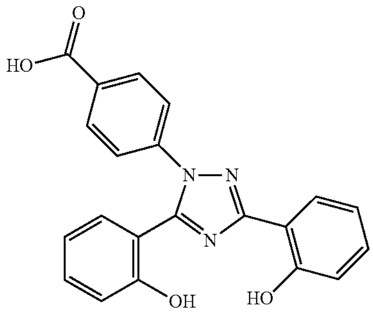 [SMILES: O=C(O)c1ccc(-n2nc(-c3ccccc3O)nc2-c2ccccc2O)cc1] | WO 1997/049395 |
| A12 | Letrozole<br>FEMARA ® | 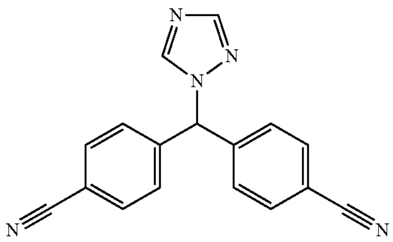 [SMILES: N#Cc1ccc(C(c2ccc(C#N)cc2)n2cncn2)cc1] | U.S. Pat. No. 4,978,672 |

-continued
| Compound Designation | Generic Name Tradename | Compound Structure | Patents/Patent Application Publications |
|---|---|---|---|
| A13 | | 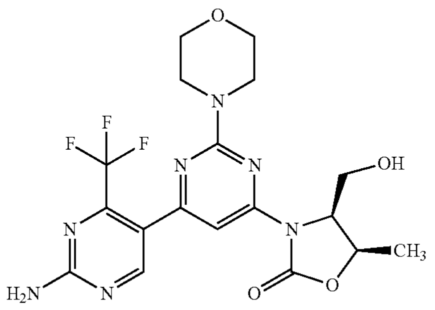 [SMILES: C[C@H]1OC(=O)N(c2cc(-c3cnc(N)nc3C(F)(F)F)nc(N3CCOCC3)n2)[C@H]1CO] | WO 2013/124826<br>US 2013/0225574 |
| A14 | | 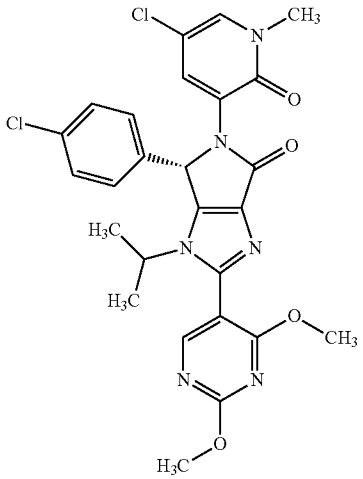 [SMILES: COc1ncc(-c2nc3c(n2C(C)C)[C@H](c2ccc(Cl)cc2)N(c2cc(Cl)cn(C)c2=O)C3=O)c(OC)n1] | WO 2013/111105 |
| A15 | | 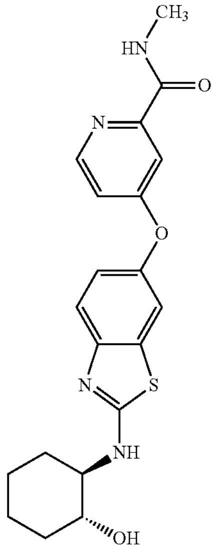 [SMILES: CNC(=O)c1cc(Oc2ccc3nc(N[C@@H]4CCCC[C@H]4O)sc3c2)ccn1] | WO 2005/073224 |

-continued
| Compound Designation | Generic Name Tradename | Compound Structure | Patents/Patent Application Publications |
|---|---|---|---|
| A16 | Imatinib mesylate GLEEVEC ® | 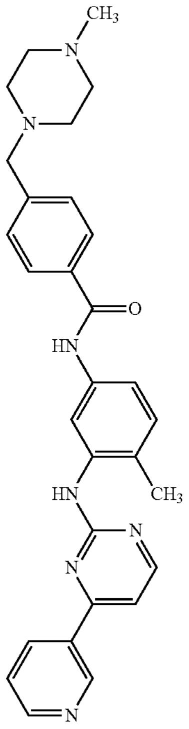 Mesylate | WO 1999/003854 |
| A17 | | 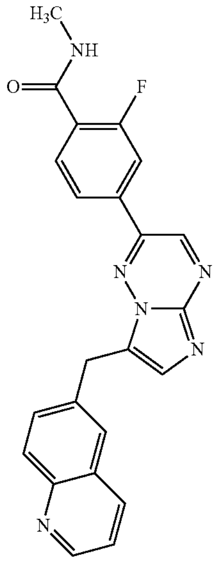 Dihydrochloric salt | EP 2099447 U.S. Pat. No. 7,767,675 U.S. Pat. No. 8,420,645 |

-continued
| Compound Designation | Generic Name Tradename | Compound Structure | Patents/Patent Application Publications |
|---|---|---|---|
| A18 | Ruxolitinib Phosphate JAKAFI ® | 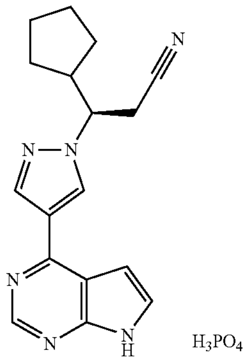 | WO 2007/070514 EP 2474545 U.S. Pat. No. 7,598,257 WO 2014/018632 |
| A19 | Panobinostat | 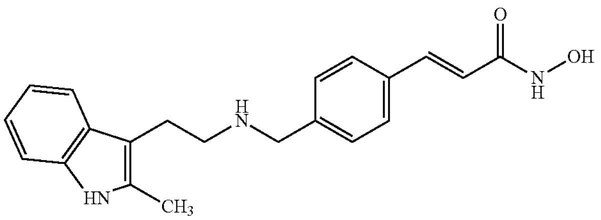 [SMILES: Cc1[nH]c2ccccc2c1CCNCc1ccc(/C=C/C(=O)NO)cc1] | WO 2014/072493 WO 2002/022577 EP 1870399 |
| A20 | Osilodrostat | 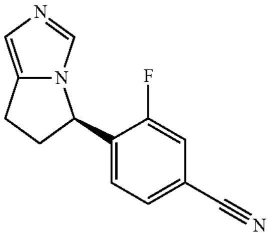 [SMILES: N#Cc1ccc([C@H]2CCc3cncn32)c(F)c1] | WO 2007/024945 |
| A21 | | 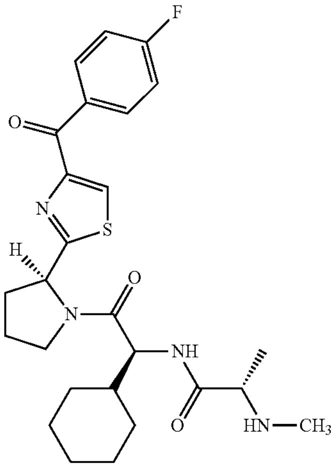 [SMILES: CN[C@@H](C)C(=O)N[C@H](C(=O)N1CCC[C@H]1c1nc(C(=O)c2ccc(F)cc2)cs1)C1CCCCC1] | WO 2008/016893 EP 2051990 U.S. Pat. No. 8,546,336 |

-continued
| Compound Designation | Generic Name Tradename | Compound Structure | Patents/Patent Application Publications |
|---|---|---|---|
| A22 | Sonidegib phosphate | 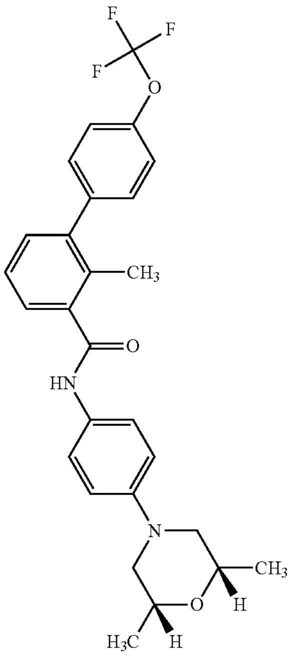 [SMILES: Cc1c(C(=O)Nc2ccc(N3C[C@@H](C)O[C@@H](C)C3)cc2)cccc1-c1ccc(OC(F)(F)F)cc1] | WO 2007/131201<br>EP 2021328<br>U.S. Pat. No. 8,178,563 |
| A23 | ceritinib<br>ZYKADIA ™ | 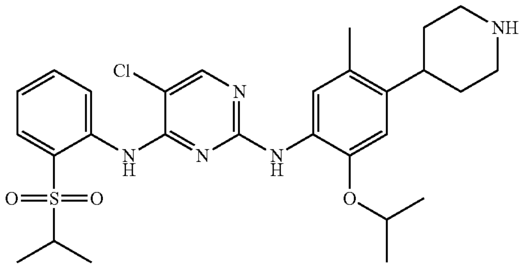 [SMILES: Cc1cc(Nc2ncc(Cl)c(Nc3ccccc3S(=O)(=O)C(C)C)n2)c(OC(C)C)cc1C1CCNCC1] | WO 2008/073687<br>U.S. Pat. No. 8,039,479 |
| A24 | | 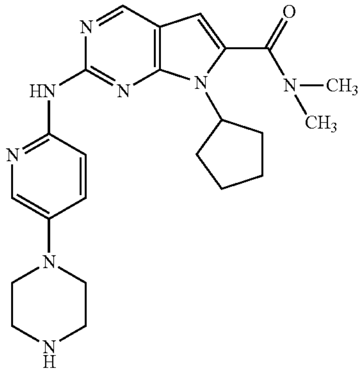 [SMILES: CN(C)C(=O)c1cc2cnc(Nc3ccc(N4CCNCC4)cn3)nc2n1C1CCCC1] | U.S. Pat. No. 8,415,355<br>U.S. Pat. No. 8,685,980 |

-continued
| Compound Designation | Generic Name Tradename | Compound Structure | Patents/Patent Application Publications |
|---|---|---|---|
| A25 | | 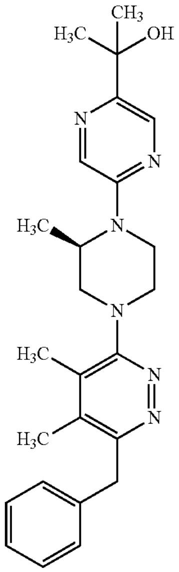 [SMILES: Cc1c(Cc2ccccc2)nnc(N2CCN(c3cnc(C(C)(C)O)cn3)[C@H](C)C2)c1C] | WO 2010/007120 |
| A26 | | Human monoclonal antibody to PRLR | U.S. Pat. No. 7,867,493 |
| A27 | | 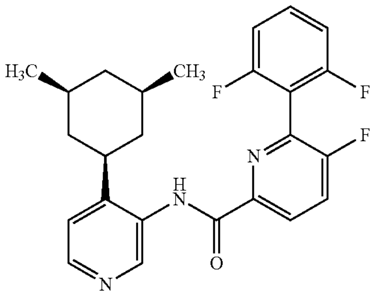 [SMILES: C[C@@H]1C[C@H](C)C[C@H](c2ccncc2NC(=O)c2ccc(F)c(-c3c(F)cccc3F)n2)C1] | WO 2010/026124<br>EP 2344474<br>U.S. Pat. No. 2010/0056576<br>WO 2008/106692 |
| A28 | | 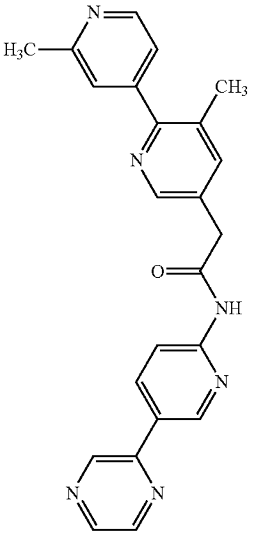 | WO 2010/101849 |

-continued

| Compound Designation | Generic Name Tradename | Compound Structure | Patents/Patent Application Publications |
|---|---|---|---|
| A29 | Encorafenib | 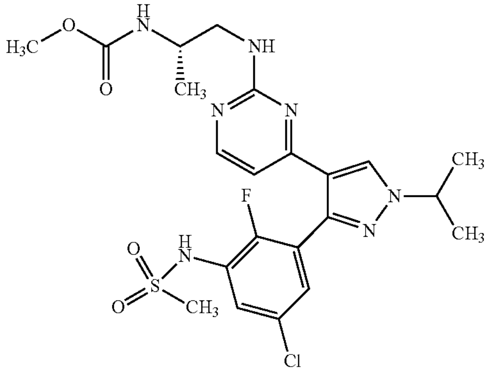 [SMILES: COC(=O)N[C@@H](C)CNc1nccc(-c2cn(C(C)C)nc2-c2cc(Cl)cc(NS(C)(=O)=O)c2F)n1] | WO 2011/025927 |
| A30 | | 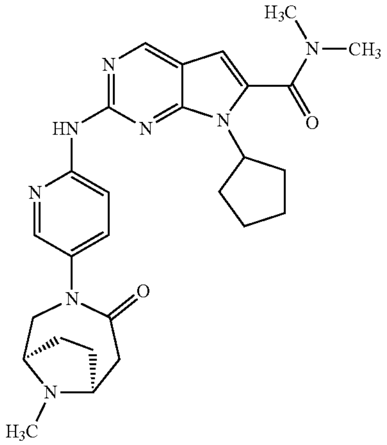 [SMILES: CN(C)C(=O)c1cc2cnc(Nc3ccc(N4C[C@H]5CC[C@@H](CC4=O)N5C)cn3)nc2n1C1CCCC1] | WO 2011/101409 |
| A31 | | Human monoclonal antibody to HER3 | WO 2012/022814<br>EP 2606070<br>U.S. Pat. No. 8,735,551 |
| A32 | | Antibody Drug Conjugate (ADC) | WO 2014/160160<br>Ab: 12425 (see Table 1, paragraph [001911])<br>Linker: SMCC (see paragraph [00117]<br>Payload: DM1 (see paragraph [00111]<br>See also Claim 29 |
| A33 | | Monoclonal antibody or Fab to M-CSF | WO 2004/045532 |
| A34 | Binimetinib | 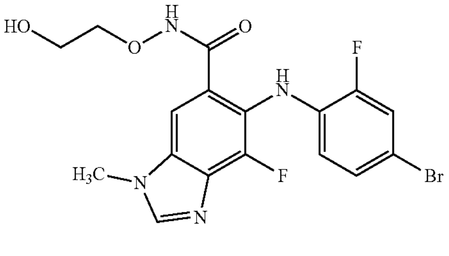 [SMILES: Cn1cnc2c(F)c(Nc3ccc(Br)cc3F)c(C(=O)NOCCO)cc21] | WO 2003/077914 |

-continued
| Compound Designation | Generic Name Tradename | Compound Structure | Patents/Patent Application Publications |
|---|---|---|---|
| A35 | Midostaurin | 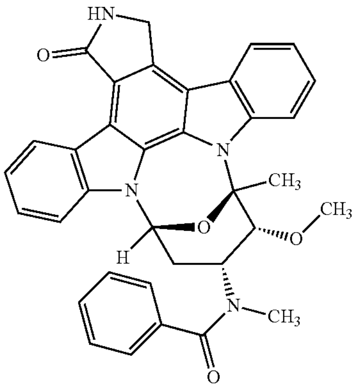 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] | WO 2003/037347<br>EP 1441737<br>US 2012/252785 |
| A36 | Everolimus<br>®AFINITOR | 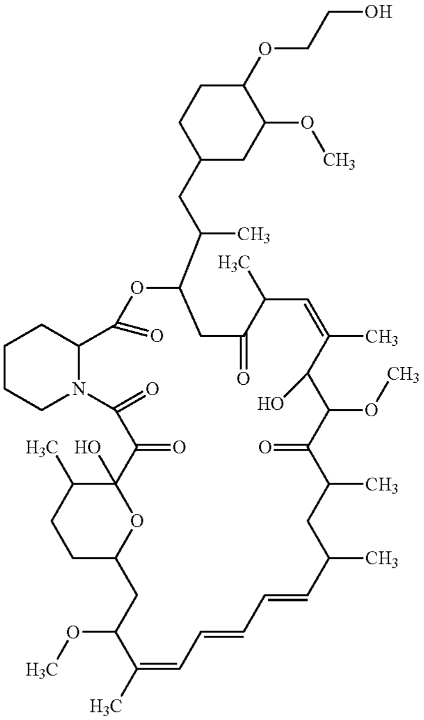 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] | WO 2014/085318 |

-continued
| Compound Designation | Generic Name Tradename | Compound Structure | Patents/Patent Application Publications |
|---|---|---|---|
| A37 | | 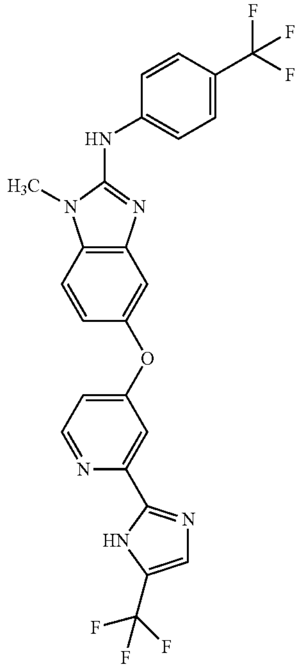 [SMILES: Cn1c(Nc2ccc(C(F)(F)F)cc2)nc2cc(Oc3ccnc(-c4ncc(C(F)(F)F)[nH]4)c3)ccc21] | WO 2007/030377 U.S. Pat. No. 7,482,367 |
| A38 | Pasireotide diaspartate SIGNIFOR ® | 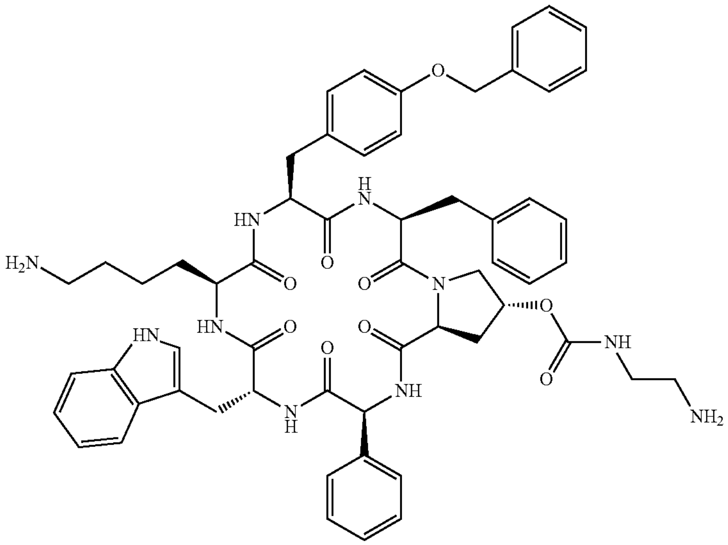 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O] | WO 2002/010192 U.S. Pat. No. 7,473,761 |

-continued
| Compound Designation | Generic Name Tradename | Compound Structure | Patents/Patent Application Publications |
|---|---|---|---|
| A39 | Dovitinib | 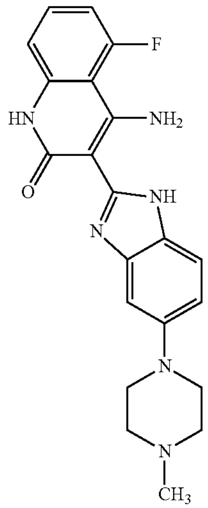 [SMILES: CN1CCN(c2ccc3[nH]c(-c4c(N)c5c(F)cccc5[nH]c4=O)nc3c2)CC1] | WO 2009/115562<br>U.S. Pat. No. 8,563,556 |
| A40 | | 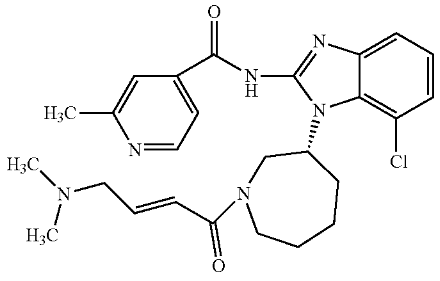 [SMILES: Cc1cc(C(=O)Nc2nc3cccc(Cl)c3n2[C@@H]2CCCCN(C(=O)/C=C/CN(C)C)C2)ccn1] | WO 2013/184757 |
| A41 | | 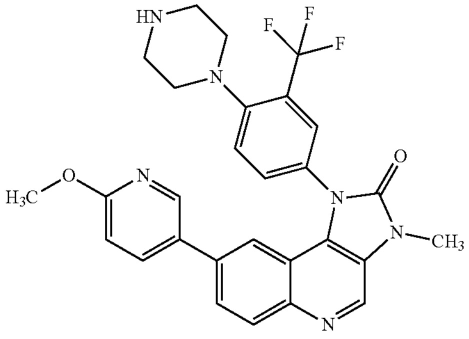 | WO 2006/122806 |

-continued
| Compound Designation | Generic Name Tradename | Compound Structure | Patents/Patent Application Publications |
|---|---|---|---|
| A42 | | 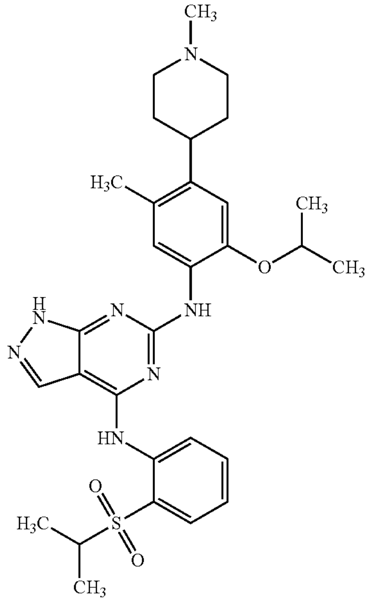 [SMILES: Cc1cc(Nc2nc(Nc3ccccc3S(=O)(=O)C(C)C)c3cn[nH]c3n2)c(OC(C)C)cc1C1CCN(C)CC1] | WO 2008/073687 U.S. Pat. No. 8,372,858 |
| A43 | | 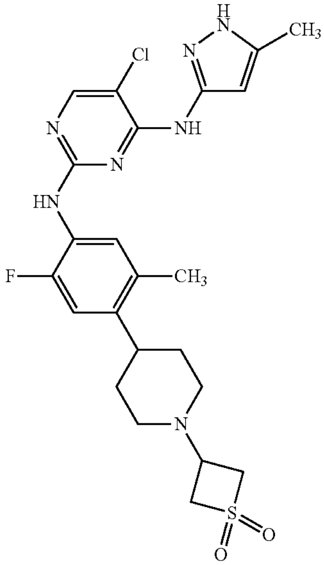 [SMILES: Cc1cc(Nc2nc(Nc3cc(C)c(C4CCN(C5CS(=O)(=O)C5)CC4)cc3F)ncc2Cl)n[nH]1] | WO 2010/002655 U.S. Pat. No. 8,519,129 |

-continued
| Compound Designation | Generic Name Tradename | Compound Structure | Patents/Patent Application Publications |
|---|---|---|---|
| A44 | | 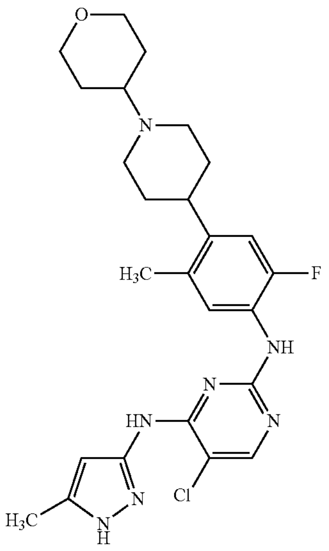 [SMILES: Cc1cc(Nc2nc(Nc3cc(C)c(C4CCN(C5CCOCC5)CC4)cc3F)ncc2Cl)n[nH]1] | WO 2010/002655 U.S. Pat. No. 8,519,129 |
| A45 | | 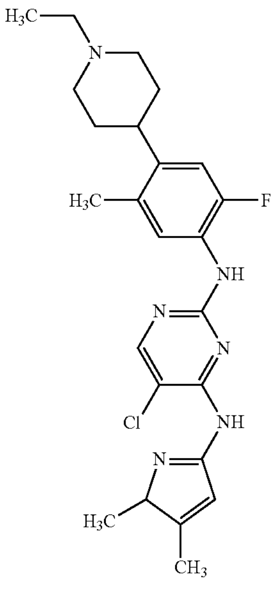 [SMILES: CCN1CCC(c2cc(F)c(Nc3ncc(Cl)c(NC4=NC(C)C(C)=C4)n3)cc2C)CC1] | WO 2010/002655 |

-continued

| Compound Designation | Generic Name Tradename | Compound Structure | Patents/Patent Application Publications |
|---|---|---|---|
| A46 | Valspodar AMDRAY ™ | 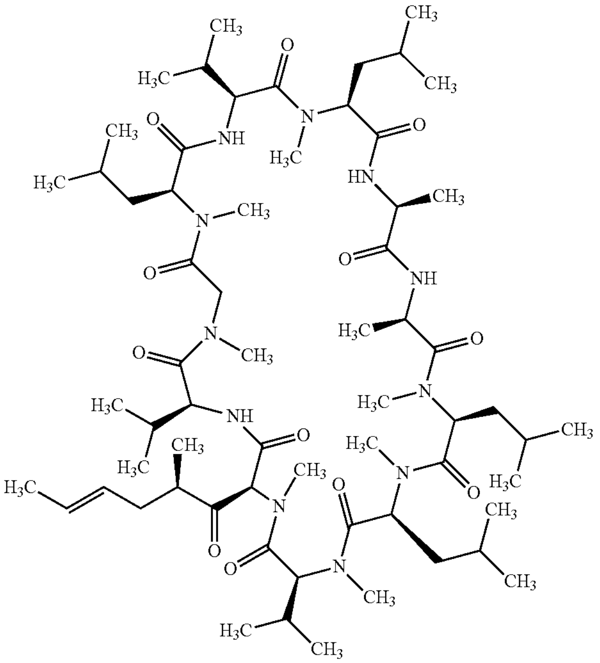 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | EP 296122 |
| A47 | Vatalanib succinate | 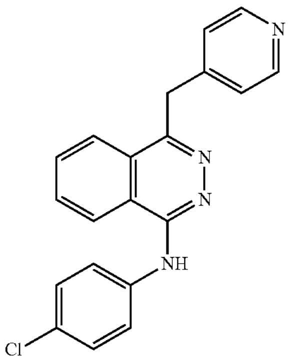 succinate | WO 98/35958 |
| A48 | | IDH inhibitor | WO2014/141104 |
| A4 | | BCR-ABL inhibitor | WO2013/171639 WO2013/171640 WO2013/171641 WO2013/171642 |
| A50 | | cRAF inhibitor | WO2014/151616 |
| A51 | | ERK1/2 ATP competitive inhibitor | PCT/US2014/062913 |

EXAMPLES

The Examples below are set forth to aid in the understanding of the inventions but are not intended to, and should not be construed to, limit its scope in any way.

Example 1: Humanization of Anti-PD-1 Antibody, BAP049

Murine anti-PD-1 monoclonal antibody BAP049 was humanized. The sequences and test samples of sixteen humanized BAP049 clones with unique variable region sequences were obtained. These clones were further analyzed for their biological functions (e.g., antigen binding and ligand blocking), structural features, and transcient expression in CHO cells.

Example 1.1: Humanization Technology and Process

Humanization of BAP049 was performed using a combinatorial library of human germline variable region frameworks (FWs). The technology entails transferring the murine CDRs in frame to a library of human variable regions (VRs)

that had been constructed by randomly combining human germ line FW1, FW2 and FW3 sequences. Only one FW4 sequence was used, which is WGQGTTVTVSS (SEQ ID NO: 169) for the heavy chain (HC) (Kabat human HC subgroup I, No. 21) and FGQGTKVEIK (SEQ ID NO: 208) for the light chain (LC) (Kabat human κ subgroup I, No. 5). The library of VR sequences was fused to human constant region (CR) sequences, human IgG4(S228P) of HC and human κ CR of LC, and the resulting library of whole IgG was expressed in CHO cells for screening. Screening was performed with tissue culture supernatants measuring binding avidity on antigen-expressing cells in a whole cell ELISA format or on FACS.

The humanization process was performed in a stepwise manner starting with the construction and expression of the appropriate chimeric mAb (murine VR, IgG4(S228P), human κ), which can serve as a comparator for the screening of the humanized clones. The constant region amino acid sequences for human IgG4(S228P) heavy chain and human kappa light chain are shown in Table 3.

Humanization of the VR of LC and HC were performed in two independent steps. The library of humanized LC (huLC) was paired with the chimeric HC (murine VR, IgG4(S228P)) and the resulting "half-humanized" mAbs were screened for binding activity by ELISA. The huLC of clones with adequate binding activity (≥binding of chimeric mAb) were selected. Analogously, the library of humanized HC (huHC) was paired with the chimeric LC (murine VR, human κ) and screened for binding activity by ELISA. The huHC of clones with appropriate binding activity (≥binding of chimeric mAb) were selected.

The variable regions of the selected huLC and huHC were then sequenced to identify the huLC and huHC with unique sequences (some clones from the initial selection process may share the same LC or HC). The unique huLC and huHC were then randomly combined to form a small library of humanized mAbs (humAbs), which was expressed in CHO cells and screened on antigen-expressing cells in an ELISA and FACS format. Clones with binding activities that were equal or better than the binding of the chimeric comparator mAb are the final product of the humanization process.

Example 1.2: Sequence of Murine mAb BAP049

The LC and HC variable region sequences of murine anti-PD-1 mAb were determined. The sequences obtained from two independent analyses were identical and are shown in FIG. 1.

Germline analysis was performed and part of the result is shown in FIG. 2A as an amino acid sequence alignment. For the light chain, the V-gene is 98.65% identical to mIGKV8-19*01F (293/297 nts) and the J-gene is 97.30% identical to mIGKJ2*01F (36/37 nts). For the heavy chain, the V-gene is 92.83% identical to mIGHV1S22*01F (259/279 nts), the J-gene is 82.98% identical to mIGHJ3*01F (39/47 nts), and the D-gene is mIGHD2-14*01F. As shown in FIG. 2B, the LC sequence of the murine mAb contains an unpaired Cys at position 102, which is in CDRL3 and arose through a point mutation in the murine J2 gene (tac→tgc; Y→C).

Example 1.3: Construction of Chimeric Antibody

Figure 3B:
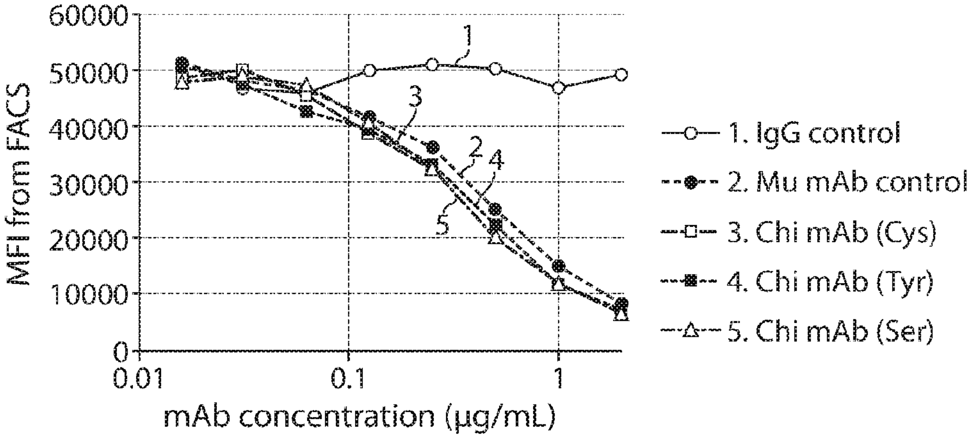

Three variants of the chimeric antibody were prepared that either had a Cys, Tyr or Ser residue at position 102 of the LC sequence. The three chimeric antibodies, i.e., BAP049-chi (Cys), BAP049-chi (Tyr), and BAP049-chi (Ser) (also known as BAP049-chi, BAP049-chi-Y, and BAP049-chi-S, respectively), were expressed in CHO cells and tested for their ability to compete with labeled murine antibody for binding to PD-1 expressing Jurkat cells. As shown in FIGS. 3A-3B, the three variants were indistinguishable in the competition experiment. The results show that the three chimeric mAbs (Cys, Tyr, Ser) compete equally well with the binding of the labeled murine mAb BAP049. The slight difference between the chimeric mAb curves and the murine mAb curve is probably due to the different methods used for determining mAb concentrations. The concentration of the murine mAb was determined by OD280 measurement, whereas the chimeric mAb concentrations in supernatants were determined with an ELISA using an IgG4 standard. The germline residue Tyr was selected for humanized antibodies.

The amino acid sequences of the heavy and light chains for chimeric mAb BAP049-chi (Cys) are shown in Table 1. The nucleotide sequences of the heavy and light chains for chimeric mAb BAP049-chi (Cys) are shown in Table 1. In BAP049-chi (Tyr) and BAP049-chi (Ser), the unpaired Cys residue at position 102 of the LC were replaced with a Tyr or Ser residue.

Example 1.4: Humanized Antibody Clones

Figure 4:
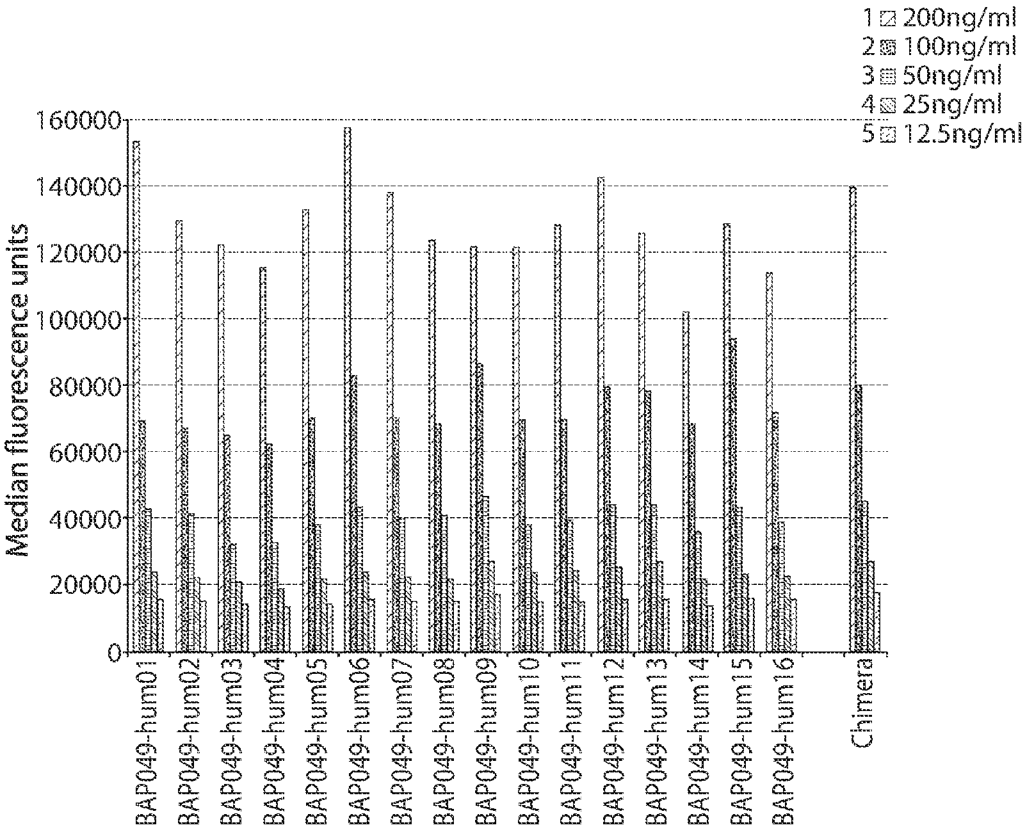
FIG. 4 is a bar graph showing the results of FACS binding analysis for the sixteen humanized BAP049 clones (BAP049-hum01 to BAP049-hum16). The antibody concentrations are 200, 100, 50, 25 and 12.5 ng/ml from the leftmost bar to the rightmost bar for each tested mAb.

As shown in FIG. 4, the process of humanization yielded sixteen clones with binding affinities comparable to that of the chimeric antibody. In addition to binding data, for each clone, the VR sequences were provided along with a sample of the mAb. The samples had been prepared by transient transfections of CHO cells and were concentrated tissue culture supernatants. The antibody concentrations in the solutions had been determined by an IgG4-specific ELISA.

As shown in FIG. 5, the sixteen unique clones are combinations of four unique HC sequences and nine unique LC sequences. For the HC FW regions, the HC sequences are combinations of one of two different VHFW1, one of three different VHFW2, and one of two different VHFW3 sequences. For the LC FW regions, the LC sequences are combinations of one of five different VLFW1, one of three different VLFW2, and one of four different VLFW3 sequences. The amino acid and nucleotide sequences of the heavy and light chain variable domains for the humanized BAP049 clones are shown in Table 1. The amino acid and nucleotide sequences of the heavy and light chain CDRs of the humanized BAP049 clones are also shown in Table 1.

FIG. 5 indicates that the samples varied in the concentration of the mAb, ranging from 7.9 μg/mL to 61.5 μg/mL. These numbers were representative of several transient expression experiments.

Example 1.5: Analysis of Humanized Clones

Example 1.5.1: Analysis of Binding Activity and Binding Specificity

Figure 6A:
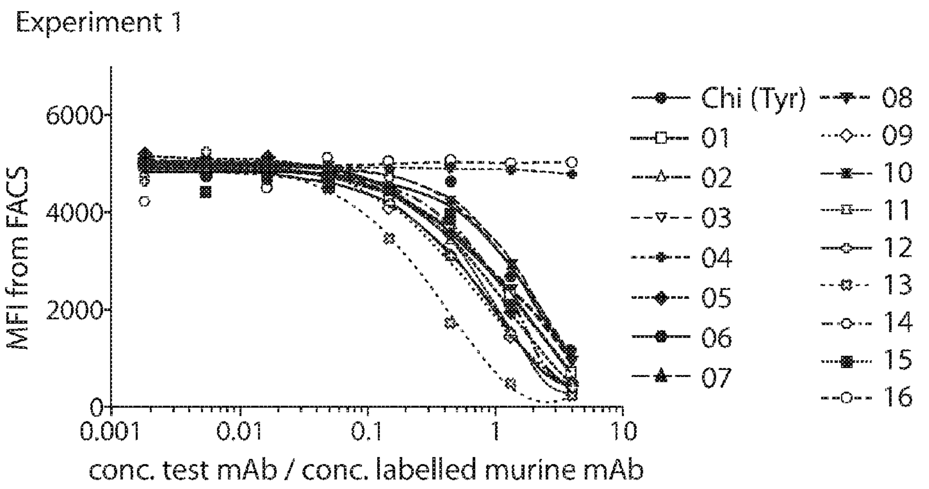
FIG. 6A-6B depicts the binding affinity and specificity of humanized BAP049 mAbs measured in a competition binding assay using a constant concentration of Alexa 488-labeled murine mAb BAP049, serial dilutions of the test antibodies, and PD-1-expressing 300.19 cells. Experiment was performed twice, and the results are shown in FIGS. 6A and 6B, respectively.
Figure 6B:
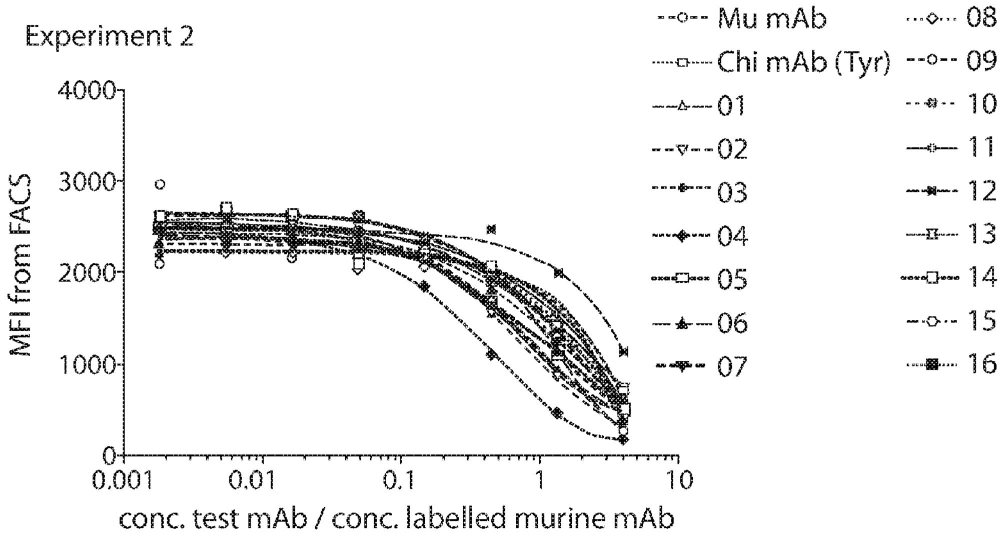

The binding activity and specificity was measured in a competition binding assay using a constant concentration of Alexa 488-labeled murine mAb, serial dilutions of the test mAbs, and PD-1-expressing 300.19 cells. Incubations with the mAb mixtures having different concentration ratios of test mAb to labeled mAb was at 4° C. for 30 min. Bound labeled murine mAb was then quantified using a FACS machine. The experiment was performed twice. The results are shown in FIGS. 6A-6B.

Within the accuracy of the experiment, all humanized clones show similar activity for competing with binding of labeled murine mAb. The activity is also comparable to the activity of the parent murine mAb and chimeric mAb. MAbs were ranked relative to each other. For example, it can be a weaker competitor if in both experiments the curve of a certain clone is to the right of the chimeric mAb curve or it can be a better competitor if the curve of a certain clone is to the left of the chimeric mAb curve. Such a ranking system was used in FIG. 7.

Example 1.5.2: Sequence Analysis

Based on structural features, the sixteen humanized mAbs were divided into four groups and ranked from A to E. The results are shown in FIG. 7.

Example 1.5.3: Selection of Humanized Clones

FIG. 7 summarizes the data which was considered for the selection of humanized clones. Expression data ($2^{nd}$ column), the diversity in the composition of the variable regions ($3^{rd}$ column), relative rankings in binding studies ($4^{th}$ and $5^{th}$ columns), and structural analysis ($6^{th}$ column), were considered.

Selected clones were further tested for their ability to block the binding of PD-L1 and PD-L2 to PD-1 and for enhancing T cell activity in vitro assays with human PBMC.

Example 1.5.4: Blocking of Ligand Binding

Murine anti-PD-1 mAb blocks the binding of the natural ligands PD-L1 and PD-L2 to PD-1 expressed on cells at low concentrations. Whether the humanized clones had preserved the blocking capacity of the parent murine mAb was tested in comparative experiments with murine and chimeric antibodies.

Figure 8A:
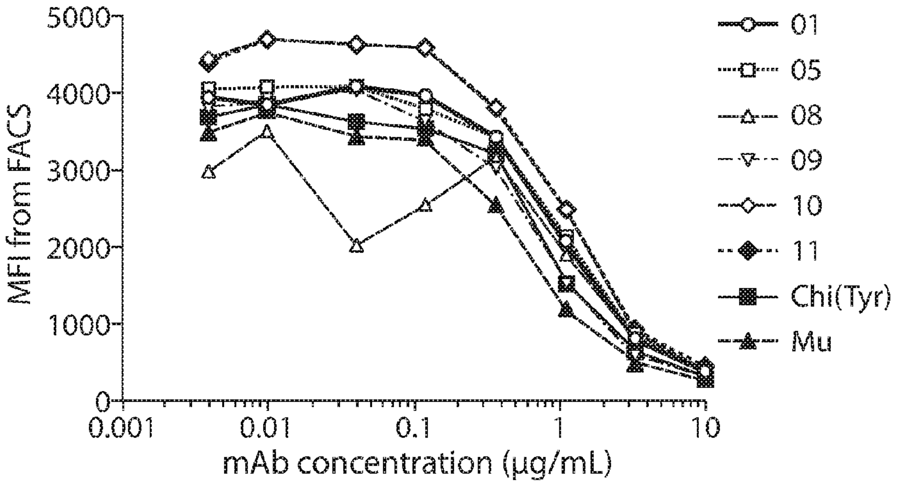
FIGS. 8A-8B depict blocking of ligand binding to PD-1 by selected humanized BAP049 clones. Blocking of PD-L1-Ig and PD-L2-Ig binding to PD-1 is shown in FIG. 8A. Blocking of PD-L2-Ig binding to PD-1 is shown in FIG. 8B. BAP049-hum01, BAP049-hum05, BAP049-hum08, BAP049-hum09, BAP049-hum10, and BAP049-hum11 were evaluated. Murine mAb BAP049 and chimeric mAb having Tyr at position 102 of the light chain variable region were also included in the analyses.
Figure 8B:
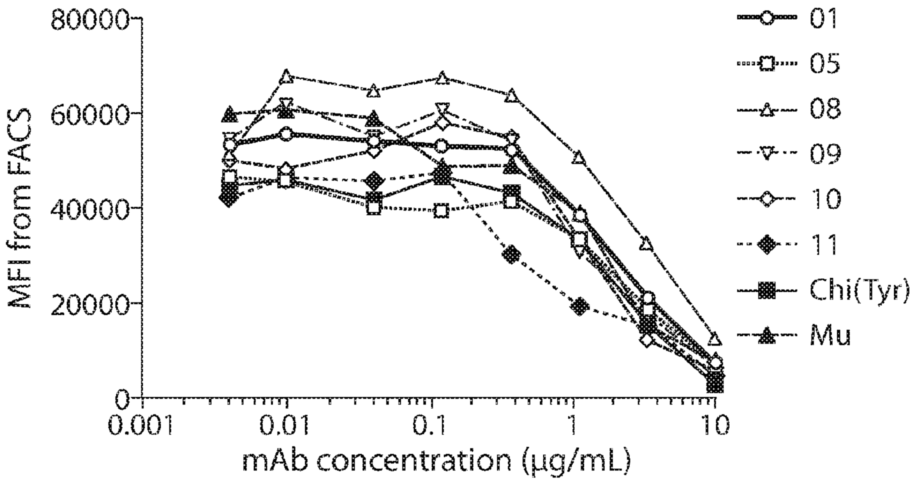

The blocking capacity of the mAbs was evaluated in a competition binding assay using a constant concentration of PD-L1-huIgG1 Fc fusion protein or PD-L2-hulgG1 Fc fusion protein, serial dilutions of the mAbs to be tested, and PD-1-expressing 300.19 cells. Incubation was at 4° C. for 30 min. Bound ligand fusion proteins were detected with PE-conjugated F(ab')2 fragment of goat anti-human IgG which doesn't recognize IgG4 mAbs (Southern Biotech 2043-09), and flow cytometry. The results are shown in FIGS. 8A-8B.

Within the accuracy of the experiments, the humanized clones, chimeric antibody and murine parent mAb demonstrated comparable blocking activity for both the PD-L1 and PD-L2 ligands.

Example 1.5.5: T-Cell Epitope Analysis

Humanized mAbs were analyzed for T cell epitopes using Epibase™. The algorithm analyzes each possible peptide (each 10-mer along the protein advancing by one amino acid) for binding to HLA class II. It estimates free energy of binding ($\Delta G_{bind}$) for each peptide and calculates a putative $K_D$ ($\Delta G_{bind}$=RT ln $K_D$). Then peptides are labeled S, M, or N for strong, medium, and non-binders. Threshold values used for this classification are different for each allotype.

The data was normalized to a risk score. The overall "risk score" is the sum of all potential epitopes to all tested alleles, weighted by the affinities of the respective peptides but leaving out all potential epitopes in germ line sequences (lower value therefor is "better").

There are roughly three categories of mAbs, derived from a large set of mAbs of different composition as described below.

Risk score of around 500: fully human mAbs generated from humans, "humanized" mice, and phage libraries ("values below 500 are really good even for fully human antibodies"). Humanized mAbs specifically engineered (even the CDRs) to have a low score are typically in the 500-700 risk category.

Risk score around 900: typical CDR-grafted antibodies, which have fully murine CDRs with or without changes in the FW region; approved CDR-grafted mAbs are basically all in this category.

Risk score around 1500: chimeric mAbs.

The results for selected humanized BAP049 mAbs are:

| Clone No. | Risk score |
|---|---|
| 01 | 476 |
| 05 | 479 |
| 08 | 472 |
| 09 | 503 |
| 10 | 583 |
| 11 | 614 |

Selected humanized clones have low scores. Typically, values below 500 indicate low risk of immunogenicity even for fully human antibodies. For example, the human mAb, adalimumab (Humira®), has a score of 654, which is relatively high for human mAbs (at the upper end of the Gaussian curve) but low in comparison to a typical CDR-grafted mAb.

Summary and Conclusions

Murine anti-PD-1 monoclonal antibody, BAP049, was humanized. The technology entails the cloning of the murine CDRs in-frame into an ordered library of human germ line variable region frameworks, expressing the library of cloned variable regions as intact IgG4(S228P) humanized mAbs in CHO cells, and selecting clones that bind with comparable or higher affinity to the target as the parent mAb. Therefore, the murine CDRs were asked to select proper human germline framework sequences that preserve their conformations and thus the binding affinity and specificity of the parent murine mAb. The sequences and test samples of sixteen humanized mAbs with unique variable region sequences were obtained, which had passed a binding test with PD-1-transfected CHO cells. These clones were further analyzed for their biological functions (e.g., antigen binding and ligand blocking), structural features, and transcient expression in CHO cells.

Example 2: Expression of Humanized Anti-PD-1 Antibody, BAP049

Five humanized clones described in Example 1 were selected for evaluation of expression in Chinese Hamster Ovary (CHO) cells.

Single gene vectors (SGVs) were constructed using Lonza's GS Xceed vectors (IgG4proΔk for heavy chain and Kappa for light chain). The SGVs were amplified and transiently co-transfected into CHOK1SV GS-KO cells for expression at a volume of 2.8 L.

Expression cultures were harvested Day 6 post-transfection and clarified by centrifugation and sterile filtration. The clarified cell culture supernatant was purified using one-step Protein A chromatography. Product quality analysis in the form of SE-HPLC, SDS-PAGE, IEF, and LAL was carried out using purified material at a concentration of 1 mg/ml including an antibody as a control sample.

Example 2.1: Vector Construction

The sequences of the light and heavy chain variable domain encoding regions were synthesised by GeneArt AG. Light chain variable domain encoding regions were sub-cloned into pXC-Kappa and heavy chain variable domain encoding regions into pXC-IgG4pro ΔK vectors respectively using the N-terminal restriction site Hind III and the C-terminal restriction sites BsiWI (light chain) and ApaI (heavy chain). Positive clones were screened by PCR amplification (primers 1053: GCTGACAGACTAACAGACTGT-TCC (SEQ ID NO: 226) and 1072: CAAATGTGGTATG-GCTGA (SEQ ID NO: 227)) and verified by restriction digest (using a double digest of EcoRI-HF and HindIII-HF) and nucleotide sequencing of the gene of interest.

Example 2.2: DNA Amplification

A single bacterial colony was picked into 15 ml Luria Bertani (LB) medium (LB Broth, Sigma-Aldrich, L7275) containing 50 μg/ml ampicillin and incubated at 37° C. overnight with shaking at 220 rpm. The resulting starter culture was used to inoculate 1 L Luria Bertani (LB) medium containing 50 μg/ml ampicillin and incubated at 37° C. overnight with shaking at 220 rpm. Vector DNA was isolated using the QIAGEN Plasmid Plus Gigaprep system (QIAGEN, 12991). In all instances, DNA concentration was measured using a Nanodrop 1000 spectrophotometer (Thermo-Scientific) and adjusted to 1 mg/ml with EB buffer (10 mM Tris-C1, pH 8.5). DNA quality for the single gene vectors was assessed by measuring the absorbance ratio A260/A280. This was found to be between 1.88 and 1.90.

Example 2.3: Culture of CHOK1SV GS-KO Cells

CHOK1SV GS-KO cells were cultured in CD-CHO media (Invitrogen, 10743-029) supplemented with 6 mM glutamine (Invitrogen, 25030-123). Cells were incubated in a shaking incubator at 36.5° C., 5% $CO_2$, 85% humidity, 140 rpm. Cells were routinely sub-cultured every 3-4 days, seeding at $2\times10^5$ cells/ml and were propagated in order to have sufficient cells available for transfection. Cells were discarded by passage 20.

Example 2.4: Transient Transfections of CHOK1SV GS-KO Cells

Transient transfections were performed using CHOK1SV GS-KO cells which had been in culture a minimum two weeks. Cells were sub-cultured 24 h prior to transfection and cell viability was >99% at the time of transfection.

All transfections were carried out via electroporation using a Gene Pulse MXCell (Bio-Rad), a plate based system for electroporation. For each transfection, viable cells were resuspended in pre-warmed media to $2.86\times10^7$ cells/ml. 80 μg DNA (1:1 ratio of heavy and light chain SGVs) and 700 μl cell suspension were aliquotted into each cuvette/well. Cells were electroporated at 300 V, 1300 μF. Transfected cells were transferred to pre-warmed media in Erlenmeyer flasks and the cuvette/wells rinsed twice with pre-warmed media which was also transferred to the flasks. Transfected cell cultures were incubated in a shaking incubator at 36.5° C., 5% $CO_2$, 85% humidity, 140 rpm for 6 days. Cell viability and viable cell concentrations were measured at the time of harvest using a Cedex HiRes automated cell counter (Roche).

Example 2.5: Protein A Affinity Chromatography

Cell culture supernatant was harvested and clarified by centrifugation at 2000 rpm for 10 min, then filtered through a 0.22 μm PES membrane filter. Clarified supernatant was purified using a pre-packed 5 ml HiTrap MabSelect SuRE column (GE Healthcare, 11-0034-94) on an AKTA purifier (10 ml/min). The column was equilibrated with 50 mM sodium phosphate, 125 mM sodium chloride, pH 7.0 (equilibration buffer) for 5 column volumes (CVs). After sample loading, the column was washed with 2 CVs of equilibration buffer followed by 3 CVs of 50 mM sodium phosphate, 1 M sodium chloride pH 7.0 and a repeat wash of 2 CVs of equilibration buffer. The Product was then eluted with 10 mM sodium formate, pH 3.5 over 5 CVs. Protein containing, eluted fractions were immediately pH adjusted to pH 7.2 and filtered through a 0.2 μm filter.

A single protein-containing peak was observed during the elution phase. This peak was shown to contain the mAb, when analyzed by SE-HPLC and SDS-PAGE. Recovered protein yield is shown in Table 5. The clones expressed transiently in a range from 32.4 to 43.0 mg/L.

TABLE 5

Summary of yield, titre, monomer content and endotoxin levels

| Product | Yield* (mg) | Titre* (mg/L) | Monomer Content (%) | Endotoxin levels (EU/mg) |
|---|---|---|---|---|
| Clone A | 107.5 | 38.38 | 93.94 | 0.04 |
| Clone B | 93.8 | 33.50 | 95.28 | 0.63 |
| Clone C | 90.7 | 32.38 | 97.83 | 0.04 |
| Clone D | 108.9 | 38.88 | 96.53 | 0.35 |
| Clone E | 120.4 | 43.00 | 97.73 | 0.14 |

*Post Protein A purification

Example 2.6: SE-HPLC Analysis

Samples of Protein A purified antibodies were analyzed in duplicate by SE-HPLC on an Agilent 1200 series HPLC system, using a Zorbax GF-250 4 μm 9.4 mm ID×250 mm column (Agilent). Aliquots of sample at a concentration of 1 mg/ml were filtered through a 0.2 μm filter prior to injection. 80 μl aliquots were injected respectively and run at 1 ml/min for 15 minutes. Soluble aggregate levels were analysed using Chemstation (Agilent) software.

Chromatography profiles with retention time showing the percentage of the overall detected peak areas were obtained for the tested antibodies and a control IgG4 antibody. The products show a single protein peak at approximately 8.65 to 8.72 min comparable to the human IgG4 antibody control (about 8.64 min) and consistent with a monomeric antibody. Small amounts (up to about 4-5%) of higher molecular weight impurities, consistent with soluble aggregates, were detected at retention times between about 7.43 and 8.08 min.

Example 2.7: SDS-PAGE Analysis

Reduced samples were prepared for analysis by mixing with NuPage 4×LDS sample buffer (Invitrogen, NP0007) and NuPage 10× sample reducing agent (Invitrogen, NP0009), and incubated at 70° C., 10 min. For non-reduced samples, the reducing agent and heat incubation were omitted. Samples were electrophoresed on 1.5 mm NuPage 4-12% Bis-Tris Novex pre-cast gels (Invitrogen, NP0335PK2) with NuPage MES SDS running buffer under denaturing conditions. 10 μl aliquots of SeeBlue Plus 2 pre-stained molecular weight standard (Invitrogen, LC5925) and a control IgG4 antibody at 1 mg/ml were included on the gel. 1 μl of each sample at 1 mg/ml were loaded onto the gel. Once electrophoresed, gels were stained with InstantBlue (TripleRed, ISBOlL) for 30 min at room temperature. Images of the stained gels were analysed on a BioSpectrum Imaging System (UVP).

The analysis confirmed the presence of the antibody products and good levels of purity. Under non-reducing conditions, a predominant protein band close to 98 kDa was observed comparable with the control IgG4 antibody. The control IgG4 antibody and one tested clone display an additional fainter band corresponding to a heavy plus light chain half-antibody at approximately 70 kDa under non-reducing conditions. This is expected for the control antibody. Two bands were observed under reducing conditions consistent with the size of heavy (close to the position of the 49 kDa marker) and light chains (close to the position of the 28 kDa marker) and comparable with the bands found for the control IgG4 antibody.

Example 2.8: Iso-Electric Focussing (IEF) Analysis

Non-reduced samples of Protein A purified antibody were electrophoresed as described below.

5 μg of Protein A purified samples were electrophoresed on a 1.0 mm Novex pH 3-10 gradient gel (Invitrogen, EC66552BOX) using manufacturers recommended running conditions. A 10 μl aliquot of IEF pH 3-10 markers (Invitrogen, 39212-01) was included on the gel. Once electrophoresed, gels were fixed with 10% TCA solution for 30 min and then stained with InstantBlue (TripleRed, ISBOlL) over night at room temperature. Images of the stained gels were analysed on a BioSpectrum Imaging System (UVP).

As shown in Table 6, the tested clones show charge isoforms between pH 7.4 and 8.0 markers. The detected charge isoforms are slightly more basic than the theoretically calculated pIs for these antibodies which were predicted to be between 6.99 and 7.56. The general shift to more basic charge isoforms suggests the presence of post-translational modifications such as glycosylation on the molecules. Clone C and Clone E show comparable charge isoforms, which is also consistent with the theoretically calculated pI being the same for both (6.99). The control IgG4 antibody behaved as expected.

TABLE 6

Charge isoforms as detected by Novex IEF analysis

| Product | pI of predominant charge isoform* | Acidic charge isoforms* | Basic charge isoforms* |
|---|---|---|---|
| Clone A | 7.6 | 2x; 7.5 to 7.55 | 7.7 |
| Clone B | 7.75 | 2x; 7.5 to 7.6 | 7.8 |
| Clone C | 7.5 | 2x; 7.4 to 7.5 | 7.55 |
| Clone D | 8.0 | 7.9 | 8.1 |
| Clone E | 7.5 | 2x; 7.4 to 7.5 | 7.55 |

*pI readings are estimated from the staining positions correlated against the IEF 3-10 marker.

Example 2.9: Endotoxin Analysis

Endotoxin levels of purified proteins were measured at final concentrations (up to 3.44 mg/ml) using an Endosafe-PTS instrument, a cartridge based method based on the LAL assay (Charles River).

As shown in Table 5, the endotoxin content was found to range from 0.04 to 0.63 EU/mg.

CONCLUSION

GS single gene expression vectors for selected humanized anti-PD-1 mAbs were constructed and used to transiently transfect CHOK1SV GS-KO cells. 2.6 to 2.8 liters of expression culture were incubated under standard conditions for 6 days and the resulting cell culture supernatant purified using Protein A chromatography. Post-purification titres are indicated in Table 5 and were found to be ranging from 32.38 to 43.0 mg/L. The recovered yields range from 90.7 to 120.4 mg.

SDS-PAGE and SE-HPLC analysis indicated the presence of a small amount (up to 6.06%) of soluble aggregates present in the products being predominantly consistent with dimeric antibody for the mAb. The mAbs also showed higher molecular weight impurities at retention times consistent with that of trimeric antibodies.

Iso-electric focusing detected a number of charge isoforms for all mAbs. The mAbs showed isoforms generally more basic when based on theoretically calculated pI for these molecules indicating some level of post translation modification. The mAbs were found to be comparable to their theoretically calculated pI values.

The endotoxin levels for all samples were measured prior to provision of samples and found to be below 0.63 EU/mg.

Example 3: Characterization of Murine and Humanized Anti-PD-1 Antibodies

Example 3.1: Characterization of Murine Anti-PD-1 Antibody

The binding affinity of murine anti-PD-1 antibody BAP049 to PD-1 was investigated. The murine anti-PD-1 antibody binds to human PD-1-Ig fusion protein with a $K_D$ of 0.04 nM as measured by ELISA. As shown by FACS analyses, the murine anti-PD-1 antibody binds to human PD-1 transfected Jurkat cells with a $K_D$ of 0.06 nM, to cynomolgus T cells (e.g., CD3/CD28 activated CD4 T cells) with a $K_D$ of 0.4 nM, and to cells transfected with cynomolgus PD-1 with a $K_D$ of 0.6 nM.

The blocking activity of murine anti-PD-1 antibody BAP049 was examined by competition binding assays. The murine anti-PD-1 antibody blocked PD-L1 binding to human PD-1-expressing 300.19 cells with an IC50 of 0.3 nM. It blocked PD-L2 binding to human PD-1-expressing 300.19 cells with an IC50 of 0.9 nM.

The effect of murine anti-PD-1 antibody BAP049 on interferon gamma (IFN-γ) expression was tested. The murine anti-PD-1 antibody resulted in 2.3±1.1 fold increase in IFN-γ expression on cells stimulated with anti-CD3 (0.1 μg/mL), 2.5±2.0 fold increase on cells stimulated with Staphylococcal enterotoxin B (SEB) (3 pg/mL), and 2.8±0.8 fold increase on cells stimulated with CMV peptides.

The murine anti-PD-1 antibody BAP049 was also found to increase proliferation of $CD8^+$ T cells activated with CMV peptides as indicated by the percentages of $CD8^+$ cells that passed through at least certain number (n) of cell divisions (e.g., n=2, 4, 6).

Example 3.2: Characterization of Humanized Anti-PD-1 Antibody

Binding Affinity and Specificity

The binding of an exemplary humanized anti-PD-1 antibody on human PD-1 protein was measured using Biacore method. The results are: Ka=$2.78\times10^5$ $M^{-1}s^{-1}$; Kd=$2.13\times10^{-4}$ $s^{-1}$; $K_D$=0.0827±0.005505 nM.

The binding of the same humanized anti-PD-1 antibody on human PD-1-expressing 300.19 cells was measured using FACS analysis. The result shows that the anti-PD-1 antibody (human IgG4) binds with high affinity to human PD-1 compared to a human IgG4 isotype control.

The exemplary humanized anti-PD-1 antibody was found to exhibit high affinity to cynomolgus PD-1 protein and cynomolgus PD-1-expressing 300.19 cells. As measured by Biacore method, the anti-PD-1 antibody binds to cynomolgus PD-1 with a $K_D$ of 0.093±0.015 nM. The binding affinity to cynomolgus PD-1 is comparable to its binding affinity to human PD-1.

Additional binding analyses show that the exemplary humanized anti-PD-1 antibody is not cross-reactive with mouse PD-1 or cross-reactive with parental cell line.

Blocking of Interactions Between PD-1 and its Ligands

The ability of the exemplary humanized anti-PD-1 antibody to block the interactions between PD-1 and both of its known ligands, PD-L1 and PD-L2 was examined. The results show that the anti-PD-1 antibody blocked the binding of PD-L1 and PD-L2 on human PD-1-expressing 300.19 cells compared to human IgG4 isotype control and no antibody control. The anti-PD-1 antibody blocked PD-L1 binding on the 300.19 cells with an IC50 of 0.94±0.15 nM. The same antibody blocked PD-L2 binding on the 300.19 cells with an IC50 of 1.3±0.25 nM.

Cellular Activity

The ability of the exemplary humanized anti-PD-1 antibody to enhance the Staphylococcal enterotoxin B (SEB)-stimulated expression of IL-2 was tested in human whole blood ex vivo assay. Diluted human whole blood was incubated with the anti-PD-1 antibody in the presence or absence of SEB at 37° C. for 48 hours prior to IL-2 measurement. The result shows that the anti-PD-1 antibody increased SEB-stimulated IL-2 expression by 2.28±0.32 fold compared to a human IgG4 isotype control (25 μg/ml SEB; n=5 donors).

Example 4: Patient Selection Based on PD-L1/CD8/IFN-γ Status

Figure 11:
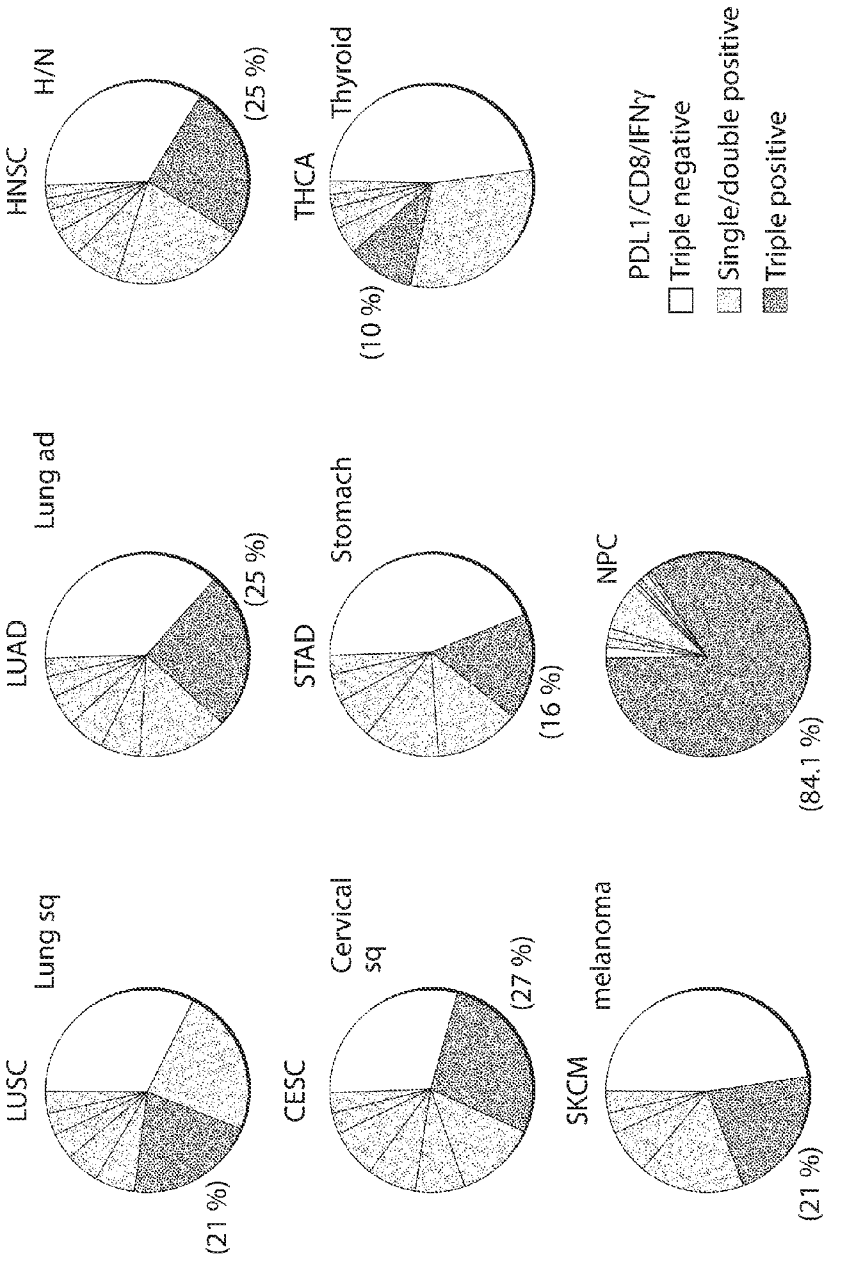
FIG. 11 shows exemplary cancers having relatively high proportions of patients that are triple-positive for PD-L1/CD8/IFN-γ.

For each of several types of cancer, samples from multiple patients were tested for PD-L1/CD8/IFN-γ status. Each sample was classified as: triple-negative for PD-L1/CD8/1FN-γ, single or double positive for these markers, or triple-positive for these markers. FIG. 11 shows that in this experiment, within a population of patients, the following types of cancer are frequently triple-positive for PD-L1/CD8/IFN-γ: Lung cancer (squamous), lung cancer (adenocarcinoma), head and neck cancer, cervical cancer (squamous), stomach cancer, thyroid cancer, melanoma, and nasopharyngeal cancer. Patients having these types of cancer are good candidates for therapy with anti PD-1 antibodies and combination therapies as described herein. The likelihood of successful treatment can be further boosted by determining which patients are triple-positive for PD-L1/CD8/1FN-γ, and treating the triple-positive patients with anti PD-1 antibodies and combination therapies as described herein.

Figure 12:
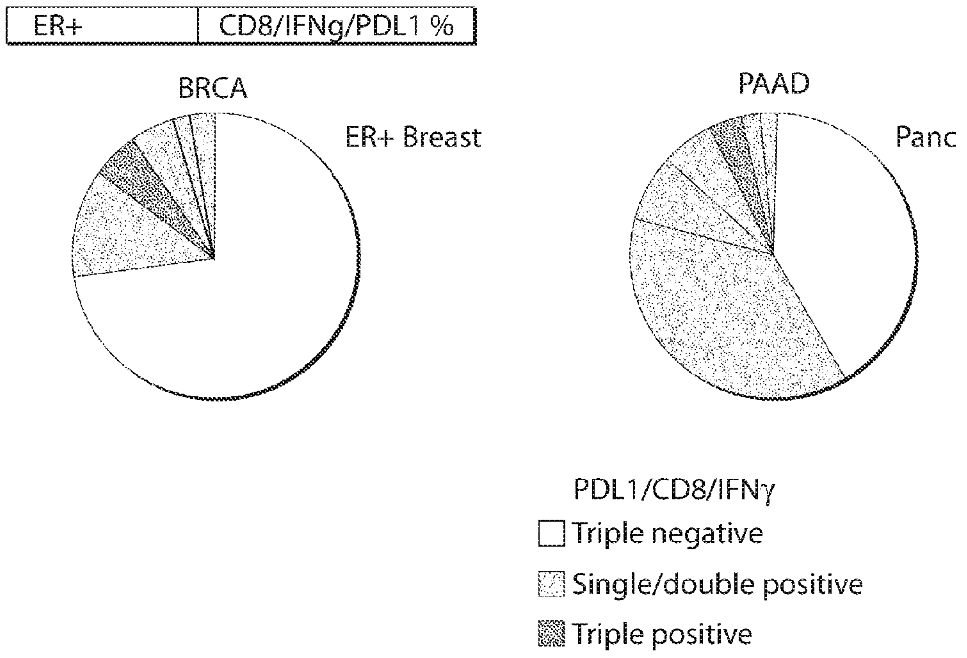
FIG. 12 shows exemplary ER+ breast cancer and pancreatic cancer having relatively low proportions for patients that are triple positive for PD-L1/CD8/IFN-γ.

FIG. 12 shows that within a population of patients, the following types of cancer are rarely triple positive for PD-L1/CD8/IFN-γ: ER+ breast cancer and pancreatic cancer. Notably, even in cancers that are generally not positive for PD-L1/CD8/IFN-γ, one can increase the likelihood of successful treatment by determining which patients are triple-positive for PD-L1/CD8/IFN-γ, and treating the triple-positive patients with anti PD-1 antibodies and combination therapies as described herein.

Figure 13:
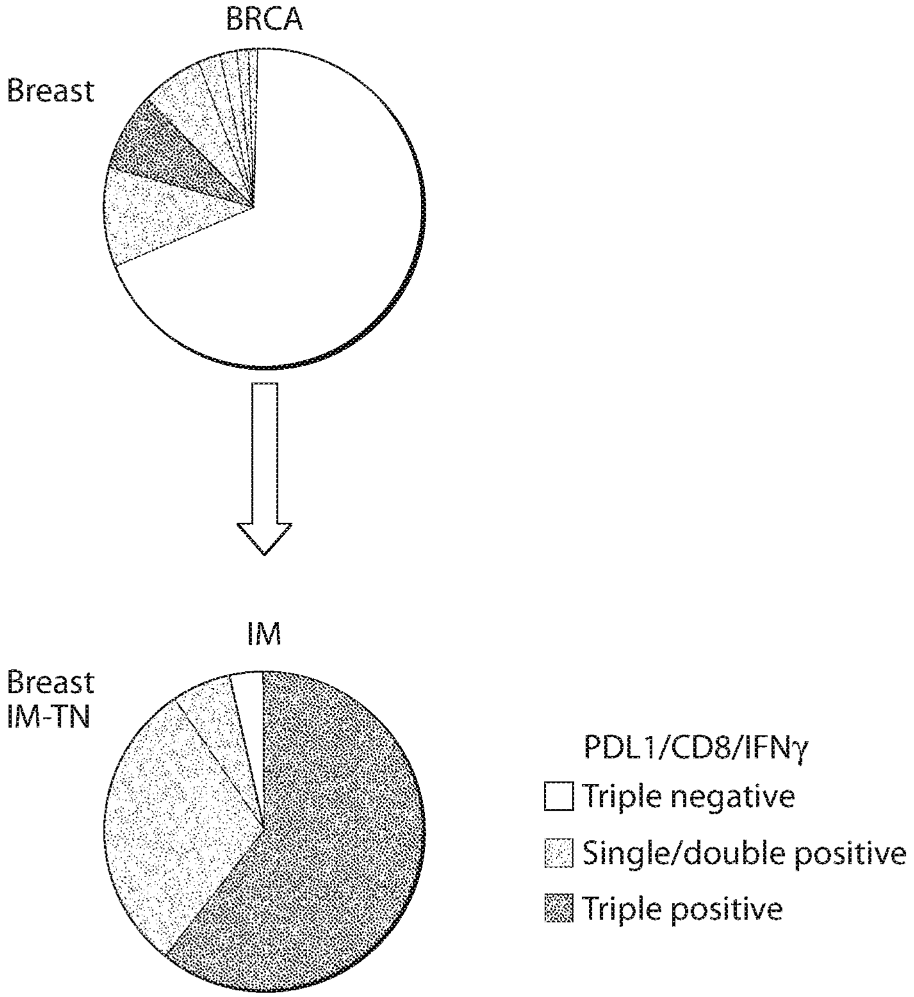
FIG. 13 shows the proportion of exemplary breast cancer patients that are triple positive for PD-L1/CD8/IFN-γ.

FIG. 13 shows the proportion of breast cancer patients that are triple positive for PD-L1/CD8/IFN-γ. Considering breast cancer in general, the proportion of triple-positives is somewhat low. However, when one focuses only on IM-TN breast cancer, it can be seen that a much larger percentage of patients is triple positive for PD-L1/CD8/IFN-γ. IM-TN breast cancer is particularly difficult to treat with conventional therapies. The discovery that IM-TN breast cancer is often triple-positive for PD-L1/CD8/IFN-γ opens up new avenues of therapy for this cancer with anti PD-1 antibodies and combination therapies as described herein.

Figure 14:
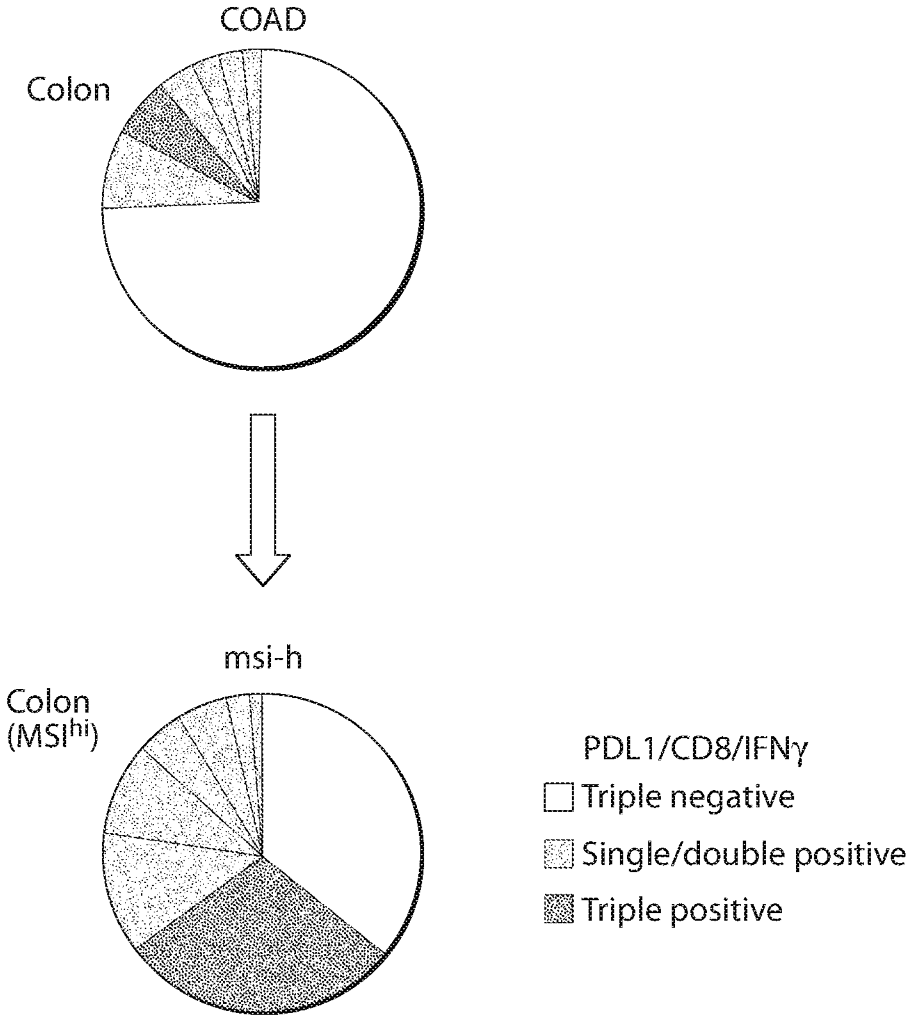
FIG. 14 shows the proportion of exemplary colon cancer patients that are triple positive for PD-L1/CD8/IFN-γ.

FIG. 14 shows the proportion of colon cancer patients that are triple positive for PD-L1/CD8/IFN-γ. Considering colon cancer in general, the proportion of triple-positive is somewhat low. However, when one focuses only on MSI-high (high microsatellite instability) breast cancer, it can be seen that a much larger percentage of patients is triple positive for PD-L1/CD8/IFN-γ. MSI levels can be assayed using, e.g., commercially available PCR-based methods.

Gastric cancer samples were tested for levels of PD-L1/CD8/IFN-γ (data not shown). It was found that in MSI-high or EBV+ gastric cancers, about 49% were positive for PD-L1, and a high proportion of the PD-L1-positive cells were triple positive for PD-L1/CD8/IFN-γ. It was also found that a proportion of PD-L1-positive cells and PD-L1/CD8/IFN-γ positive cells were also positive for PIK3CA. This finding suggests that these cancers may be treated with a PD-1 antibody, optionally in combination with a PIK3 therapeutic.

MSI-high CRC samples were tested for a combination of markers (data not shown). It was found that in MSI-high CRC samples, a high proportion of the PD-L1/CD8/IFN-γ samples are also positive for LAG-3, PD-1 (also called PDCD1), RNF43, and BRAF. This finding suggests that these cancers may be treated with a PD-1 antibody, optionally in combination with a therapeutic that targets one or more of LAG-3, PDCD1, RNF43, and BRAF.

Squamous cell lung cancers were tested for a combination of markers (data not shown). It was found that in squamous cell lung cancer samples, a high proportion of the PD-L1/CD8/IFN-γ samples are also positive for LAG-3. This finding suggests that these cancers may be treated with a PD-1 antibody, optionally in combination with a therapeutic that targets LAG-3, e.g., a LAG-3 antibody.

Papillary thyroid cancers were tested for a combination of markers including the BRAF V600E mutation (data not shown). It was found that a high proportion of thyroid cancer samples that are positive for PD-L1 are also positive for BRAF V600E. This finding suggests that these cancers may be treated with a PD-1 antibody, optionally in combination with a therapeutic that targets BRAF.

Example 5: Patient Selection Based on PD-L1 Status

To enable broad examination of cancer indications for PD-1/PD-L1 based therapies, we evaluated PD-L1 expression at both the protein and mRNA level in human cancers including both lung and hepatic tumors.

PD-L1 protein expression was evaluated in a set of formalin-fixed paraffin-embedded non-small cell lung (NSCLC) adenocarcinoma (ACA), NSCLC squamous cell carcinoma (SCC), and hepatocellular carcinoma (HCC) tumors by immunohistochemistry (IHC). PD-L1 expression was scored semi-quantitatively by a manual histo-score (H-score) methodology based on staining intensity and percentage of positive tumor cells. In our IHC analysis, PD-L1 positivity (PD-L1+) was defined as an H-score ≥20. In parallel, PD-L1 mRNA expression data was examined from The Cancer Genome Atlas (TCGA) in these same indications (503 NSCLC ACA, 489 NSCLC SCC, and 191 HCC) and analyzed by comparing the expression in matched normal tissues from TCGA.

With RNAseq analysis, data was calculated as log 2 (RPKM+0.1) after RSEM normalization, utilizing OmicSoft RNASeq pipelines across TCGA tumor indications. The expression of PD-L1 is elevated in NSCLC ACA and SCC, relative to that in HCC. By overlaying the distributions and comparing the expression levels across all indications in TCGA, we ranked overexpression profiles for PD-L1 and found the TCGA HCC cohort to have much reduced PD-L1 mRNA levels, with a median level of −0.8 compared to 1.3 for ACA and 1.5 for SCC, which amounts to more than a 2-fold change of median level expression. With RNAseq, our analysis defines 50% of NSCLC adenocarcinoma, 54% of NSCLC squamous cell carcinoma, and 6% of HCC as high expressers for PD-L1.

Tumor cell PD-L1 protein expression was measured in 45 lung adenocarcinoma (ACA) samples, 47 lung squamous cell carcinoma (SCC) samples, and 36 hepatocellular carcinoma (HCC) samples. 16/45 (35.6%) lung ACA, 21/47 (44.7%) lung SCC were PD-L1 positive. In contrast, PD-L1 positivity was seen in only 2/36 (5.6%) HCC samples.

In summary, with IHC and RNAseq analysis in large and independent human NSCLC and HCC sample sets, we have found PD-L1 expression to be more enriched in NSCLC than in HCC. Within NSCLC, there are comparable findings between adenocarcinoma and squamous cell carcinomas. Importantly, amongst the large number of samples (128 for IHC and 1183 for RNAseq) in the 3 indications, very good concordance is observed between protein- and mRNA-based analyses. Our finding thus establishes the basis for large scale mRNA-based data mining in TCGA for indications and patient segments that may be enriched for responses to PD-1/PD-L1-based immune therapies.

Example 6: Effects of Targeted Agents on PD-L1 Modulation

This example evaluates the effects of selected therapeutic agents (e.g., a cMET inhibitor, a MEK inhibitor, a bRAF inhibitor, and an ALK inhibitor) on PD-L1 (CD274) modulation. Compound A17 can be prepared as disclosed in Example 21 of U.S. Pat. No. 8,420,645. The following compounds: Compound A18 (ruxolitinib phosphate), Compound A23 (ceritinib), Compound A34 (Binimetinib), and Compound A29 (Encorafenib) are available from Novartis AG, Basel, Switzerland. Selected therapeutic agents were examined by real time PCR and flow cytometry on PD-L1 levels. Significant inhibition of PD-L1 by Compound A17, Compound A18, Compound A34, Compound A29, and Compound A23 on tumor cells was observed.

Compound A11 Downregulation of PD-L1 Protein in Non-Small Cell Lung Cancer Cells PD-L1 (CD274) expression was analyzed in cancer cell lines treated with Compound A17. Cells were obtained from ATCC and cultured in vitro following ATCC directions. The cell lines used were previously characterized by the Cancer Cell Line Encyclopedia Project (http://www.broadinstitute.org/ccle/home).

Cells plated in six-well culture plates were treated with the Compound A17 at different concentrations (10 nM, 100 nM, and 1000 nM) for 24, 48 and 72 hours. Equal amount of vehicle (DMSO) was used as a control. Cells were washed with PBS and then harvested using a cell scraper.

For each reaction, 0.5-1×$10^6$ cells were stained with 20 μL of anti-human monoclonal PD-L1-PE antibody, clone M1H1 (BD) for 30-60 minutes at 4° C. Cells were washed twice and data was acquired using a Canto II with FACSDiva software (BD Bioscience). Data analysis was performed using FlowJo software (Tree Star). Mean fluorescence intensity (MFI) was determined by gating on single cells. Unstained cells were used as a gating control.

Figure 15:
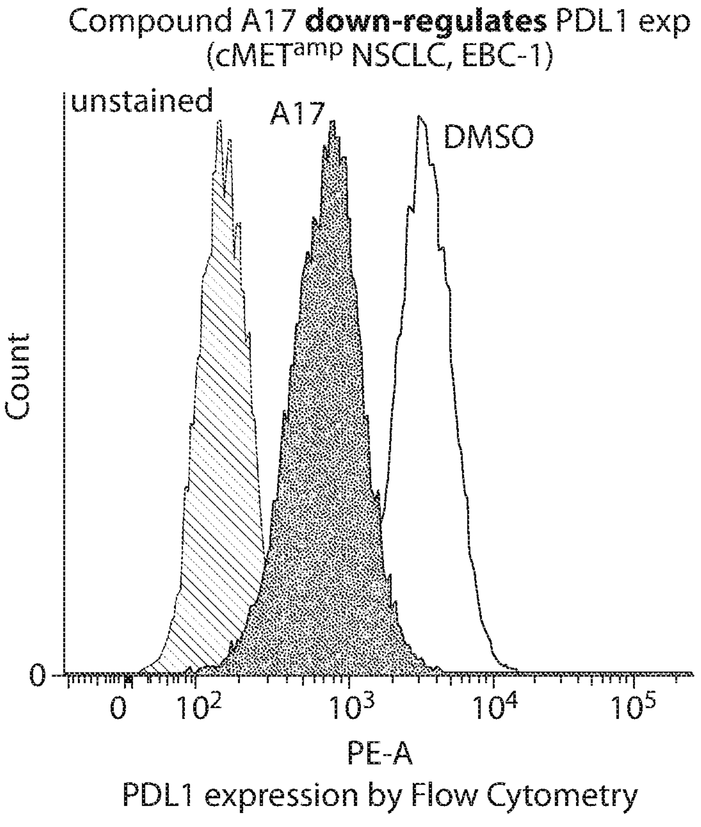
FIG. 15 shows a graphical representation of flow cytometry of PD-L1 surface expression in EBC-1 cells in vitro with or without Compound A17 treatment. EBC-1 cells are non-small cell lung cancer cells with a cMET amplification.

In vitro treatment of EBC-1 cells (Non-Small Cell Lung Cancer (NSCLC) with cMET amplification) with Compound A17 led to significant downregulation of surface expression of PD-L1 as observed by flow cytometry (FIG. 15). The results presented herein suggest that Compound A17 functions as a PD-L1/PD-1 inhibitor.

Compound A17, Compound A34, Compound A18, Compound A29, and Compound A23 Downregulate PD-L1 mRNA TaqMan RT PCR assays were developed to detect changes of expression levels of PD-L1 (CD274) in cell lines and xenograft tumors. mRNA was isolated from frozen cell pellets or tumor fragments using the Qiagen RNeasy Mini kit. Isolated RNA was frozen at −80° C. RNA quality was checked and RNA was quantified using a 2100 Agilent Bioanalyzer following the protocol for the Agilent RNA 6000 Nano Kit. cDNA was prepared using a High Capacity RNA− to cDNA Kit (Applied Biosystems).

Real-time PCR reactions were carried out in 20 μl total volume, including 10 μl of Universal PCR master mix (Applied Biosystems), 10 of human PD-L1 (CD274) probe/primer set (Applied Biosystems), and 8 μl of cDNA. Each sample was run in triplicate. The amount of cDNA produced from 25-50 ng of RNA in the reverse transcription reaction was used in each PCR reaction. Due to difference in mRNA levels between PD-L1 and GAPDH, the two real-time PCR reactions were done in separate tubes using same amount of cDNA. The real-time PCR reaction was run on the C1000 Thermal Cycle (BioRad) with the cycle program as follows: a 10 minute incubation at 95° C. followed by 40 cycles of 95° C. for 15 seconds and 60° C. for 1 minute. After the reaction was complete, the PD-L1 average Ct was normalized relative to each Ct value from the GAPDH reference reaction. Each normalized logarithmic value was then converted into a linear value.

Figure 16:
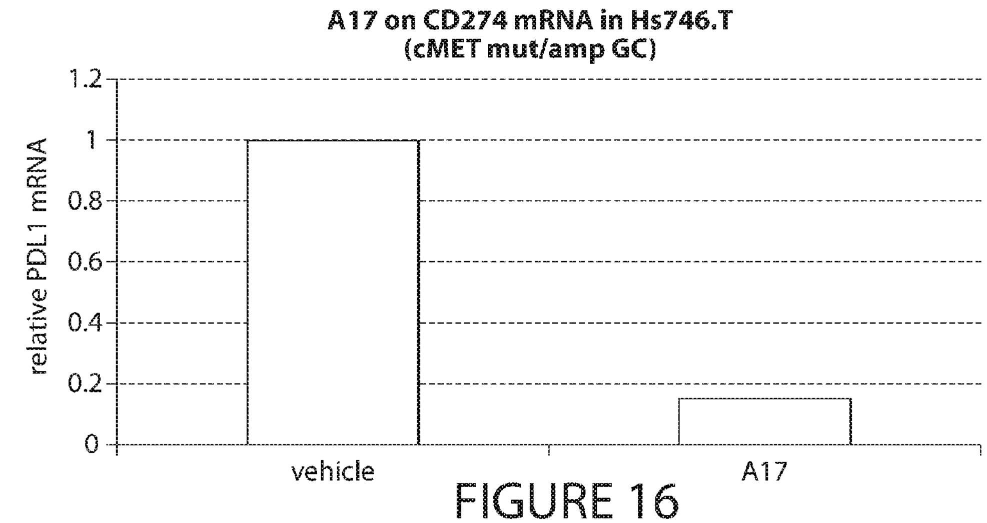
FIG. 16 shows a graphical representation of PD-L1 mRNA expression in Hs.746.T cells in a tumor xenograft model with or without Compound A17 treatment. Hs.746.T cells are gastric cancer cells with a c-MET amplification and a c-MET mutation.
Figure 17:
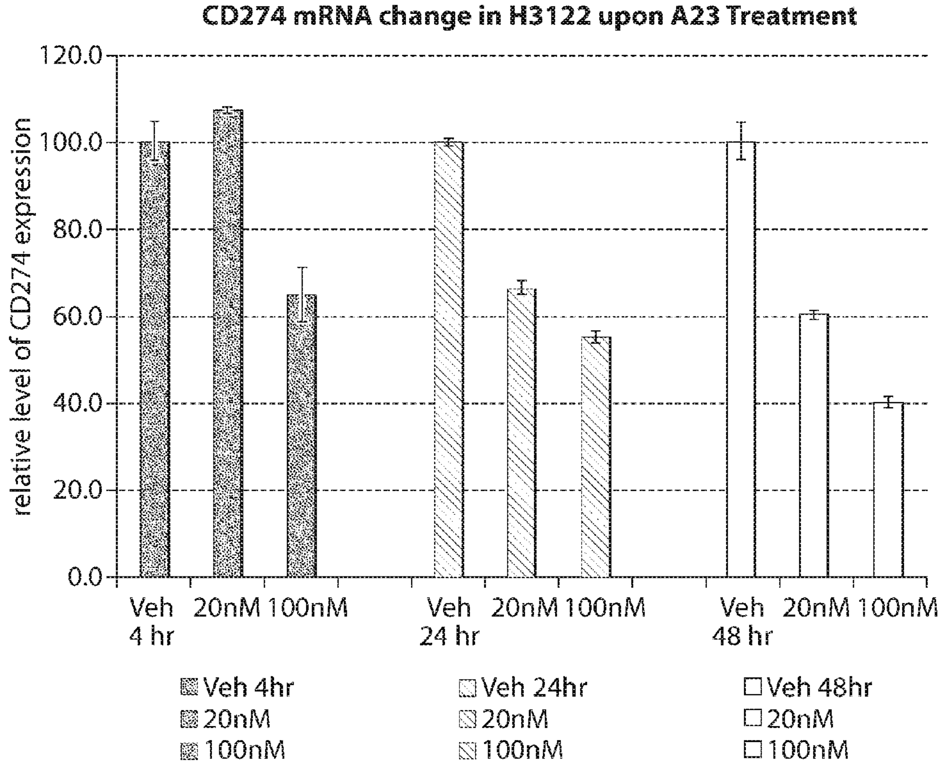
FIG. 17 shows a graphical representation of PD-L1 mRNA expression in H3122 cells in vitro with or without Compound A23. H3122 cells are non-small cell lung cancer (NSCLC) cells with an ALK translocation.
Figure 18:
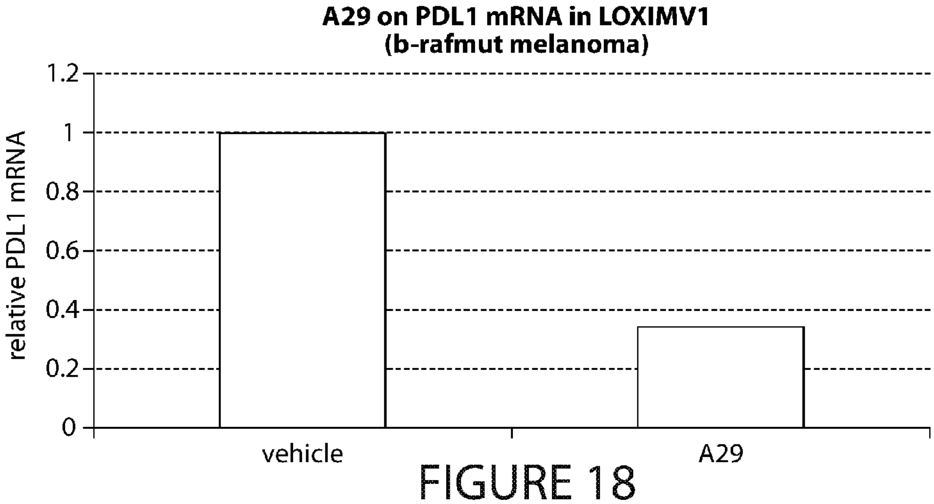
FIG. 18 shows a graphical representation of PD-L1 mRNA expression in LOXIMV1 cells (BRAF mutant melanoma cells) in a tumor xenograft model with or without Compound A29 treatment.
Figure 19:
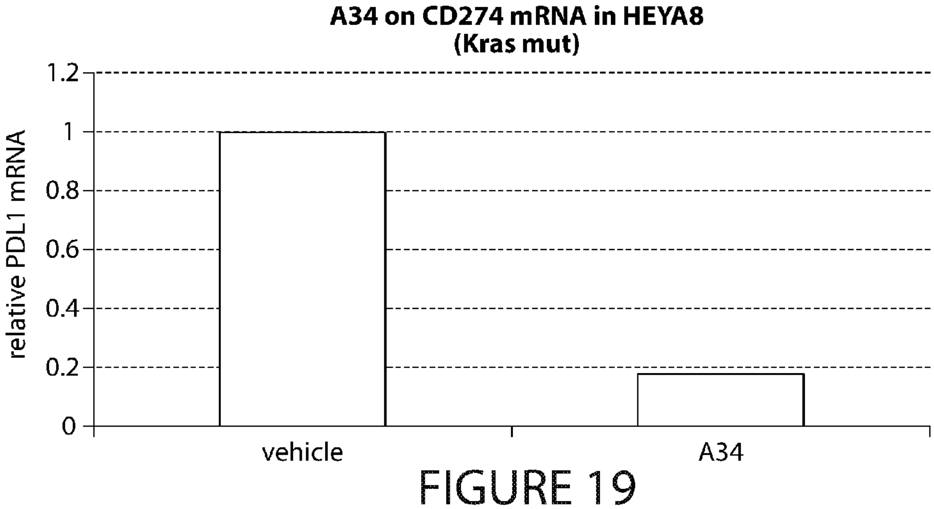
FIG. 19 shows a graphical representation of PD-L1 mRNA expression in HEYA8 cells (KRAS mutant ovarian cancer cells) in a tumor xenograft model with or without Compound A34 treatment.
Figure 20:
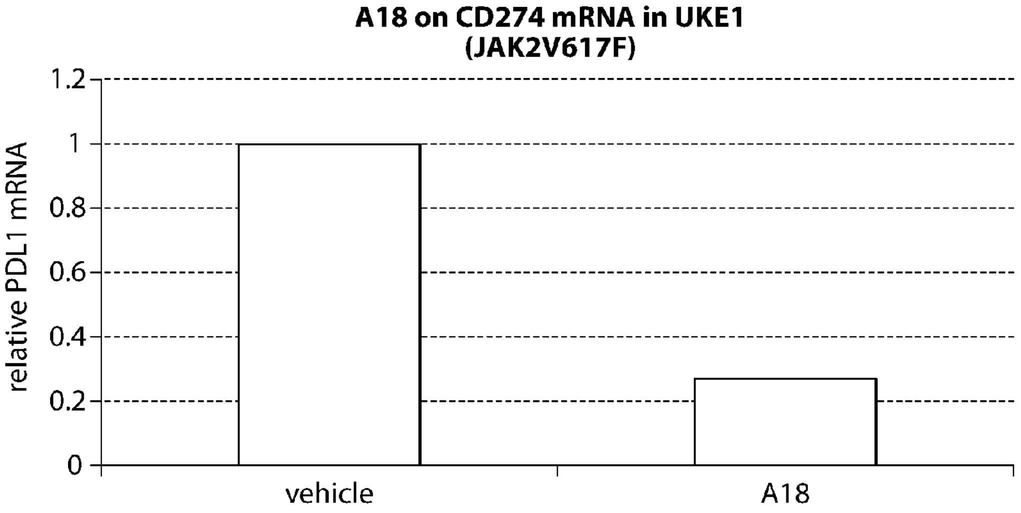
FIG. 20 shows a graphical representation of PD-L1 mRNA expression in UKE-1 cells (JAK2 V617F mutant myeloproliferative neoplasm cells) in a tumor xenograft model with or without Compound A18 treatment.

Inhibition of PD-L1 expression (mRNA) by Compound A17 was observed in a Hs.746.T tumor (gastric cancer cell with cMET amplification & mutation) xenograft (FIG. 16). Inhibition of PD-L1 mRNA by Compound A23 was observed in H3122 (Non-Small Cell Lung Cancer (NSCLC) with ALK translocation) in vitro (FIG. 17). Downregulation of PD-L1 mRNA by Compound A29, and Compound A34 was observed in tumor xenograft models bearing LOXIMV1 (BRAF mutant melanoma, FIG. 18) and HEYA8 (KRAF mutant ovarian cancer, FIG. 19) tumors, respectively. Downregulation of PD-L1 mRNA by Compound A18 was observed in tumor xenograft models bearing UKE-1 (Myeloproliferative Neoplasm (MPN) line with JAK2V617F mutation, FIG. 20).

The results presented herein demonstrate a role of Compound A17, Compound A34, Compound A18, Compound A29, and Compound A23 in the regulation of immunecheckpoint molecules on cancer. The observed inhibition of PD-L1 expression by these agents suggests that these targeted agents may have immune-modulatory activities, in addition to their effects on cancer signaling. Thus, the results presented herein suggest that administration of targeted agents with inhibitors of immunecheckpoint inhibitors such as PD-1, PD-L1, LAG-3 and/or TIM-3 will achieve a more potent reversal of the immunecheckpoint-mediated immune suppression.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. An antibody molecule capable of binding to human Programmed Death-1 (PD-1), comprising:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

2. The antibody molecule of claim 1, comprising a VH comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33.

3. The antibody molecule of claim 1, comprising a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

4. The antibody molecule of claim 1, comprising a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33.

5. The antibody molecule of claim 1, comprising a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

6. The antibody molecule of claim 1, wherein said antibody molecule is a humanized antibody molecule.

7. The antibody molecule of claim 1, which comprises a VH comprising an amino acid sequence at least 85% identical to any of the amino acid sequence of SEQ ID NO: 38, 50, 82, or 86.

8. The antibody molecule of claim 1, which comprises a VH comprising the amino acid sequence of SEQ ID NO: 38, 50, 82, or 86.

9. The antibody molecule of claim 1, which comprises a VL comprising an amino acid sequence at least 85% identical to any of the amino acid sequence of SEQ ID NO: 42, 46, 54, 58, 62, 66, 70, 74, or 78.

10. The antibody molecule of claim 1, which comprises a VL comprising the amino acid sequence of SEQ ID NO: 42, 46, 54, 58, 62, 66, 70, 74, or 78.

11. The antibody molecule of claim 1, which comprises:

(a) a VH comprising the amino acid sequence of SEQ ID NO: 38 and a VL comprising the amino acid sequence of SEQ ID NO: 54;

(b) a VH comprising the amino acid sequence of SEQ ID NO: 38 and a VL comprising the amino acid sequence of SEQ ID NO: 42;

(c) a VH comprising the amino acid sequence of SEQ ID NO: 38 and a VL comprising the amino acid sequence of SEQ ID NO: 66;

(d) a VH comprising the amino acid sequence of SEQ ID NO: 38 and a VL comprising the amino acid sequence of SEQ ID NO: 70;

(e) a VH comprising the amino acid sequence of SEQ ID NO: 50 and a VL comprising the amino acid sequence of SEQ ID NO: 70;

(f) a VH comprising the amino acid sequence of SEQ ID NO: 38 and a VL comprising the amino acid sequence of SEQ ID NO: 46;

(g) a VH comprising the amino acid sequence of SEQ ID NO: 50 and a VL comprising the amino acid sequence of SEQ ID NO: 46;

(h) a VH comprising the amino acid sequence of SEQ ID NO: 50 and a VL comprising the amino acid sequence of SEQ ID NO: 54;

(i) a VH comprising the amino acid sequence of SEQ ID NO: 38 and a VL comprising the amino acid sequence of SEQ ID NO: 58;

(j) a VH comprising the amino acid sequence of SEQ ID NO: 38 and a VL comprising the amino acid sequence of SEQ ID NO: 62;

(k) a VH comprising the amino acid sequence of SEQ ID NO: 50 and a VL comprising the amino acid sequence of SEQ ID NO: 66;

(l) a VH comprising the amino acid sequence of SEQ ID NO: 38 and a VL comprising the amino acid sequence of SEQ ID NO: 74;

(m) a VH comprising the amino acid sequence of SEQ ID NO: 38 and a VL comprising the amino acid sequence of SEQ ID NO: 78;

(n) a VH comprising the amino acid sequence of SEQ ID NO: 82 and a VL comprising the amino acid sequence of SEQ ID NO: 70;

(o) a VH comprising the amino acid sequence of SEQ ID NO: 82 and a VL comprising the amino acid sequence of SEQ ID NO: 66; or (p) a VH comprising the amino acid sequence of SEQ ID NO: 86 and a VL comprising the amino acid sequence of SEQ ID NO: 66.

12. The antibody molecule of claim 1, which comprises a heavy chain comprising the amino acid sequence of SEQ ID NO: 40, 52, 84, 88, 91, or 102.

13. The antibody molecule of claim 1, which comprises a light chain comprising the amino acid sequence of SEQ ID NO: 44, 48, 56, 60, 64, 68, 72, 76, or 80.

14. The antibody molecule of claim 1, which comprises:

(a) a heavy chain comprising the amino acid sequence of SEQ ID NO: 91 and a light chain comprising the amino acid sequence of SEQ ID NO: 44;

(b) a heavy chain comprising the amino acid sequence of SEQ ID NO: 91 and a light chain comprising the amino acid sequence of SEQ ID NO: 56;

(c) a heavy chain comprising the amino acid sequence of SEQ ID NO: 91 and a light chain comprising the amino acid sequence of SEQ ID NO: 68;

(d) a heavy chain comprising the amino acid sequence of SEQ ID NO: 91 and a light chain comprising the amino acid sequence of SEQ ID NO: 72;

(e) a heavy chain comprising the amino acid sequence of SEQ ID NO: 102 and a light chain comprising the amino acid sequence of SEQ ID NO: 72;

(f) a heavy chain comprising the amino acid sequence of SEQ ID NO: 40 and a light chain comprising the amino acid sequence of SEQ ID NO: 44;

(g) a heavy chain comprising the amino acid sequence of SEQ ID NO: 40 and a light chain comprising the amino acid sequence of SEQ ID NO: 48;

(h) a heavy chain comprising the amino acid sequence of SEQ ID NO: 52 and a light chain comprising the amino acid sequence of SEQ ID NO: 48;

(i) a heavy chain comprising the amino acid sequence of SEQ ID NO: 52 and a light chain comprising the amino acid sequence of SEQ ID NO: 56;

(j) a heavy chain comprising the amino acid sequence of SEQ ID NO: 40 and a light chain comprising the amino acid sequence of SEQ ID NO: 56;

(k) a heavy chain comprising the amino acid sequence of SEQ ID NO: 40 and a light chain comprising the amino acid sequence of SEQ ID NO: 60;

(l) a heavy chain comprising the amino acid sequence of SEQ ID NO: 40 and a light chain comprising the amino acid sequence of SEQ ID NO: 64;

(m) a heavy chain comprising the amino acid sequence of SEQ ID NO: 52 and a light chain comprising the amino acid sequence of SEQ ID NO: 68;

(n) a heavy chain comprising the amino acid sequence of SEQ ID NO: 40 and a light chain comprising the amino acid sequence of SEQ ID NO: 68;

(o) a heavy chain comprising the amino acid sequence of SEQ ID NO: 52 and a light chain comprising the amino acid sequence of SEQ ID NO: 72;

(p) a heavy chain comprising the amino acid sequence of SEQ ID NO: 40 and a light chain comprising the amino acid sequence of SEQ ID NO: 72;

(q) a heavy chain comprising the amino acid sequence of SEQ ID NO: 40 and a light chain comprising the amino acid sequence of SEQ ID NO: 76;

(r) a heavy chain comprising the amino acid sequence of SEQ ID NO: 40 and a light chain comprising the amino acid sequence of SEQ ID NO: 80;

(s) a heavy chain comprising the amino acid sequence of SEQ ID NO: 84 and a light chain comprising the amino acid sequence of SEQ ID NO: 72;

(t) a heavy chain comprising the amino acid sequence of SEQ ID NO: 84 and a light chain comprising the amino acid sequence of SEQ ID NO: 68; or (u) a heavy chain comprising the amino acid sequence of SEQ ID NO: 88 and a light chain comprising the amino acid sequence of SEQ ID NO: 68.

15. The antibody molecule of claim 1, which comprises a Fab, F(ab')2, Fv, or a single chain Fv fragment (scFv).

16. The antibody molecule of claim 1, which comprises (a) a heavy chain constant region of IgG1, IgG2, IgG3, or IgG4, (b) a light chain constant region of kappa or lambda, or both (a) and (b).

17. The antibody molecule of claim 16, which comprises a human IgG4 heavy chain constant region with a Serine to Proline mutation at position 108 of SEQ ID NO: 212 or 214 and a kappa light chain constant region.

18. The antibody molecule of claim 16, which comprises one or more of:

(a) a human IgG1 heavy chain constant region with an Asparagine to Alanine mutation at position 180 of SEQ ID NO: 216 and a kappa light chain constant region;

(b) a human IgG1 heavy chain constant region with an Aspartate to Alanine mutation at position 148 and Proline to Alanine mutation at position 212 of SEQ ID NO: 217, and a kappa light chain constant region; or (c) a human IgG1 heavy chain constant region with a Leucine to Alanine mutation at position 117 and Leucine to Alanine mutation at position 118 of SEQ ID NO: 218, and a kappa light chain constant region.

19. The antibody molecule of claim 1, which is capable of binding to human PD-1 with a dissociation constant ($K_D$) of less than about 0.2 nM.

20. The antibody molecule of claim 1, wherein the VH comprises the amino acid sequence of SEQ ID NO: 38 and the VL comprises the amino acid sequence of SEQ ID NO: 54.

21. The antibody molecule of claim 1, wherein the VH comprises the amino acid sequence of SEQ ID NO: 38 and the VL comprises the amino acid sequence of SEQ ID NO: 70.

22. The antibody molecule of claim 1, wherein the heavy chain comprises the amino acid sequence of SEQ ID NO: 91 and the light chain comprises the amino acid sequence of SEQ ID NO: 56.

23. The antibody molecule of claim 1, wherein the heavy chain comprises the amino acid sequence of SEQ ID NO: 91 and the light chain comprises the amino acid sequence of SEQ ID NO: 72.

24. An antibody molecule capable of binding to human PD-1, comprising a VH comprising the amino acid sequence of SEQ ID NO: 38 and a VL comprising the amino acid sequence of SEQ ID NO: 54.

25. An antibody molecule capable of binding to human PD-1, comprising a VH comprising the amino acid sequence of SEQ ID NO: 38 and a VL comprising the amino acid sequence of SEQ ID NO: 70.

26. A bispecific antibody molecule having a first binding specificity for PD-1 and a second binding specificity for TIM-3, LAG-3, CEACAM-1, CEACAM-5, PD-L1 or PD-L2, wherein the bispecific antibody molecule comprises:

(a) a VH comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

27. The bispecific antibody molecule of claim 26, which comprises:

(a) a VH comprising the amino acid sequence of SEQ ID NO: 38 and a VL comprising the amino acid sequence of SEQ ID NO: 54;

(b) a VH comprising the amino acid sequence of SEQ ID NO: 38 and a VL comprising the amino acid sequence of SEQ ID NO: 42;

(c) a VH comprising the amino acid sequence of SEQ ID NO: 38 and a VL comprising the amino acid sequence of SEQ ID NO: 66;

(d) a VH comprising the amino acid sequence of SEQ ID NO: 38 and a VL comprising the amino acid sequence of SEQ ID NO: 70;

(e) a VH comprising the amino acid sequence of SEQ ID NO: 50 and a VL comprising the amino acid sequence of SEQ ID NO: 70;

(f) a VH comprising the amino acid sequence of SEQ ID NO: 38 and a VL comprising the amino acid sequence of SEQ ID NO: 46;

(g) a VH comprising the amino acid sequence of SEQ ID NO: 50 and a VL comprising the amino acid sequence of SEQ ID NO: 46;

(h) a VH comprising the amino acid sequence of SEQ ID NO: 50 and a VL comprising the amino acid sequence of SEQ ID NO: 54;

(i) a VH comprising the amino acid sequence of SEQ ID NO: 38 and a VL comprising the amino acid sequence of SEQ ID NO: 58;

(j) a VH comprising the amino acid sequence of SEQ ID NO: 38 and a VL comprising the amino acid sequence of SEQ ID NO: 62;

(k) a VH comprising the amino acid sequence of SEQ ID NO: 50 and a VL comprising the amino acid sequence of SEQ ID NO: 66;

(l) a VH comprising the amino acid sequence of SEQ ID NO: 38 and a VL comprising the amino acid sequence of SEQ ID NO: 74;

(m) a VH comprising the amino acid sequence of SEQ ID NO: 38 and a VL comprising the amino acid sequence of SEQ ID NO: 78;

(n) a VH comprising the amino acid sequence of SEQ ID NO: 82 and a VL comprising the amino acid sequence of SEQ ID NO: 70;

(o) a VH comprising the amino acid sequence of SEQ ID NO: 82 and a VL comprising the amino acid sequence of SEQ ID NO: 66; or (p) a VH comprising the amino acid sequence of SEQ ID NO: 86 and a VL comprising the amino acid sequence of SEQ ID NO: 66.

28. The bispecific antibody molecule of claim 26, which comprises:

(a) a heavy chain comprising the amino acid sequence of SEQ ID NO: 91 and a light chain comprising the amino acid sequence of SEQ ID NO: 44;

(b) a heavy chain comprising the amino acid sequence of SEQ ID NO: 91 and a light chain comprising the amino acid sequence of SEQ ID NO: 56;

(c) a heavy chain comprising the amino acid sequence of SEQ ID NO: 91 and a light chain comprising the amino acid sequence of SEQ ID NO: 68;

(d) a heavy chain comprising the amino acid sequence of SEQ ID NO: 91 and a light chain comprising the amino acid sequence of SEQ ID NO: 72;

(e) a heavy chain comprising the amino acid sequence of SEQ ID NO: 102 and a light chain comprising the amino acid sequence of SEQ ID NO: 72;

(f) a heavy chain comprising the amino acid sequence of SEQ ID NO: 40 and a light chain comprising the amino acid sequence of SEQ ID NO: 44;

(g) a heavy chain comprising the amino acid sequence of SEQ ID NO: 40 and a light chain comprising the amino acid sequence of SEQ ID NO: 48;

(h) a heavy chain comprising the amino acid sequence of SEQ ID NO: 52 and a light chain comprising the amino acid sequence of SEQ ID NO: 48;

(i) a heavy chain comprising the amino acid sequence of SEQ ID NO: 52 and a light chain comprising the amino acid sequence of SEQ ID NO: 56;

(j) a heavy chain comprising the amino acid sequence of SEQ ID NO: 40 and a light chain comprising the amino acid sequence of SEQ ID NO: 56;

(k) a heavy chain comprising the amino acid sequence of SEQ ID NO: 40 and a light chain comprising the amino acid sequence of SEQ ID NO: 60;

(l) a heavy chain comprising the amino acid sequence of SEQ ID NO: 40 and a light chain comprising the amino acid sequence of SEQ ID NO: 64;

(m) a heavy chain comprising the amino acid sequence of SEQ ID NO: 52 and a light chain comprising the amino acid sequence of SEQ ID NO: 68;

(n) a heavy chain comprising the amino acid sequence of SEQ ID NO: 40 and a light chain comprising the amino acid sequence of SEQ ID NO: 68;

(o) a heavy chain comprising the amino acid sequence of SEQ ID NO: 52 and a light chain comprising the amino acid sequence of SEQ ID NO: 72;

(p) a heavy chain comprising the amino acid sequence of SEQ ID NO: 40 and a light chain comprising the amino acid sequence of SEQ ID NO: 72;

(q) a heavy chain comprising the amino acid sequence of SEQ ID NO: 40 and a light chain comprising the amino acid sequence of SEQ ID NO: 76;

(r) a heavy chain comprising the amino acid sequence of SEQ ID NO: 40 and a light chain comprising the amino acid sequence of SEQ ID NO: 80;

(s) a heavy chain comprising the amino acid sequence of SEQ ID NO: 84 and a light chain comprising the amino acid sequence of SEQ ID NO: 72;

(t) a heavy chain comprising the amino acid sequence of SEQ ID NO: 84 and a light chain comprising the amino acid sequence of SEQ ID NO: 68; or (u) a heavy chain comprising the amino acid sequence of SEQ ID NO: 88 and a light chain comprising the amino acid sequence of SEQ ID NO: 68.

29. A pharmaceutical composition comprising the antibody molecule of claim 1 and a pharmaceutically acceptable carrier, excipient or stabilizer.

30. A pharmaceutical composition comprising the antibody molecule of claim 26 and a pharmaceutically acceptable carrier, excipient or stabilizer.

* * * * *